US012780946B2

(12) United States Patent
Lee et al.

(10) Patent No.: US 12,780,946 B2
(45) Date of Patent: Nov. 3, 2026

(54) ANTI-MERTK ANTIBODIES AND METHODS OF USE THEREOF

(71) Applicant: ALECTOR LLC, South San Francisco, CA (US)

(72) Inventors: Seung-Joo Lee, Benicia, CA (US); Spencer Liang, San Mateo, CA (US); Angie Yee, San Francisco, CA (US); Marina Roell, Concord, CA (US); Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 480 days.

(21) Appl. No.: 18/392,569

(22) Filed: Dec. 21, 2023

(65) Prior Publication Data

US 2024/0287204 A1 Aug. 29, 2024

Related U.S. Application Data

(62) Division of application No. 17/118,921, filed on Dec. 11, 2020, now Pat. No. 11,897,968.

(60) Provisional application No. 63/121,773, filed on Dec. 4, 2020, provisional application No. 63/016,821, filed on Apr. 28, 2020, provisional application No. 62/947,855, filed on Dec. 13, 2019.

(51) Int. Cl.

| | |
|---|---|
| ***C07K 16/40*** | (2006.01) |
| ***A61P 35/00*** | (2006.01) |
| ***C07K 16/28*** | (2006.01) |
| *A61K 39/00* | (2006.01) |

(52) U.S. Cl.

CPC .............. *C07K 16/40* (2013.01); *A61P 35/00* (2018.01); *C07K 16/2818* (2013.01); *C07K 16/2827* (2013.01); *A61K 2039/507* (2013.01); *C07K 2317/56* (2013.01); *C07K 2317/622* (2013.01); *C07K 2317/76* (2013.01)

(58) Field of Classification Search

None

See application file for complete search history.

(56) References Cited

U.S. PATENT DOCUMENTS

| | | | | |
|---|---|---|---|---|
| 10,017,564 | B2 | 7/2018 | Sahin et al. | |
| 10,221,248 | B2 * | 3/2019 | Tavazoie ................ | C07K 16/40 |
| 11,897,968 | B2 | 2/2024 | Lee et al. | |
| 2018/0002444 | A1 | 1/2018 | Tavazoie et al. | |
| 2020/0291135 | A1 | 9/2020 | Tavazoie et al. | |

FOREIGN PATENT DOCUMENTS

| | | | | |
|---|---|---|---|---|
| WO | WO-2006058202 A2 | 6/2006 | | |
| WO | WO-2009062112 A2 | 5/2009 | | |
| WO | WO-2016001830 A1 | 1/2016 | | |
| WO | WO-2016106221 A1 * | 6/2016 | ............. | A61K 31/44 |
| WO | WO-2019005756 A1 | 1/2019 | | |
| WO | WO-2019084307 A1 | 5/2019 | | |
| WO | WO-2020076799 A1 | 4/2020 | | |
| WO | WO-2020106461 A2 | 5/2020 | | |
| WO | WO-2020176497 A1 | 9/2020 | | |
| WO | WO-2020214995 A1 | 10/2020 | | |
| WO | WO-2021119508 A1 | 6/2021 | | |
| WO | WO-2021202590 A1 | 10/2021 | | |
| WO | WO-2022266221 A1 | 12/2022 | | |
| WO | WO-2022266223 A1 | 12/2022 | | |

OTHER PUBLICATIONS

Al-Khersan, H., et al., "A novel MERTK mutation causing retinitis pigmentosa," Graefe's Archive for Clinical and Experimental Ophthalmology 255(8):1613-1619, Springer Verlag, Germany (May 2017).

Audo, I., et al., "MERTK mutation update in inherited retinal diseases," Hum Mutat 39(7):887-913, Wiley-Liss Inc., United States (May 2018).

Binder, M. D., et al., "Common and Low Frequency Variants in MERTK Are Independently Associated with Multiple Sclerosis Susceptibility with Discordant Association Dependent upon HLA-DRB1*15:01 Status," PLoS Genetics 12(3):e1005853, 25 pages, Public Library of Science, United States (Mar. 2016).

Cook, R. S., et al., "MerTK inhibition in tumor leukocytes decreases tumor growth and metastasis," Journal of Clinical Investigation 123(8):3231-3242, American Society for Clinical Investigation, United States (Jul. 2013).

Cummings, C. T., et al., "Molecular pathways: MERTK signaling in cancer," Clinical Cancer Research 19(19):5275-5280, American Association for Cancer Research Inc., United States (Jul. 2013).

Cummings, C. T., et al., "Mer590, a novel monoclonal antibody targeting MER receptor tyrosine kinase, decreases colony formation and increases chemosensitivity in non-small cell lung cancer," Oncotarget 5(21):10434-10445, Impact Journals LLC, United States (Jun. 2014).

Dayoub, A. S., and Brekken, R. A., "TIMs, TAMs, and PS-antibody targeting: implications for cancer immunotherapy ," Cell Communication and Signaling 18:29, 11 pages, Signal Transduction Society, United Kingdom (Feb. 2020).

Graham, D. K., et al., "The TAM family: phosphatidylserine-sensing receptor tyrosine kinases gone awry in cancer," Nat Rev Cancer 14(12):769-785, Nature Publishing Group, United Kingdom (Dec. 2014).

Healy, L. M., et al., "MerTK Is a Functional Regulator ofMyelin Phagocytosis by Human Myeloid Cells," Journal of Immunology 196(8):3375-3384, American Association of Immunologists, United States (Mar. 2016).

Healy, L. M., et al., "MerTK-mediated regulation of myelin phagocytosis by macrophages generated from patients with MS," Neurology: Neuroimmunology & Neuroinflammation 4(6):e402, 7 pages, Lippincott Williams and Wilkins Ltd., United States (Oct. 2017).

(Continued)

*Primary Examiner* — Laura B Goddard

(74) *Attorney, Agent, or Firm* — Sterne, Kessler, Goldstein & Fox P.L.L.C.

(57) ABSTRACT

The present disclosure is generally directed to compositions that include antibodies, e.g., monoclonal, antibodies, antibody fragments, etc., that specifically bind a MerTK polypeptide, e.g., a mammalian MerTK or human MerTK, and use of such compositions in treating an individual in need thereof.

20 Claims, 26 Drawing Sheets

Specification includes a Sequence Listing.

(56) References Cited

OTHER PUBLICATIONS

Huey, M. G., et al., "Targeting the TAM Receptors in Leukemia," Cancers (Basel) 8(11):101, 22 pages, MDPI Multidisciplinary Digital Publishing Institute, Switzerland (Nov. 2016).
Kedage, V., et al., "Harnessing MerTK agonism for targeted therapeutics," MAbs 12(1):e1685832, 8 pages, Landes Bioscience, United States (Dec. 2019).
Lavail, M. M., et al., "Gene Therapy for MERTK-Associated Retinal Degenerations," Advances in Experimental Medicine and Biology 854:487-493, Springer New York, United States (Oct. 2015).
Lorach, H., et al., "Long-term Rescue of Photoreceptors in a Rodent Model of Retinitis Pigmentosa Associated with MERTK Mutation," Sci Rep 8:11312, 10 pages, Nature Publishing Group, United Kingdom (Jul. 2018).
Ma, G. Z. M., et al., "Polymorphisms in the Receptor Tyrosine Kinase MERTK Gene Are Associated with Multiple Sclerosis Susceptibility," PLoS One 6(2):e16964, 6 pages, Public Library of Science, United States (Feb. 2011).
Rothlin, C. V., et al., "TAM receptor signaling in immune homeostasis," Annual Review of Immunology 33:355-391, Annual Reviews Inc., United States (Jan. 2015).
Shafit-Zagardo, B., et al., "The role of TAM family receptors and ligands in the nervous system: From development to pathobiology," Pharmacol Ther 188:97-117, Elsevier, Netherlands (Mar. 2018).
Shen, K., et al., "Multiple sclerosis risk gene Mertk is required for microglial activation and subsequent remyelination," Cell Rep 34(10):108835, 20 pages, Cell Press, United States (Mar. 2021).
Tondo, G., et al., "TAM Receptor Pathways at the Crossroads ofNeuroinflammation and Neurodegeneration," Disease Markers 2019(4):2387614, 14 pages, Hindawi Ltd., Egypt (Sep. 2019).
Ubil, E., et al., "Tumor-secreted Prosl inhibits macrophage M1 polarization to reduce antitumor immune response," Journal of Clinical Investigation 128(6):2356-2369, American Society for Clinical Investigation, United States (Apr. 2018).
Verma, A., et al., "Targeting Axl and Mer kinases in cancer," Mal Cancer Ther 10(10):1763-1773, American Association for Cancer Research Inc., United States (Sep. 2011).
Weinger, J. G., et al., "Up-regulation of soluble Axl and Mer receptor tyrosine kinases negatively correlates with Gas6 in established multiple sclerosis lesions," Am J Pathol 175(1):283-293, Elsevier, Netherlands (Jun. 2009).
Zhou, Y., et al., "Blockade of the Phagocytic Receptor MerTK on Tumor-Associated Macrophages Enhances P2X7R-Dependent STING Activation by Tumor-Derived cGAMP," Immunity 52(2):357-373, Cell Press, United States (Feb. 2020).
Alvarado, D., et al., "Monoclonal Antibodies Targeting the MerTK receptor de-repress the innate immune response," J. Immunother. Cancer 6(SI), 2 pages, BioMed Central Ltd., Netherlands (Nov. 2018).
Dondelinger, M., et al., "Understanding the Significance and Implications of Antibody Numbering and Antigen-Binding Surface/ Residue Definition," Front. Immunol. 9:2278, 15 pages, Frontiers Media S.A., Switzerland (Oct. 2018).
Ginisty, A., et al., "Evidence for a subventricular zone neural stem cell phagocytic activity stimulated by the vitamin K-dependent factor protein S," Stem Cells 33(2):515-525, Wiley, United States (Oct. 2014).
Karl, M.O., et al., "Endogenous Gas6 and Ca2+-channel activation modulate phagocytosis by retinal pigment epithelium," Cellular Signaling 20(6):1159-1168, Elsevier, Netherlands (Jun. 2008).
Santulli-Marotto, S., et al., "Discovering Molecules That Regulate Efferocytosis Using Primary Human Macrophages and High Content Imaging," PLOS One 10(12):e0145078, 21 pages, Public Library of Science, United States (Dec. 2015).
Stanford, J.C., et al., "Efferocytosis produces a prometastatic landscape during postpartum mammary gland involution," J. Clin. Invest. 124(11):4737-4752, American Society for Clinical Investigation, United States (Sep. 2014).
Qin, S., et al., "Roles of av5, FAK and MerTK in oxidative stress inhibition of RPE cell phagocytosis," Experimental Eye Research 94(1):63-70, Academic Press Ltd., United Kingdom (Nov. 2011).
Takeda, S., et al., "Characterization of the anti-cancer and immunologic activity of RGX-019, a novel pre-clinical stage humanized monoclonal antibody targeting the MERTK receptor," Cancer Res. 79(S13): 1 page, American Association for Cancer Research, United States (Jul. 2019).
Todt, J.C., et al., "The receptor tyrosine kinase MerTK activates phospholipase C y2 during recognition of apoptotic thymocytes by murine macrophages," J. Leukoc. Biol. 75(4):705-713, Wiley, United States (Apr. 2004).
Waterborg, C.E., et al., "Protective Role of the MER Tyrosine Kinase via Efferocytosis in Rheumatoid Arthritis Models," Front. Immunol. 9:742, 14 pages, Frontiers Media S.A., Switzerland (Apr. 2018).
White, K.F., et al., "MERTK-specific antibodies that have therapeutic antitumor activity in mice disrupt the integrity of the retinal pigmented epithelium in cynomolgus monkeys," Cancer Res 79:S13, 2 pages, American Association for Cancer Research, United States (Jul. 2019).
Zhang, B., et al., "MerTK Downregulates Lipopolysaccharide-Induced Inflammation Through SOCS1 Protein but Does Not Affect Phagocytosis of *Escherichia coli* in Macrophages," Inflanunation 42(1):113-123, SpringerLink, United States (Feb. 2019).
International Search Report and Written Opinion for International Application No. PCT/US2020/064640, mailed May 11, 2021, European Patent Office, Netherlands, 27 pages.
Abcam. Com, "Anti-MERTK (phospho Y749 + Y753 +Y754) antibody (abl4921)," Abeam.com, accessed at https://www.abcam.com/mertk-phospho-y749--y753--y754-antibody-ab14921.html, (Jun. 2021) accessed on Dec. 23, 2022, 3 pages.
Murase, H., et al., "TUDCA Promotes Phagocytosis by Retinal Pigment Epithelium via MerTK Activation," Invest. Ophthalmol. Vis. Sci. 56(4):2511-2518, Association for Research in Vision and Ophthalmology, United States (Apr. 2015).
R&D Systems, "Mouse Mer Antibody AF591: R&D Systems," Rndsystems.com, accessed at https://www.mdsystems.com/products/mouse-mer-antibody_af591, (Jun. 2021) accessed on Dec. 23, 2022, 7 pages.
International Search Report and Written Opinion for International Application No. PCT/US2021/024970, mailed on Aug. 27, 2021, European Patent Office, Netherlands, 28 pages.
Blander, J.M., et al., "MerTK Blockade Fuels Anti-tumor Immunity," Immunity 52(2):212-214, Cell Press, Netherlands (Feb. 2020).
International Search Report and Written Opinion for International Application No. PCT/US2022/033629, mailed Sep. 16, 2022, European Patent Office, Netherlands, 18 pages.
Akalu, Y.T., et al., "TAM receptor tyrosine kinases as emerging targets of innate immune checkpoint blockade for cancer therapy," Immunological Reviews 276(1):165-177, Wiley, United States (Mar. 2017).
Brinkmann, U., et al., "The making ofbispecific antibodies," mAbs 9(2):182-212, Taylor & Francis, United Kingdom (Feb./Mar. 2017).
Huelse, J.M., et al., "MERTK in cancer therapy: Targeting the receptor tyrosine kinase in tumor cells and the immune system," Pharmacology & Therapeutics 213:107577, 22 pages, Elsevier, United Kingdom (Sep. 2020).
International Search Report and Written Opinion for International Application No. PCT/US2022/033632, mailed Oct. 28, 2022, European Patent Office, Netherlands, 28 pages.
Silva, J.S., et al., "The S228P mutation prevents in vivo and in vitro IgG4 Fab-arm exchange as demonstrated using a combination of novel quantitative immunoassays and physiological matrix preparation," J Biol Chem 290(9):5462-5469, American Society for Biochemistry and Molecular Biology, United States (Feb. 2015).
Grabiec, A.M., et al., "Axl and MerTK receptor tyrosine kinases maintain human macrophage efferocytic capacity in the presence of viral triggers," Eur J Immunol 48(5):855-860, Wiley-VCH Verlag, Germany (May 2018).
R&D Systems product datasheet on antibody AF891 (Dec. 4, 2018).

(56) References Cited

OTHER PUBLICATIONS

Eken, C., et al., "Ectosomes released by polymorphonuclear neutrophils induce a MerTK-dependent anti-inflammatory pathway in macrophages," J Biol Chem 285(51):39914-39921, Elsevier, Inc., United States (Dec. 2010).
Office Action mailed Feb. 13, 2023, in U.S. Appl. No. 17/118,921, Lee, S.-J., et al., filed Dec. 11, 2020, 16 pages.
Co-pending Application, U.S. Appl. No. 17/995,189, inventors Kurnellas, M., et al., international filing date: Mar. 30, 2021 (Not yet Published).
Co-pending Application, U.S. Appl. No. 18/570,888, inventors Lee, S-J., et al., international filing date: Jun. 15, 2022 (Not yet Published).
Co-pending Application, U.S. Appl. No. 18/570,865, inventors Lee, S-J., et al., international filing date: Jun. 15, 2022 (Not yet Published).

* cited by examiner

ANTI-MERTK ANTIBODIES AND METHODS OF USE THEREOF

CROSS REFERENCE TO RELATED APPLICATIONS

This application is a divisional application of U.S. application Ser. No. 17/118,921, filed Dec. 11, 2020, which claims the benefit of U.S. Provisional Application No. 62/947,855, filed Dec. 13, 2019, U.S. Provisional Application No. 63/016,821, filed Apr. 28, 2020, and U.S. Provisional Application No. 63/121,773, filed Dec. 4, 2020, each of which is herein incorporated by reference in its entirety.

SUBMISSION OF SEQUENCE LISTING ON XML FILE

The content of the following submission on XML file is incorporated herein by reference in its entirety: a computer readable form (CRF) of the Sequence Listing (file name: 4503_0100004_SeqListing_ST26.xml, date created: Dec. 18, 2023, size: 636,944 bytes).

FIELD OF THE PRESENT DISCLOSURE

The present disclosure relates to anti-MerTK antibodies and uses (e.g., therapeutic uses) of such antibodies.

BACKGROUND OF THE PRESENT DISCLOSURE

Mer Tyrosine Kinase (MerTK) belongs to the TAM (Tyro3, Axl, and MerTK) family of receptor tyrosine kinases. MerTK is a single-pass type 1 transmembrane protein with an extracellular domain having two immunoglobulin (Ig)-like and two fibronectin (FN) type III motifs (Graham et al, 2014, Nat Rev Cancer, 14:769-785; Rothlin et al, 2015, Annu Rev Immunol, 33:355-391).

Several ligands of MerTK have been identified, including Protein S (ProS or ProS1), Growth arrest specific gene 6 (Gas6), Tubby, Tubby-like protein 1 (TULP-1), and Galectin-3. MerTK transduces signals from the extracellular space via activation following ligand binding, leading to MerTK tyrosine auto-phosphorylation (Cummings et al, 2013, Clin Cancer Res, 19:5275-5280; Verma et al, 2011, Mol Cancer Ther, 10:1763-1773) and subsequent ERK and AKT-associated signal transduction.

MerTK regulates various physiological processes including cell survival, migration, and differentiation. MerTK ligands ProS and Gas6 contribute to several oncogenic processes, such as cell survival, invasion, migration, chemoresistance, and metastasis, in which their expression often correlates with poor clinical outcomes. Additionally, MerTK is implicated in numerous cancers, and MerTK or ProS deficiency is associated with anti-tumor effects (Cook et al, 2013, J Clin Invest, 123:3231-3242; Ubil et al, 2018, J Clin Invest, 128:2356-2369; Huey et al, 2016, Cancers, 8:101). However, MerTK is also expressed on retinal pigment epithelial cells and plays a critical role in clearing shed photoreceptor outer segment in the eye; loss of function mutations in MerTK result in retinitis pigmentosa and other retinal dystrophies (see, e.g. Al-khersan et al, Graefes Arch Clim Exp Ophthalmol, 2017, 255:1613-1619; Lorach et al, Nature Scientific Reports, 2018, 8:11312; Audo et al, Human Mutation, Wiley, 2018, 39:997-913; LaVail et al, Adv Exp Med Biol, 2016, 854:487-493).

MerTK plays an essential role in phagocytosis of apoptotic cells (efferocytosis) by phagocytic cells, leading to M2-like macrophage polarization, production of anti-inflammatory cytokines, and promoting an immunosuppressive tumor microenvironment. Reducing efferocytosis by phagocytic cells increases M1-like macrophage polarization, leading to the production of pro-inflammatory cytokines and an immune-active milieu. Modulating efferocytosis can provide an effective means for anti-tumor activity.

Anti-MerTK antibodies have been previously described in, e.g., International Patent Application Publication Nos: WO2020/214995, WO2020/076799, WO2020/106461, WO2020/176497, WO2019/084307, WO2019/005756, WO2016/106221, WO2016/001830, WO2009/062112, and WO2006/058202; and in, e.g., Dayoub and Brekken, 2020, Cell Communications and Signaling, 18:29; Zhou et al, 2020, Immunity, 52:1-17; Kedage et al, 2020, MABS, 12:e1685832; Cummings et al, 2014, Oncotarget, 5:10434-10445.

There is a need for novel therapeutic anti-MerTK antibodies that are effective at treating conditions such as cancer. The present disclosure meets this need by providing anti-MerTK antibodies effective at mediating anti-tumor immunity, reducing efferocytosis, and promoting M1-like macrophage polarization.

All references cited herein, including patent applications and publications, are hereby incorporated by reference in their entirety.

SUMMARY OF THE PRESENT DISCLOSURE

The present disclosure is generally directed to anti-Mer Tyrosine Kinase (MerTK) antibodies and methods of using such antibodies. The methods provided herein find use in treating an individual having cancer. In some embodiments, the present disclosure provides a method for treating an individual having cancer, the method including administering to the individual in need thereof a therapeutically effective amount of an anti-MerTK antibody.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:83; b) an HVR-H2 comprising an amino acid sequence selected from the group consisting of SEQ ID NOs: 329, 330, 331, 332, and 333; and c) an HVR-H3 comprising an amino acid sequence selected from the group consisting of SEQ ID NOs: 138, 334, 335, 336, 337, 338, and 339; and wherein the light chain variable region comprises: d) an HVR-L1 comprising an amino acid sequence selected from the group consisting of SEQ ID NOs: 158, 340, 341, 342, 343, and 344; e) an HVR-L2 comprising the amino acid sequence of SEQ ID NO:187; and f) an HVR-L3 comprising the amino acid sequence of SEQ ID NO:210.

In one aspect, the present disclosure relates to an isolated anti-MerTK antibody that binds to a MerTK protein, wherein the antibody comprises: (a) HVR-H1 comprising the amino acid sequence of SEQ ID NO:83; (b) HVR-H2 comprising the amino acid sequence of SEQ ID NO:99; (c) HVR-H3 comprising the amino acid sequence of SEQ ID NO: 138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b)

HVR-H2 comprising the amino acid sequence of SEQ ID NO:329; (c) HVR-H3 comprising the amino acid sequence of SEQ ID NO:334; (d) HVR-L1 comprising the amino acid sequence of SEQ ID NO: 158; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:330; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:340; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:335; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:331; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:342; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:337; (d) HVR-L1 comprising the amino acid sequence of SEQ ID NO:343; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:338; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:339; (d) HVR-L1 comprising the amino acid sequence of SEQ ID NO:344; (e) HVR-L2 comprising the amino acid sequence of SEQ ID NO: 187; and (f) HVR-L3 comprising the amino acid sequence of SEQ ID NO:210; or (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO: 19 and VL comprising the amino acid sequence of SEQ ID NO:54; VH comprising the amino acid sequence of SEQ ID NO:234 and VL comprising the amino acid sequence of SEQ ID NO:247; VH comprising the amino acid sequence of SEQ ID NO:235 and VL comprising the amino acid sequence of SEQ ID NO:247; VH comprising the amino acid sequence of SEQ ID NO:236 and VL comprising the amino acid sequence of SEQ ID NO:248; VH comprising the amino acid sequence of SEQ ID NO:236 and VL comprising the amino acid sequence of SEQ ID NO:249; VH comprising the amino acid sequence of SEQ ID NO:237 and VL comprising the amino acid sequence of SEQ ID NO:249; VH comprising the amino acid sequence of SEQ ID NO:238 and VL comprising the amino acid sequence of SEQ ID NO:249; VH comprising the amino acid sequence of SEQ ID NO:239 and VL comprising the amino acid sequence of SEQ ID NO:250; VH comprising the amino acid sequence of SEQ ID NO:240 and VL comprising the amino acid sequence of SEQ ID NO:251; VH comprising the amino acid sequence of SEQ ID NO:241 and VL comprising the amino acid sequence of SEQ ID NO:252; VH comprising the amino acid sequence of SEQ ID NO:242 and VL comprising the amino acid sequence of SEQ ID NO: 249; VH comprising the amino acid sequence of SEQ ID NO:243 and VL comprising the amino acid sequence of SEQ ID NO:247; VH comprising the amino acid sequence of SEQ ID NO:244 and VL comprising the amino acid sequence of SEQ ID NO:251; VH comprising the amino acid sequence of SEQ ID NO:245 and VL comprising the amino acid sequence of SEQ ID NO:253; VH comprising the amino acid sequence of SEQ ID NO:246 and VL comprising the amino acid sequence of SEQ ID NO:247; and VH comprising the amino acid sequence of SEQ ID NO:246 and VL comprising the amino acid sequence of SEQ ID NO:254.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:84; b) an HVR-H2 comprising an amino acid sequence selected from the group consisting of SEQ ID NOs: 99 and 329; and c) an HVR-H3 comprising the amino acid sequence of SEQ ID NO: 139; and wherein the light chain variable region comprises: d) an HVR-L1 comprising an amino acid sequence selected from the group consisting of SEQ ID NOs: 169 and 345; e) an HVR-L2 comprising the amino acid sequence of SEQ ID NO:195; and f) an HVR-L3 comprising the amino acid sequence of SEQ ID NO:219.

In one aspect, the present disclosure relates to an isolated anti-MerTK antibody that binds to a MerTK protein, wherein the antibody comprises (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO: 139; (d) HVR-L1 comprising the amino acid sequence of SEQ ID NO: 169; (e) HVR-L2 comprising the amino acid sequence of SEQ ID NO:195; and (f) HVR-L3 comprising the amino acid sequence of SEQ ID NO:219; or (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO: 195; and (f) HVR-L3 comprising the amino acid sequence of SEQ ID NO:219.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:255 and VL comprising the amino acid sequence of SEQ ID NO:257; and VH comprising the amino acid sequence of SEQ ID NO:256 and VL comprising the amino acid sequence of SEQ ID NO:258.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising an amino acid sequence selected from the group consisting of SEQ ID NOs:95, 346, and 347; b) an HVR-H2 comprising an amino acid sequence selected from the group consisting of SEQ ID NOs: 119, 348, 349, 350, 351, 352, 353, and 354; and c) an HVR-H3 comprising an amino acid sequence selected from the group consisting of SEQ ID NOs: 151, 355, and 356; and wherein the light chain variable region comprises: d) an HVR-L1 comprising an amino acid sequence selected from the group consisting of SEQ ID NOs: 181, 341, 357, and 358; e) an HVR-L2 comprising an amino acid sequence selected from the group consisting of SEQ ID NOs:187 and 359; and f) an HVR-L3 comprising an amino acid sequence selected from the group consisting of SEQ ID NOs:208, 360, 361, and 362.

In one aspect, the present disclosure relates to an isolated anti-MerTK antibody that binds to a MerTK protein, wherein the antibody comprises (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:360; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:361; (a) HVR-H1 comprising the amino acid sequence of SEQ ID NO:95; (b) HVR-H2 comprising the amino acid sequence of SEQ ID NO:349; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:350 (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:347; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:352; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:353; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:363; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:356; (d) HVR-L1 comprising the amino acid sequence of SEQ ID NO:357; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:358; (e) HVR-L2 comprising the amino acid sequence of SEQ ID NO: 187; and (f) HVR-L3 comprising the amino acid sequence of SEQ ID NO:362; or (a) HVR-H1 comprising the amino acid sequence of SEQ ID NO:95; (b) HVR-H2 comprising the amino acid sequence of SEQ ID NO:348; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO:187; and (f) HVR-L3 comprising the amino acid sequence of SEQ ID NO:208.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:33 and VL comprising the amino acid sequence of SEQ ID NO:68; VH comprising the amino acid sequence of SEQ ID NO:259 and VL comprising the amino acid sequence of SEQ ID NO:274; VH comprising the amino acid sequence of SEQ ID NO:260 and VL comprising the amino acid sequence of SEQ ID NO: 275; VH comprising the amino acid sequence of SEQ ID NO:261 and VL comprising the amino acid sequence of SEQ ID NO:276; VH comprising the amino acid sequence of SEQ ID NO:262 and VL comprising the amino acid sequence of SEQ ID NO:277; VH comprising the amino acid sequence of SEQ ID NO:263 and VL comprising the amino acid sequence of SEQ ID NO:277; VH comprising the amino acid sequence of SEQ ID NO:264 and VL comprising the amino acid sequence of SEQ ID NO:277; VH comprising the amino acid sequence of SEQ ID NO:265 and VL comprising the amino acid sequence of SEQ ID NO:277; VH comprising the amino acid sequence of SEQ ID NO:266 and VL comprising the amino acid sequence of SEQ ID NO:277; VH comprising the amino acid sequence of SEQ ID NO:267 and VL comprising the amino acid sequence of SEQ ID NO:278; VH comprising the amino acid sequence of SEQ ID NO:268 and VL comprising the amino acid sequence of SEQ ID NO:279; VH comprising the amino acid sequence of SEQ ID NO:269 and VL comprising the amino acid sequence of SEQ ID NO:279; VH comprising the amino acid sequence of SEQ ID NO:264 and VL comprising the amino acid sequence of SEQ ID NO:280; VH comprising the amino acid sequence of SEQ ID NO:270 and VL comprising the amino acid sequence of SEQ ID NO:281; VH comprising the amino acid sequence of SEQ ID NO:265 and VL comprising the amino acid sequence of SEQ ID NO:282; VH comprising the amino acid sequence of SEQ ID NO:264 and VL comprising the amino acid sequence of SEQ ID NO:283; VH comprising the amino acid sequence of SEQ ID NO:271 and VL comprising the amino acid sequence of SEQ ID NO:284; VH comprising the amino acid sequence of SEQ ID NO:272 and VL comprising the amino acid sequence of SEQ ID NO:285; VH comprising the amino acid sequence of SEQ ID NO:271 and VL comprising the amino acid sequence of SEQ ID NO:286; VH comprising the amino acid sequence of SEQ ID NO:273 and VL comprising the amino acid sequence of SEQ ID NO:287; VH comprising the amino acid sequence of SEQ ID NO:273 and VL comprising the amino acid sequence of SEQ ID NO:288; and VH comprising the amino acid sequence of SEQ ID NO:273 and VL comprising the amino acid sequence of SEQ ID NO:289.

In one aspect, the present disclosure relates to an isolated anti-MerTK antibody that binds to a MerTK protein, wherein the antibody comprises a heavy chain variable region and a light chain variable region, wherein the heavy chain variable region comprises: a) an HVR-H1 comprising the amino acid sequence of SEQ ID NO:90; b) an HVR-H2 comprising an amino acid sequence selected from the group consisting of SEQ ID NOs: 122, 364, 365, 366, 367, and 368; and c) an HVR-H3 comprising an amino acid sequence selected from the group consisting of SEQ ID NOs: 155, 373, 374, and 375; and wherein the light chain variable region comprises: d) an HVR-L1 comprising an amino acid sequence selected from the group consisting of SEQ ID NOs: 184, 376, 377, 378, 379, 380, 381, 382, 383, 384, 385, 386, and 387; e) an HVR-L2 comprising an amino acid sequence selected from the group consisting of SEQ ID NOs:203, 388, 389, 390, and 391; and f) an HVR-L3 comprising an amino acid sequence selected from the group consisting of SEQ ID NOs:231, 392, 393, and 394.

In one aspect, the present disclosure relates to an isolated anti-MerTK antibody that binds to a MerTK protein, wherein the antibody comprises (a) HVR-H1 comprising the amino acid sequence of SEQ ID NO:90; (b) HVR-H2 comprising the amino acid sequence of SEQ ID NO: 122; (c) HVR-H3 comprising the amino acid sequence of SEQ ID NO: 155; (d) HVR-L1 comprising the amino acid sequence of SEQ ID NO: 184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:376; (e) HVR-L2 comprising the amino acid sequence of SEQ ID NO:388; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:377; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:90; (b) HVR-H2 comprising the amino acid sequence of SEQ ID NO:365; (c) HVR-H3 comprising the amino acid sequence of SEQ ID NO:155; (d) HVR-L1 comprising the amino acid sequence of SEQ ID NO:276; (e) HVR-L2 comprising the amino acid sequence of SEQ ID NO:203; and (f) HVR-L3 comprising the amino acid sequence of SEQ ID NO:392; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:389; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:379; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:366; (c) HVR-H3 comprising the amino acid sequence of SEQ ID NO:155; (d) HVR-L1 comprising the amino acid sequence of SEQ ID NO:380; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:381; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:367; (c) HVR-H3 comprising the amino acid sequence of SEQ ID NO:155; (d) HVR-L1 comprising the amino acid sequence of SEQ ID NO:382; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:384; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:369; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:370; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:371; (c) HVR-H3 comprising the amino acid sequence of SEQ ID NO:155; (d) HVR-L1 comprising the amino acid sequence of SEQ ID NO:178; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:385; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:395; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:390; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:372; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:391; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:375; (d) HVR-L1 comprising the amino acid sequence of SEQ ID NO:386; (e) HVR-L2 comprising the amino acid sequence of SEQ ID NO:203; and (f) HVR-L3 comprising the amino acid sequence of SEQ ID NO:394; or (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:387; (e) HVR-L2 comprising the amino acid sequence of SEQ ID NO:203; and (f) HVR-L3 comprising the amino acid sequence of SEQ ID NO:394.

In one aspect, the present disclosure relates to an isolated anti-MerTK antibody that binds to a MerTK protein, wherein the antibody comprises a heavy chain variable domain (VH) and a light chain variable domain (VL), wherein the VH and VL are selected from the group consisting of: VH comprising the amino acid sequence of SEQ ID NO:37 and VL comprising the amino acid sequence of SEQ ID NO:72; VH comprising the amino acid sequence of SEQ ID NO:290 and VL comprising the amino acid sequence of SEQ ID NO:309; VH comprising the amino acid sequence of SEQ ID NO:291 and VL comprising the amino acid sequence of SEQ ID NO:310; VH comprising the amino acid sequence of SEQ ID NO:292 and VL comprising the amino acid sequence of SEQ ID NO:311; VH comprising the amino acid sequence of SEQ ID NO:293 and VL comprising the amino acid sequence of SEQ ID NO:312; VH comprising the amino acid sequence of SEQ ID NO:294 and VL comprising the amino acid sequence of SEQ ID NO:313; VH comprising the amino acid sequence of SEQ ID NO:295 and VL comprising the amino acid sequence of SEQ ID NO:314; VH comprising the amino acid sequence of SEQ ID NO:296 and VL comprising the amino acid sequence of SEQ ID NO:315; VH comprising the amino acid sequence of SEQ ID NO:290 and VL comprising the amino acid sequence of SEQ ID NO:316; VH comprising the amino acid sequence of SEQ ID NO:297 and VL comprising the amino acid sequence of SEQ ID NO:317; VH comprising the amino acid sequence of SEQ ID NO:298 and VL comprising the amino acid sequence of SEQ ID NO:318; VH comprising the amino acid sequence of SEQ ID NO:292 and VL comprising the amino acid sequence of SEQ ID NO:319; VH comprising the amino acid sequence of SEQ ID NO:299 and VL comprising the amino acid sequence of SEQ ID NO:320; VH comprising the amino acid sequence of SEQ ID NO:300 and VL comprising the amino acid sequence of SEQ ID NO:311; VH comprising the amino acid sequence of SEQ ID NO:301 and VL comprising the amino acid sequence of SEQ ID NO:321; VH comprising the amino acid sequence of SEQ ID NO:302 and VL comprising the amino acid sequence of SEQ ID NO:322; VH comprising the amino acid sequence of SEQ ID NO:303 and VL comprising the amino acid sequence of SEQ ID NO:311; VH comprising the amino acid sequence of SEQ ID NO:304 and VL comprising the amino acid sequence of SEQ ID NO:322; VH comprising the amino acid sequence of SEQ ID NO:305 and VL comprising the amino acid sequence of SEQ ID NO:322; VH comprising the amino acid sequence of SEQ ID NO:301 and VL comprising the amino acid sequence of SEQ ID NO:323; VH comprising the amino acid sequence of SEQ ID NO:301 and VL comprising the amino acid sequence of SEQ ID NO:324; VH comprising the amino acid sequence of SEQ ID NO:301 and VL comprising the amino acid sequence of SEQ ID NO:325; VH comprising the amino acid sequence of SEQ ID NO:306 and VL comprising the amino acid sequence of SEQ ID NO:326; VH comprising the amino acid sequence of SEQ ID NO:307 and VL comprising the amino acid sequence of SEQ ID NO:327; and VH comprising the amino acid sequence of SEQ ID NO:308 and VL comprising the amino acid sequence of SEQ ID NO:328.

In one aspect, the present disclosure relates to an isolated anti-MerTK antibody that binds to a MerTK protein, wherein the antibody includes a heavy chain variable region and a light chain variable region, wherein the heavy chain variable region includes: an HVR-H1 comprising an amino acid sequence selected from the group consisting of SEQ ID NOs:75, 76, 77, 78, 79, 80, 81, 82, 83, 84, 85, 86, 87, 88, 89, 90, 91, 92, 93, 94, 95, 96, 97, and 98; an HVR-H2 comprising an amino acid sequence selected from the group consisting of SEQ ID NOs:99, 100, 101, 102, 103, 104, 105, 106, 107, 108, 109, 110, 111, 112, 113, 114, 115, 116, 117, 118, 119, 120, 121, 122, 123, and 124; and an HVR-H3 comprising an amino acid sequence selected from the group consisting of SEQ ID NOs:125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157; and the light chain variable region includes: an HVR-L1 comprising an amino acid sequence selected from the group consisting of SEQ ID NOs:158, 159, 160, 161, 162, 163, 164, 165, 166, 167, 168, 169, 170, 171, 172, 173, 174, 175, 176, 177, 178, 179, 180, 181, 182, 183, 184, 185, and 186; an HVR-L2 comprising an amino acid sequence selected from the group consisting of SEQ ID NOs:187, 188, 189, 190, 191, 192, 193, 194, 195, 196, 197, 198, 199, 200, 201, 202, 203, 204, and 205; and an HVR-L3 comprising an amino acid sequence selected from the group consisting of SEQ ID NOs:207, 208, 209, 210, 211, 212, 213, 214, 215, 216, 217, 218, 219, 220, 221, 222, 223, 224, 225, 226, 227, 228, 229, 230, 231, 232, and 233.

In one aspect, the present disclosure relates to an isolated anti-MerTK antibody that binds to a MerTK protein, wherein the antibody comprises an HVR-H1, HVR-H2, HVR-H3, HVR-L1, HVR-L2, and HVR-L3 comprising the amino acid sequences of (i) SEQ ID NOs: 75, 99, 125, 158, 187, and 207, respectively; (ii) SEQ ID NOs: 76, 100, 126, 159, 187, and 208, respectively; (iii) SEQ ID NOs: 77, 101, 127, 160, 188, and 209, respectively; (iv) SEQ ID NOs: 75, 99, 128, 158, 187, and 210, respectively; (v) SEQ ID NOs: 78, 102, 129, 161, 189, and 211, respectively; (vi) SEQ ID NOs: 75, 103, 130, 158, 187, and 212, respectively; (vii) SEQ ID NOs: 77, 101, 127, 162, 188, and 209, respectively; (viii) SEQ ID NOs: 75, 99, 131, 163, 187, and 213, respectively; (ix) SEQ ID NOs: 79, 104, 132, 164, 190, and 214, respectively; (x) SEQ ID NOs: 80, 105, 133, 165, 191, and 215, respectively; (xi) SEQ ID NOs: 81, 106, 134, 166, 192, and 216, respectively; (xii) SEQ ID NOs: 82, 107, 135, 167, 193, and 217, respectively; (xiii) SEQ ID NOs: 77, 108, 136, 167, 194, and 209, respectively; (xiv) SEQ ID NOs: 75, 109, 137, 168, 187, and 218, respectively; (xv) SEQ ID NOs: 83, 99, 138, 158, 187, and 210, respectively; (xvi) SEQ ID NOs: 84, 99, 139, 169, 195, and 219, respectively; (xvii) SEQ ID NOs: 85, 99, 140, 170, 196, and 220, respectively; (xviii) SEQ ID NOs: 86, 99, 141, 171, 191, and 221, respectively; (xix) SEQ ID NOs:87, 110, 142, 172, 197, and 222, respectively; (xx) SEQ ID NOs: 88, 99, 143, 173, 191, and 223, respectively; (xxi) SEQ ID NOs: 89, 111, 143, 173, 198, and 221, respectively; (xxii) SEQ ID NOs: 90, 112, 144, 174, 199, and 224, respectively; (xxiii) SEQ ID NOs: 91, 113, 145, 175, 200, and 225, respectively; (xxiv) SEQ ID NOs: 90, 114, 146, 176, 201, and 226, respectively; (xxv) SEQ ID NOs: 92, 115, 147, 177, 195, and 227, respectively; (xxvi) SEQ ID NOs: 93, 116, 148, 178, 188, and 209, respectively; (xxvii) SEQ ID NOs: 94, 117, 149, 179, 195, and 228, respectively; (xxviii) SEQ ID NOs: 95, 118, 150, 180, 187, and 229, respectively; (xxix) SEQ ID NOs: 95, 119, 151, 181, 187, and 208, respectively; (xxx) SEQ ID NOs: 90, 120, 152, 182, 202, and 230, respectively; (xxxi) SEQ ID NOs: 96, 118, 153, 183, 202, and 230, respectively; (xxxii) SEQ ID NOs: 96, 121, 154, 181, 187, and 210, respectively; (xxxiii) SEQ ID NOs: 90, 122, 155, 184, 203, and 231, respectively; (xxxiv) SEQ ID NOs: 90, 122, 155, 184, 203, and 231, respectively; (xxxv) SEQ ID NOs:97, 123, 156, 185, 204, and 232, respectively; or (xxxvi) SEQ ID NOs: 98, 124, 157, 186, 205, and 233, respectively.

In some embodiments that may be combined with any of the embodiments provided herein, an anti-MerTK antibody of the present disclosure is an isolated antibody that binds to a MerTK protein, wherein the antibody comprises the HVR-H1, HVR-H2, HVR-H3, HVR-L1, HVR-L2 and HVR-L3 sequences of MTK-01, MTK-02, MTK-03, MTK-04, MTK-05, MTK-06, MTK-07, MTK-08, MTK-09, MTK-10, MTK-11, MTK-12, MTK-13, MTK-14, MTK-15, MTK-16, MTK-17, MTK-18, MTK-19, MTK-20, MTK-21, MTK-22, MTK-23, MTK-24, MTK-25, MTK-26, MTK-27, MTK-28, MTK-29, MTK-30, MTK-31, MTK-32, MTK-33, MTK-34, MTK-35, or MTK-36 antibody. In some embodiments, the HVRs are the Kabat-defined HVRs, the Chothia-defined HVRs, or the AbM-defined HVRs.

In some embodiments that may be combined with any of the embodiments provided herein, an anti-MerTK antibody of the present disclosure is an isolated antibody that binds to a MerTK protein, wherein the antibody comprises the HVR-H1, HVR-H2, HVR-H3, HVR-L1, HVR-L2 and HVR-L3 sequences of MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15, MTK-16.1 and MTK-16.2, MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21, MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK-33.22, MTK-33.23, or MTK-33.24 antibody. In some embodiments, the HVRs are the Kabat-defined HVRs, the Chothia-defined HVRs, or the AbM-defined HVRs.

In some embodiments that may be combined with any of the embodiments provided herein, an anti-MerTK antibody of the present disclosure is an isolated antibody that binds to a MerTK protein, wherein the antibody includes a heavy chain variable region, wherein the heavy chain variable region includes an amino acid sequence selected from the group consisting of SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39.

In some embodiments that may be combined with any of the embodiments provided herein, an anti-MerTK antibody of the present disclosure is an isolated antibody that binds to a MerTK protein, wherein the antibody includes a heavy chain variable region, wherein the heavy chain variable region includes an amino acid sequence selected from the group consisting of SEQ ID NOs:234-246, 255, 256, 259-379, and 290-308.

In some embodiments that may be combined with any of the embodiments provided herein, an anti-MerTK antibody of the present disclosure is an isolated antibody that binds to a MerTK protein, wherein the antibody includes a light chain variable region, wherein the light chain variable region includes an amino acid sequence selected from the group consisting of SEQ ID NOs:40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74.

In some embodiments that may be combined with any of the embodiments provided herein, an anti-MerTK antibody of the present disclosure is an isolated antibody that binds to a MerTK protein, wherein the antibody includes a light chain variable region, wherein the light chain variable region includes an amino acid sequence selected from the group consisting of SEQ ID NOs:247-254, 257, 258, 274-289, and 309-328.

In some embodiments that may be combined with any of the embodiments provided herein, an anti-MerTK antibody of the present disclosure is an isolated antibody that binds to a MerTK protein, wherein the antibody includes a heavy chain variable region and a light chain variable region, wherein the heavy chain variable region includes an amino acid sequence selected from SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39, and the light chain variable region includes an amino acid sequence selected from SEQ ID NOs: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74.

In some embodiments that may be combined with any of the embodiments provided herein, an anti-MerTK antibody of the present disclosure is an isolated antibody that binds to a MerTK protein, wherein the antibody includes a heavy chain variable region and a light chain variable region, wherein the heavy chain variable region includes an amino acid sequence selected from 234-246, 255, 256, 259-379, and 290-308, and the light chain variable region includes an amino acid sequence selected from SEQ ID NOs: 247-254, 257, 258, 274-289, and 309-328.

In some embodiments that may be combined with any of the embodiments provided herein, an anti-MerTK antibody of the present disclosure is an isolated antibody that binds to a MerTK protein, wherein the antibody a heavy chain variable region and a light chain variable region comprising the amino acid sequences of SEQ ID NOs:5 and 40, respectively; SEQ ID NOs:6 and 41, respectively; SEQ ID NOs:7 and 42, respectively; respectively; SEQ ID NOs:8 and 43, respectively; SEQ ID NOs:9 and 44, respectively; SEQ ID NOs:10 and 45, respectively; SEQ ID NOs: 11 and 46, respectively; SEQ ID NOs:12 and 47, respectively; SEQ ID NOs:13 and 48, respectively; SEQ ID NOs:14 and 49, respectively; SEQ ID NOs:15 and 50, respectively; SEQ ID NOs:16 and 51, respectively; SEQ ID NOs:17 and 52, respectively; SEQ ID NOs:18 and 53, respectively; SEQ ID NOs:19 and 54, respectively; SEQ ID NOs:20 and 55, respectively; SEQ ID NOs:21 and 56, respectively; SEQ ID NOs:22 and 57, respectively; SEQ ID NOs:23 and 58, respectively; SEQ ID NOs:24 and 59, respectively; SEQ ID NOs:25 and 60, respectively; SEQ ID NOs:26 and 61, respectively; SEQ ID NOs:27 and 62, respectively; SEQ ID NOs:28 and 63, respectively; SEQ ID NOs:29 and 64, respectively; SEQ ID NOs:30 and 65, respectively; SEQ ID NOs:31 and 66, respectively; SEQ ID NOs:32 and 67, respectively; SEQ ID NOs:33 and 68, respectively; SEQ ID NOs:34 and 69, respectively; SEQ ID NOs:35 and 70, respectively; SEQ ID NOs:36 and 71, respectively; SEQ ID NOs:37 and 72, respectively; SEQ ID NOs:38 and 73, respectively; and SEQ ID NOs:39 and 74, respectively.

In one aspect, the present disclosure relates to an isolated antibody that binds to a MerTK protein, wherein the antibody competitively inhibits binding of one or more of the antibodies of any of the embodiments herein for binding to MerTK.

In another aspect, the present disclosure relates to an isolated antibody that binds to a MerTK protein, wherein the antibody binds essentially the same or an overlapping epitope on MerTK as an antibody of any of the embodiments herein.

In certain embodiments that may be combined with any of the embodiments herein, the MerTK protein is a mammalian protein or a human protein. In certain embodiments that may be combined with any of the embodiments herein, the MerTK protein is a wild-type protein. In certain embodiments that may be combined with any of the embodiments herein, the MerTK protein is a naturally occurring variant. In certain embodiments that may be combined with any of the embodiments herein, an anti-MerTK antibody binds to human MerTK and to cynomolgus monkey MerTK and/or murine MerTK. In certain embodiments that may be combined with any of the embodiments herein, an anti-MerTK antibody binds to human MerTK and murine MerTK, binds to human MerTK and cynomolgus MerTK, or binds to human MerTK, murine MerTK, and cynomolgus MerTK.

In some embodiments that may be combined with any of the embodiments herein, an anti-MerTK antibody of the present disclosure inhibits or reduces binding of one or more ligands to MerTK.

In some embodiments that may be combined with any of the embodiments herein, an anti-MerTK antibody of the present disclosure inhibits or reduces binding of ProS to MerTK. In some embodiments that may be combined with any of the embodiments herein, an anti-MerTK antibody of the present disclosure inhibits or reduces binding of ProS to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of ProS to MerTK with an IC50 value of 0.58 nM to 25.9 nM. %. In some embodiments that may be combined with any of the embodiments herein, an anti-MerTK antibody of the present disclosure inhibits or reduces binding of ProS to MerTK with an IC50 value of 0.58 nM to 1 nM, 1 nM to 2.5 nM, 2.5 nM to 5 nM, 5 nM to 10 nM, or 10 nM to 25 nM.

In some embodiments that may be combined with any of the embodiments herein, an anti-MerTK antibody of the present disclosure inhibits or reduces binding of Gas6 to MerTK. In some embodiments that may be combined with any of the embodiments herein, an anti-MerTK antibody of the present disclosure inhibits or reduces binding of Gas6 to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of Gas6 to MerTK with an IC50 value of 0.29 nM to 32 nM. In some embodiments that may be combined with any of the embodiments herein, an anti-MerTK antibody of the present disclosure inhibits or reduces binding of Gas6 to MerTK with an IC50 value of 0.29 nM to 1 nM, 1 nM to 5 nM, 5 nM to 10 nM, 10 nM to 25 nM, or 25 nM to 32 nM.

In some embodiments that may be combined with any of the embodiments herein, an anti-MerTK antibody of the present disclosure inhibits or reduces binding of Gas6 to MerTK and inhibits or reduces binding of ProS to MerTK. In some embodiments that may be combined with any of the embodiments herein, an anti-MerTK antibody of the present disclosure inhibits or reduces binding of Gas6 to MerTK and inhibits or reduces binding of ProS to MerTK by at least 20%, by at least 25%, by at least 30%, by at least 40%, by at least 50%, by at least 60%, by at least 70%, by at least 80%, by at least 90%, or by at least 95% and wherein the antibody reduces or inhibits binding of Gas6 to MerTK by at least 20%, by at least 25%, by at least 30%, by at least 40%, by at least 50%, by at least 60%, by at least 70%, by at least 80%, by at least 90%, or by at least 95%. In some embodiments that may be combined with any of the embodiments herein, an anti-MerTK antibody of the present disclosure inhibits or reduces binding of Gas6 to MerTK and inhibits or reduces binding of ProS to MerTK with an IC50 value of 0.58 nM to 25.9 nM and wherein the antibody reduces or inhibits binding of Gas6 to MetTK with an IC50 value of 0.29 nM to 32 nM.

In some embodiments that may be combined with any of the embodiments herein, an anti-MerTK antibody of the present disclosure inhibits or reduces binding of ProS to MerTK and does not inhibit or reduce binding of Gas6 to MerTK.

In some embodiments that may be combined with any of the embodiments herein, an anti-MerTK antibody of the present disclosure does not inhibit or reduce binding of ProS to MerTK and does not inhibit binding of Gas6 to MerTK.

In some embodiments that may be combined with any of the embodiments herein, an anti-MerTK antibody of the present disclosure reduces Gas6-mediated phosphorylation of AKT. In some embodiments that may be combined with any of the embodiments herein, an anti-MerTK antibody of the present disclosure reduces Gas6-mediated phosphorylation of AKT with an IC50 value of 0.019 nM to 7.74 nM. In some embodiments that may be combined with any of the embodiments herein, an anti-MerTK antibody of the present disclosure reduces Gas6-mediated phosphorylation of AKT with an IC50 value of 0.019 nM to 0.25 nM, 0.25 nM to 0.5 nM, 0.5 nM to 1 nM, 1 nM to 2.5 nM, 2.5 nM to 5 nM, or 5 nM to 7.74 nM.

In some embodiments that may be combined with any of the embodiments herein, an anti-MerTK antibody of the present disclosure binds to human MerTK with a binding affinity of 1.4 nM to 81 nM. In some embodiments that may be combined with any of the embodiments herein, an anti-MerTK antibody of the present disclosure binds to human MerTK with a binding affinity of 1.6 nM to 107 nM. In some embodiments that may be combined with any of the embodiments herein, an anti-MerTK antibody of the present disclosure binds to human MerTK with a binding affinity of 30 nM to 186 nM.

In some embodiments that may be combined with any of the embodiments herein, an anti-MerTK antibody of the present disclosure is at least 1.7 times, at least 2.3 times, at least 2.4 times, at least 5 times, at least 7.7 times, or at least 8.5 times more effective at reducing or inhibiting the binding of ProS to MerTK than at reducing or inhibiting the binding of Gas6 to MerTK.

In some embodiments that may be combined with any of the embodiments provided here, an anti-MerTK antibody of the present disclosure decreases or reduces efferocytosis by phagocytic cells (e.g., by at least 50%). In some embodiments that may be combined with any of the embodiments provided here, an anti-MerTK antibody of the present disclosure decreases or reduces efferocytosis by phagocytic cells by at least 60%, by at least 70%, by at least 80%, by at least 90%, or by at least 95%.%). In some embodiments that may be combined with any of the embodiments provided here, an anti-MerTK antibody of the present disclosure decreases or reduces efferocytosis by phagocytic cells with an IC50 value of 0.13 nM to 30 nM. In some embodiments that may be combined with any of the embodiments provided here, an anti-MerTK antibody of the present disclosure decreases or reduces efferocytosis by phagocytic cells with an IC50 value of 0.13 nM to 1 nM, 1 nM to 5 nM, 5 nM to 10 nM, or 10 nM to 30 nM. In some embodiments, the phagocytic cells are macrophages. In some embodiments, the phagocytic cells are tumor-associated macrophages. In some embodiments, the phagocytic cells are dendritic cells.

In some embodiments that may be combined with any of the embodiments provided herein, an anti-MerTK antibody of the present disclosure increases or induces M1-like macrophage polarization. In some embodiments that may be combined with any of the embodiments provided herein, an anti-MerTK antibody of the present disclosure increases production, expression, and/or secretion of pro-inflammatory cytokines. In certain embodiments, the pro-inflammatory cytokines are tumor necrosis factor (TNF), interferon (IFN), or interleukin-12 (IL-12). In certain embodiments, the pro-inflammatory cytokines are chemokine (C-X-C motif) ligand 1 (CXCL-1, KC), monocyte chemoattractant protein-1 (MCP1, CCL2), macrophage inflammatory protein-1-alpha (MIP-Ilt, CCL3), macrophage inflammatory protein-1-beta (MIP-1β, CCL4), or interleukin-6 (IL-6). In some embodiments that may be combined with any of the embodiments provided herein, an anti-MerTK antibody of the present disclosure increases production, expression, and/or secretion of pro-inflammatory cytokines in vitro. In some embodiments that may be combined with any of the embodiments provided herein, an anti-MerTK antibody of the present disclosure increases production, expression, and/or secretion of pro-inflammatory cytokines in vivo.

In some embodiments that may be combined with any of the embodiments herein, the anti-MerTK antibody of the present disclosure is a monoclonal antibody. In some embodiments that may be combined with any of the embodiments herein, the antibody is a human antibody. In some embodiments that may be combined with any of the embodiments herein, the antibody is a humanized antibody. In some embodiments that may be combined with any of the embodiments herein, the antibody is a bispecific antibody. In some embodiments that may be combined with any of the embodiments herein, the antibody is a multivalent antibody. In some embodiments that may be combined with any of the embodiments herein, the antibody is a chimeric antibody.

In one aspect, the present disclosure relates to an isolated anti-MerTK antibody that binds to a MerTK protein, wherein the antibody is a humanized form of an anti-MerTK antibody provided herein.

In some embodiments that may be combined with any of the embodiments herein, the anti-MerTK antibody of the present disclosure is of the IgG class, the IgM class, or the IgA class. In some embodiments, the antibody is of the IgG class and has an IgG1, IgG2, or IgG4 isotype. In some embodiments, the antibody is of an IgG1 isotype with an Fc amino acid sequence selected from the group consisting of SEQ ID NOs: 396, 397, 398, 399, 400, and 401.

In certain embodiments that may be combined with any of the embodiments herein, the antibody is a full-length antibody. In certain embodiments that may be combined with any of the embodiments herein, the antibody is an antibody fragment. In certain embodiments that may be combined with any of the embodiments herein, the antibody is an antibody fragment that binds to an epitope on human MerTK or a mammalian MerTK protein. In certain embodiments that may be combined with any of the embodiments herein, the antibody fragment is a Fab, Fab', Fab'-SH, F(ab')2, Fv, or scFv fragment.

In another aspect, the present disclosure relates to an isolated nucleic acid including a nucleic acid sequence encoding an anti-MerTK antibody of any of the preceding embodiments. In some embodiments, the present disclosure relates to a vector including the nucleic acid of any of the preceding embodiments. In some embodiments, the present disclosure relates to an isolated host cell including the nucleic acid of any of the preceding embodiments or the vector of any of the preceding embodiments. In some embodiments, the present disclosure relates to an isolated host cell comprising (i) a nucleic acid comprising a nucleic acid sequence encoding the VH of an anti-MerTK antibody of any of the preceding embodiments and (ii) a nucleic acid comprising a nucleic acid sequence encoding the VL of the anti-MerTK antibody.

In another aspect, the present disclosure relates to a method of producing an antibody that binds to human MerTK antibody, including culturing the host cell of any of the preceding embodiments so that the anti-MerTK antibody is produced. In certain embodiments, the method further includes recovering the anti-MerTK antibody produced by the cell.

In another aspect, the present disclosure relates to a pharmaceutical composition including an anti-MerTK antibody of any one of the preceding embodiments and a pharmaceutically acceptable carrier.

In one aspect, the present disclosure relates to a method of treating an individual having cancer, the method comprising administering to an individual in need thereof a therapeutically effective amount of an anti-MerTK antibody of any of the preceding embodiments. In some embodiments, the cancer is colon cancer, ovarian cancer, liver cancer, or endometrial cancer. In some embodiments, the cancer is selected from sarcoma, bladder cancer, breast cancer, colon cancer, endometrial cancer, kidney cancer, renal cancer, leukemia, lung cancer, non-small cell lung cancer, melanoma, lymphoma, pancreatic cancer, prostate cancer, ovarian cancer, stomach cancer, thyroid cancer, cancer of the uterus, liver cancer, cervical cancer, testicular cancer, squamous cell carcinoma, glioma, glioblastoma, adenoma, and neuroblastoma. In some embodiments, the cancer is selected from glioblastoma multiforme, bladder carcinoma, and esophageal carcinoma. In some embodiments, the cancer is triple-negative breast carcinoma. In some embodiments, the cancer may be a primary tumor. In some embodiments, the cancer may be a metastatic tumor at a second site derived from any of the above types of cancer. In some embodiments, an anti-MerTK antibody of the present disclosure is useful for treating cancer in s subject in need thereof, wherein the cancer expresses MerTK. In some embodiments, the administration of an anti-MerTK antibody of the present disclosure which reduces efferocytosis does not lead to a retinal pathology in the individual. In some embodiments, the method further comprises administering an anti-PD-L1 antibody, an anti-PD-L2 antibody, or anti-PD antibody (e.g., simultaneously or sequentially) to the individual.

In one aspect, the present disclosure relates to a method of detecting MerTK in a sample comprising contacting said sample with an anti-MerTK antibody of any of the preceding embodiments, optionally wherein the method further comprises detecting the binding of the antibody to MerTK in the sample.

It is to be understood that one, some, or all of the properties of the various embodiments described herein may be combined to form other embodiments of the present disclosure. These and other aspects of the disclosure will become apparent to one of skill in the art. These and other aspects of the disclosure are further described by the detailed description that follows.

DETAILED DESCRIPTION OF THE PRESENT DISCLOSURE

Figure 1:
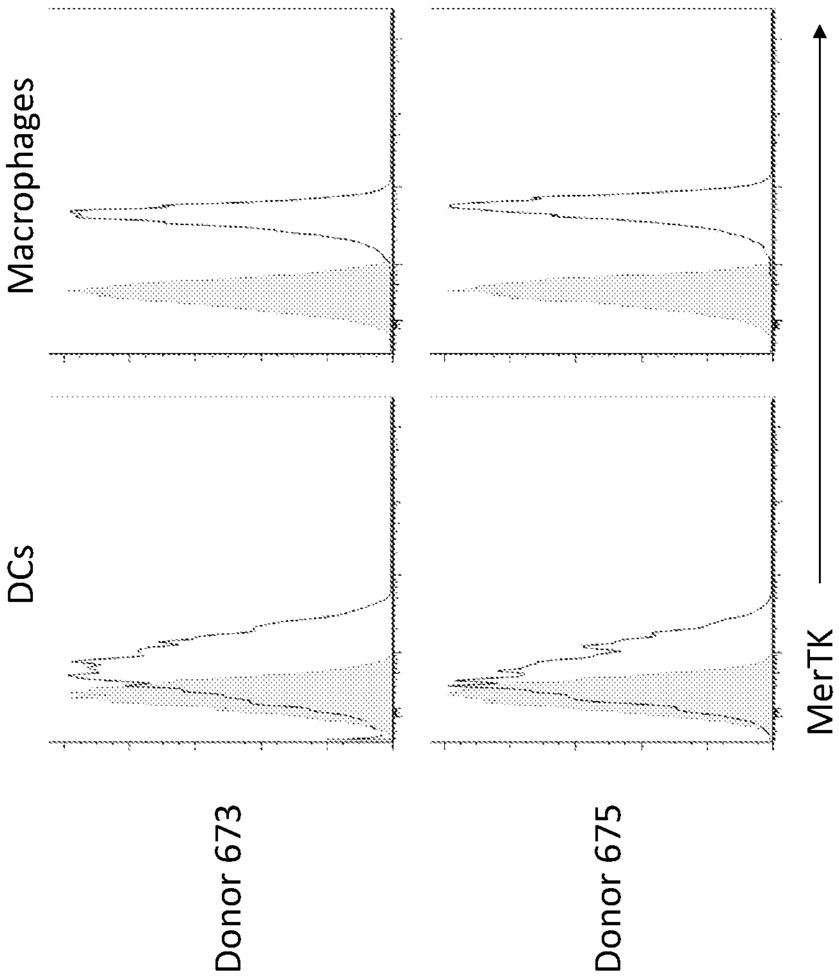
FIG. 1 sets forth data showing FACS analysis of human MerTK expression on dendritic cells (DCs) and macrophages from two human donors.

The present disclosure relates to anti-MerTK antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies such as those described in Sambrook et al. *Molecular Cloning: A Laboratory Manual* 3d edition (2001)

Cold Spring Harbor Laboratory Press, Cold Spring Harbor, N.Y.; *Current Protocols in Molecular Biology* (F. M. Ausubel, et al. eds., (2003); *Monoclonal Antibodies: A Practical Approach* (P. Shepherd and C. Dean, eds., Oxford University Press, 2000).

I. Definitions

The terms "MerTK" or "MerTK polypeptide" or "MerTK protein" are used interchangeably herein refer herein to any native MerTK from any vertebrate source, including mammals such as primates (e.g., humans and cynomolgus monkeys (cynos)) and rodents (e.g., mice and rats), unless otherwise indicated. MerTK is also referred to as c-mer, MER, Proto-oncogene c-Mer, Receptor Tyrosine Kinase MerTK, Tyrosine-protein Kinase Mer, STK Kinase, RP38, and MGC133349. In some embodiments, the term encompasses both wild-type sequences and naturally occurring variant sequences, e.g., splice variants or allelic variants. In some embodiments, the term encompasses "full-length," unprocessed MerTK as well as any form of MerTK that results from processing in the cell. In some embodiments, the MerTK is human MerTK. As used herein, the term "human MerTK" refers to a polypeptide with the amino acid sequence of SEQ ID NO: 1.

The terms "anti-MerTK antibody," an "antibody that binds to MerTK," and "antibody that specifically binds MerTK" refer to an antibody that is capable of binding MerTK with sufficient affinity such that the antibody is useful as a diagnostic and/or therapeutic agent in targeting MerTK. In one embodiment, the extent of binding of an anti-MerTK antibody to an unrelated, non-MerTK polypeptide is less than about 10% of the binding of the antibody to MerTK as measured, e.g., by a radioimmunoassay (RIA). In certain embodiments, an antibody that binds to MerTK has a dissociation constant (KD) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-MerTK antibody binds to an epitope of MerTK that is conserved among MerTK from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antigen-binding antibody fragments so long as they exhibit the desired biological activity.

"Native antibodies" are usually heterotetrameric glycoproteins of about 150,000 Daltons, composed of two identical light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology,* 8th Ed., Daniel P. Stites, Abba I. Terr and Tristram G. Parslow (eds.), Appleton & Lange, Norwalk, C T, 1994, page 71 and Chapter 6.

The light chain from any vertebrate species can be assigned to one of two clearly distinct types, called kappa ("K") and lambda ("X"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., *Cellular and Molecular Immunology,* $4^{th}$ ed. (W.B. Saunders Co., 2000).

The "variable region" or "variable domain" of an antibody, such as an anti-MerTK antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-MerTK antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-MerTK antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, but not limited to one or more of the following methods, immunization methods of animals including, but not limited to rats, mice, rabbits, guinea pigs, hamsters and/or chickens with one or more of DNA(s), virus-like particles, polypeptide(s), and/or cell(s), the hybridoma methods, B-cell cloning methods, recombinant DNA methods, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody, such as an anti-MerTK antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', $F(ab')_2$ and Fv fragments; diabodies; linear antibodies (see U.S. Pat. 5641870, Example 2; Zapata et al., *Protein Eng.* 8(10):1057-1062 (1995)); single-chain antibody molecules and multi-specific antibodies formed from antibody fragments.

Papain digestion of antibodies, such as anti-MerTK antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-MerTK antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-MerTK antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-MerTK antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-MerTK antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology.

The term "hypervariable region," "HVR," or "HV," when used herein refers to the regions of an antibody-variable domain, such as that of an anti-MerTK antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J Mol. Biol.* 196:901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

An "acceptor human framework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, *Bethesda, MD* (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-MerTK antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least 80% homology with a native sequence Fc region and/or with an Fc region of a parent polypeptide, and most preferably at least 90% homology therewith, more preferably at least 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies that compete for the same epitope or overlapping epitopes means competition between antibody as determined by an assay in which the antibody being tested prevents or inhibits (e.g., reduces) specific binding of a reference molecule (e.g., a ligand, or a reference antibody) to a common antigen (e.g., MerTK or a fragment thereof). Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a MerTK polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of polypeptides and/or macromolecules.

An "isolated" antibody, such as an isolated anti-MerTK antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-MerTK antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are nontoxic to the cell or mammal being exposed thereto at the dosages and concentrations employed.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic result. An effective amount can be provided in one or more administrations. An effective amount is also one in which any toxic or detrimental effects of the treatment are outweighed by the therapeutically beneficial effects. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

I. Anti-MerTK Antibodies

Provided herein are anti-MerTK antibodies. Antibodies provided herein are useful, e.g., for the diagnosis or treatment of the MerTK associated disorders.

In one aspect, the present disclosure provides isolated (e.g., monoclonal) antibodies that bind to an epitope within a MerTK protein or polypeptide of the present disclosure. MerTK proteins or polypeptides of the present disclosure include, without limitation, a mammalian MerTK protein or polypeptide, human MerTK protein or polypeptide, mouse (murine) MerTK protein or polypeptide, and cynomolgus MerTK protein or polypeptide. MerTK proteins and polypeptides of the present disclosure include naturally occurring variants of MerTK. In some embodiments, MerTK proteins and polypeptides of the present disclosure are membrane bound. In some embodiments, MerTK proteins and polypeptides of the present disclosure are a soluble extracellular domain of MerTK.

In some embodiments, MerTK is expressed in a cell. In some embodiments, MerTK is expressed in phagocytic cells, including without limitation, macrophages and dendritic cells. In some embodiments, MerTK is expressed in monocytes, natural killer cells, natural killer T cells, microglia, endothelial cells, megakaryocytes, and platelets. In some embodiments, high levels of MerTK expression are also found in ovary, prostate, testis, lung, retina, and kidney. Additionally, MerTK displays ectopic or overexpression in numerous cancers (Linger et al, 2008, Adv Cancer Res, 100:35-83).

Antibody Activities

In some embodiments, an anti-MerTK antibody is provided that binds to human MerTK but does not bind to cynomolgus MerTK. In some embodiments, an anti-MerTK antibody is provided that binds to human MerTK but does not bind to murine MerTK. In some embodiments, an anti-MerTK antibody is provided that binds to human MerTK but does not bind to cynomolgus MerTK and does not bind to murine MerTK. In some embodiments, an anti-MerTK antibody is provided that binds to human MerTK and binds to cynomolgus MerTK. In some embodiments, an anti-MerTK antibody is provided that binds to human MerTK and binds to cynomolgus MerTK but does not bind to murine MerTK. In some embodiments, an anti-MerTK antibody is provide that binds to human MerTK and binds to murine MerTK. In some embodiments, an anti-MerTK antibody is provide that binds to human MerTK and binds to murine MerTK but does not bind cynomolgus MerTK. In some embodiments, an anti-MerTK antibody is provide that binds to human MerTK, cynomolgus MerTK, and murine MerTK. An anti-MerTk antibody that binds to human, cynomolgus, and murine MerTK is advantageous for performing in vivo studies in mammalian animal models of disease (e.g., cancer) as well as studies in non-human primates.

MerTK Binding Partners

MerTK proteins of the present disclosure interact with (e.g., bind) one or more ligands or binding partners, including, without limitation, Protein S (ProS or ProS1), Growth arrest specific gene 6 (Gas6), Tubby, Tubby-like protein 1 (TULP-1), and Galectin-3. Anti-MerTK antibodies of the present disclosure can affect the interaction of MerTK with one or more of its various ligands and binding partners.

Anti-MerTK antibodies of the present disclosure that blocked both ProS binding and Gas6 binding to MerTK, that blocked only ProS binding to MerTK, or that did not block binding of either ProS or Gas6 binding to MerTK were identified. The ProS only blocking anti-MerTK antibodies did not bin with the ProS/Gas6 double blocking anti-MerTK antibodies (as shown in the Examples below), suggesting non-overlapping epitopes for these two classes of anti-MerTK antibodies identified herein.

Accordingly, in some embodiments, an anti-MerTK antibody of the present disclosure inhibits (i.e., blocks) or reduces binding between MerTK and one or more MerTK ligands. In some embodiments, an anti-MerTK antibody of the present disclosure inhibits or reduces binding of ProS to MerTK. In some embodiments, an anti-MerTK antibody of the present disclosure inhibits or reduces binding of ProS to MerTK but does not inhibit or reduce binding of Gas6 to MerTK. In some embodiments, an anti-MerTK antibody of the present disclosure inhibits or reduces binding of Gas6 to MerTK. In some embodiments, an anti-MerTK antibody of the present disclosure inhibits or reduces binding to Gas6 to MerTK but does not inhibit or reduce binding of ProS to MerTK. In yet other embodiments, an anti-MerTK antibody of the present disclosure inhibits or reduces binding of ProS to MerTK and inhibits or reduces binding of Gas6 to MerTK. In other embodiments, an anti-MerTK antibody of the present disclosure does not inhibit or reduce binding of ProS to MerTK and does not inhibit or reduce binding of Gas6 to MerTK.

An IC50 value for inhibition or blocking of Gas6 ligand binding to MerTK or for inhibition or blocking of ProS ligand binding to MerTK can be determined using methods known by one of skill in the art, such as that described herein in the Example below (e.g., Example 13). In some embodiments, an anti-MerTK antibody of the present disclosure inhibits or reduces Gas6 ligand binding or inhibits or reduces ProS ligand binding to MerTK in vitro. In some embodiments, an anti-MerTK antibody of the the present disclosure inhibits or reduces Gas6 ligand binding to human MerTK with an IC50 value in the range of 0.29 nM to 32 nM. In some embodiments, an anti-MerTK antibody of the present disclosure inhibits or reduces Gas6 ligand binding to human MerTK with an IC50 value in the range of 0.29 nM to 1.0 nM, in the range of 1.0 nM to 5 nM, in the range of 5 nM to 10 nM, in the range of 10 nM to 25 nM, or in the range of 25 nM to 32 nM. In some embodiments, an anti-MerTK antibody of the present disclosure inhibits or reduces ProS ligand binding to human MerTK with an IC50 value in the range of 0.58 nM to 25.9 nM. In some embodiments, an anti-MerTK antibody of the present disclosure inhibits or reduces ProS ligand binding to human MerTK with an IC50 value in the range of 0.58 nM to 1 nM, in the range of 1 nM to 2.5 nM, in the range of 2.5 nM to 5 nM, in the range of 5 nM to 10 nM, in the range of 10 nM to 25 nM.

The relative effectiveness of an antibody at reducing or inhibiting the binding of ProS and Gas6 to MerTK can be determined using such IC50 values. For example, an antibody that inhibits binding of Gas6 to MerTK at an IC50 value that is 1.7 times greater than its IC50 value for inhibiting binding of ProS to MerTK is 1.7 times more effective at reducing or inhibiting the binding of ProS to MerTK than at reducing or inhibiting the binding of Gas6 to MerTK. In some embodiments, an anti-MerTK antibody is at least 1.7 times, at least 2.3 times, at least 2.4 times, at least 5 times, at least 7.7 times, or at least 8.5 times more effective at reducing or inhibiting the binding of ProS to MerTK than at reducing or inhibiting the binding of Gas6 to MerTK.

In some embodiments, an anti-MerTK antibody of the present disclosure inhibits or reduces Gas6 ligand binding to MerTK by at least 20%, by at least 25, by at least 30%, by at least 40%, by at least 50%, by at least 60%, by at least 70%, by at least 80%, by at least 90%, or by at least 95% compared to Gas6 ligand binding to MerTK in the absence of an anti-MerTK antibody of the present disclosure. In some embodiments, an anti-MerTK antibody of the present disclosure inhibits or reduces ProS ligand binding to MerTK by at least 20%, by at least 25%, by at least 30%, by at least 40%, by at least 50%, by at least 60%, by at least 70%, by at least 80%, by at least 90%, or by at least 95% compared to ProS ligand binding to MerTK in the absence of an anti-MerTK antibody of the present disclosure. Percent inhibition or reduction of Gas6 ligand binding to MerTK or of ProS ligand binding to MerTK can be determined by measuring IC50 values using standard methods known by one of skill in the art, such as described herein in Example 13.

Further provided herein are methods of screening for anti-MerTK antibodies that bind MerTK and that block or reduce the interactions between MerTK and one or more MerTK ligands or binding partners.

pAKT

AKT activity is a downstream target of Gas6 binding to MerTK, Axl, or Tyro-3 receptors. For example, the binding of MerTK ligand Gas6 to MerTK induces AKT phosphorylation (pAKT) (see, e.g., Angelillo-Scherrer et al, 2008, J Clin Invest, 118:583-596; Moody et al, 2016, Int J Cancer, 139:1340-1349). Anti-MerTK antibodies of the present disclosure were effective at inhibiting Gas6-mediated phospho-AKT (pAKT) activity in human macrophages (e.g., M2c macrophages) in a dose-dependent manner. Accordingly, anti-MerTK antibodies of the present disclosure were effective at inhibiting Gas6-mediated MerTK signaling as evidenced by inhibition of pAKT levels. In some embodiments, an anti-MerTK antibody of the present disclosure inhibits or reduces Gas6-mediated pAKT activity in vitro.

The relative effectiveness of an anti-MerTK antibody at reducing or inhibiting pAKT activity in a cell can be determined by measuring the IC50 values. IC50 values for inhibition of Gas6-mediated pAKT activity can be determined using methods known by one of skill in the art, such as that described herein in Example 22 below. In some embodiments, an anti-MerTK antibody of the present disclosure inhibits Gas6-mediated pAKT activity in macrophages (e.g., M2c macrophages) with an IC50 value ranging from 0.019 nM to 7.74 nM. In some embodiments, an anti-MerTK antibody of the present disclosure inhibits Gas6-mediated pAKT activity in macrophages (e.g., M2c macrophages) with an IC50 value of 0.019 nM to 0.25 nM, 0.25 nM to 0.50 nM, 0.50 nM to 1.0 nM, 1.0 nM to 2.5 nM, 2.5 nM to 5.0 nM, or 5.0 nM to 10 nM.

Efferocytosis

Efferocytosis refers to phagocytic clearance of dying or apoptotic cells. Efferocytosis can be accomplished by professional phagocytes (e.g., macrophages, dendritic cells, microglia), non-professional phagocytes (e.g., epithelial cells, fibroblasts, retinal pigment epithelial cells), or specialized phagocytes. (Elliott et al, 2017, J Immunol, 198: 1387-1394). Efferocytosis leads to the removal of dead or dying cells before their membrane integrity is breached and their cellular contents leak into the surrounding tissue, thus preventing exposure of tissue to toxic enzymes, oxidants, and other intracellular components.

Apoptotic cells expose a variety of molecules on their cell surface ("eat-me" signals) that are recognized by receptors on phagocytic cells. One such "eat me" signaling molecules is phosphatidylserine (PtdSer), which is normally confined to the inner leaflet of the cell membrane. During apoptosis, PtdSer is exposed to the outer leaflet of the cell membrane. MerTK ligands ProS and Gas6 contain gamma-carboxylated glutamic acid residues near their N-terminal domains; gamma-carboxylation of the glutamic acid domain enables binding to phosphatidylserine. Gas6 or ProS bind to PtdSer on apoptotic cells and simultaneously bind MerTK on phagocytes. Such ligand engagement with MerTK activates efferocytosis.

As shown in the Examples below, anti-MerTK antibodies of the present disclosure were effective at reducing or decreasing efferocytosis in various phagocytic cells. Anti-MerTK antibodies that that block ProS only binding to MerTK showed robust inhibition of efferocytosis, having an IC50 comparable to anti-MerTK antibodies that block both ProS and Gas6 binding to MerTK. Considering that genetic deficiency of both ProS and Gas6 is required to develop vision loss by retinal degradation (ProS or Gas6 single genetic knockouts did not lead to retinal pathologies), anti-MerTK antibodies that are ProS-specific blockers may provide improved therapeutic index for use in anti-tumor responses without inducing eye toxicity issues.

Accordingly, in some embodiments, an anti-MerTK antibody of the present disclosure decreases or reduces efferocytosis by phagocytic cells. In some embodiments, an anti-MerTK antibody of the present disclosure decreases or reduces efferocytosis by macrophages. In some embodiments, an anti-MerTK antibody of the present disclosure decreases or reduces efferocytosis by dendritic cells. In some embodiments, an anti-MerTK antibody of the present disclosure decreases or reduces efferocytosis by bone marrow-derived macrophages. In some embodiments, an anti-MerTK antibody of the present disclosure decreases or reduces efferocytosis by phagocytic cells by at least 10%, by at least 20%, by at least 25%, by at least 30%, by at least 40%, by at least 50%, by at least 60%, by at least 70%, by at least 80%, by at least 90%, or by at least 95% compared to the level of efferocytosis in phagocytic cells in the absence of an anti-MerTK antibody. Percent reduction of efferocytosis can be determined using standard methods known to one of skill in the art, such as described herein in Example 11.

In some embodiments, an anti-MerTK antibody of the present disclosure decreases or reduces efferocytosis by a phagocytic cell (e.g., a human macrophage) with an IC50 in the range of about 0.13 nM to about 30 nM, as assessed by methods described herein in the Example below (e.g., Example 11). In some embodiments, an anti-MerTK antibody of the present disclosure decreases or reduces efferocytosis by a phagocytic cell with an IC50 value in the range of 0.13 nM to 1.0 nM, in the range of 1 nM to 5 nM, in the range of 5 nM to 10 nM, or in the range of 10 nM to 30 nM.

Blocking efferocytosis drives M1-like macrophage polarization, resulting in increased production of pro-inflammatory cytokines (e.g., TNF, IFN, IL-12) and recruitment of cytotoxic cells, such as CD8+ T cells and natural killer cells, that mediate anti-tumor immunity. By reducing efferocytosis by phagocytic cells, anti-MerTK antibodies of the present disclosure are effective at increasing M1-like macrophage polarization and at increasing production, expression, and/or secretion of pro-inflammatory cytokines/chemokines, including TNF, IFN, IL-6, IL-1, IL-12, chemokine (C-X-C motif) ligand 1 (CXCL-1, KC), monocyte chemoattractant protein-1 (MCP1, CCL2), macrophage inflammatory protein-1-alpha (MIP-1α, CCL3), and/or macrophage inflammatory protein-1-beta (MIP-1β, CCL4). Accordingly, in some embodiments, an anti-MerTK antibody of the present disclosure increases M1-like macrophage polarization. In some embodiments, an anti-MerTK antibody of the present disclosure increases macrophage production, expression, or secretion of one or more pro-inflammatory cytokines. In some embodiments, an anti-MerTK antibody of the present disclosure increases macrophage production, expression, or secretion of TNF, IFN, IL-6, IL-1, IL-12, CXCL-1, MCP1, MIP-1α, and/or MIP-1β.

Accordingly, in some embodiments, provided herein is a method for increasing pro-inflammatory cytokine production, expression, and/or secretion in a subject in need thereof, the method comprising administering to the subject an anti-MerTK antibody of the present disclosure such that the production, expression, and/or secretion of one or more pro-inflammatory cytokines in the subject is increased. In some embodiments, the production, expression, and/or secretion of TNF is increased. In some embodiments, the production, expression, and/or secretion of IFN is increased. In some embodiments, the production, expression, and/or secretion of IL-12 is increased. In some embodiments, the production, expression, and/or secretion of CXCL-1 is increased. In some embodiments, the production, expression, and/or secretion of MCP1 is increased. In some embodiments, the production, expression, and/or secretion of MIP-1α is increased. In some embodiments, the production, expression, and/or secretion of MIP-1β is increased.

In some embodiments, provided herein is a method for increasing M1-like macrophage polarization in a subject in need thereof, the method comprising administering to the subject an anti-MerTK antibody of the present disclosure such that M1-like macrophage polarization in the subject is increased. Increased M1-like macrophage polarization is measured by various methods known to one of skill in the art, such as increased production, expression, or secretion of one or more pro-inflammatory cytokines, including TNF, IFN, IL-12, CXCL1, MCP1, MIP-1α, and/or MIP-1.

A link between efferocytosis and cancer progression has been described. For example, blockade of efferocytosis using Annexin V, which blocks PtdSer from interacting with the efferocytosis machinery of phagocytes, sufficiently reduces tumor progression and metastasis (Stach et al, 2000, Cell Death Diff, 7:911; Bondanza et al, 2004, J Exp Med, 200:1157; Werfel and Cook, 2018, Sem Immunopathology, 40:545-554). Further, MerTK correlates with poor prognosis and survival in numerous human cancers, as does its PtdSer bridging ligand Gas6 (Graham et al, 2014, Nat Rev Cancer, 14:769; Linger et al, 2010, Expert Opin Ther Targets, 14:1073-1090; Wang et al, 2013, Oncogene, 32:872; Jansen et al, 2011, J Proteome Res, 11:728-735; Tworkoski et al, 2011, Mol Cancer Res, p. molcanres-0512; Graham et al, 2006, Clin Cancer Res, 12:2662-2669; Keating et al, 2006, Oncogene, 25:6092). Accordingly, anti-MerTK antibodies of the present disclosure, which reduce efferocytosis by phagocytic cells, are thus effective at reducing tumor progression and metastasis.

Cynomolgus studies indicated that in some instances, anti-MerTK antibodies that block binding to both Gas6 and ProS (e.g., anti-MerTK antibody MTK-16) showed less in vivo toxicity (e.g., weight loss) compared to that observed in cynomolgus monkeys administered an anti-MerTK antibody that blocks ProS binding to MerTK but does not block binding of Gas6 to MerTK (e.g., anti-MerTK antibody MTK-15 or MTK-29). Accordingly, in some embodiments, an anti-MertK antibody of the present disclosure that blocks binding of both Gas6 and ProS to MerTK may display less systemic in vivo toxicity compared to an anti-MerTK antibody of the present disclosure that blocks binding of ProS to MerTK but does not block binding of Gas6 to MerTK. Anti-MerTk antibody MTK-16 (which blocks binding of both Gas6 and ProS to MerTK) binds to the Ig1 domain of MerTK protein, while anti-MerTK antibodies MTK-15 and MTK-29 (which block binding of ProS to MerTK but which do not block binding of Gas6 to MerTK) bind to both the Ig2 and the FN1 domain of MerTK protein. Accordingly, in some embodiments, an anti-MerTK antibody that binds to the Ig 1 domain of MerTK may display less systemic in vivo toxicity than an anti-MerTK antibody that binds to both the Ig2 and FN1 domains of MerTK.

A. Exemplary Antibodies and Certain Other Antibody Embodiments

In some embodiments, provided herein are anti-MerTK antibodies comprising at least one, two, three, four, five, or six HVRs selected from: (a) HVR-H1 comprising an amino acid sequence selected from the group consisting of SEQ ID NOs:75, 76, 77, 78, 79, 80, 81, 82, 83, 84, 85, 86, 87, 88, 89, 90, 91, 92, 93, 94, 95, 96, 97, and 98; (b) HVR-H2 comprising an amino acid sequence selected from the group consisting of SEQ ID NOs:99, 100, 101, 102, 103, 104, 105, 106, 107, 108, 109, 110, 111, 112, 113, 114, 115, 116, 117, 118, 119, 120, 121, 122, 123, and 124; (c) HVR-H3 comprising an amino acid sequence selected from the group consisting of SEQ ID NOs:125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157; (d) HVR-L1 comprising an amino acid sequence selected from the group consisting of SEQ ID NOs:158, 159, 160, 161, 162, 163, 164, 165, 166, 167, 168, 169, 170, 171, 172, 173, 174, 175, 176, 177, 178, 179, 180, 181, 182, 183, 184, 185, and 186; (e) HVR-L2 comprising an amino acid sequence selected from the group consisting of SEQ ID NOs:187, 188, 189, 190, 191, 192, 193, 194, 195, 196, 197, 198, 199, 200, 201, 202, 203, 204, and 205; and (f) HVR-L3 comprising an amino acid sequence selected from the group consisting of SEQ ID NOs:207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising at least one, at least two, or all three $V_H$ HVR sequences selected from (a) HVR-H1 comprising an amino acid sequence selected from the group consisting of SEQ ID NOs: 75, 76, 77, 78, 79, 80, 81, 82, 83, 84, 85, 86, 87, 88, 89, 90, 91, 92, 93, 94, 95, 96, 97, and 98; (b) HVR-H2 comprising an amino acid sequence selected from the group consisting of SEQ ID NOs: 99, 100, 101, 102, 103, 104, 105, 106, 107, 108, 109, 110, 111, 112, 113, 114, 115, 116, 117, 118, 119, 120, 121, 122, 123, and 124; and (c) HVR-H3 comprising an amino acid sequence selected from the group consisting of SEQ ID NOs: 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs: 158, 159, 160, 161, 162, 163, 164, 165, 166, 167, 168, 169, 170, 171, 172, 173, 174, 175, 176, 177, 178, 179, 180, 181, 182, 183, 184, 185, and 186; (b) HVR-L2 comprising an amino acid sequence selected from the group consisting of SEQ ID NOs: 187, 188, 189, 190, 191, 192, 193, 194, 195, 196, 197, 198, 199, 200, 201, 202, 203, 204, and 205; and (c) HVR-L3 comprising an amino acid sequence selected from the group consisting of SEQ ID NOs: 207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising (a) a $V_H$ domain comprising at least one, at least two, or all three $V_H$ HVR sequences selected from (i) HVR-H1 comprising an amino acid sequence selected from the group consisting of SEQ ID NOs: 75, 76, 77, 78, 79, 80, 81, 82, 83, 84, 85, 86, 87, 88, 89, 90, 91, 92, 93, 94, 95, 96, 97, and 98, (ii) HVR-H2 comprising an amino acid sequence selected from the group consisting of SEQ ID NOs: 99, 100, 101, 102, 103, 104, 105, 106, 107, 108, 109, 110, 111, 112, 113, 114, 115, 116, 117, 118, 119, 120, 121, 122, 123, and 124, and (iii) HVR-H3 comprising an amino acid sequence selected from the group consisting of SEQ ID NOs: 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, and 157, and (b) a $V_L$ domain comprising at least one, at least two, or all three $V_L$ HVR sequences selected from (i) HVR-L1 comprising an amino acid sequence selected from the group consisting of SEQ ID NOs: 158, 159, 160, 161, 162, 163, 164, 165, 166, 167, 168, 169, 170, 171, 172, 173, 174, 175, 176, 177, 178, 179, 180, 181, 182, 183, 184, 185, and 186, (ii) HVR-L2 comprising an amino acid sequence selected from the group consisting of SEQ ID NOs: 187, 188, 189, 190, 191, 192, 193, 194, 195, 196, 197, 198, 199, 200, 201, 202, 203, 204, and 205, and (iii) HVR-L3 comprising an amino acid sequence selected from the group consisting of SEQ ID NOs: 207, 208, 209, 210, 211, 212, 213, 214, 215, 216, 217, 218, 219, 220, 221, 222, 223, 224, 225, 226, 227, 228, 229, 230, 231, 232, and 233.

In some embodiments, provided herein are anti-MerTK antibodies comprising: (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO:125; (d) HVR-L1 comprising the amino acid sequence of SEQ ID NO: 158; (e) HVR-L2 comprising the amino acid sequence of SEQ ID NO: 187; and (f) HVR-L3 comprising the amino acid sequence of SEQ ID NO:207; (a) HVR-H1 comprising the amino acid sequence of SEQ ID NO:76; (b) HVR-H2 comprising the amino acid sequence of SEQ ID NO: 100; (c) HVR-H3 comprising the amino acid sequence of SEQ ID NO: 126; (d) HVR-L1 comprising the amino acid sequence of SEQ ID NO: 159; (e) HVR-L2 comprising the amino acid sequence of SEQ ID NO: 187; and (f) HVR-L3 comprising the amino acid sequence of SEQ ID NO:208; (a) HVR-H1 comprising the amino acid sequence of SEQ ID NO:77; (b) HVR-H2 comprising the amino acid sequence of SEQ ID NO:101; (c) HVR-H3 comprising the amino acid sequence of SEQ ID NO: 127; (d) HVR-L1 comprising the amino acid sequence of SEQ ID NO: 160; (e) HVR-L2 comprising the amino acid sequence of SEQ ID NO:188; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO: 128; (d) HVR-L1 comprising the amino acid sequence of SEQ ID NO: 158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:78; (b) HVR-H2 comprising the amino acid sequence of SEQ ID NO: 102; (c) HVR-H3 comprising the amino acid sequence of SEQ ID NO: 129; (d) HVR-L1 comprising the amino acid sequence of SEQ ID NO: 161; (e) HVR-L2 comprising the amino acid sequence of SEQ ID NO:189; and (f) HVR-L3 comprising the amino acid sequence of SEQ ID NO:211; (a) HVR-H1 comprising the amino acid sequence of SEQ ID NO:75; (b) HVR-H2 comprising the amino acid sequence of SEQ ID NO:103; (c) HVR-H3 comprising the amino acid sequence of SEQ ID NO:130; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:212; (a) HVR-H1 comprising the amino acid sequence of SEQ ID NO:77; (b) HVR-H2 comprising the amino acid sequence of SEQ ID NO:101; (c) HVR-H3 comprising the amino acid sequence of SEQ ID NO: 127; (d) HVR-L1 comprising the amino acid sequence of SEQ ID NO: 162; (e) HVR-L2 comprising the amino acid sequence of SEQ ID NO: 188; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO:99; (c) HVR-H3 comprising the amino acid sequence of SEQ ID NO:131; (d) HVR-L1 comprising the amino acid sequence of SEQ ID NO: 163; (e) HVR-L2 comprising the amino acid sequence of SEQ ID NO:187; and (f) HVR-L3 comprising the amino acid sequence of SEQ ID NO:213; (a) HVR-H1 comprising the amino acid sequence of SEQ ID NO:79; (b) HVR-H2 comprising the amino acid sequence of SEQ ID NO:104; (c) HVR-H3 comprising the amino acid sequence of SEQ ID NO: 132; (d) HVR-L1 comprising the amino acid sequence of SEQ ID NO: 164; (e) HVR-L2 comprising the amino acid sequence of SEQ ID NO: 190; and (f) HVR-L3 comprising the amino acid sequence of SEQ ID NO:214; (a) HVR-H1 comprising the amino acid sequence of SEQ ID NO:80; (b) HVR-H2 comprising the amino acid sequence of SEQ ID NO:105; (c) HVR-H3 comprising the amino acid sequence of SEQ ID NO:133; (d) HVR-L1 comprising the amino acid sequence of SEQ ID NO: 165; (e) HVR-L2 comprising the amino acid sequence of SEQ ID NO:191; and (f) HVR-L3 comprising the amino acid sequence of SEQ ID NO:215; (a) HVR-H1 comprising the amino acid sequence of SEQ ID NO:81; (b) HVR-H2 comprising the amino acid sequence of SEQ ID NO: 106; (c) HVR-H3 comprising the amino acid sequence of SEQ ID NO:134; (d) HVR-L1 comprising the amino acid sequence of SEQ ID NO: 166; (e) HVR-L2 comprising the amino acid sequence of SEQ ID NO: 192; and (f) HVR-L3 comprising the amino acid sequence of SEQ ID NO:216; (a) HVR-H1 comprising the amino acid sequence of SEQ ID NO:82; (b) HVR-H2 comprising the amino acid sequence of SEQ ID NO: 107; (c) HVR-H3 comprising the amino acid sequence of SEQ ID NO:135; (d) HVR-L1 comprising the amino acid sequence of SEQ ID NO: 167; (e) HVR-L2 comprising the amino acid sequence of SEQ ID NO: 193; and (f) HVR-L3 comprising the amino acid sequence of SEQ ID NO:217; (a) HVR-H1 comprising the amino acid sequence of SEQ ID NO:77; (b) HVR-H2 comprising the amino acid sequence of SEQ ID NO:108; (c) HVR-H3 comprising the amino acid sequence of SEQ ID NO:136; (d) HVR-L1 comprising the amino acid sequence of SEQ ID NO: 167; (e) HVR-L2 comprising the amino acid sequence of SEQ ID NO: 194; and (f) HVR-L3 comprising the amino acid sequence of SEQ ID NO:209; (a) HVR-H1 comprising the amino acid sequence of SEQ ID NO:75; (b) HVR-H2 comprising the amino acid sequence of SEQ ID NO: 109; (c) HVR-H3 comprising the amino acid sequence of SEQ ID NO:137; (d) HVR-L1 comprising the amino acid sequence of SEQ ID NO: 168; (e) HVR-L2 comprising the amino acid sequence of SEQ ID NO: 187; and (f) HVR-L3 comprising the amino acid sequence of SEQ ID NO:218; (a) HVR-H1 comprising the amino acid sequence of SEQ ID NO:83; (b) HVR-H2 comprising the amino acid sequence of SEQ ID NO:999; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO: 169; (e) HVR-L2 comprising the amino acid sequence of SEQ ID NO: 195; and (f) HVR-L3 comprising the amino acid sequence of SEQ ID NO:219; (a) HVR-H1 comprising the amino acid sequence of SEQ ID NO:85; (b) HVR-H2 comprising the amino acid sequence of SEQ ID NO:99; (c) HVR-H3 comprising the amino acid sequence of SEQ ID NO: 140; (d) HVR-L1 comprising the amino acid sequence of SEQ ID NO: 170; (e) HVR-L2 comprising the amino acid sequence of SEQ ID NO: 196; and (f) HVR-L3 comprising the amino acid sequence of SEQ ID NO:222; (a) HVR-H1 comprising the amino acid sequence of SEQ ID NO:86; (b) HVR-H2 comprising the amino acid sequence of SEQ ID NO:99; (c) HVR-H3 comprising the amino acid sequence of SEQ ID NO:141; (d) HVR-L1 comprising the amino acid sequence of SEQ ID NO:171; (e) HVR-L2 comprising the amino acid sequence of SEQ ID NO:191; and (f) HVR-L3 comprising the amino acid sequence of SEQ ID NO:221; (a) HVR-H1 comprising the amino acid sequence of SEQ ID NO:87; (b) HVR-H2 comprising the amino acid sequence of SEQ ID NO:110; (c) HVR-H3 comprising the amino acid sequence of SEQ ID NO: 142; (d) HVR-L1 comprising the amino acid sequence of SEQ ID NO: 172; (e) HVR-L2 comprising the amino acid sequence of SEQ ID NO:197; and (f) HVR-L3 comprising the amino acid sequence of SEQ ID NO:222; (a) HVR-H1 comprising the amino acid sequence of SEQ ID NO:88; (b) HVR-H2 comprising the amino acid sequence of SEQ ID NO:99; (c) HVR-H3 comprising the amino acid sequence of SEQ ID NO: 143; (d) HVR-L1 comprising the amino acid sequence of SEQ ID NO: 173; (e) HVR-L2 comprising the amino acid sequence of SEQ ID NO:191; and (f) HVR-L3 comprising the amino acid sequence of SEQ ID NO:223; (a) HVR-H1 comprising the amino acid sequence of SEQ ID NO:89; (b) HVR-H2 comprising the amino acid sequence of SEQ ID NO:111; (c) HVR-H3 comprising the amino acid sequence of SEQ ID NO:143; (d) HVR-L1 comprising the amino acid sequence of SEQ ID NO: 173; (e) HVR-L2 comprising the amino acid sequence of SEQ ID NO: 198; and (f) HVR-L3 comprising the amino acid sequence of SEQ ID NO:221; (a) HVR-H1 comprising the amino acid sequence of SEQ ID NO:90; (b) HVR-H2 comprising the amino acid sequence of SEQ ID NO: 112; (c) HVR-H3 comprising the amino acid sequence of SEQ ID NO: 144; (d) HVR-L1 comprising the amino acid sequence of SEQ ID NO: 174; (e) HVR-L2 comprising the amino acid sequence of SEQ ID NO: 199; and (f) HVR-L3 comprising the amino acid sequence of SEQ ID NO:224; (a) HVR-H1 comprising the amino acid sequence of SEQ ID NO:91; (b) HVR-H2 comprising the amino acid sequence of SEQ ID NO: 113; (c) HVR-H3 comprising the amino acid sequence of SEQ ID NO: 145; (d) HVR-L1 comprising the amino acid sequence of SEQ ID NO:175; (e) HVR-L2 comprising the amino acid sequence of SEQ ID NO:200; and (f) HVR-L3 comprising the amino acid sequence of SEQ ID NO:225; (a) HVR-H1 comprising the amino acid sequence of SEQ ID NO:90; (b) HVR-H2 comprising the amino acid sequence of SEQ ID NO:114; (c) HVR-H3 comprising the amino acid sequence of SEQ ID NO: 146; (d) HVR-L1 comprising the amino acid sequence of SEQ ID NO: 176; (e) HVR-L2 comprising the amino acid sequence of SEQ ID NO:201; and (f) HVR-L3 comprising the amino acid sequence of SEQ ID NO:226; (a) HVR-H1 comprising the amino acid sequence of SEQ ID NO:92; (b) HVR-H2 comprising the amino acid sequence of SEQ ID NO: 115; (c) HVR-H3 comprising the amino acid sequence of SEQ ID NO: 147; (d) HVR-L1 comprising the amino acid sequence of SEQ ID NO: 177; (e) HVR-L2 comprising the amino acid sequence of SEQ ID NO: 195; and (f) HVR-L3 comprising the amino acid sequence of SEQ ID NO:227; (a) HVR-H1 comprising the amino acid sequence of SEQ ID NO:93; (b) HVR-H2 comprising the amino acid sequence of SEQ ID NO: 116; (c) HVR-H3 comprising the amino acid sequence of SEQ ID NO:148; (d) HVR-L1 comprising the amino acid sequence of SEQ ID NO:178; (e) HVR-L2 comprising the amino acid sequence of SEQ ID NO:188; and (f) HVR-L3 comprising the amino acid sequence of SEQ ID NO:209; (a) HVR-H1 comprising the amino acid sequence of SEQ ID NO:94; (b) HVR-H2 comprising the amino acid sequence of SEQ ID NO: 117; (c) HVR-H3 comprising the amino acid sequence of SEQ ID NO: 149; (d) HVR-L1 comprising the amino acid sequence of SEQ ID NO: 179; (e) HVR-L2 comprising the amino acid sequence of SEQ ID NO: 195; and (f) HVR-L3 comprising the amino acid sequence of SEQ ID NO:228; (a) HVR-H1 comprising the amino acid sequence of SEQ ID NO:95; (b) HVR-H2 comprising the amino acid sequence of SEQ ID NO:118; (c) HVR-H3 comprising the amino acid sequence of SEQ ID NO:150; (d) HVR-L1 comprising the amino acid sequence of SEQ ID NO: 180; (e) HVR-L2 comprising the amino acid sequence of SEQ ID NO: 187; and (f) HVR-L3 comprising the amino acid sequence of SEQ ID NO:229; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO: 187; and (f) HVR-L3 comprising the amino acid sequence of SEQ ID NO:208; (a) HVR-H1 comprising the amino acid sequence of SEQ ID NO:90; (b) HVR-H2 comprising the amino acid sequence of SEQ ID NO: 120; (c) HVR-H3 comprising the amino acid sequence of SEQ ID NO: 152; (d) HVR-L1 comprising the amino acid sequence of SEQ ID NO:182; (e) HVR-L2 comprising the amino acid sequence of SEQ ID NO:202; and (f) HVR-L3 comprising the amino acid sequence of SEQ ID NO:230; (a) HVR-H1 comprising the amino acid sequence of SEQ ID NO:96; (b) HVR-H2 comprising the amino acid sequence of SEQ ID NO:118; (c) HVR-H3 comprising the amino acid sequence of SEQ ID NO:153; (d) HVR-L1 comprising the amino acid sequence of SEQ ID NO: 183; (e) HVR-L2 comprising the amino acid sequence of SEQ ID NO:202; and (f) HVR-L3 comprising the amino acid sequence of SEQ ID NO:230; (a) HVR-H1 comprising the amino acid sequence of SEQ ID NO:96; (b) HVR-H2 comprising the amino acid sequence of SEQ ID NO:121; (c) HVR-H3 comprising the amino acid sequence of SEQ ID NO:154; (d) HVR-L1 comprising the amino acid sequence of SEQ ID NO:181; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:90; (b) HVR-H2 comprising the amino acid sequence of SEQ ID NO: 122; (c) HVR-H3 comprising the amino acid sequence of SEQ ID NO: 155; (d) HVR-L1 comprising the amino acid sequence of SEQ ID NO: 184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:97; (b) HVR-H2 comprising the amino acid sequence of SEQ ID NO: 123; (c) HVR-H3 comprising the amino acid sequence of SEQ ID NO: 156; (d) HVR-L1 comprising the amino acid sequence of SEQ ID NO: 185; (e) HVR-L2 comprising the amino acid sequence of SEQ ID NO:204; and (f) HVR-L3 comprising the amino acid sequence of SEQ ID NO:232; (a) HVR-H1 comprising the amino acid sequence of SEQ ID NO:98; (b) HVR-H2 comprising the amino acid sequence of SEQ ID NO:124; (c) HVR-H3 comprising the amino acid sequence of SEQ ID NO:157; (d) HVR-L1 comprising the amino acid sequence of SEQ ID NO: 186; (e) HVR-L2 comprising the amino acid sequence of SEQ ID NO:205; and (f) HVR-L3 comprising the amino acid sequence of SEQ ID NO:233.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, and 39 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. In certain embodiments, a total of 1 to 5 amino acids have been substituted, inserted and/or deleted in SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. In certain embodiments, substitutions, insertions, or deletions occur in regions outside the HVRs (i.e., in the FRs). Optionally, the anti-MerTK antibody comprises the $V_H$ sequence of SEQ ID NO: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. including post-translational modifications of that sequence. In a particular embodiment, the $V_H$ comprises one, two or three HVRs selected from: (a) HVR-H1 comprising an amino acid sequence selected from the group consisting of SEQ ID NOs:75-98, (b) HVR-H2 comprising an amino acid sequence selected from the group consisting of SEQ ID NOs:99-124, and (c) HVR-H3 comprising an amino acid sequence selected from the group consisting of SEQ ID NOs:125-157.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, and 74, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In certain embodiments, a total of 1 to 5 amino acids have been substituted, inserted and/or deleted in SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In certain embodiments, the substitutions, insertions, or deletions occur in regions outside the HVRs (i.e., in the FRs). Optionally, the anti-MerTK antibody comprises the $V_L$ sequence of SEQ ID NO: 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74, including post-translational modifications of that sequence. In a particular embodiment, the $V_L$ comprises one, two or three HVRs selected from (a) HVR-L1 comprising an amino acid sequence selected from the group consisting of SEQ ID NOs:158-186, (b) HVR-L2 comprising an amino acid sequence selected from the group consisting of SEQ ID NOs: 187-205, and (c) HVR-L3 comprising an amino acid sequence selected from the group consisting of SEQ ID NOs: 207-233.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:5-39 and SEQ ID NOs: 40-74, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:5 and $V_L$ comprising the amino acid sequence of SEQ ID NO:40; $V_H$ comprising the amino acid sequence of SEQ ID NO:6 and $V_L$ comprising the amino acid sequence of SEQ ID NO:41; $V_H$ comprising the amino acid sequence of SEQ ID NO:7 and $V_L$ comprising the amino acid sequence of SEQ ID NO:42; $V_H$ comprising the amino acid sequence of SEQ ID NO:8 and $V_L$ comprising the amino acid sequence of SEQ ID NO:43; $V_H$ comprising the amino acid sequence of SEQ ID NO:9 and $V_L$ comprising the amino acid sequence of SEQ ID NO:44; $V_H$ comprising the amino acid sequence of SEQ ID NO: 10 and $V_L$ comprising the amino acid sequence of SEQ ID NO:45; $V_H$ comprising the amino acid sequence of SEQ ID NO:11 and $V_L$ comprising the amino acid sequence of SEQ ID NO:46; $V_H$ comprising the amino acid sequence of SEQ ID NO: 12 and $V_L$ comprising the amino acid sequence of SEQ ID NO:47; $V_H$ comprising the amino acid sequence of SEQ ID NO: 13 and $V_L$ comprising the amino acid sequence of SEQ ID NO:48; $V_H$ comprising the amino acid sequence of SEQ ID NO: 14 and $V_L$ comprising the amino acid sequence of SEQ ID NO:49; $V_H$ comprising the amino acid sequence of SEQ ID NO: 15 and $V_L$ comprising the amino acid sequence of SEQ ID NO:50; $V_H$ comprising the amino acid sequence of SEQ ID NO:16 and $V_L$ comprising the amino acid sequence of SEQ ID NO:51; $V_H$ comprising the amino acid sequence of SEQ ID NO: 17 and $V_L$ comprising the amino acid sequence of SEQ ID NO:52; $V_H$ comprising the amino acid sequence of SEQ ID NO: 18 and $V_L$ comprising the amino acid sequence of SEQ ID NO:53; $V_H$ comprising the amino acid sequence of SEQ ID NO: 19 and $V_L$ comprising the amino acid sequence of SEQ ID NO:54; $V_H$ comprising the amino acid sequence of SEQ ID NO:20 and $V_L$ comprising the amino acid sequence of SEQ ID NO:55; $V_H$ comprising the amino acid sequence of SEQ ID NO:21 and $V_L$ comprising the amino acid sequence of SEQ ID NO:56; $V_H$ comprising the amino acid sequence of SEQ ID NO:22 and $V_L$ comprising the amino acid sequence of SEQ ID NO:57; $V_H$ comprising the amino acid sequence of SEQ ID NO:23 and $V_L$ comprising the amino acid sequence of SEQ ID NO:58; $V_H$ comprising the amino acid sequence of SEQ ID NO:24 and $V_L$ comprising the amino acid sequence of SEQ ID NO:59; $V_H$ comprising the amino acid sequence of SEQ ID NO:25 and $V_L$ comprising the amino acid sequence of SEQ ID NO:60; $V_H$ comprising the amino acid sequence of SEQ ID NO:26 and $V_L$ comprising the amino acid sequence of SEQ ID NO:61; $V_H$ comprising the amino acid sequence of SEQ ID NO:27 and $V_L$ comprising the amino acid sequence of SEQ ID NO:62; $V_H$ comprising the amino acid sequence of SEQ ID NO:28 and $V_L$ comprising the amino acid sequence of SEQ ID NO:63; $V_H$ comprising the amino acid sequence of SEQ ID NO:29 and $V_L$ comprising the amino acid sequence of SEQ ID NO:64; $V_H$ comprising the amino acid sequence of SEQ ID NO:30 and $V_L$ comprising the amino acid sequence of SEQ ID NO:65; $V_H$ comprising the amino acid sequence of SEQ ID NO:31 and $V_L$ comprising the amino acid sequence of SEQ ID NO:66; $V_H$ comprising the amino acid sequence of SEQ ID NO:32 and $V_L$ comprising the amino acid sequence of SEQ ID NO:67; $V_H$ comprising the amino acid sequence of SEQ ID NO:33 and $V_L$ comprising the amino acid sequence of SEQ ID NO:68; $V_H$ comprising the amino acid sequence of SEQ ID NO:34 and $V_L$ comprising the amino acid sequence of SEQ ID NO:69; $V_H$ comprising the amino acid sequence of SEQ ID NO:35 and $V_L$ comprising the amino acid sequence of SEQ ID NO:70; $V_H$ comprising the amino acid sequence of SEQ ID NO:36 and $V_L$ comprising the amino acid sequence of SEQ ID NO:71; $V_H$ comprising the amino acid sequence of SEQ ID NO:37 and $V_L$ comprising the amino acid sequence of SEQ ID NO:72; $V_H$ comprising the amino acid sequence of SEQ ID NO:38 and $V_L$ comprising the amino acid sequence of SEQ ID NO:73; and $V_H$ comprising the amino acid sequence of SEQ ID NO:39 and $V_L$ comprising the amino acid sequence of SEQ ID NO:74.

In some embodiments, provided herein are anti-MerTK antibodies comprising at least one, two, three, four, five, or six HVRs selected from: (a) HVR-H1 comprising the amino acid sequence of SEQ ID NO:83; (b) HVR-H2 comprising an amino acid sequence selected from the group consisting of SEQ ID NOs:99, 329, 330, 331, 332, and 333; (c) HVR-H3 comprising an amino acid sequence selected from the group consisting of SEQ ID NOs: 138, 334, 335, 336, 337, 338, and 339; (d) HVR-L1 comprising an amino acid sequence selected from the group consisting of SEQ ID NOs: 158, 340, 341, 342, 343, and 344; (e) HVR-L2 comprising the amino acid sequence of SEQ ID NO:187; and (f) HVR-L3 comprising the amino acid sequence of SEQ ID NO:210.

In some embodiments, provided herein are anti-MerTK antibodies comprising at least one, at least two, or all three $V_H$ HVR sequences selected from (a) HVR-H1 comprising the amino acid sequence of SEQ ID NO:83; (b) HVR-H2 comprising an amino acid sequence selected from the group consisting of SEQ ID NOs:99, 329, 330, 331, 332, and 333; and (c) HVR-H3 comprising an amino acid sequence selected from the group consisting of SEQ ID NOs: 138, 334, 335, 336, 337, 338, and 339.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs: 158, 340, 341, 342, 343, and 344; (b) HVR-L2 comprising the amino acid sequence of SEQ ID NO: 187; and (c) HVR-L3 comprising the amino acid sequence of SEQ ID NO:210.

In some embodiments, provided herein are anti-MerTK antibodies comprising (a) a $V_H$ domain comprising at least one, at least two, or all three $V_H$ HVR sequences selected from (i) HVR-H1 comprising the amino acid sequence of SEQ ID NO: 83, (ii) HVR-H2 comprising an amino acid sequence selected from the group consisting of SEQ ID NOs: 99, 329, 330, 331, 332, and 333, and (iii) HVR-H3 comprising an amino acid sequence selected from the group consisting of SEQ ID NOs: 138, 334, 335, 336, 337, 338, and 339, and (b) a $V_L$ domain comprising at least one, at least two, or all three $V_L$ HVR sequences selected from (i) HVR-L1 comprising an amino acid sequence selected from the group consisting of SEQ ID NOs: 158, 340, 341, 342, 343, and 344, (ii) HVR-L2 comprising the amino acid sequence of SEQ ID NO: 187, and (iii) HVR-L3 comprising the amino acid sequence of SEQ ID NO: 210.

In some embodiments, provided herein are anti-MerTK antibodies comprising: (a) HVR-H1 comprising the amino acid sequence of SEQ ID NO:83; (b) HVR-H2 comprising the amino acid sequence of SEQ ID NO:99; (c) HVR-H3 comprising the amino acid sequence of SEQ ID NO:138; (d) HVR-L1 comprising the amino acid sequence of SEQ ID NO: 158; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:334; (d) HVR-L1 comprising the amino acid sequence of SEQ ID NO: 158; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:330; (c) HVR-H3 comprising the amino acid sequence of SEQ ID NO:138; (d) HVR-L1 comprising the amino acid sequence of SEQ ID NO:158; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:340; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:335; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:331; (c) HVR-H3 comprising the amino acid sequence of SEQ ID NO:138; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO: 138; (d) HVR-L1 comprising the amino acid sequence of SEQ ID NO:342; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:337; (d) HVR-L1 comprising the amino acid sequence of SEQ ID NO:343; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:338; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:333; (c) HVR-H3 comprising the amino acid sequence of SEQ ID NO:334; (d) HVR-L1 comprising the amino acid sequence of SEQ ID NO:158; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:332; (c) HVR-H3 comprising the amino acid sequence of SEQ ID NO:336; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO:339; (d) HVR-L1 comprising the amino acid sequence of SEQ ID NO:344; (e) HVR-L2 comprising the amino acid sequence of SEQ ID NO:187; and (f) HVR-L3 comprising the amino acid sequence of SEQ ID NO:210; (a) HVR-H1 comprising the amino acid sequence of SEQ ID NO:83; (b) HVR-H2 comprising the amino acid sequence of SEQ ID NO:329; (c) HVR-H3 comprising the amino acid sequence of SEQ ID NO: 138; (d) HVR-L1 comprising the amino acid sequence of SEQ ID NO: 158; (e) HVR-L2 comprising the amino acid sequence of SEQ ID NO: 187; and (f) HVR-L3 comprising the amino acid sequence of SEQ ID NO:210.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:19, 234, 235, 236, 237, 238, 239, 240, 241, 242, 243, 244, 245, and 246. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 19, 234, 235, 236, 237, 238, 239, 240, 241, 242, 243, 244, 245, and 246 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 19, 234, 235, 236, 237, 238, 239, 240, 241, 242, 243, 244, 245, or 246. In certain embodiments, a total of 1 to 5 amino acids have been substituted, inserted and/or deleted in SEQ ID NO: 19, 234, 235, 236, 237, 238, 239, 240, 241, 242, 243, 244, 245, or 246. In certain embodiments, substitutions, insertions, or deletions occur in regions outside the HVRs (i.e., in the FRs). Optionally, the anti-MerTK antibody comprises the $V_H$ sequence of SEQ ID NO: 19, 234, 235, 236, 237, 238, 239, 240, 241, 242, 243, 244, 245, or 246, including post-translational modifications of that sequence. In a particular embodiment, the $V_H$ comprises one, two or three HVRs selected from: (a) HVR-H1 comprising the amino acid sequence of SEQ ID NO:83, (b) HVR-H2 comprising an amino acid sequence selected from the group consisting of SEQ ID NOs:99, 329, 330, 331, 332, and 333, and (c) HVR-H3 comprising an amino acid sequence selected from the group consisting of SEQ ID NOs:138, 334, 335, 336, 337, 338, and 339.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:54, 247, 248, 249, 250, 251, 252, 253, and 254. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 54, 247, 248, 249, 250, 251, 252, 253, and 254, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 54, 247, 248, 249, 250, 251, 252, 253, or 254. In certain embodiments, a total of 1 to 5 amino acids have been substituted, inserted and/or deleted in SEQ ID NO: 54, 247, 248, 249, 250, 251, 252, 253, or 254. In certain embodiments, the substitutions, insertions, or deletions occur in regions outside the HVRs (i.e., in the FRs). Optionally, the anti-MerTK antibody comprises the $V_L$ sequence of SEQ ID NO: 54, 247, 248, 249, 250, 251, 252, 253, or 254, including post-translational modifications of that sequence. In a particular embodiment, the $V_L$ comprises one, two or three HVRs selected from (a) HVR-L1 comprising an amino acid sequence selected from the group consisting of SEQ ID NOs:158, 340, 341, 342, 343, and 344, (b) HVR-L2 comprising the amino acid sequence of SEQ ID NO: 187, and (c) HVR-L3 comprising the amino acid sequence of SEQ ID NO: 210.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:19, 234, 235, 236, 237, 238, 239, 240, 241, 242, 243, 244, 245, and 246 and SEQ ID NOs:54, 247, 248, 249, 250, 251, 252, 253, and 258, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:19 and $V_L$ comprising the amino acid sequence of SEQ ID NO:54; $V_H$ comprising the amino acid sequence of SEQ ID NO:234 and $V_L$ comprising the amino acid sequence of SEQ ID NO:247; $V_H$ comprising the amino acid sequence of SEQ ID NO:235 and $V_L$ comprising the amino acid sequence of SEQ ID NO:247; $V_H$ comprising the amino acid sequence of SEQ ID NO:236 and $V_L$ comprising the amino acid sequence of SEQ ID NO:248; $V_H$ comprising the amino acid sequence of SEQ ID NO:236 and $V_L$ comprising the amino acid sequence of SEQ ID NO:249; $V_H$ comprising the amino acid sequence of SEQ ID NO:237 and $V_L$ comprising the amino acid sequence of SEQ ID NO:249; $V_H$ comprising the amino acid sequence of SEQ ID NO:238 and $V_L$ comprising the amino acid sequence of SEQ ID NO:249; $V_H$ comprising the amino acid sequence of SEQ ID NO:239 and $V_L$ comprising the amino acid sequence of SEQ ID NO:250; $V_H$ comprising the amino acid sequence of SEQ ID NO:240 and $V_L$ comprising the amino acid sequence of SEQ ID NO:251; $V_H$ comprising the amino acid sequence of SEQ ID NO:241 and $V_L$ comprising the amino acid sequence of SEQ ID NO:252; $V_H$ comprising the amino acid sequence of SEQ ID NO:242 and $V_L$ comprising the amino acid sequence of SEQ ID NO:249; $V_H$ comprising the amino acid sequence of SEQ ID NO:243 and $V_L$ comprising the amino acid sequence of SEQ ID NO:247; $V_H$ comprising the amino acid sequence of SEQ ID NO:244 and $V_L$ comprising the amino acid sequence of SEQ ID NO:251; $V_H$ comprising the amino acid sequence of SEQ ID NO:245 and $V_L$ comprising the amino acid sequence of SEQ ID NO:253; $V_H$ comprising the amino acid sequence of SEQ ID NO:246 and $V_L$ comprising the amino acid sequence of SEQ ID NO:247; and $V_H$ comprising the amino acid sequence of SEQ ID NO:246 and $V_L$ comprising the amino acid sequence of SEQ ID NO:254.

In some embodiments, provided herein are anti-MerTK antibodies comprising at least one, two, three, four, five, or six HVRs selected from: (a) HVR-H1 comprising the amino acid sequence of SEQ ID NO:84; (b) HVR-H2 comprising an amino acid sequence selected from the group consisting of SEQ ID NOs:99 and 329; (c) HVR-H3 comprising the amino acid sequence of SEQ ID NO:139; (d) HVR-L1 comprising an amino acid sequence selected from the group consisting of SEQ ID NOs:169 and 345; (e) HVR-L2 comprising the amino acid sequence of SEQ ID NO:195; and (f) HVR-L3 comprising the amino acid sequence of SEQ ID NO:219.

In some embodiments, provided herein are anti-MerTK antibodies comprising at least one, at least two, or all three $V_H$ HVR sequences selected from (a) HVR-H1 comprising the amino acid sequence of SEQ ID NO:84; (b) HVR-H2 comprising an amino acid sequence selected from the group consisting of SEQ ID NOs:99 and 329; and (c) HVR-H3 comprising the amino acid sequence of SEQ ID NO: 139.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs:169 and 345; (b) HVR-L2 comprising the amino acid sequence of SEQ ID NO: 195; and (c) HVR-L3 comprising the amino acid sequence of SEQ ID NO:219.

In some embodiments, provided herein are anti-MerTK antibodies comprising (a) a $V_H$ domain comprising at least one, at least two, or all three $V_H$ HVR sequences selected from (i) HVR-H1 comprising the amino acid sequence of SEQ ID NO: 84, (ii) HVR-H2 comprising an amino acid sequence selected from the group consisting of SEQ ID NOs: 99, 329, and (iii) HVR-H3 comprising the amino acid sequence of SEQ ID NO: 139, and (b) a $V_L$ domain comprising at least one, at least two, or all three $V_L$ HVR sequences selected from (i) HVR-L1 comprising an amino acid sequence selected from the group consisting of SEQ ID NOs: 169 and 345, (ii) HVR-L2 comprising the amino acid sequence of SEQ ID NO: 195, and (iii) HVR-L3 comprising the amino acid sequence of SEQ ID NO: 219.

In some embodiments, provided herein are anti-MerTK antibodies comprising: (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d)

HVR-L1 comprising the amino acid sequence of SEQ ID NO: 169; (e) HVR-L2 comprising the amino acid sequence of SEQ ID NO: 195; and (f) HVR-L3 comprising the amino acid sequence of SEQ ID NO:219; (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO: 139; (d) HVR-L1 comprising the amino acid sequence of SEQ ID NO: 169; (e) HVR-L2 comprising the amino acid sequence of SEQ ID NO: 195; and (f) HVR-L3 comprising the amino acid sequence of SEQ ID NO:219; and (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO:195; and (f) HVR-L3 comprising the amino acid sequence of SEQ ID NO:219.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:20, 255, and 256. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 20, 255, and 256 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 20, 255, or 256. In certain embodiments, a total of 1 to 5 amino acids have been substituted, inserted and/or deleted in SEQ ID NO: 20, 255, or 256. In certain embodiments, substitutions, insertions, or deletions occur in regions outside the HVRs (i.e., in the FRs). Optionally, the anti-MerTK antibody comprises the $V_H$ sequence of SEQ ID NO: 20, 255, or 256, including post-translational modifications of that sequence. In a particular embodiment, the $V_H$ comprises one, two or three HVRs selected from: (a) HVR-H1 comprising the amino acid sequence of SEQ ID NO:84, (b) HVR-H2 comprising an amino acid sequence selected from the group consisting of SEQ ID NOs:99 and 329, and (c) HVR-H3 comprising the amino acid sequence of SEQ ID NO:139.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:55, 257, and 258. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 55, 257, and 258, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 55, 257, or 258. In certain embodiments, a total of 1 to 5 amino acids have been substituted, inserted and/or deleted in SEQ ID NO: 55, 257, or 258. In certain embodiments, the substitutions, insertions, or deletions occur in regions outside the HVRs (i.e., in the FRs). Optionally, the anti-MerTK antibody comprises the $V_L$ sequence of SEQ ID NO: 55, 257, or 258, including post-translational modifications of that sequence. In a particular embodiment, the $V_L$ comprises one, two or three HVRs selected from (a) HVR-L1 comprising an amino acid sequence selected from the group consisting of SEQ ID NOs:169 and 345, (b) HVR-L2 comprising the amino acid sequence of SEQ ID NO: 195, and (c) HVR-L3 comprising the amino acid sequence of SEQ ID NO: 219.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:20, 255, and 256 and SEQ ID NOs:55, 257, and 258, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:20 and $V_L$ comprising the amino acid sequence of SEQ ID NO:55; $V_H$ comprising the amino acid sequence of SEQ ID NO:255 and $V_L$ comprising the amino acid sequence of SEQ ID NO:257; and $V_H$ comprising the amino acid sequence of SEQ ID NO:256 and $V_L$ comprising the amino acid sequence of SEQ ID NO:258.

In some embodiments, provided herein are anti-MerTK antibodies comprising at least one, two, three, four, five, or six HVRs selected from: (a) HVR-H1 comprising an amino acid sequence selected from the group consisting of SEQ ID NOs:95, 346, and 347; (b) HVR-H2 comprising an amino acid sequence selected from the group consisting of SEQ ID NOs:119, 348, 349, 350, 351, 352, 353, and 354; (c) HVR-H3 comprising an amino acid sequence selected from the group consisting of SEQ ID NOs:151, 355, and 356; (d) HVR-L1 comprising an amino acid sequence selected from the group consisting of SEQ ID NOs:181, 341, 357, and 358; (e) HVR-L2 comprising an amino acid sequence selected from the group consisting of SEQ ID NOs:187 and 359; and (f) HVR-L3 comprising an amino acid sequence selected from the group consisting of SEQ ID NOs:208, 360, 361, and 362.

In some embodiments, provided herein are anti-MerTK antibodies comprising at least one, at least two, or all three $V_H$ HVR sequences selected from (a) HVR-H1 comprising an amino acid sequence selected from the group consisting of SEQ ID NOs:95, 346, and 347; (b) HVR-H2 comprising an amino acid sequence selected from the group consisting of SEQ ID NOs:119, 348, 349, 350, 351, 352, 353, and 354; and (c) HVR-H3 comprising an amino acid sequence selected from the group consisting of SEQ ID NOs:151, 355, and 356.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs:181, 341, 357, and 358; (b) HVR-L2 comprising an amino acid sequence selected from the group consisting of SEQ ID NOs:187 and 359; and (c) HVR-L3 comprising an amino acid sequence selected from the group consisting of SEQ ID NO:208. 360, 361, and 362.

In some embodiments, provided herein are anti-MerTK antibodies comprising (a) a $V_H$ domain comprising at least one, at least two, or all three $V_H$ HVR sequences selected from (i) HVR-H1 comprising an amino acid sequence selected from the group consisting of SEQ ID NOs: 95, 346, and 347, (ii) HVR-H2 comprising an amino acid sequence selected from the group consisting of SEQ ID NOs: 119, 348, 349, 350, 351, 352, 353, and 354, and (iii) HVR-H3 comprising an amino acid sequence selected from the group consisting of SEQ ID NOs: 151, 355, and 356, and (b) a $V_L$ domain comprising at least one, at least two, or all three $V_L$ HVR sequences selected from (i) HVR-L1 comprising an amino acid sequence selected from the group consisting of SEQ ID NOs: 181, 341, 357, and 358, (ii) HVR-L2 comprising an amino acid sequence selected from the group consisting of SEQ ID NOs: 187 and 359, and (iii) HVR-L3 comprising an amino acid sequence selected from the group consisting of SEQ ID NOs: 208, 360, 361, and 362.

In some embodiments, provided herein are anti-MerTK antibodies comprising: (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO: 187; and (f) HVR-L3 comprising the amino acid sequence of SEQ ID NO:208; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:360; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:355; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:361; (a) HVR-H1 comprising the amino acid sequence of SEQ ID NO:95; (b) HVR-H2 comprising the amino acid sequence of SEQ ID NO:349; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:350 (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:347; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO: 119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO: 187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:352; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:353; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:363; (a) HVR-H1 comprising the amino acid sequence of SEQ ID NO:346; (b) HVR-H2 comprising the amino acid sequence of SEQ ID NO:348; (c) HVR-H3 comprising the amino acid sequence of SEQ ID NO:356; (d) HVR-L1 comprising the amino acid sequence of SEQ ID NO:357; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:346; (b) HVR-H2 comprising the amino acid sequence of SEQ ID NO:354; (c) HVR-H3 comprising the amino acid sequence of SEQ ID NO:356; (d) HVR-L1 comprising the amino acid sequence of SEQ ID NO:358; (e) HVR-L2 comprising the amino acid sequence of SEQ ID NO: 187; and (f) HVR-L3 comprising the amino acid sequence of SEQ ID NO:362; (a) HVR-H1 comprising the amino acid sequence of SEQ ID NO:95; (b) HVR-H2 comprising the amino acid sequence of SEQ ID NO:348; (c) HVR-H3 comprising the amino acid sequence of SEQ ID NO:151; (d) HVR-L1 comprising the amino acid sequence of SEQ ID NO:181; (e) HVR-L2 comprising the amino acid sequence of SEQ ID NO: 187; and (f) HVR-L3 comprising the amino acid sequence of SEQ ID NO:208.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:33, 259, 260, 261, 262, 263, 264, 265, 266, 267, 268, 269, 270, 271, 272, and 273. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 33, 259, 260, 261, 262, 263, 264, 265, 266, 267, 268, 269, 270, 271, 272, and 273 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 33, 259, 260, 261, 262, 263, 264, 265, 266, 267, 268, 269, 270, 271, 272, or 273. In certain embodiments, a total of 1 to 5 amino acids have been substituted, inserted and/or deleted in SEQ ID NO: 33, 259, 260, 261, 262, 263, 264, 265, 266, 267, 268, 269, 270, 271, 272, or 273. In certain embodiments, substitutions, insertions, or deletions occur in regions outside the HVRs (i.e., in the FRs). Optionally, the anti-MerTK antibody comprises the $V_H$ sequence of SEQ ID NO: 33, 259, 260, 261, 262, 263, 264, 265, 266, 267, 268, 269, 270, 271, 272, or 273, including post-translational modifications of that sequence. In a particular embodiment, the $V_H$ comprises one, two or three HVRs selected from: (a) HVR-H1 comprising an amino acid sequence selected from the group consisting of SEQ ID NOs:95, 346, and 347, (b) HVR-H2 comprising an amino acid sequence selected from the group consisting of SEQ ID NOs:119, 348, 349, 350, 351, 352, 353, and 354, and (c) HVR-H3 comprising an amino acid sequence selected from the group consisting of SEQ ID NOs:151, 355, and 356.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:68, 274, 275, 276, 277, 278, 279, 280, 281, 282, 283, 284, 285, 286, 287, 288, and 289. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 68, 274, 275, 276, 277, 278, 279, 280, 281, 282, 283, 284, 285, 286, 287, 288, and 289, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 68, 274, 275, 276, 277, 278, 279, 280, 281, 282, 283, 284, 285, 286, 287, 288, or 289. In certain embodiments, a total of 1 to 5 amino acids have been substituted, inserted and/or deleted in SEQ ID NO: 68, 274, 275, 276, 277, 278, 279, 280, 281, 282, 283, 284, 285, 286, 287, 288, or 289. In certain embodiments, the substitutions, insertions, or deletions occur in regions outside the HVRs (i.e., in the FRs). Optionally, the anti-MerTK antibody comprises the $V_L$ sequence of SEQ ID NO: 68, 274, 275, 276, 277, 278, 279, 280, 281, 282, 283, 284, 285, 286, 287, 288, or 289, including post-translational modifications of that sequence. In a particular embodiment, the $V_L$ comprises one, two or three HVRs selected from (a) HVR-L1 comprising an amino acid sequence selected from the group consisting of SEQ ID NOs:181, 341, 357, and 358, (b) HVR-L2 comprising an amino acid sequence selected from the group consisting of SEQ ID NOs: 187 and 359, and (c) HVR-L3 comprising an amino acid sequence selected from the group consisting of SEQ ID NOs: 208, 360, 361, and 362.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 33, 259, 260, 261, 262, 263, 264, 265, 266, 267, 268, 269, 270, 271, 272, and 273 and SEQ ID NOs: 68, 274, 275, 276, 277, 278, 279, 280, 281, 282, 283, 284, 285, 286, 287, 288, and 289, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:33 and $V_L$ comprising the amino acid sequence of SEQ ID NO:68; $V_H$ comprising the amino acid sequence of SEQ ID NO:259 and $V_L$ comprising the amino acid sequence of SEQ ID NO:274; $V_H$ comprising the amino acid sequence of SEQ ID NO:260 and $V_L$ comprising the amino acid sequence of SEQ ID NO:275; $V_H$ comprising the amino acid sequence of SEQ ID NO:261 and $V_L$ comprising the amino acid sequence of SEQ ID NO:276; $V_H$ comprising the amino acid sequence of SEQ ID NO:262 and $V_L$ comprising the amino acid sequence of SEQ ID NO:277; $V_H$ comprising the amino acid sequence of SEQ ID NO:263 and $V_L$ comprising the amino acid sequence of SEQ ID NO:277; $V_H$ comprising the amino acid sequence of SEQ ID NO:264 and $V_L$ comprising the amino acid sequence of SEQ ID NO:277; $V_H$ comprising the amino acid sequence of SEQ ID NO:265 and $V_L$ comprising the amino acid sequence of SEQ ID NO:277; $V_H$ comprising the amino acid sequence of SEQ ID NO:266 and $V_L$ comprising the amino acid sequence of SEQ ID NO:277; $V_H$ comprising the amino acid sequence of SEQ ID NO:267 and $V_L$ comprising the amino acid sequence of SEQ ID NO:278; $V_H$ comprising the amino acid sequence of SEQ ID NO:268 and $V_L$ comprising the amino acid sequence of SEQ ID NO:279; $V_H$ comprising the amino acid sequence of SEQ ID NO:269 and $V_L$ comprising the amino acid sequence of SEQ ID NO:279; $V_H$ comprising the amino acid sequence of SEQ ID NO:264 and $V_L$ comprising the amino acid sequence of SEQ ID NO:280; $V_H$ comprising the amino acid sequence of SEQ ID NO:270 and $V_L$ comprising the amino acid sequence of SEQ ID NO:281; $V_H$ comprising the amino acid sequence of SEQ ID NO:265 and $V_L$ comprising the amino acid sequence of SEQ ID NO:282; $V_H$ comprising the amino acid sequence of SEQ ID NO:264 and $V_L$ comprising the amino acid sequence of SEQ ID NO:283; $V_H$ comprising the amino acid sequence of SEQ ID NO:271 and $V_L$ comprising the amino acid sequence of SEQ ID NO:284; $V_H$ comprising the amino acid sequence of SEQ ID NO:272 and $V_L$ comprising the amino acid sequence of SEQ ID NO:285; $V_H$ comprising the amino acid sequence of SEQ ID NO:271 and $V_L$ comprising the amino acid sequence of SEQ ID NO:286; $V_H$ comprising the amino acid sequence of SEQ ID NO:273 and $V_L$ comprising the amino acid sequence of SEQ ID NO:287; $V_H$ comprising the amino acid sequence of SEQ ID NO:273 and $V_L$ comprising the amino acid sequence of SEQ ID NO:288; and $V_H$ comprising the amino acid sequence of SEQ ID NO:273 and $V_L$ comprising the amino acid sequence of SEQ ID NO:289.

In some embodiments, provided herein are anti-MerTK antibodies comprising at least one, two, three, four, five, or six HVRs selected from: (a) HVR-H1 comprising the amino acid sequence of SEQ ID NO:90; (b) HVR-H2 comprising an amino acid sequence selected from the group consisting of SEQ ID NOs:122, 364, 365, 366, 367, and 368; (c) HVR-H3 comprising an amino acid sequence selected from the group consisting of SEQ ID NOs:155, 373, 374, and 375; (d) HVR-L1 comprising an amino acid sequence selected from the group consisting of SEQ ID NOs:184, 376, 377, 378, 379, 380, 381, 382, 383, 384, 385, 386, and 387; (e) HVR-L2 comprising an amino acid sequence selected from the group consisting of SEQ ID NOs:203, 388, 389, 390, and 391; and (f) HVR-L3 comprising an amino acid sequence selected from the group consisting of SEQ ID NOs:231, 392, 393, and 394.

In some embodiments, provided herein are anti-MerTK antibodies comprising at least one, at least two, or all three $V_H$ HVR sequences selected from (a) HVR-H1 comprising the amino acid sequence of SEQ ID NO:90; (b) HVR-H2 comprising an amino acid sequence selected from the group consisting of SEQ ID NOs: 122, 364, 365, 366, 367, and 368; and (c) HVR-H3 comprising an amino acid sequence selected from the group consisting of SEQ ID NOs: 155, 373, 374, and 375.

In some embodiments, provided herein are anti-MerTK antibodies comprising at least one, at least two, or all three $V_L$ HVR sequences selected from (a) HVR-L1 comprising an amino acid sequence selected from the group consisting of SEQ ID NOs: 184, 376, 377, 378, 379, 380, 381, 382, 383, 384, 385, 386, and 387; (b) HVR-L2 comprising an amino acid sequence selected from the group consisting of SEQ ID NOs: 203, 388, 389, 390, and 391 and (c) HVR-L3 comprising an amino acid sequence selected from the group consisting of SEQ ID NOs: 203, 388, 389, 390, and 391

In some embodiments, provided herein are anti-MerTK antibodies comprising (a) a $V_H$ domain comprising at least one, at least two, or all three $V_H$ HVR sequences selected from (i) HVR-H1 comprising the amino acid sequence of SEQ ID NO: 90, (ii) HVR-H2 comprising an amino acid sequence selected from the group consisting of SEQ ID NOs: 122, 364, 365, 366, 367, and 368, and (iii) HVR-H3 comprising an amino acid sequence selected from the group consisting of SEQ ID NOs: 155, 373, 374, and 375, and (b) a $V_L$ domain comprising at least one, at least two, or all three $V_L$ HVR sequences selected from (i) HVR-L1 comprising an amino acid sequence selected from the group consisting of SEQ ID NOs: 184, 376, 377, 378, 379, 380, 381, 382, 383, 384, 385, 386, and 387, (ii) HVR-L2 comprising an amino acid sequence selected from the group consisting of SEQ ID NOs: 203, 388, 389, 390, and 391, and (iii) HVR-L3 comprising an amino acid sequence selected from the group consisting of SEQ ID NOs: 231, 392, 393, and 394.

In some embodiments, provided herein are anti-MerTK antibodies comprising: (a) HVR-H1 comprising the amino acid sequence of SEQ ID NO:90; (b) HVR-H2 comprising the amino acid sequence of SEQ ID NO:122; (c) HVR-H3 comprising the amino acid sequence of SEQ ID NO:155; (d) HVR-L1 comprising the amino acid sequence of SEQ ID NO: 184; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:376; (e) HVR-L2 comprising the amino acid sequence of SEQ ID NO:388; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:377; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:95; (b) HVR-H2 comprising the amino acid sequence of SEQ ID NO:119; (c) HVR-H3 comprising the amino acid sequence of SEQ ID NO:356; (d) HVR-L1 comprising the amino acid sequence of SEQ ID NO:341; (e) HVR-L2 comprising the amino acid sequence of SEQ ID NO:359; and (f) HVR-L3 comprising the amino acid sequence of SEQ ID NO:362; (a) HVR-H1 comprising the amino acid sequence of SEQ ID NO:90; (b) HVR-H2 comprising the amino acid sequence of SEQ ID NO:365; (c) HVR-H3 comprising the amino acid sequence of SEQ ID NO:155; (d) HVR-L1 comprising the amino acid sequence of SEQ ID NO:276; (e) HVR-L2 comprising the amino acid sequence of SEQ ID NO:203; and (f) HVR-L3 comprising the amino acid sequence of SEQ ID NO:392; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:389; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:379; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:366; (c) HVR-H3 comprising the amino acid sequence of SEQ ID NO: 155; (d) HVR-L1 comprising the amino acid sequence of SEQ ID NO:380; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:373; (d) HVR-L1 comprising the amino acid sequence of SEQ ID NO:381; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:367; (c) HVR-H3 comprising the amino acid sequence of SEQ ID NO:155; (d) HVR-L1 comprising the amino acid sequence of SEQ ID NO:382; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:374; (d) HVR-L1 comprising the amino acid sequence of SEQ ID NO:384; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO: 155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393; (a) HVR-H1 comprising the amino acid sequence of SEQ ID NO:90; (b) HVR-H2 comprising the amino acid sequence of SEQ ID NO:364; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:231; (a) HVR-H1 comprising the amino acid sequence of SEQ ID NO:90; (b) HVR-H2 comprising the amino acid sequence of SEQ ID NO:369; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:370; (c) HVR-H3 comprising the amino acid sequence of SEQ ID NO:155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:371; (c) HVR-H3 comprising the amino acid sequence of SEQ ID NO:155; (d) HVR-L1 comprising the amino acid sequence of SEQ ID NO: 178; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:385; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO: 155; (d) HVR-L1 comprising the amino acid sequence of SEQ ID NO:378; (e) HVR-L2 comprising the amino acid sequence of SEQ ID NO:203; and (f) HVR-L3 comprising the amino acid sequence of SEQ ID NO:395; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO: 155; (d) HVR-L1 comprising the amino acid sequence of SEQ ID NO:378; (e) HVR-L2 comprising the amino acid sequence of SEQ ID NO:390; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:372; (c) HVR-H3 comprising the amino acid sequence of SEQ ID NO: 155; (d) HVR-L1 comprising the amino acid sequence of SEQ ID NO:378; (e) HVR-L2 comprising the amino acid sequence of SEQ ID NO:391; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:375; (d) HVR-L1 comprising the amino acid sequence of SEQ ID NO:386; (e) HVR-L2 comprising the amino acid sequence of SEQ ID NO:203; and (f) HVR-L3 comprising the amino acid sequence of SEQ ID NO:394; (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO:155; (d) HVR-L1 comprising the amino acid sequence of SEQ ID NO:387; (e) HVR-L2 comprising the amino acid sequence of SEQ ID NO:203; and (f) HVR-L3 comprising the amino acid sequence of SEQ ID NO:394.

In another aspect, an anti-MerTK antibody comprises a heavy chain variable domain ($V_H$) sequence having at least 90%, 91%, 92%, 93%, 94%, 95%, 96%, 97%, 98%, 99%, or 100% sequence identity to an amino acid sequence selected from the group consisting of SEQ ID NOs:37, 290, 291, 292, 293, 294, 295, 296, 297, 298, 299, 300, 301, 302, 303, 304, 305, 306, 307, and 308. In certain embodiments, a $V_H$ sequence having at least 90%, 91%, 92%, 93%, 94%, 95%, 96%, 97%, 98%, or 99% identity to an amino acid sequence selected from the group consisting of SEQ ID NOs: 37, 290, 291, 292, 293, 294, 295, 296, 297, 298, 299, 300, 301, 302, 303, 304, 305, 306, 307, and 308 contains substitutions (e.g., conservative substitutions), insertions, or deletions relative to the reference sequence, but an anti-MerTK antibody comprising that sequence retains the ability to bind to MerTK. In certain embodiments, a total of 1 to 10 amino acids have been substituted, inserted, and/or deleted in SEQ ID NO: 37, 290, 291, 292, 293, 294, 295, 296, 297, 298, 299, 300, 301, 302, 303, 304, 305, 306, 307, or 308. In certain embodiments, a total of 1 to 5 amino acids have been substituted, inserted and/or deleted in SEQ ID NO: 37, 290, 291, 292, 293, 294, 295, 296, 297, 298, 299, 300, 301, 302, 303, 304, 305, 306, 307, or 308. In certain embodiments, substitutions, insertions, or deletions occur in regions outside the HVRs (i.e., in the FRs). Optionally, the anti-MerTK antibody comprises the $V_H$ sequence of SEQ ID NO: 37, 290, 291, 292, 293, 294, 295, 296, 297, 298, 299, 300, 301, 302, 303, 304, 305, 306, 307, or 308, including post-translational modifications of that sequence. In a particular embodiment, the $V_H$ comprises one, two or three HVRs selected from: (a) HVR-H1 comprising the amino acid sequence of SEQ ID NO:90, (b) HVR-H2 comprising an amino acid sequence selected from the group consisting of SEQ ID NOs:122, 364, 365, 366, 367, and 368, and (c)

HVR-H3 comprising an amino acid sequence selected from the group consisting of SEQ ID NOs:155, 373, 374, and 375.

In another aspect, an anti-MerTK antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from the group consisting of SEQ ID NOs:72, 309, 310, 311, 312, 313, 314, 315, 316, 316, 318, 319, 320, 321, 322, 323, 324, 325, 326, 327, and 328. In certain embodiments, a $V_L$ sequence having at least 90%, 91%, 92%, 93%, 94%, 95%, 96%, 97%, 98%, or 99% identity to an amino acid sequence selected from the group consisting of SEQ ID NOs: 72, 309, 310, 311, 312, 313, 314, 315, 316, 316, 318, 319, 320, 321, 322, 323, 324, 325, 326, 327, and 328, and contains substitutions (e.g., conservative substitutions), insertions, or deletions relative to the reference sequence, but an anti-MerTK antibody comprising that sequence retains the ability to bind to MerTK. In some embodiments, a total of 1 to 10 amino acids have been substituted, inserted and/or deleted in SEQ ID NO: 72, 309, 310, 311, 312, 313, 314, 315, 316, 316, 318, 319, 320, 321, 322, 323, 324, 325, 326, 327, or 328. In certain embodiments, a total of 1 to 5 amino acids have been substituted, inserted and/or deleted in SEQ ID NO: 72, 309, 310, 311, 312, 313, 314, 315, 316, 316, 318, 319, 320, 321, 322, 323, 324, 325, 326, 327, or 328. In certain embodiments, the substitutions, insertions, or deletions occur in regions outside the HVRs (i.e., in the FRs). Optionally, the anti-MerTK antibody comprises the $V_L$ sequence of SEQ ID NO: 72, 309, 310, 311, 312, 313, 314, 315, 316, 316, 318, 319, 320, 321, 322, 323, 324, 325, 326, 327, or 328, including post-translational modifications of that sequence. In a particular embodiment, the $V_L$ comprises one, two or three HVRs selected from (a) HVR-L1 comprising an amino acid sequence selected from the group consisting of SEQ ID NOs:184, 376, 377, 378, 379, 380, 381, 382, 383, 384, 385, 386, and 387, (b) HVR-L2 comprising an amino acid sequence selected from the group consisting of SEQ ID NOs: 203, 388, 389, 390, and 391, and (c) HVR-L3 comprising an amino acid sequence selected from the group consisting of SEQ ID NOs: 231, 392, 393, and 394.

In some embodiments, an anti-MerTK antibody is provided, wherein the antibody comprises a $V_H$ as in any of the embodiments provided above, and a $V_L$ as in any of the embodiments provided above. In some embodiments, provided herein are anti-MerTK antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs: 37, 290, 291, 292, 293, 294, 295, 296, 297, 298, 299, 300, 301, 302, 303, 304, 305, 306, 307, and 308 and SEQ ID NOs: 72, 309, 310, 311, 312, 313, 314, 315, 316, 316, 318, 319, 320, 321, 322, 323, 324, 325, 326, 327, and 328, respectively, including post-translational modifications of those sequences.

In some embodiments, provided herein are anti-MerTK antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:37 and $V_L$ comprising the amino acid sequence of SEQ ID NO:72; $V_H$ comprising the amino acid sequence of SEQ ID NO:290 and $V_L$ comprising the amino acid sequence of SEQ ID NO:309; $V_H$ comprising the amino acid sequence of SEQ ID NO:291 and $V_L$ comprising the amino acid sequence of SEQ ID NO:310; $V_H$ comprising the amino acid sequence of SEQ ID NO:292 and $V_L$ comprising the amino acid sequence of SEQ ID NO:311; $V_H$ comprising the amino acid sequence of SEQ ID NO:293 and $V_L$ comprising the amino acid sequence of SEQ ID NO:312; $V_H$ comprising the amino acid sequence of SEQ ID NO:294 and $V_L$ comprising the amino acid sequence of SEQ ID NO:313; $V_H$ comprising the amino acid sequence of SEQ ID NO:295 and $V_L$ comprising the amino acid sequence of SEQ ID NO:314; $V_H$ comprising the amino acid sequence of SEQ ID NO:296 and $V_L$ comprising the amino acid sequence of SEQ ID NO:315; $V_H$ comprising the amino acid sequence of SEQ ID NO:290 and $V_L$ comprising the amino acid sequence of SEQ ID NO:316; $V_H$ comprising the amino acid sequence of SEQ ID NO:297 and $V_L$ comprising the amino acid sequence of SEQ ID NO:317; $V_H$ comprising the amino acid sequence of SEQ ID NO:298 and $V_L$ comprising the amino acid sequence of SEQ ID NO:318; $V_H$ comprising the amino acid sequence of SEQ ID NO:292 and $V_L$ comprising the amino acid sequence of SEQ ID NO:319; $V_H$ comprising the amino acid sequence of SEQ ID NO:299 and $V_L$ comprising the amino acid sequence of SEQ ID NO:320; $V_H$ comprising the amino acid sequence of SEQ ID NO:300 and $V_L$ comprising the amino acid sequence of SEQ ID NO:311; $V_H$ comprising the amino acid sequence of SEQ ID NO:301 and $V_L$ comprising the amino acid sequence of SEQ ID NO:321; $V_H$ comprising the amino acid sequence of SEQ ID NO:302 and $V_L$ comprising the amino acid sequence of SEQ ID NO:322; $V_H$ comprising the amino acid sequence of SEQ ID NO:303 and $V_L$ comprising the amino acid sequence of SEQ ID NO:311; $V_H$ comprising the amino acid sequence of SEQ ID NO:304 and $V_L$ comprising the amino acid sequence of SEQ ID NO:322; $V_H$ comprising the amino acid sequence of SEQ ID NO:305 and $V_L$ comprising the amino acid sequence of SEQ ID NO:322; $V_H$ comprising the amino acid sequence of SEQ ID NO:301 and $V_L$ comprising the amino acid sequence of SEQ ID NO:323; $V_H$ comprising the amino acid sequence of SEQ ID NO:301 and $V_L$ comprising the amino acid sequence of SEQ ID NO:324; $V_H$ comprising the amino acid sequence of SEQ ID NO:301 and $V_L$ comprising the amino acid sequence of SEQ ID NO:325; $V_H$ comprising the amino acid sequence of SEQ ID NO:306 and $V_L$ comprising the amino acid sequence of SEQ ID NO:326; $V_H$ comprising the amino acid sequence of SEQ ID NO:307 and $V_L$ comprising the amino acid sequence of SEQ ID NO:327; and $V_H$ comprising the amino acid sequence of SEQ ID NO:308 and $V_L$ comprising the amino acid sequence of SEQ ID NO:328.

In some embodiments, an anti-MerTK antibody of the present disclosure competitively inhibits binding of at least one reference antibody selected from MTK-01, MTK-02, MTK-03, MTK-04, MTK-05, MTK-06, MTK-07, MTK-08, MTK-09, MTK-10, MTK-11, MTK-12, MTK-13, MTK-14, MTK-15 (including MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15), MTK-16 (including MTK-16.1 and MTK-16.2), MTK-17, MTK-18, MTK-19, MTK-20, MTK-21, MTK-22, MTK-23, MTK-24, MTK-25, MTK-26, MTK-27, MTK-28, MTK-29 (including MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21), MTK-30, MTK-31, MTK-32, MTK-33 (including MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK- 33.22, MTK-33.23, and MTK-33.24), MTK-34, MTK-35, and MTK-36, and any combination thereof, for binding to MerTK.

In some embodiments, an anti-MerTK antibody of the present disclosure binds to an epitope of human MerTK that is the same as or overlaps with the MerTK epitope bound by at least one reference antibody selected from MTK-01, MTK-02, MTK-03, MTK-04, MTK-05, MTK-06, MTK-07, MTK-08, MTK-09, MTK-10, MTK-11, MTK-12, MTK-13, MTK-14, MTK-15 (including MTK-15.1, MTK-15.2, MTK-15.3, MTK-15.4, MTK-15.5, MTK-15.6, MTK-15.7, MTK-15.8, MTK-15.9, MTK-15.10, MTK-15.11, MTK-15.12, MTK-15.13, MTK-15.14, and MTK-15.15), MTK-16 (including MTK-16.1 and MTK-16.2), MTK-17, MTK-18, MTK-19, MTK-20, MTK-21, MTK-22, MTK-23, MTK-24, MTK-25, MTK-26, MTK-27, MTK-28, MTK-29 (including MTK-29.1, MTK-29.2, MTK-29.3, MTK-29.4, MTK-29.5, MTK-29.6, MTK-29.7, MTK-29.8, MTK-29.9, MTK-29.10, MTK-29.11, MTK-29.12, MTK-29.13, MTK-29.14, MTK-29.15, MTK-29.16, MTK-29.17, MTK-29.18, MTK-29.19, MTK-29.20, and MTK-29.21), MTK-30, MTK-31, MTK-32, MTK-33 (including MTK-33.1, MTK-33.2, MTK-33.3, MTK-33.4, MTK-33.5, MTK-33.6, MTK-33.7, MTK-33.8, MTK-33.9, MTK-33.10, MTK-33.11, MTK-33.12, MTK-33.13, MTK-33.14, MTK-33.15, MTK-33.16, MTK-33.17, MTK-33.18, MTK-33.19, MTK-33.20, MTK-33.21, MTK-33.22, MTK-33.23, and MTK-33.24), MTK-34, MTK-35, and MTK-36. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:5 and $V_L$ comprising the amino acid sequence of SEQ ID NO:40; $V_H$ comprising the amino acid sequence of SEQ ID NO:6 and $V_L$ comprising the amino acid sequence of SEQ ID NO:41; $V_H$ comprising the amino acid sequence of SEQ ID NO:7 and $V_L$ comprising the amino acid sequence of SEQ ID NO:42; $V_H$ comprising the amino acid sequence of SEQ ID NO:8 and $V_L$ comprising the amino acid sequence of SEQ ID NO:43; $V_H$ comprising the amino acid sequence of SEQ ID NO:9 and $V_L$ comprising the amino acid sequence of SEQ ID NO:44; $V_H$ comprising the amino acid sequence of SEQ ID NO: 10 and $V_L$ comprising the amino acid sequence of SEQ ID NO:45; $V_H$ comprising the amino acid sequence of SEQ ID NO: 11 and $V_L$ comprising the amino acid sequence of SEQ ID NO:46; $V_H$ comprising the amino acid sequence of SEQ ID NO:12 and $V_L$ comprising the amino acid sequence of SEQ ID NO:47; $V_H$ comprising the amino acid sequence of SEQ ID NO: 13 and $V_L$ comprising the amino acid sequence of SEQ ID NO:48; $V_H$ comprising the amino acid sequence of SEQ ID NO: 14 and $V_L$ comprising the amino acid sequence of SEQ ID NO:49; $V_H$ comprising the amino acid sequence of SEQ ID NO: 15 and $V_L$ comprising the amino acid sequence of SEQ ID NO:50; $V_H$ comprising the amino acid sequence of SEQ ID NO: 16 and $V_L$ comprising the amino acid sequence of SEQ ID NO:51; $V_H$ comprising the amino acid sequence of SEQ ID NO:17 and $V_L$ comprising the amino acid sequence of SEQ ID NO:52; $V_H$ comprising the amino acid sequence of SEQ ID NO: 18 and $V_L$ comprising the amino acid sequence of SEQ ID NO:53; $V_H$ comprising the amino acid sequence of SEQ ID NO: 19 and $V_L$ comprising the amino acid sequence of SEQ ID NO:54; $V_H$ comprising the amino acid sequence of SEQ ID NO:20 and $V_L$ comprising the amino acid sequence of SEQ ID NO:55; $V_H$ comprising the amino acid sequence of SEQ ID NO:21 and $V_L$ comprising the amino acid sequence of SEQ ID NO:56; $V_H$ comprising the amino acid sequence of SEQ ID NO:22 and $V_L$ comprising the amino acid sequence of SEQ ID NO:57; $V_H$ comprising the amino acid sequence of SEQ ID NO:23 and $V_L$ comprising the amino acid sequence of SEQ ID NO:58; $V_H$ comprising the amino acid sequence of SEQ ID NO:24 and $V_L$ comprising the amino acid sequence of SEQ ID NO:59; $V_H$ comprising the amino acid sequence of SEQ ID NO:25 and $V_L$ comprising the amino acid sequence of SEQ ID NO:60; $V_H$ comprising the amino acid sequence of SEQ ID NO:26 and $V_L$ comprising the amino acid sequence of SEQ ID NO:61; $V_H$ comprising the amino acid sequence of SEQ ID NO:27 and $V_L$ comprising the amino acid sequence of SEQ ID NO:62; $V_H$ comprising the amino acid sequence of SEQ ID NO:28 and $V_L$ comprising the amino acid sequence of SEQ ID NO:63; $V_H$ comprising the amino acid sequence of SEQ ID NO:29 and $V_L$ comprising the amino acid sequence of SEQ ID NO:64; $V_H$ comprising the amino acid sequence of SEQ ID NO:30 and $V_L$ comprising the amino acid sequence of SEQ ID NO:65; $V_H$ comprising the amino acid sequence of SEQ ID NO:31 and $V_L$ comprising the amino acid sequence of SEQ ID NO:66; $V_H$ comprising the amino acid sequence of SEQ ID NO:32 and $V_L$ comprising the amino acid sequence of SEQ ID NO:67; $V_H$ comprising the amino acid sequence of SEQ ID NO:33 and $V_L$ comprising the amino acid sequence of SEQ ID NO:68; $V_H$ comprising the amino acid sequence of SEQ ID NO:34 and $V_L$ comprising the amino acid sequence of SEQ ID NO:69; $V_H$ comprising the amino acid sequence of SEQ ID NO:35 and $V_L$ comprising the amino acid sequence of SEQ ID NO:70; $V_H$ comprising the amino acid sequence of SEQ ID NO:36 and $V_L$ comprising the amino acid sequence of SEQ ID NO:71; $V_H$ comprising the amino acid sequence of SEQ ID NO:37 and $V_L$ comprising the amino acid sequence of SEQ ID NO:72; $V_H$ comprising the amino acid sequence of SEQ ID NO:38 and $V_L$ comprising the amino acid sequence of SEQ ID NO:73; and $V_H$ comprising the amino acid sequence of SEQ ID NO:39 and $V_L$ comprising the amino acid sequence of SEQ ID NO:74.

In some embodiments, an anti-MerTK antibody of the present disclosure comprises a full-length heavy chain amino acid sequence comprising a variable heavy chain amino acid sequence of SEQ ID NO: 234, 235, 236, 237, 238, 239, 240, 241, 242, 243, 244, 245, or 246, and a heavy chain Fc selected from the group consisting of SEQ ID NOs: 396-411; and comprises a full-length light chain amino acid sequence comprising a variable light chain amino acid sequence of SEQ ID NO:247, 248, 249, 250, 251, 252, 253, or 254, and a light chain Fc comprising the amino acid sequence of SEQ ID NO:412.

In some embodiments, an anti-MerTK antibody of the present disclosure comprises a full-length heavy chain amino acid sequence comprising a variable heavy chain amino acid sequence of SEQ ID NO:255 or 256 and a heavy chain Fc selected from the group consisting of SEQ ID NOs: 396-411; and comprises a full-length light chain amino acid sequence comprising a variable light chain amino acid sequence of SEQ ID NO:257 or 258 and a light chain Fc comprising the amino acid sequence of SEQ ID NO:412.

In some embodiments, an anti-MerTK antibody of the present disclosure comprises a full-length heavy chain amino acid sequence of SEQ ID NO:413, 414, 415, 416, 417, 418, 419, or 420 and a full-length light chain amino acid sequence of SEQ ID NO: 421. Accordingly, in some embodiments, an anti-MerTK antibody comprises the heavy chain amino acid sequence of SEQ ID NO:413 and the light chain amino acid sequence of SEQ ID NO:421; the heavy chain amino acid sequence of SEQ ID NO:414 and the light chain amino acid sequence of SEQ ID NO:421; the heavy chain amino acid sequence of SEQ ID NO:415 and the light chain amino acid sequence of SEQ ID NO:421; the heavy chain amino acid sequence of SEQ ID NO:416 and the light chain amino acid sequence of SEQ ID NO:421; the heavy chain amino acid sequence of SEQ ID NO:417 and the light chain amino acid sequence of SEQ ID NO:421; the heavy chain amino acid sequence of SEQ ID NO:418 and the light chain amino acid sequence of SEQ ID NO:421; the heavy chain amino acid sequence of SEQ ID NO:419 and the light chain amino acid sequence of SEQ ID NO:421; or the heavy chain amino acid sequence of SEQ ID NO:420 and the light chain amino acid sequence of SEQ ID NO:421.

In some embodiments, an anti-MerTK antibody of the present disclosure comprises a full-length heavy chain amino acid sequence of SEQ ID NO:422, 423, 424, 425, 426, 427, 428, or 429 and a full-length light chain amino acid sequence of SEQ ID NO: 430. Accordingly, in some embodiments, an anti-MerTK antibody comprises the heavy chain amino acid sequence of SEQ ID NO:422 and the light chain amino acid sequence of SEQ ID NO:430; the heavy chain amino acid sequence of SEQ ID NO:423 and the light chain amino acid sequence of SEQ ID NO:430; the heavy chain amino acid sequence of SEQ ID NO:424 and the light chain amino acid sequence of SEQ ID NO:430; the heavy chain amino acid sequence of SEQ ID NO:425 and the light chain amino acid sequence of SEQ ID NO:430; the heavy chain amino acid sequence of SEQ ID NO:426 and the light chain amino acid sequence of SEQ ID NO:430; the heavy chain amino acid sequence of SEQ ID NO:427 and the light chain amino acid sequence of SEQ ID NO:430; the heavy chain amino acid sequence of SEQ ID NO:428 and the light chain amino acid sequence of SEQ ID NO:430; or the heavy chain amino acid sequence of SEQ ID NO:429 and the light chain amino acid sequence of SEQ ID NO:430.

In some embodiments, an anti-MerTK antibody of the present disclosure comprises a full-length heavy chain amino acid sequence comprising a variable heavy chain amino acid sequence of SEQ ID NO:259, 260, 261, 262, 263, 264, 265, 266, 267, 268, 269, 270, 271, 272, or 273, and a heavy chain Fc selected from the group consisting of SEQ ID NOs: 396-411; and comprises a full-length light chain amino acid sequence comprising a variable light chain amino acid sequence of SEQ ID NO:274, 275, 276, 277, 278, 279, 280, 281, 282, 283, 284, 285, 286, 287, 288, or 289, and a light chain Fc comprising the amino acid sequence of SEQ ID NO:412.

In some embodiments, an anti-MerTK antibody of the present disclosure comprises a full-length heavy chain amino acid sequence comprising a variable heavy chain amino acid sequence of SEQ ID NO: 290, 291, 292, 293, 294, 295, 296, 297, 298, 299, 300, 301, 302, 303, 304, 305, 306, 307, or 308, and a heavy chain Fc selected from the group consisting of SEQ ID NOs: 396-411; and comprises a full-length light chain amino acid sequence comprising a variable light chain amino acid sequence of SEQ ID NO:309, 310, 311, 312, 313, 314, 315, 316, 317, 318, 319, 320, 321, 322, 323, 324, 325, 326, 327, or 328, and a light chain Fc comprising the amino acid sequence of SEQ ID NO:412.

In some embodiments, an anti-MerTK antibody of the present disclosure comprises a full-length heavy chain amino acid sequence of SEQ ID NO: 431, 432, 433, 434, 435, 436, 437, or 438 and a full-length light chain amino acid sequence of SEQ ID NO:439. Accordingly, in some embodiments, an anti-MerTK antibody comprises the heavy chain amino acid sequence of SEQ ID NO:431 and the light chain amino acid sequence of SEQ ID NO:439; the heavy chain amino acid sequence of SEQ ID NO:432 and the light chain amino acid sequence of SEQ ID NO:439; the heavy chain amino acid sequence of SEQ ID NO:433 and the light chain amino acid sequence of SEQ ID NO:439; the heavy chain amino acid sequence of SEQ ID NO:434 and the light chain amino acid sequence of SEQ ID NO:439; the heavy chain amino acid sequence of SEQ ID NO:435 and the light chain amino acid sequence of SEQ ID NO:439; the heavy chain amino acid sequence of SEQ ID NO:436 and the light chain amino acid sequence of SEQ ID NO:439; the heavy chain amino acid sequence of SEQ ID NO:437 and the light chain amino acid sequence of SEQ ID NO:439; or the heavy chain amino acid sequence of SEQ ID NO:438 and the light chain amino acid sequence of SEQ ID NO:439.

In some embodiments, an anti-MerTK antibody of the present disclosure comprises a full-length heavy chain amino acid sequence of SEQ ID NO: 464, 465, 466, 467, 468, 469, 470, and 471 and a full-length light chain amino acid sequence of SEQ ID NO:472. Accordingly, in some embodiments, an anti-MerTK antibody comprises the heavy chain amino acid sequence of SEQ ID NO:464 and the light chain amino acid sequence of SEQ ID NO:472; the heavy chain amino acid sequence of SEQ ID NO:465 and the light chain amino acid sequence of SEQ ID NO:472; the heavy chain amino acid sequence of SEQ ID NO:466 and the light chain amino acid sequence of SEQ ID NO:472; the heavy chain amino acid sequence of SEQ ID NO:467 and the light chain amino acid sequence of SEQ ID NO:472; the heavy chain amino acid sequence of SEQ ID NO:468 and the light chain amino acid sequence of SEQ ID NO:472; the heavy chain amino acid sequence of SEQ ID NO:469 and the light chain amino acid sequence of SEQ ID NO:472; the heavy chain amino acid sequence of SEQ ID NO:470 and the light chain amino acid sequence of SEQ ID NO:472; or the heavy chain amino acid sequence of SEQ ID NO:471 and the light chain amino acid sequence of SEQ ID NO:472.

In some embodiments, an anti-MerTK antibody of the present disclosure comprises a full-length heavy chain amino acid sequence of SEQ ID NO: 440, 441, 442, 443, 444, 445, 446, or 447 and a full-length light chain amino acid sequence of SEQ ID NO:448. Accordingly, in some embodiments, an anti-MerTK antibody comprises the heavy chain amino acid sequence of SEQ ID NO:440 and the light chain amino acid sequence of SEQ ID NO:448; the heavy chain amino acid sequence of SEQ ID NO:441 and the light chain amino acid sequence of SEQ ID NO:448; the heavy chain amino acid sequence of SEQ ID NO:442 and the light chain amino acid sequence of SEQ ID NO:448; the heavy chain amino acid sequence of SEQ ID NO:443 and the light chain amino acid sequence of SEQ ID NO:448; the heavy chain amino acid sequence of SEQ ID NO:444 and the light chain amino acid sequence of SEQ ID NO:448; the heavy chain amino acid sequence of SEQ ID NO:445 and the light chain amino acid sequence of SEQ ID NO:448; the heavy chain amino acid sequence of SEQ ID NO:446 and the light chain amino acid sequence of SEQ ID NO:448; or the heavy chain amino acid sequence of SEQ ID NO:447 and the light chain amino acid sequence of SEQ ID NO:448.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:19 and $V_L$ comprising the amino acid sequence of SEQ ID NO:54; $V_H$ comprising the amino acid sequence of SEQ ID NO:234 and $V_L$ comprising the amino acid sequence of SEQ ID NO:247; $V_H$ comprising the amino acid sequence of SEQ ID NO:235 and $V_L$ comprising the amino acid sequence of SEQ ID NO:247; $V_H$ comprising the amino acid sequence of SEQ ID NO:236 and $V_L$ comprising the amino acid sequence of SEQ ID NO:248; $V_H$ comprising the amino acid sequence of SEQ ID NO:236 and $V_L$ comprising the amino acid sequence of SEQ ID NO:249; $V_H$ comprising the amino acid sequence of SEQ ID NO:237 and $V_L$ comprising the amino acid sequence of SEQ ID NO:249; $V_H$ comprising the amino acid sequence of SEQ ID NO:238 and $V_L$ comprising the amino acid sequence of SEQ ID NO:249; $V_H$ comprising the amino acid sequence of SEQ ID NO:239 and $V_L$ comprising the amino acid sequence of SEQ ID NO:250; $V_H$ comprising the amino acid sequence of SEQ ID NO:240 and $V_L$ comprising the amino acid sequence of SEQ ID NO:251; $V_H$ comprising the amino acid sequence of SEQ ID NO:241 and $V_L$ comprising the amino acid sequence of SEQ ID NO:252; $V_H$ comprising the amino acid sequence of SEQ ID NO:242 and $V_L$ comprising the amino acid sequence of SEQ ID NO:249; $V_H$ comprising the amino acid sequence of SEQ ID NO:243 and $V_L$ comprising the amino acid sequence of SEQ ID NO:247; $V_H$ comprising the amino acid sequence of SEQ ID NO:244 and $V_L$ comprising the amino acid sequence of SEQ ID NO:251; $V_H$ comprising the amino acid sequence of SEQ ID NO:245 and $V_L$ comprising the amino acid sequence of SEQ ID NO:253; $V_H$ comprising the amino acid sequence of SEQ ID NO:246 and $V_L$ comprising the amino acid sequence of SEQ ID NO:247; and $V_H$ comprising the amino acid sequence of SEQ ID NO:246 and $V_L$ comprising the amino acid sequence of SEQ ID NO:254.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:20 and $V_L$ comprising the amino acid sequence of SEQ ID NO:55; $V_H$ comprising the amino acid sequence of SEQ ID NO:255 and $V_L$ comprising the amino acid sequence of SEQ ID NO:257; and $V_H$ comprising the amino acid sequence of SEQ ID NO:256 and $V_L$ comprising the amino acid sequence of SEQ ID NO:258.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:33 and $V_L$ comprising the amino acid sequence of SEQ ID NO:68; $V_H$ comprising the amino acid sequence of SEQ ID NO:259 and $V_L$ comprising the amino acid sequence of SEQ ID NO:274; $V_H$ comprising the amino acid sequence of SEQ ID NO:260 and $V_L$ comprising the amino acid sequence of SEQ ID NO:275; $V_H$ comprising the amino acid sequence of SEQ ID NO:261 and $V_L$ comprising the amino acid sequence of SEQ ID NO:276; $V_H$ comprising the amino acid sequence of SEQ ID NO:262 and $V_L$ comprising the amino acid sequence of SEQ ID NO:277; $V_H$ comprising the amino acid sequence of SEQ ID NO:263 and $V_L$ comprising the amino acid sequence of SEQ ID NO:277; $V_H$ comprising the amino acid sequence of SEQ ID NO:264 and $V_L$ comprising the amino acid sequence of SEQ ID NO:277; $V_H$ comprising the amino acid sequence of SEQ ID NO:265 and $V_L$ comprising the amino acid sequence of SEQ ID NO:277; $V_H$ comprising the amino acid sequence of SEQ ID NO:266 and $V_L$ comprising the amino acid sequence of SEQ ID NO:277; $V_H$ comprising the amino acid sequence of SEQ ID NO:267 and $V_L$ comprising the amino acid sequence of SEQ ID NO:278; $V_H$ comprising the amino acid sequence of SEQ ID NO:268 and $V_L$ comprising the amino acid sequence of SEQ ID NO:279; $V_H$ comprising the amino acid sequence of SEQ ID NO:269 and $V_L$ comprising the amino acid sequence of SEQ ID NO:279; $V_H$ comprising the amino acid sequence of SEQ ID NO:264 and $V_L$ comprising the amino acid sequence of SEQ ID NO:280; $V_H$ comprising the amino acid sequence of SEQ ID NO:270 and $V_L$ comprising the amino acid sequence of SEQ ID NO:281; $V_H$ comprising the amino acid sequence of SEQ ID NO:265 and $V_L$ comprising the amino acid sequence of SEQ ID NO:282; $V_H$ comprising the amino acid sequence of SEQ ID NO:264 and $V_L$ comprising the amino acid sequence of SEQ ID NO:283; $V_H$ comprising the amino acid sequence of SEQ ID NO:271 and $V_L$ comprising the amino acid sequence of SEQ ID NO:284; $V_H$ comprising the amino acid sequence of SEQ ID NO:272 and $V_L$ comprising the amino acid sequence of SEQ ID NO:285; $V_H$ comprising the amino acid sequence of SEQ ID NO:271 and $V_L$ comprising the amino acid sequence of SEQ ID NO:286; $V_H$ comprising the amino acid sequence of SEQ ID NO:273 and $V_L$ comprising the amino acid sequence of SEQ ID NO:287; $V_H$ comprising the amino acid sequence of SEQ ID NO:273 and $V_L$ comprising the amino acid sequence of SEQ ID NO:288; and $V_H$ comprising the amino acid sequence of SEQ ID NO:273 and $V_L$ comprising the amino acid sequence of SEQ ID NO:289.

In some embodiments, an anti-MerTK antibody of the present disclosure competitively inhibits binding of at least one reference antibody, or binds to an epitope of human MerTK that is the same as or overlaps with the MerTK epitope bound by at least one reference antibody, wherein the reference antibody is an anti-MerTK antibody comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:37 and $V_L$ comprising the amino acid sequence of SEQ ID NO:72; $V_H$ comprising the amino acid sequence of SEQ ID NO:290 and $V_L$ comprising the amino acid sequence of SEQ ID NO:309; $V_H$ comprising the amino acid sequence of SEQ ID NO:291 and $V_L$ comprising the amino acid sequence of SEQ ID NO:310; $V_H$ comprising the amino acid sequence of SEQ ID NO:292 and $V_L$ comprising the amino acid sequence of SEQ ID NO:311; $V_H$ comprising the amino acid sequence of SEQ ID NO:293 and $V_L$ comprising the amino acid sequence of SEQ ID NO:312;

$V_H$ comprising the amino acid sequence of SEQ ID NO:294 and $V_L$ comprising the amino acid sequence of SEQ ID NO:313; $V_H$ comprising the amino acid sequence of SEQ ID NO:295 and $V_L$ comprising the amino acid sequence of SEQ ID NO:314; $V_H$ comprising the amino acid sequence of SEQ ID NO:296 and $V_L$ comprising the amino acid sequence of SEQ ID NO:315; $V_H$ comprising the amino acid sequence of SEQ ID NO:290 and $V_L$ comprising the amino acid sequence of SEQ ID NO:316; $V_H$ comprising the amino acid sequence of SEQ ID NO:297 and $V_L$ comprising the amino acid sequence of SEQ ID NO:317; $V_H$ comprising the amino acid sequence of SEQ ID NO:298 and $V_L$ comprising the amino acid sequence of SEQ ID NO:318; $V_H$ comprising the amino acid sequence of SEQ ID NO:292 and $V_L$ comprising the amino acid sequence of SEQ ID NO:319; $V_H$ comprising the amino acid sequence of SEQ ID NO:299 and $V_L$ comprising the amino acid sequence of SEQ ID NO:320; $V_H$ comprising the amino acid sequence of SEQ ID NO:300 and $V_L$ comprising the amino acid sequence of SEQ ID NO:311; $V_H$ comprising the amino acid sequence of SEQ ID NO:301 and $V_L$ comprising the amino acid sequence of SEQ ID NO:321; $V_H$ comprising the amino acid sequence of SEQ ID NO:302 and $V_L$ comprising the amino acid sequence of SEQ ID NO:322; $V_H$ comprising the amino acid sequence of SEQ ID NO:303 and $V_L$ comprising the amino acid sequence of SEQ ID NO:311; $V_H$ comprising the amino acid sequence of SEQ ID NO:304 and $V_L$ comprising the amino acid sequence of SEQ ID NO:322; $V_H$ comprising the amino acid sequence of SEQ ID NO:305 and $V_L$ comprising the amino acid sequence of SEQ ID NO:322; $V_H$ comprising the amino acid sequence of SEQ ID NO:301 and $V_L$ comprising the amino acid sequence of SEQ ID NO:323; $V_H$ comprising the amino acid sequence of SEQ ID NO:301 and $V_L$ comprising the amino acid sequence of SEQ ID NO:324; $V_H$ comprising the amino acid sequence of SEQ ID NO:301 and $V_L$ comprising the amino acid sequence of SEQ ID NO:325; $V_H$ comprising the amino acid sequence of SEQ ID NO:306 and $V_L$ comprising the amino acid sequence of SEQ ID NO:326; $V_H$ comprising the amino acid sequence of SEQ ID NO:307 and $V_L$ comprising the amino acid sequence of SEQ ID NO:327; and $V_H$ comprising the amino acid sequence of SEQ ID NO:308 and $V_L$ comprising the amino acid sequence of SEQ ID NO:328.

In some embodiments, an anti-MerTK antibody of the present disclosure comprises: (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO: 155; (d) HVR-L1 comprising the amino acid sequence of SEQ ID NO:383; (e) HVR-L2 comprising the amino acid sequence of SEQ ID NO:203; and (f) HVR-L3 comprising the amino acid sequence of SEQ ID NO:232. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 298 and the $V_L$ comprises the amino acid sequence of SEQ ID NO:318. In some embodiments, an anti-MerTK antibody of the present disclosure comprises a heavy chain and a light chain, wherein the heavy chain comprises the amino acid sequence of SEQ ID NO: 464 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 465 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 466 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 467 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 468 and the light chain comprises the amino acid sequence of SEQ ID NO:472. In some embodiments, an anti-MerTK antibody of the present disclosure comprises a heavy chain and a light chain, wherein the heavy chain comprises the amino acid sequence of SEQ ID NO: 469 and the light chain comprises the amino acid sequence of SEQ ID NO:472.

In some embodiments, an anti-MerTK antibody of the present disclosure comprises: (a) HVR-H1 comprising the amino acid sequence of SEQ ID NO:84; (b) HVR-H2 comprising the amino acid sequence of SEQ ID NO:99; (c) HVR-H3 comprising the amino acid sequence of SEQ ID NO:139; (d) HVR-L1 comprising the amino acid sequence of SEQ ID NO:345; (e) HVR-L2 comprising the amino acid sequence of SEQ ID NO: 195; and (f) HVR-L3 comprising the amino acid sequence of SEQ ID NO:219. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 256 and the $V_L$ comprises the amino acid sequence of SEQ ID NO:258. In some embodiments, an anti-MerTK antibody of the present disclosure comprises a heavy chain and a light chain, wherein the heavy chain comprises the amino acid sequence of SEQ ID NO: 422 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 423 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 424 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 425 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 426 and the light chain comprises the amino acid sequence of SEQ ID NO:430. In some embodiments, an anti-MerTK antibody of the present disclosure comprises a heavy chain and a light chain, wherein the heavy chain comprises the amino acid sequence of SEQ ID NO: 427 and the light chain comprises the amino acid sequence of SEQ ID NO:430.

In some embodiments, an anti-MerTK antibody of the present disclosure comprises: (a) HVR-H1 comprising the amino acid sequence of SEQ ID NO:90; (b) HVR-H2 comprising the amino acid sequence of SEQ ID NO:368; (c) HVR-H3 comprising the amino acid sequence of SEQ ID NO: 155; (d) HVR-L1 comprising the amino acid sequence of SEQ ID NO:376; (e) HVR-L2 comprising the amino acid sequence of SEQ ID NO:203; and (f) HVR-L3 comprising the amino acid sequence of SEQ ID NO:393. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 299 and the $V_L$ comprises the amino acid sequence of SEQ ID NO:320. In some embodiments, an anti-MerTK antibody of the present disclosure comprises a heavy chain and a light chain, wherein the heavy chain comprises the amino acid sequence of SEQ ID NO: 440 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 441 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 442 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 443 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 444 and the light chain comprises the amino acid sequence of SEQ ID NO:448. In some embodiments, an anti-MerTK antibody of the present disclosure comprises a heavy chain and a light chain, wherein the heavy chain comprises the amino acid sequence of SEQ ID NO: 445 and the light chain comprises the amino acid sequence of SEQ ID NO:448.

In some embodiments, an anti-MerTK antibody of the present disclosure comprises: (a) HVR-H1 comprising the amino acid sequence of SEQ ID NO:84; (b) HVR-H2 comprising the amino acid sequence of SEQ ID NO:329; (c) HVR-H3 comprising the amino acid sequence of SEQ ID NO: 139; (d) HVR-L1 comprising the amino acid sequence of SEQ ID NO: 169; (e) HVR-L2 comprising the amino acid sequence of SEQ ID NO: 195; and (f) HVR-L3 comprising the amino acid sequence of SEQ ID NO:219. In some embodiments, an anti-MerTK antibody of the present disclosure comprises a heavy chain variable domain ($V_H$) and a light chain variable domain ($V_L$), wherein the $V_H$ comprises the amino acid sequence of SED ID NO: 225 and the $V_L$ comprises the amino acid sequence of SEQ ID NO:257. In some embodiments, an anti-MerTK antibody of the present disclosure comprises a heavy chain and a light chain, wherein the heavy chain comprises the amino acid sequence of SEQ ID NO: 413 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 414 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 415 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 416 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 417 and the light chain comprises the amino acid sequence of SEQ ID NO:421. In some embodiments, an anti-MerTK antibody of the present disclosure comprises a heavy chain and a light chain, wherein the heavy chain comprises the amino acid sequence of SEQ ID NO: 418 and the light chain comprises the amino acid sequence of SEQ ID NO:421.

In some embodiments, an anti-MerTK antibody of the present disclosure binds to the extracellular domain (ECD) of human MerTK. In some embodiments, an anti-MerTK antibody of the present disclosure binds to the N-terminal domain of human MerTK. In some embodiments, an anti-MerTK antibody of the present disclosure binds to one or more amino acids within the amino acid sequence of SEQ ID NO:449. In some embodiments, an anti-MerTK antibody of the present disclosure binds to the immunoglobulin-like domain 1 (Ig1) of human MerTK. In some embodiments, an anti-MerTK antibody of the present disclosure binds to one or more amino acid residues within the amino acid sequence of SED ID NO:450. In some embodiments, an anti-MerTK antibody of the present disclosure binds to the immunoglobulin-like domain 2 (Ig2) of human MerTK. In some embodiments, an anti-MerTK antibody of the present disclosure binds to one or more amino acid residues within the amino acid sequence of SEQ ID NO:451. In some embodiments, an anti-MerTK antibody of the present disclosure binds to the fibronectin type III domain 1 (FN1) of human MerTK. In some embodiments, an anti-MerTK antibody of the present disclosure binds to one or more amino acid residues within the amino acid sequence of SEQ ID NO: 452. In some embodiments, an anti-MerTK antibody of the present disclosure binds to the juxta membrane domain (JM) of human MerTK. In some embodiments, an anti-MerTK antibody of the present disclosure binds to one or more amino acid residues within the amino acid sequence of SEQ ID NO:454. In some embodiments, an anti-MerTK antibody of the present disclosure binds to the extracellular domain of human MerTK protein but does not bind to the extracellular domain of human Axl protein.

In some embodiments, an anti-MerTK antibody of the present disclosure binds to one or more domains within the extracellular domain of human MerTK. In some embodiments, an anti-MerTK antibody of the present disclosure binds to the immunoglobulin-like 1 domain 1 (Ig1) and the fibronectin type III domain 1 (FN1) of human MerTK. In some embodiments, an anti-MerTK antibody of the present disclosure binds to the immunoglobulin-like domain 2 (Ig2) and the fibronectin type III domain 1 (FN1) of human MerTK.

In some embodiments, the anti-MerTK antibody according to any of the above embodiments is a monoclonal antibody, including a humanized and/or human antibody. In some embodiments, the anti-MerTK antibody is an antibody fragment, e.g., a Fv, Fab, Fab', scFv, diabody, or F(ab')2 fragment. In some embodiments, the anti-MerTK antibody is a substantially full-length antibody, e.g., an IgG1 antibody, IgG2a antibody or other antibody class or isotype as defined herein.

In some embodiments, an anti-MerTK antibody according to any of the above embodiments may incorporate any of the features, singly or in combination, as described in Sections 1-7 below:

(1) Anti-MerTK Antibody Binding Affinity

In some embodiments of any of the antibodies provided herein, the antibody has a dissociation constant ($K_D$) of <1 μM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g., from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. *J. Mol. Biol.* 293:865-881(1999)). In some embodiments, $K_D$ is measured using a BIACORE surface plasmon resonance assay, for example, an assay using a BIACORE-2000 or a BIACORE-3000 (BIAcore, Inc., Piscataway, NJ) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

In some embodiments, an anti-MerTK antibody of the present disclosure binds to human MerTK, wherein the $K_D$ of binding to human MerTK is from about 1.4 nM to about 81 nM. In some embodiments, an anti-MerTK antibody binds to cyno MerTK, wherein the $K_D$ of binding to cyno MerTK is from about 1.6 nM to about 107 nM. In some embodiments, an anti-MerTK antibody of the present disclosure binds to murine MerTK, wherein the $K_D$ of binding to murine MerTK is from about 30 nM to about 186 nM.

(2) Antibody Fragments

In some embodiments of any of the antibodies provided herein, the antibody is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

(3) Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087,409. Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J. Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J Biol. Chem.* 271:22611-22618 (1996)).

(4) Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human MAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J Immunol.* 133:3001 (1984) and Boerner et al. *J Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. Histology and Histopathology 20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; *Fellouse Proc. Natl. Acad. Sci. USA* 101(34):12467-12472 (2004); and Lee et al. J. *Immunol*. Methods 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. J. *Mol. Biol.,* 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

(5) Constant Regions Including Fc Regions

In some embodiments of any of the antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the antibodies provided herein, the antibody has an IgG2 isotype. In some embodiments, the antibody contains a human IgG2 constant region. In some embodiments, the human IgG2 constant region includes an Fc region. In some embodiments, the antibody induces the one or more MerTK activities or independently of binding to an Fc receptor. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG4 isotype. In some embodiments, the antibody contains a human IgG4 constant region. In some embodiments, the human IgG4 constant region includes an Fc region. In some embodiments, the antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has a hybrid IgG2/4 isotype. In some embodiments, the antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to MerTK.

It may also be desirable to modify an anti-MerTK antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRI, and/or FcγRIII to reduce Antibody-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-MerTK antibody of the present disclosure to modify effector function to increase finding selectivity toward the ITIM-containing FcgRIIb (CD32b) to increase clustering of MerTK antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term “salvage receptor binding epitope” refers to an epitope of the Fc region of an IgG molecule (e.g., $IgG_1$, $IgG_2$, $IgG_3$, or $IgG_4$) that is responsible for increasing the in vivo serum half-life of the IgG molecule. Other amino acid sequence modifications.

(6) Antibody Variants

In some embodiments of any of the antibodies provided herein, amino acid sequence variants of the antibodies are contemplated. For example, it may be desirable to improve the binding affinity and/or other biological properties of the antibody.

(i) Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE A

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J Mol. Biol.,* 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within +2 is included. In certain embodiments, those which are within ±1 are included, and in certain embodiments, those within +0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within +2 is included, in certain embodiments, those which are within ±1 are included, and in certain embodiments, those within +0.5 are included. One can also identify epitopes from primary amino acid sequences on the basis of hydrophilicity. These regions are also referred to as “epitopic core regions”.

In certain embodiments of the variant VH and VL sequences provided above, each HVR is unaltered.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue outside the HVRs and not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

(ii) Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered.

Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

(iii) Modified Constant Regions

In some embodiments of any of the antibodies provided herein, the antibody Fc is an antibody Fc isotypes and/or modifications. In some embodiments, the antibody Fc isotype and/or modification is capable of binding to Fc gamma receptor.

In some embodiments of any of the antibodies provided herein, the modified antibody Fc is an IgG1 modified Fc. In some embodiments, the IgG1 modified Fc comprises one or more modifications.

For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J Biol. Chem.* 276, 6591-6604), L234A, L235A (Hutchins et al. (1995) *Proc Natl Acad Sci USA,* 92:11980-11984; Alegre et al., (1994) *Transplantation* 57:1537-1543. 31; Xu et al., (2000) *Cell Immunol,* 200:16-26), G237A (Alegre et al. (1994) *Transplantation* 57:1537-1543. 31; Xu et al. (2000) *Cell Immunol,* 200:16-26), C226S, C229S, E233P, L234V, L234F, L235E (McEarchern et al., (2007) *Blood,* 109:1185-1192), P331S (Sazinsky et al., (2008) *Proc Natl Acad Sci USA* 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises N325S and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fe comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA,* 103:4005-4010 (2006)), or one or more of L234F, L235E, and/or P331S mutations (Sazinsky et al. *Proc Natl Acad Sci USA,* 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-MerTK antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. Transplantation 57:1537-1543 (1994); Xu et al. *Cell Immunol,* 200:16-26 (2000)); G237A (Cole et al. Transplantation, 68:563-571 (1999)); H268Q, V309L, A330S, P331S (US 2007/0148167; Armour et al. *Eur J Immunol* 29: 2613-2624 (1999); Armour et al. *The Haematology Journal* 1(Suppl. 1):27 (2000); Armour et al. *The Haematology Journal* 1(Suppl. 1):27 (2000)), C219S, and/or C220S (White et al. *Cancer Cell* 27, 138-148 (2015)); S267E, L328F (Chu et al. *Mol Immunol,* 45:3926-3933 (2008)); and M252Y, S254T, and/or T256E according to the EU numbering convention. In some embodiments of any of the IgG2 modified Fe, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1(CH1) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fe, the Fe comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

(7) Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.,* 15:29 (1986); and Evans et al. J. *Med. Chem.,* 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH-(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.,* 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g. a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. Bioconjugate Chemistry 21 (1):5-13 (2010).

II. Nucleic Acids, Vectors, and Host Cells

Anti-MerTK antibodies of the present disclosure may be produced using recombinant methods and compositions, e.g., as described in U.S. Pat. No. 4,816,567. In some embodiments, isolated nucleic acids having a nucleotide sequence encoding any of the anti-MerTK antibodies of the present disclosure are provided. Such nucleic acids may encode an amino acid sequence comprising the $V_L$ and/or an amino acid sequence comprising the $V_H$ of the anti-MerTK antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-MerTK antibody of the present disclosure are provided. In some embodiments, the method includes culturing a host cell of the present disclosure comprising a nucleic acid encoding the anti-MerTK antibody, under conditions suitable for expression of the antibody. In some embodiments, the antibody is subsequently recovered from the host cell (or host cell culture medium).

For recombinant production of an anti-MerTK antibody of the present disclosure, a nucleic acid encoding the anti-MerTK antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-MerTK antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-MerTK antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gemgross *Nat. Biotech.* 22:1409-1414 (2004); and Li et al. *Nat. Biotech.* 24:210$^{-215}$ (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. *Annals N. Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

III. Pharmaceutical Compositions/Formulations

Provided herein are pharmaceutical compositions and/or pharmaceutical formulations comprising the anti-MerTK antibodies of the present disclosure and a pharmaceutically acceptable carrier.

In some embodiments, pharmaceutically acceptable carrier preferably are nontoxic to recipients at the dosages and concentrations employed. The pharmaceutical compositions and/or pharmaceutical formulations to be used for in vivo administration can be sterile. This is readily accomplished by filtration through, e.g., sterile filtration membranes Pharmaceutical compositions and/or pharmaceutical formulations provided herein are useful as a medicament, e.g., for treating cancer.

IV. Therapeutic Uses

As disclosed herein, anti-MerTK antibodies of the present disclosure may be used for treating diseases and disorders. In some embodiments, the present disclosure provides methods for treating an individual having cancer comprising administering to the individual a therapeutically effective amount of an anti-MerTK antibody of the present disclosure.

Ectopic or expression of MerTK has been observed in various tumors; overexpression and activation of MerTK has been implicated in lymphoid leukemia, lymphoma, adenoma, melanoma, gastric, prostate, and breast cancers; and MerTK overexpression has been associated with metastasis. (Schlegel et al, 2013, *J Clin Invest,* 123:2257-2267; Tworkoski et al, 2013, *Pigment Cell Melanoma,* 26:527-541; Yi et al, 2017, *Oncotarget,* 8:96656-96667; Linger et al, 2013, *Blood,* 122:1599-1609; Lee-Sherick et al, 2013, *Oncogene,* 32:5359-5368; Brandao et al, 2013, *Blood Cancer,* 3:e101; Xie et al, 2015, *Oncotarget,* 6:9206-9219; Shi et al, 2018, *J Hematology & Oncology,* 11:43). Accordingly, modulating the activity of MerTK with an anti-MerTK antibody of the present disclosure is an effective means of treating cancer.

In certain aspects, provided herein are methods for treating cancer in a subject in need thereof, the method comprising administering to the subject an anti-MerTK antibody of the present disclosure, or a pharmaceutical composition comprising an anti-MerTK antibody of the present disclosure. In some embodiments, a method is provided for treating cancer in a subject in need thereof, the method comprising administering to the subject an anti-MerTK antibody of the present disclosure, wherein the anti-MerTK antibody reduces efferocytosis by phagocytic cells. In some embodiments, a method is provided for treating cancer in a subject in need thereof, the method comprising administering to the subject an anti-MerTK antibody of the present disclosure, wherein the anti-MerTK antibody induces M1-like macrophage polarization.

In some embodiments, the cancer is selected from sarcoma, bladder cancer, breast cancer, colon cancer, endometrial cancer, kidney cancer, renal cancer, leukemia, lung cancer, non-small cell lung cancer, melanoma, lymphoma, pancreatic cancer, prostate cancer, ovarian cancer, stomach cancer, thyroid cancer, cancer of the uterus, liver cancer, cervical cancer, testicular cancer, squamous cell carcinoma, glioma, glioblastoma, adenoma, and neuroblastoma. In some embodiments, the cancer is selected from glioblastoma multiforme, bladder carcinoma, and esophageal carcinoma. In some embodiments, the cancer is triple-negative breast carcinoma. In some embodiments, the cancer may be a primary tumor. In some embodiments, the cancer may be a metastatic tumor at a second site derived from any of the above types of cancer. In some embodiments, an anti-MerTK antibody of the present disclosure is useful for treating cancer in s subject in need thereof, wherein the cancer expresses MerTK.

In some embodiments, an anti-MerTK antibody of the present disclosure may be administered in conjunction with one or more therapeutic agents that act as a checkpoint inhibitor. In some embodiments, the method further includes administering to the individual at least one antibody that specifically binds to an inhibitory immune checkpoint molecule, and/or another standard or investigational anti-cancer therapy. In some embodiments, the inhibitory checkpoint molecule is selected from PD1, PD-L1, and PD-L2, In some embodiments, the at least one antibody that specifically binds to an inhibitory checkpoint molecule is administered in combination with the anti-MerTK antibody of the present disclosure In some embodiments, the at least one antibody that specifically binds to an inhibitory checkpoint molecule is selected from an anti-PD-L1 antibody, an anti-PD-L2 antibody, and an anti-PD-1 antibody In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

V. Diagnostic Uses

In some embodiments of any of the antibodies, any of the anti-MerTK antibodies provided herein is useful for detecting the presence of MerTK in a sample or an individual. The term "detecting" as used herein encompasses quantitative or qualitative detection. Provided herein are methods of using the antibodies of this disclosure for diagnostic purposes, such as the detection of MerTK in an individual or in tissue samples derived from an individual. In some embodiments, the individual is a human. In some embodiments, the tissue sample is phagocytic cells (e.g., macrophages, dendritic cells), tumor tissue, cancer cells, etc.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

VI. Articles of Manufacture

Provided herein are articles of manufacture (e.g., kit) comprising an anti-MerTK antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment. In some embodiments, these instructions comprise a description of administration of the isolated antibody of the present disclosure (e.g., an anti-MerTK antibody described herein) to treat an individual having a disease, disorder, or injury, such as for example cancer, according to any methods of this disclosure. In some embodiments, the instructions include instructions for use of the anti-MerTK antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

Example 1: Production of his-Conjugated and Murine Fc-Conjugated MerTK Polypeptides Human, cyno, and murine MerTK polypeptides containing polyHis or TEVS/Thrombin/murine IgG2a-Fc tagged fusion proteins for use in the generation and characterization of anti-MerTK antibodies of the present disclosure were generated as follows. Nucleic acid encoding the extracellular domain (ECD) of human MerTK (SEQ ID NO: 2), cyno MerTK (SEQ ID NO: 3), and murine MerTK (SEQ ID NO: 4) were each cloned into a mammalian expression vector containing nucleic acid encoding a heterologous signal peptide as well as containing either a PolyHis Fc tag or TEVS/Thrombin/murine IgG2a Fc tag.

The amino acid sequences of human MerTK, human MerTK extracellular domain, cyno MerTK extracellular domain, and murine MerTK extracellular domain are set forth below.

```
Human MerTK amino acid sequence (SEQ ID NO: 1):

MGPAPLPLLLGLFLPALWRRAITEAREEAKPYPLFPGPFPGSLQTDHTP

LLSLPHASGYQPALMFSPTQPGRPHTGNVAIPQVTSVESKPLPPLAFKH
```

-continued

TVGHIILSEHKGVKFNCSISVPNIYQDTTISWWKDGKELLGAHHAITQF

YPDDEVTAIIASFSITSVQRSDNGSYICKMKINNEEIVSDPIYIEVQGL

PHFTKQPESMNVTRNTAFNLTCQAVGPPEPVNIFWVQNSSRVNEQPEKS

PSVLTVPGLTEMAVFSCEAHNDKGLTVSKGVQINIKAIPSPPTEVSIRN

STAHSILISWVPGFDGYSPFRNCSIQVKEADPLSNGSVMIFNTSALPHL

YQIKQLQALANYSIGVSCMNEIGWSAVSPWILASTTEGAPSVAPLNVTV

FLNESSDNVDIRWMKPPTKQQDGELVGYRISHVWQSAGISKELLEEVGQ

NGSRARISVQVHNATCTVRIAAVTRGGVGPFSDPVKIFIPAHGWVDYAP

SSTPAPGNADPVLIIFGCFCGFILIGLILYISLAIRKRVQETKFGNAFT

EEDSELVVNYIAKKSFCRRAIELTLHSLGVSEELQNKLEDVVIDRNLLI

LGKILGEGEFGSVMEGNLKQEDGTSLKVAVKTMKLDNSSQREIEEFLSE

AACMKDFSHPNVIRLLGVCIEMSSQGIPKPMVILPFMKYGDLHTYLLYS

RLETGPKHIPLQTLLKFMVDIALGMEYLSNRNFLHRDLAARNCMLRDDM

TVCVADFGLSKKIYSGDYYRQGRIAKMPVKWIAIESLADRVYTSKSDVW

AFGVTMWELATRGMTPYPGVQNHEMYDYLLHGHRLKQPEDCLDELYEIM

YSCWRTDPLDRPTFSVLRLQLEKLLESLPDVRNQADVIYVNTQLLESSE

GLAQGSTLAPLDLNIDPDSIIASCTPRAAISVVTAEVHDSKPHEGRYIL

NGGSEEWEDLTSAPSAAVTAEKNSVLPGERLVRNGVSWSHSSMLPLGSS

LPDELLFADDSSEGSEVLM

Human MerTK ECD amino acid sequence
(SEQ ID NO: 2):
MGPAPLPLLLGLFLPALWRRAITEAREEAKPYPLFPGPFPGSLQTDHTP

LLSLPHASGYQPALMFSPTQPGRPHTGNVAIPQVTSVESKPLPPLAFKH

TVGHIILSEHKGVKFNCSISVPNIYQDTTISWWKDGKELLGAHHAITQF

YPDDEVTAIIASFSITSVQRSDNGSYICKMKINNEEIVSDPIYIEVQGL

PHFTKQPESMNVTRNTAFNLTCQAVGPPEPVNIFWVQNSSRVNEQPEKS

PSVLTVPGLTEMAVFSCEAHNDKGLTVSKGVQINIKAIPSPPTEVSIRN

STAHSILISWVPGFDGYSPFRNCSIQVKEADPLSNGSVMIFNTSALPHL

YQIKQLQALANYSIGVSCMNEIGWSAVSPWILASTTEGAPSVAPLNVTV

FLNESSDNVDIRWMKPPTKQQDGELVGYRISHVWQSAGISKELLEEVGQ

NGSRARISVQVHNATCTVRIAAVTRGGVGPFSDPVKIFIPAHGWVDYAP

SSTPAPGNADPVLII

Cyno MerTK ECD amino acid sequence
(SEQ ID NO: 3):
MGLAPLPLPLLLGLFLPALWSRAITEAREEAKPYPLFPGPLPGSLQTDH

TSLLSLPHTSGYQPALMFSPTQPGRPYTGNVAIPRVTSAGSKLLPPLAF

KHTVGHIILSEHKDVKFNCSISVPNIYQDTTISWWKDGKELLGAHHAIT

QFYPDDEVTAIIASFSITSVQRSDNGSYICKMKINNEEIVSDPIYIEVQ

GLPHFTKQPESMNVTRNTAFNLTCQAVGPPEPVNIFWVQNSSRVNEQPE

KSPSVLTVPGLTEMAVFSCEAHNDKGLTVSKGVQINIKAIPSPPTEVSI

-continued

HNSTAHSILISWVPGFDGYSPFRNCSVQVKEVDPLSNGSVMIFNTSASP

HMYQIKQLQALANYSIGVSCMNEIGWSAVSPWILASTTEGAPSVAPLNV

TVFLNESRDNVDIRWMKPLTKRQAGELVGYRISHVWQSAGISKELLEEV

GQNNSRAQISVQVHNATCTVRIAAVTKGGVGPFSDPVKIFIPAHGWVDH

APSSTPAPGNADPVLII

Murine MerTK ECD amino acid sequence
(SEQ ID NO: 4):
MVLAPLLLGLLLLPALWSGGTAEKWEETELDQLFSGPLPGRLPVNHRPF

SAPHSSRDQLPPPQTGRSHPAHTAAPQVTSTASKLLPPVAFNHTIGHIV

LSEHKNVKFNCSINIPNTYQETAGISWWKDGKELLGAHHSITQFYPDEE

GVSIIALFSIASVQRSDNGSYFCKMKVNNREIVSDPIYVEVQGLPYFIK

QPESVNVTRNTAFNLTCQAVGPPEPVNIFWVQNSSRVNEKPERSPSVLT

VPGLTETAVFSCEAHNDKGLTVSKGVHINIKVIPSPPTEVHILNSTAHS

ILVSWVPGFDGYSPLQNCSIQVKEADRLSNGSVMVFNTSASPHLYEIQQ

LQALANYSIAVSCRNEIGWSAVSPWILASTTEGAPSVAPLNITVFLNES

NNILDIRWTKPPIKRQDGELVGYRISHVWESAGTYKELSEEVSQNGSWA

QIPVQIHNATCTVRIAAITKGGIGPFSEPVNIIIPEHSKVDYAPSSTPA

PGNTDSM

The human, cyno, and murine MerTK nucleic acid fusion constructs were transiently transfected into HEK293 cells. The recombinant fusion polypeptides were purified from the supernatants of the cells using Mabselect resin (GE Healthcare, Cat #17519902) following the manufacturer's instructions. Additionally, commercially available DDDDK-tagged human MerTK fusion polypeptide (Sino Biological, Wayne, PA, Cat #10298-HCCH) or human IgG1 Fc-tagged murine MerTK fusion proteins (R&D systems, Minneapolis, MA, Cat #591-NMR-100) were also used for anti-MerTK antibody characterization as described below.

Example 2: Generation of Human and Murine MerTK Overexpressing CHO Cell Lines Human MerTK and murine MerTK overexpressing CHO cell lines were prepared as follows. Human MerTK open reading frame (ORF) clone Lentivirus particle (Cat #RC215289L4V) and mouse MerTK ORF clone Lentivirus particle (Cat #MR225392L4V) (Origene, Rockville, MD) (both mGFP-tagged) were used for preparing human MerTK overexpressing CHO-K1 and murine MerTK overexpressing CHO-K1 stable cell line generation, respectively.

CHO cells were cultured in F12-K media (ATCC, Cat #ATCC 30-2004) containing 10% FBS (Gibco) until >80% confluent. The cells were then dissociated with Trypsin buffer (0.25% EDTA/Trypsin, Gibco, Cat #25200056) and plated at 70-80% confluency in 6-well plates 24 hours prior to transduction with either the human or murine MerTK lentivirus construct. The following day, cells were incubated with the lentiviral particle at 4° C. for 2 hours and then the plates were incubated at 37° C. in 5% $CO_2$. Two days later, puromycin (Invivogen, San Diego, CA, Cat #ant-pr-1) was added for selection; selected puromycin-resistant cells were frozen in Cell Recovery Freezing Medium (Gibco, Cat #12648010) for subsequent use.

For FACS analysis of these cell lines, human MerTK overexpressing CHO cells (CHO-huMerTK OE cells) and mouse MerTK overexpressing CHO cells (CHO-muMerTK OE cells) generated as described above were plated at 1-2×10' cells per well in 96-well U-bottom plates and incubated with a commercially available mouse anti-human MerTK monoclonal antibody (BioLegend, Clone: 590H11G1E3, Cat #367608, San Diego, CA) or a commercially available rat anti-mouse MerTK monoclonal antibody (ThermoFisher, Clone: DS5MMER, Cat #12-5751-82) for 30 minutes on ice. Cells were rinsed twice with ice-cold FACS buffer (2% FBS+PBS) and then incubated with APC-conjugated goat anti-mouse antibody (Jackson ImmunoResearch, West Grove, PA, Cat #115-606-071) or goat-anti-rat antibody (Jackson ImmunoResearch, Cat #112-606-071) for 30 min on ice. Following the secondary antibody incubation, the cells were washed with ice-cold FACS buffer and then resuspended in a final volume of 50-200 μl of FACS buffer containing 0.25 μl/well propidium iodide (BD, Cat #556463). Analysis was performed using a FACS CantoII system (BD Biosciences).

The resulting human MerTK and murine MerTK overexpressing CHO cell lines were used for subsequent studies to characterize anti-MerTK antibodies as described below.

Example 3: MerTK Expression Profile

MerTK expression was examined on various human cell types and tissues, including U937 cells (ATCC CRL-1593.2; human macrophage cell line), SK-MEL-5 cells (ATCC HTB-70; human melanoma cell line), A375 cells (ATCC CRL-1619; human melanoma cell line), THP-1 cells (ATCC TIB-202; human monocyte-like cell line), CHO-huMerTK OE cells, human monocytes, human monocyte-derived macrophages, and human monocyte-derived dendritic cells. Additionally, MerTK expression was examined on human monocytes, macrophages, and dendritic cells obtained from human tumor samples as outlined below.

Monocytes were isolated from peripheral blood mononuclear cells (PBMCs) from healthy human donors using RosetteSep monocyte isolation antibody cocktail (StemCell Technologies). The isolated human monocytes were either differentiated into human macrophages with 50 ng/mL M-CSF (Peprotech) or were differentiated into human dendritic cells (DCs) with 100 ng/mL GM-CSF and 100 ng/mL IL-4 (Peprotech). The human macrophages or human dendritic cells were incubated with a commercially available fluorochrome-conjugated anti-human MerTK antibody (BioLegend, clone 590H11G1E3) for 30 minutes on ice in the dark. Cells were washed twice in FACS buffer (PBS+2% FBS, 2 mM EDTA), and analysis of MerTK expression on the surface of the cells was performed using a BD FACS Cantoll system.

Figure 2:
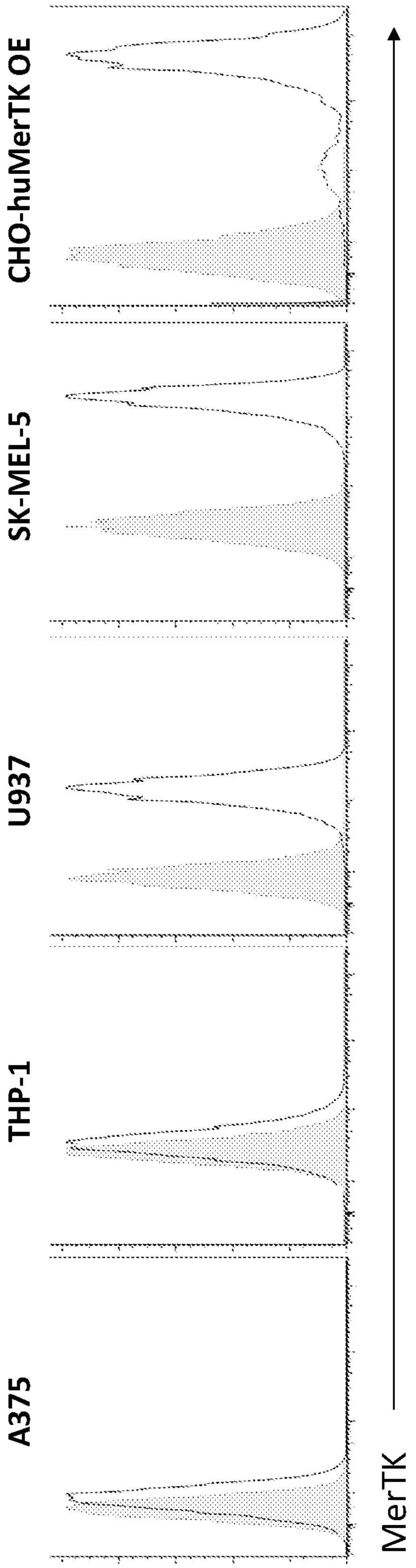
FIG. 2 sets forth data showing FACS analysis of human MerTK expression on various cell lines, including A375, THP-1, U937, SK-MEL-5, and CHO-huMerTK OE cells.

FIG. 1 shows results of FACS analysis of human MerTK expression on human myeloid cells (i.e., dendritic cells, macrophages). As shown in FIG. 1, dendritic cells (DCs) and macrophages from two different human donors displayed anti-MerTK antibody reactivity, indicating these cells express MerTK on their cell surface. FIG. 2 shows results of FACS analysis of human MerTK expression on various cell lines, including A375 cells, THP-1 cells, U937 cells, SK-MEL-5 cells, and CHO-huMerTK OE cells. As shown in FIG. 2, U937 cells, SK-MEL-5 cells, and CHO-huMerTK OE cells displayed anti-MerTK antibody reactivity, indicating that these cell lines express MerTK on their cell surface.

For analysis of MerTK expression on various myeloid cell types (e.g., monocytes, macrophages, dendritic cells) obtained from tumor samples, the following experiments were performed. Various tumor samples (from ovary, liver, and endometrial cancer) obtained from human subjects were cut into small pieces with a scalpel and transferred to GentleMACS C tubes (Miltenyi Biotec, Sunnyvale, CA) containing an enzyme mix. Samples were dissociated on GentleMACS (Miltenyi Biotec) as per the manufacturer's protocol. After dissociation, cells were filtered through a 100 m filter prior to FACS staining. Samples were then stained with Aqua Live Dead (Thermo Scientific, Cat #L34957) and a mixture of anti-human CD16 (Clone 3G8, BioLegend, Cat #302002), anti-human CD32 (Clone AT10, Thermo Scientific, Cat #MA1-81191), and anti-human CD64 (Clone 10.1, BioLegend, Cat #305002) antibodies at 4° C. for 30 min.

After washing with FACS buffer, the cells were then stained with the following antibodies for FACS sorting and analysis: anti-human CD45-Alexa Fluor 700 (Clone HI30, BioLegend, Cat #304024), anti-human CD3-APCCy7 (clone OKT3, BioLegend, Cat #317342), anti-human HLA-DR-BV711 (Clone L243, BioLegend, Cat #307644), anti-human CD15-BV605 (Clone W6D3, BioLegend, Cat #323032), anti-human CD14-BUV395 (Clone MoP9, BD bioscience, Cat #563561), anti-human CD19-BV650 (Clone HIB19, BioLegend, Cat #302238), anti-human CD56-PE Dazzle 594 (Clone HCD56, BioLegend, Cat #318348), anti-human CD1c-PerCPCy5.5 (Clone L161, BioLegend, Cat #331514), anti-human CD206-PECy5 (Clone 15-2, BioLegend, Cat #321108), and anti-human MerTK-BV421 (Clone 590H11G1E3, BioLegend, Cat #367604) at 4° C. for 30 min. Cells were washed with FACS buffer and acquired on a BD FACS Fortessa X20. All FACS data were analyzed using FlowJo software. Monocytes (defined and gated as CD45+CD3-CD14+), macrophages (defined and gated as CD45+CD3-CD14+CD206+), and dendritic cells (defined and gated as CD45+CD3-CD14-CD56-HLA-DR+CD1c+) were identified.

Figure 3:
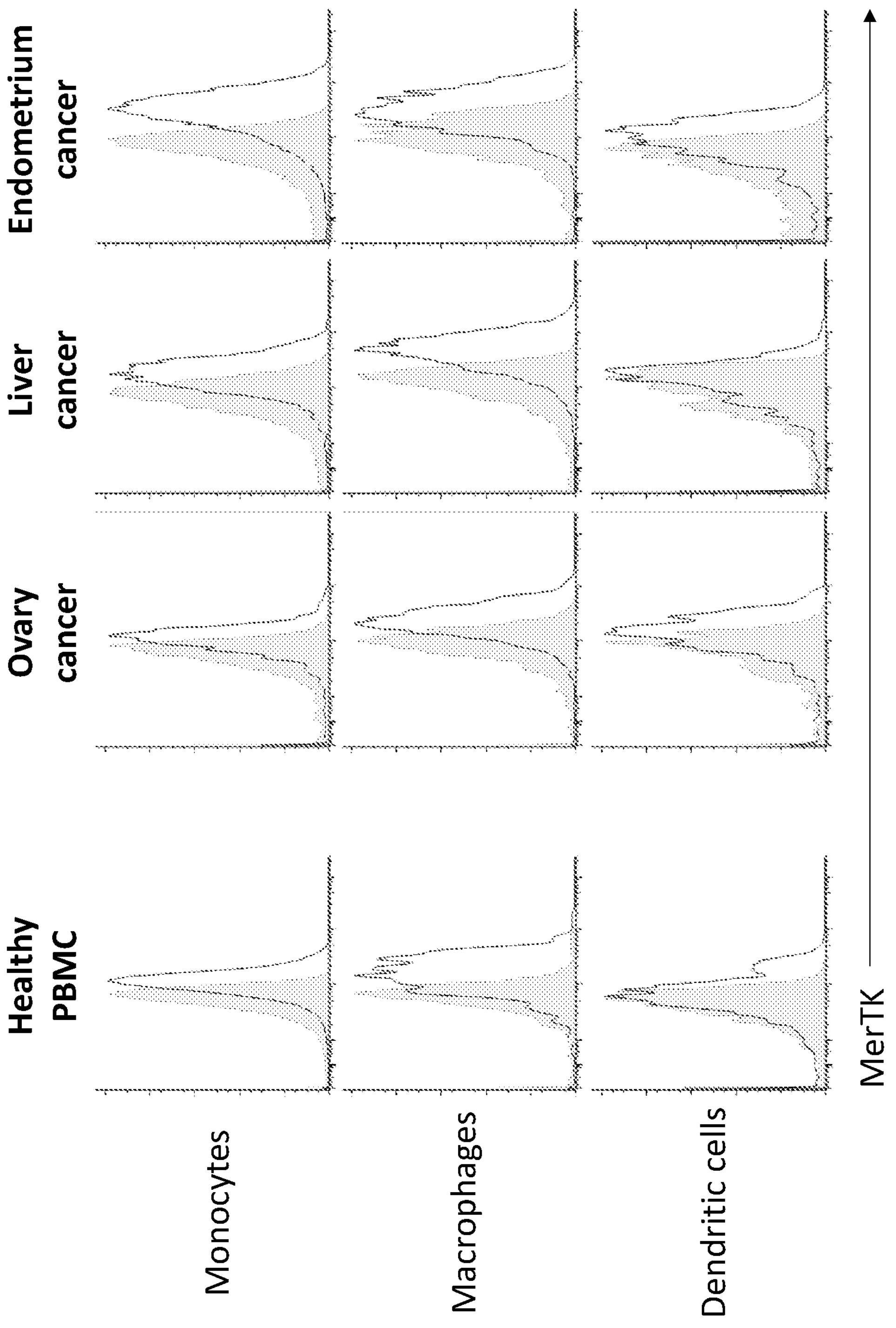
FIG. 3 sets forth data showing FACS analysis of human MerTK expression in monocytes, macrophages, and dendritic cells obtained from healthy human subjects or obtained from ovary, liver, or endometrial tumors obtained from human subjects.

As shown in FIG. 3, MerTK expression was observed by FACS analysis in monocytes, macrophages, and dendritic cells obtained from peripheral blood mononuclear cells (PBMCs) from healthy human subjects. MerTK expression was also observed in tumor-derived monocytes, macrophages, and dendritic cells obtained from ovary, liver, and endometrial cancers obtained from human subjects.

Taken together, this data showed that MerTK expression was detected on various human cells and human cell lines, on monocytes, macrophages, and dendritic cells isolated from health human subjects, and on monocytes, macrophages, and dendritic cells obtained from human ovary, liver, and endometrial cancer tumor tissue.

Example 4: Generation of Anti-MerTK Hybridoma Antibodies

In order to obtain antibodies against MerTK, the following experiments were performed in order to generate anti-MerTK hybridomas. BALB/c mice (Charles River Laboratories, Wilmington, MA) or MerTK knock-out (KO) mice (Jackson Laboratories, Bar Harbor, ME) were immunized twice a week by subcutaneous or intraperitoneal injections of purified extracellular domain polypeptides of human, cyno, and mouse MerTK (obtained as described above in Example 1) with or without adjuvant. A total of 8 injections were performed over 4 weeks. Three days following the final injection, spleens and lymph nodes were harvested from the mice for hybridoma cell line generation.

Lymphocytes from the spleens and lymph nodes of the immunized mice were isolated and then fused with P3X63Ag8.653 (CRL-1580, American Type Culture Collection, Rockville, MD) or SP2/mIL-6 (CRL-2016, American Type Culture Collection, Rockville, MD) mouse myeloma cells via electrofusion (Hybrimmune, BTX, Holliston, MA) and incubated at 37° C., 5% $CO_2$, overnight in Clonacell-HY Medium C (STEMCELL Technologies, Vancouver, BC, Canada, Cat #03803). The following day, the fused cells were centrifuged and resuspended in 10 ml of ClonaCell-HY Medium C with anti-mouse IgG Fc-FITC (Jackson ImmunoResearch, West Grove, PA) and then gently mixed with 90 ml of methylcellulose-based ClonaCell-HY Medium D (STEMCELL Technologies, Cat #03804) containing HAT components. The cells were plated into Nunc OmniTrays (Thermo Fisher Scientific, Rochester, NY) and allowed to grow at 37° C., 5% $CO_2$ for seven days. Fluorescent colonies were then selected and transferred into 96-well plates containing Clonacell-HY Medium E (STEMCELL Technologies, Cat #03805) using a Clonepix 2 (Molecular Devices, Sunnyvale, CA). In total, 1,728 IgG-secreting hybridoma clones were selected. After six days of culture, tissue culture supernatants from the hybridomas were screened by FACS analysis for specificity to bind human or mouse MerTK as described below.

Example 5: Screening of Anti-MerTK Antibody Hybridoma Supernatants by FACS

Hybridoma culture supernatants from 1,728 hybridomas obtained as described above were screened for their ability to bind MerTK on various cell types, including CHO cells stably overexpressing human MerTK (CHO-huMerTK OE cells) or stably overexpressing mouse MerTK (CHO-muMerTK OE cells) (generated as described above), and CHO parental cells; U937 cells (ATCC CRL-1593.2), SK-MEL-5 cells (ATCC HTB-70) (which endogenously express human MerTK), J774A. 1 cells (ATCC TIB-67) (which endogenously express mouse MerTK), and A375 cells (ATCC CRL-1619). THP-1 cells (ATCC TIB-202), which have no or minimal expression of MerTK, served as non-MerTK expressing negative control cells in these experiments.

For screening of the hybridoma cell culture supernatants, a multiplexed FACS experimental design was utilized to determine binding of anti-MerTK antibodies to these multiple cell lines. Briefly, cells were stained with various concentrations and combinations of CellTrace cell proliferation dyes CFSE and Violet (ThermoFisher, Cat #C34554 and Cat #34557, respectively) to create uniquely barcoded cell populations. 70,000 cells of each barcoded cell type were aliquoted into 96-well U-bottom plates and incubated with 50d of hybridoma cell culture supernatant or 5 g/ml of commercially available purified mouse anti-human MerTK monoclonal antibody (BioLegend, Cat #367602; serving as a positive anti-MerTK antibody) on ice for 30 minutes. After this primary anti-MerTK hybridoma supernatant incubation with the various MerTK expressing cell types, the supernatants were removed via centrifugation, the cells were washed twice with 175 d of ice-cold FACS buffer (PBS+1% FBS+2 mM EDTA), and the cells were then further incubated on ice for 20 minutes with anti-mouse IgG Fc-allophycocyanin (APC) (Jackson Labs, Cat #115-136-071) (diluted 1:1000). Following this secondary antibody incubation, the cells were again washed twice with ice-cold FACS buffer and resuspended in a final volume of 30 μl of FACS buffer containing 0.25 μl/well propidium iodide (BD Biosciences, Cat #556463). Binding intensity on cells was analyzed using the FACS Canto system (BD Biosciences), with sorting gates drawn to exclude dead (i.e., propidium iodide-positive) cells. The ratio of APC Mean Fluorescence Intensity (MFI) on each barcoded cell population was determined for each anti-MerTK hybridoma supernatant tested.

From this specific hybridoma supernatant screen, a total of 308 anti-MerTK hybridoma clones were identified that displayed greater than 2-fold difference in binding (as determined by MFI) to cells stably overexpressing or endogenously expressing human or mouse MerTK compared to the binding observed on parental or negative control cell types. Anti-MerTK antibodies identified using this screen were further characterized as described below.

Example 6: Screening of Anti-MerTK Antibody Hybridoma Supernatants by Recombinant MerTK Protein Binding Assay Hybridoma culture supernatants from 1,728 hybridomas obtained as described above were screened for their ability to bind polyHis-tagged human, cyno, and mouse MerTK (prepared as described above in Example 1) as compared to binding to an irrelevant His-tagged control protein. Briefly, 96-well polystyrene plates were coated with 1p g/ml of human, cyno, or mouse poly-His-tagged MerTK polypeptide in coating buffer (0.05M carbonate buffer, pH 9.6, Sigma, Cat #C3041) overnight at 4° C. Coated plates were then blocked with ELISA diluent (PBS+0.5% BSA+0.05% Tween20) for one hour and washed three times with 300 μl of PBST (PBS+0.05% Tween20, Thermo 28352). The hybridoma cell culture supernatants or two commercially available purified mouse anti-human MerTK monoclonal antibodies (BioLegend Cat #367602; R&D Cat #MAB8912) were added (50 μl/well) to each well. After 30 mins incubation (room temperature, with shaking), the plates were washed three times with 300 μl of PBST. Anti-mouse IgG Fc-HRP (Jackson Immunoresearch, Cat #115-035-071) secondary antibody was diluted 1:5000 in ELISA diluent, added to each well at 50 μl/well, and incubated for 30 minutes at room temperature with shaking. After a final set of washes (3×300 μl in PBST), 50 μl/well of TMB substrate (BioFx, Cat #TMBW-1000-01) was added to the wells. The reaction was then quenched after 5-10 mins with 50 μl/well of stop solution (BioFx, Cat #BSTP-1000-01). The quenched reaction wells were detected for absorbance at 650 nm with a BioTek Synergy Microplate Reader using GEN5 2.04 software. From this hybridoma supernatant screen, a total of 326 anti-MerTK hybridoma clones were identified that displayed greater than 10-fold difference in binding to recombinant MerTK over background. Anti-MerTK antibodies identified using this screen were further characterized as described below.

Example 7: MerTK Ligand Gas6 and Ligand ProS Blocking Assay Using Anti-MerTK Hybridoma Supernatants Anti-MerTK antibody hybridoma supernatants identified as described above were evaluated for their ability to block binding of human Gas6 ligand and/or block binding of human ProS ligand to human MerTK by ELISA. Briefly, rabbit anti-human IgG antibody (Jackson ImmunoResearch, Cat #309-005-008) was coated at 2 g/ml onto high-protein binding plates at 4° C. overnight. After washing with 0.05% Tween20 in PBS three times, 5% BSA in PBS was added for 1 hour. Recombinant human MerTK-human Fc Chimera protein (R&D systems, Cat #391-MR-100) was added at 2 g/ml for 1 hour and plates were washed before the addition of 40 μl of anti-MerTK hybridoma supernatants and 40 μl of His tag-conjugated recombinant Gas6 (R&D systems, Cat #885-GSB-050) at 3 g/ml or His tag-conjugated recombinant ProS (R&D systems, Cat #9489-PS-100) at 20 g/ml. After a further incubation for 1 hour, plates were washed and incubated for 1 hour with HRP-conjugated anti-6× His tagged antibody (Abcam, Cambridge, MA, Cat #ab 1187). Plates were then washed and an HRP substrate, TMB, was added to develop the plates. The reaction was stopped by adding 50 μl 2N $H_2SO_4$ and the OD was measured using a spectrophotometer (BioTek).

A total of 308 anti-MerTK hybridoma supernatant clones were screened for their ability to block Gas6 and/or block ProS ligand binding to MerTK. Twenty-nine (29) anti-MerTK hybridoma clones blocked the binding of both ProS ligand and Gas6 ligand to recombinant human MerTK protein. One hundred forty-five (145) anti-MerTK hybridoma clones blocked binding of ProS ligand to human MerTK protein only and did not block the binding of Gas6 ligand to recombinant human MerTK protein. The remainder of the 308 anti-MerTK hybridoma clones screened by this assay did not block either ProS ligand or Gas6 ligand binding to recombinant human MerTK protein in this assay. The hybridoma supernatants were characterized further regarding their ability to block efferocytosis by phagocytic cells as described below.

Example 8: Efferocytosis Blocking Assay Using Anti-MerTK Hybridoma Supernatants

Anti-MerTK antibody hybridoma supernatants identified above as positive for MerTK binding reactivity were evaluated for their ability to block efferocytosis by human macrophages as follows. Human macrophages were differentiated from human monocytes for 7 days in the presence of human M-CSF. Macrophages were harvested (by scraping), resuspended in PBS, and plated on 96-well plates at $5\times10^4$ cells/well. Cells were starved for 1 hour followed by the addition of anti-MerTK hybridoma supernatants to each well for 30 min at 37° C. Jurkat cells were treated with 1 M staurosporin (SigmaAldrich) for 3 hours at 37° C. (to induce apoptosis) and labeled with pHrodo (ThermoFisher) for 30 min at room temperature. After washing with PBS, pHrodo labeled Jurkat cells were added into each well at 1:4 ratio (1 macrophage cell to 4 Jurkat cells) for 1 hour. The plates were washed with PBS and then cells were stained with APC-conjugated anti-human CD14 for 30 minutes on ice in the dark. Cells were then washed twice in FACS buffer (PBS+ 2% FBS), and flow cytometry was performed on a BD FACS CantoII. Data were analyzed using FlowJo software. Macrophages that are capable of efferocytosis engulf the labeled apoptotic Jurkat cells, which are then be detected, whereas macrophages that are blocked from carrying out efferocytosis show decreased engulfment of the labeled apoptotic Jurkat cells.

In these experiments, efferocytosis-positive macrophages were identified by setting pHrodo CD14 double positive cells as an analysis gate and then applying this exact gate to all the samples. Baseline efferocytosis levels were established using macrophages cultured with media alone and this was set to 100% efferocytosis activity. Relative efferocytosis levels were calculated as a percent of efferocytosis observed in cells treated with media alone compared to that observed in cells treated with anti-MerTK hybridoma supernatants. In these experiments, the following additional anti-MerTK antibodies were used: mouse anti-human MerTK antibody H1 (BioLegend, Clone ID: 590H11G1E3, mouse IgG1) and human anti-human MerTK antibody M6 (disclosed in WO2016/106221).

Table 1 and Table 2 below show results from these efferocytosis experiments, as % efferocytosis (media alone was set to 100% efferocytosis). In Table 1 below, exemplary hybridoma supernatants tested are indicated on the left and labeled as hybridoma supernatant ID number; these supernatants were from hybridoma clones identified from immunization of wildtype BALB/c mice. In Table 2 below, exemplary hybridoma supernatants tested are indicated on the left and labeled as hybridoma supernatant ID number; these supernatants were from hybridoma clones identified from immunization of MerTK KO mice. In both Table 1 and Table 2, antibody ID refers to anti-MerTK antibodies of the present disclosure that were selected for additional characterization and thus given a specific anti-MerTK antibody name, as indicated. The third, fourth and fifth columns ("Donor" identification numbers) indicate the percent efferocytosis relative to media treatment alone. Note that in comparison to efferocytosis in macrophages in the absence of antibody (media treatment alone), no significant change in efferocytosis was observed in cells treated with isotype control mouse IgG1 antibody.

TABLE 1

| Hybridoma supernatant ID | Antibody ID | Donor 689 | Donor 692 | Donor 806 |
|---|---|---|---|---|
| 1 | | 89.4 | 80.8 | 94.4 |
| 2 | | 126.0 | 105.3 | 109.0 |
| 3 | MTK-01 | 34.1 | 34.2 | 70.1 |
| 4 | MTK-02 | 20.8 | 32.2 | 62.9 |
| 5 | | 68.9 | 101.6 | 73.1 |
| 6 | MTK-03 | 25.2 | 16.9 | 53.6 |
| 7 | MTK-04 | 23.8 | 25.6 | 58.3 |
| 8 | | 107.7 | 109.0 | 112.6 |
| 9 | | 86.3 | 109.0 | 88.3 |
| 10 | MTK-05 | 36.1 | 18.2 | 43.0 |
| 11 | MTK-06 | 16.1 | 16.0 | 67.5 |
| 12 | MTK-07 | 18.8 | 17.4 | 56.8 |
| 13 | | 68.9 | 101.6 | 73.1 |
| 14 | MTK-08 | 30.9 | 19.0 | 35.7 |
| 15 | | 65.4 | n.a. | 88.8 |
| 16 | MTK-09 | 19.9 | 17.6 | 50.5 |
| 17 | | 68.5 | 72.2 | 71.8 |
| 18 | MTK-10 | 18.8 | 12.6 | 50.0 |
| 19 | MTK-11 | 14.3 | 11.9 | 30.8 |
| 20 | MTK-12 | 14.6 | 12.4 | 38.6 |
| 21 | | 67.6 | 74.6 | 83.0 |
| 22 | MTK-13 | 21.8 | 12.2 | 45.6 |
| 23 | | 88.1 | 92.9 | 82.5 |
| 24 | MTK-14 | 25.2 | 17.5 | 55.3 |
| 25 | | 82.4 | n.a. | n.a. |
| 26 | MTK-15 | 27.2 | 23.7 | n.a. |
| 27 | | 86.8 | 61.8 | 78.9 |
| 28 | | 65.8 | 79.9 | n.a. |
| 29 | MTK-16 | 25.6 | n.a. | n.a. |
| 30 | MTK-17 | 22.7 | n.a. | n.a. |
| 31 | | 75.9 | 74.7 | 89.3 |
| 32 | MTK-18 | 24.2 | n.a. | n.a. |
| 33 | | 106.0 | 76.1 | 116.5 |
| 34 | MTK-19 | 48.0 | n.a. | n.a. |
| 35 | MTK-20 | 21.4 | n.a. | n.a. |
| 36 | | 98.1 | 86.1 | 85.7 |
| 37 | | 106.0 | 87.1 | 93.7 |
| 38 | | 74.1 | 62.8 | 90.5 |
| 39 | | 115.1 | 106.8 | 80.6 |
| 40 | | 108.1 | 62.0 | 100.2 |
| 41 | MTK-21 | 22.2 | n.a. | n.a. |
| 42 | MTK-22 | 25.7 | n.a. | n.a. |
| 43 | | 76.7 | 61.1 | 87.4 |
| 44 | | 97.2 | 71.8 | 69.4 |
| 45 | | 75.4 | 73.0 | 73.3 |

TABLE 1-continued

| Hybridoma supernatant ID | Antibody ID | Donor 689 | Donor 692 | Donor 806 |
|---|---|---|---|---|
| 46 | MTK-23 | 17.0 | n.a. | n.a. |
| 47 | | 100.3 | n.a. | 95.9 |
| 48 | | 65.4 | n.a. | 71.6 |
| 49 | | 56.7 | 66.9 | 69.9 |
| 50 | | 63.7 | n.a. | 74.0 |
| | Media | 100.0 | 100.0 | 100.0 |
| | mIgG1 | 104.5 | 95.6 | 96.0 |
| | H1 | 31.2 | 16.5 | 57.9 |
| | M6 | 14.9 | n.a. | 35.1 |

n.a. means data not available

TABLE 2

| Hybridoma supernatant ID | Antibody ID | Donor 914 | Donor 915 | Donor 916 | Donor 783 |
|---|---|---|---|---|---|
| 1 | MTK-24 | 25.42 | 40.49 | 43.39 | 70.57 |
| 2 | | 86.61 | 66.80 | 72.73 | 106.69 |
| 3 | | 80.65 | 56.68 | 55.79 | 109.36 |
| 4 | MTK-25 | 44.05 | 31.01 | 25.50 | 21.37 |
| 5 | MTK-26 | 24.67 | 24.25 | 37.73 | 30.80 |
| 6 | | 83.04 | 73.28 | 68.18 | 103.01 |
| 7 | | 77.98 | 92.31 | 114.05 | 142.47 |
| 8 | | 100.30 | 92.71 | 102.07 | 123.08 |
| 9 | MTK-27 | 33.63 | 27.49 | 34.59 | 19.26 |
| 10 | | 78.87 | 63.56 | 73.14 | 92.31 |
| 11 | MTK-28 | 38.10 | 42.91 | 51.65 | 69.23 |
| 12 | | 96.73 | 87.85 | 102.48 | 123.08 |
| 13 | MTK-29 | 32.14 | 36.40 | 28.26 | 49.83 |
| 14 | | 97.92 | 73.68 | 80.99 | 122.07 |
| 15 | | 94.64 | 73.28 | 88.84 | 126.76 |
| 16 | | 106.55 | 86.23 | 97.93 | 130.43 |
| 17 | | 98.81 | 66.80 | 87.19 | 128.76 |
| 18 | | 101.79 | 95.55 | 100.00 | 115.72 |
| 19 | MTK-30 | 30.65 | 29.27 | 34.71 | 33.78 |
| 20 | MTK-31 | 41.37 | 37.85 | 32.60 | 32.78 |
| 31 | | 89.58 | 65.59 | 72.31 | 79.60 |
| 21 | | 79.17 | 47.37 | 68.60 | 93.98 |
| 22 | MTK-32 | 63.10 | 54.25 | 57.44 | 73.24 |
| 23 | MTK-33 | 25.54 | 22.35 | 36.61 | 13.55 |
| 24 | | 80.06 | 67.61 | 66.94 | 100.00 |
| 25 | | 68.15 | 51.42 | 55.37 | 62.21 |
| 26 | MTK-35 | 40.48 | 24.21 | 39.34 | 30.37 |
| 27 | | 86.61 | 64.37 | 88.02 | 119.40 |
| 28 | | 84.82 | 83.40 | 88.84 | 112.37 |
| 29 | | 78.57 | 61.94 | 73.97 | 122.41 |
| 30 | | 75.60 | 76.92 | 71.90 | 111.04 |
| 31 | | 75.30 | 78.95 | 76.86 | 117.39 |
| 32 | | 79.76 | 89.88 | 83.06 | 118.73 |
| 33 | | 72.02 | 75.30 | 68.60 | 98.33 |
| 34 | MTK-36 | 73.51 | 93.52 | 82.23 | 120.74 |
| 35 | | 71.73 | 82.59 | 74.79 | 128.76 |
| | Media alone | 100.00 | 100.00 | 100.00 | 100.00 |
| | M6 | 17.47 | 20.40 | 28.31 | 14.82 |

TABLE 2-continued

| Hybridoma supernatant ID | Antibody ID | Donor 914 | Donor 915 | Donor 916 | Donor 783 |
|---|---|---|---|---|---|
| | Isotype control | 88.99 | 104.05 | 104.55 | 93.65 |
| | H1 | 24.76 | 34.33 | 40.79 | 34.78 |

In Table 1 and Table 2, percent of efferocytosis by human macrophages from different donors is shown, with media alone (no antibody addition) set to 100% efferocytosis in both Tables. Although the degree of efferocytosis blocking activity by various anti-MerTK antibody hybridoma supernatants was different in macrophages obtained from each donor, the efferocytosis blocking trend for anti-MerTK antibodies was consistent among macrophages from different donors. As shown in Tables 1 and 2 above, anti-MerTK hybridoma supernatants of the present disclosure reduced efferocytosis by human macrophages to varying extents (e.g., reduced efferocytosis by about 50%-~85%). These results indicated that anti-MerTK antibodies obtained as described herein were effective at reducing or blocking efferocytosis by phagocytic cells.

Example 9: Molecular Cloning of Anti-MerTK Antibodies

Anti-MerTK antibodies from the hybridomas described above were subcloned as follows. $5\times10^5$ hybridoma cells were harvested and washed with PBS and then the cell pellets were flash frozen in dry ice and stored at −20° C. Total RNA was extracted by using RNeasy Mini Kit (QIAGEN, Cat #74104) following the manufacturer's protocol. cDNA was generated using Clontech's SMARTer RACE 5'/3' Kit (Takara Bio USA, Cat #634859) following the manufacturer's protocol. Variable heavy and light immunoglobulin regions were cloned separately by touchdown PCR using the 5' UPM primer provided in the RACE kit and reverse primers recognizing the heavy chain and light chain constant regions. The resulting PCR products were purified and ligated into a pCR2.1-TOPO cloning vector (TOPO TA cloning Kit, Invitrogen Cat #450641) and transformed into *Escherichia coli* (*E. coli*) cells. Transformed colonies were isolated and the variable heavy chain (VH) and variable light chain (VL) nucleic acids were sequenced for each corresponding hybridoma cell line. Following the sequence determinations, variable heavy chain regions and variable light chain regions were amplified by PCR using primers containing endonuclease restriction sites and then subcloned into pLEV-123 (LakePharma, San Carlos, CA) mammalian expression vector encoding human IgG1-Fc-LALAPS (human IgG1 Fc comprising amino acid substitutions L234A, L235A, and P331S by EU numbering) and IgG Kappa.

Amino acid sequences of the variable heavy chains and variable light chains of anti-MerTK antibodies of the present disclosure are provided below in Table 3. In Table 3, the CDR/HVR sequences (according to Kabat) are underlined.

TABLE 3

| Antibody | Heavy Chain Variable | SEQ ID NO: | Light Chain Variable | SEQ ID NO: |
|---|---|---|---|---|
| MTK-01 | QIQLVQSGPELKKPGETVKISCKASGYTFTNYGMNWVKQAPGKGLKCMGWINTYTGEPTYADDFKGRFAFSLETSATTAYLQINNLKNEDTATYFCARRDRYTWFAYWGQGTLVTVSA | 5 | QIVLSQSPAILSASPGEKVTMTCRASSSVSYMHWYQQKPGSSPKPWIYATSNLASGVPARFSGSGSGTSYSLTISRVEAEDAATYYCQQWSSNPPTFGGGTKLEIK | 40 |

TABLE 3-continued

| Antibody | Heavy Chain Variable | SEQ ID NO: | Light Chain Variable | SEQ ID NO: |
|---|---|---|---|---|
| MTK-02 | QIQLVQSGPELKOPGETVKISC<br>KASGYTFTDYGVNWVKQAPGKG<br>LKWMGWINTYSGEPTYAGDFKG<br>RFAFSLESSASTAFLQINNLKN<br>EDMATYFCARRVRYWYFDVWGA<br>GTSVTVSS | 6 | QIVLSQSPAILSASPGERVTMTC<br>RANSSVSYMHWYQQKPGSSPKPW<br>IYATSNLASGVPARFSASGSGTS<br>YSLTVSRVEAEDAATYYCQQWGS<br>NPFTFGSGTKLEIK | 41 |
| MTK-03 | DVQLQESGPGLVKPSQSLSLTC<br>SVTGYSITSGYYWNWIRQFPGN<br>TLEWMGYMSFDGDNKFNPSLKN<br>RISITRDTSKNQFFLRLNSVTT<br>EDTATYYCARGGYNYGSTEANW<br>GQGTLVTVSA | 7 | QIVLTQSPAIMSAFPGEKVTITC<br>SASSSVNYMHWFQQKPGTSPKLW<br>IYSTSNLASGVPARFSGSGSGTS<br>YSLTISRMEAEDAATYYCQQRSS<br>YPFTFGSGTKLEIK | 42 |
| MTK-04 | QIQLVQSGPELKKPGETVKISC<br>KASGYTFTNYGMNWVKQAPGKG<br>LKCMGWINTYTGEPTYADDFKG<br>RFAFSLETSASTAYLQINNLKN<br>EDMATYFCAKYDNYAWFAYWGQ<br>GTLVTVSA | 8 | QIVLSQSPAFLSASPGEKVTMTC<br>RASSSVSYMHWYLQKPGSSPKPW<br>IYATSNLASGVPVRFSGSGSGTS<br>YSLTISRVEAEDAATYYCQQWSS<br>NPRTFGGGTKLEIR | 43 |
| MTK-05 | QVOLQQSGAELVQPGTSVRLSC<br>KTSGYTFTSYWIQWVKQRPGQG<br>LGWIGEIFPGTGTTYYNEKFKG<br>KATLTIDTSSSTAYMQLSSLTS<br>EDSAVYFCARDGAYFDVWGAGT<br>TVTVSS | 9 | DIQMTOSPASLSASVGETVTFTC<br>RASENIFSYLAWYQQKQGKSPQL<br>LVYNAKTLAEGVPSRFSGSGSGT<br>HFSLKINSLQPEDFGSYYCLHHY<br>GTPLTFGAGTKLELK | 44 |
| MTK-06 | QIQLVQSGPELKKPGETVKISC<br>KASGYTFTNYGMNWVKQAPGKG<br>LKWMGWINTNTGEPTYAEEFKG<br>RFAFSLETSASTAYLQINNLKN<br>EDTATYFCARYYNYWYFDVWGA<br>GTTVTVSS | 10 | QIVLSQSPAILSASPGEKVTMTC<br>RASSSVSYMHWYQQKPGSSPKPW<br>IYATSNLASGVPARFSGSGSGTS<br>YSLTISRVEAEDAATYYCQQWSS<br>KPPTFGGGTKLEIK | 45 |
| MTK-07 | DVQLQESGPGLVKPSQSLSLTC<br>SVTGYSITSGYYWNWIRQFPGN<br>TLEWMGYMSFDGDNKFNPSLKN<br>RISITRDTSKNQFFLRLNSVTT<br>EDTATYYCARGGYNYGSTEANW<br>GQGTLVTVST | 11 | QIVLTQSPAIMSAFPGEKVTITC<br>SASSSVTYMHWFQQKPGTSPKLW<br>IFSTSNLASGVPARFSGSGSGTS<br>YSLTISRMEAEDAATYYCQQRSS<br>YPFTFGSGTKLEIK | 46 |
| MTK-08 | QIQLVQSGPELKKPGETVKISC<br>KASGYTFTNYGMNWVKQAPGKG<br>LKWMGWINTYTGEPTYADDFKG<br>RFAFSLETSASTAYLQINNLKN<br>EDTATYFCAREVRYWYFDVWGA<br>GTTVTVSS | 12 | QIVLSQSPAILSASPGEKVTMTC<br>RATSSVSYMHWFQQKPGSSPKPW<br>IYATSNLASGVPARFSGSGSGTS<br>YSLTISRVEAEDAAAYYCQHWSG<br>NPRTFGGGTKLEIK | 47 |
| MTK-09 | QVQLQQSGAELVRPGASVKISC<br>KAFGYTFTNHHIKWVKQRPGQG<br>LDWIGYIDPYNDYTTYNQNFKG<br>KATLTVDKSSSTAYMELSSLTS<br>EDSAVYYCARRAYDGYYVDWYF<br>DVWGAGTTVTVSS | 13 | DIVMTQSHKFMSTSVGDRVSITC<br>KASQDVTTSVAWYHQKPGQSPEL<br>LIYSASYRYTGVPDRFTGSGSGT<br>DFTFTISSVQAEDLAIYYCQQHY<br>STPLTFGSGTKLQLK | 48 |
| MTK-10 | QVTLKESGPGILQPSQTLSLTC<br>SFSGFSLTTSGMGVGWIRQPSG<br>KGLEWLAHIWSDDDKRSNPALK<br>SRLTISQDSSTNQVFLKIASVD<br>TADSATYYCSHLTPVREFAYWG<br>PGTLVTVSE | 14 | DIQMTOTTSSLSASLGDRVTISC<br>SASQGISNYLNWFQQKPDGTVKL<br>LIYYTSRLHSGVPSRFSGSGSGT<br>DFSLTISNLEPEDIATYYCQQYT<br>KLPYTFGGGTKLEIK | 49 |
| MTK-11 | QVQLKQSGPGLVQPSQSLSITC<br>TVSGFSLTDYGVHWVRQSPGKG<br>LEWLGVIWSSGTTDYNEAFISR<br>LSISKDNSKSHVFFKMNSLQAI<br>DTAIYYCARKGHDPYAMDYWGQ<br>GTSVTVSS | 15 | QIVLTQSPAIMSASLGERVTMTC<br>TASSSISSSYFHWYQQKPGSSPK<br>LWIYSTSNLPSGVPARFSGSGSG<br>TSYSLTISSMEAEDAATYYCHQY<br>YRSPLTFGAGTKLELK | 50 |
| MTK-12 | QVQLQQSGPQLVRPGASVKISC<br>KASGYSFTSHWMHWVKQRPGQG<br>LEWIGMIDPSDGESRLNQKFKD<br>KATLTVDKSSSTAYMQLSSPTF<br>EDSAVYYCARGIYYYGITYAMD<br>YWGQGTSVTVSS | 16 | QIVLTQSPAIMSASPGEKVTMTC<br>SASSSVSYMYWYQQKPRSSPRLL<br>IYDTSNLASGVPVRFSGSGSGTS<br>YSLTISRMEAEDAATYYCQQWSS<br>YPLTFGAGTKLELK | 51 |

TABLE 3-continued

| Antibody | Heavy Chain Variable | SEQ ID NO: | Light Chain Variable | SEQ ID NO: |
|---|---|---|---|---|
| MTK-13 | DVQLQESGPGLVKPSQSLSLTC<br>SVTGYSITSGYYWNWIRQFPGN<br>KLEWMGNIDYDGSNKYNPSLKN<br>RISITRDTSKNHFFLKLNSVTP<br>EDTATYFCARDGGNYRSFAYWG<br>QGTLVTVSA | 17 | QIVLTQSPPIMSASPGEKVTITC<br>SASSSVSYMYWFQQKPGTSPKLW<br>IYSTFNLASGVPARFSGSGSGTS<br>YSLTISRMEAEDVATYYCQQRSS<br>YPFTFGSGTKLEIK | 52 |
| MTK-14 | QIQLVQSGPELKKPGETVKISC<br>KASGYTFTNYGMNWVKQAPGKD<br>LQWMGWINTYTGEPTYADDFTG<br>RFAFSLETSASTAYLQINNLKN<br>EDTATYFCAKGGHYAWFAYWGQ<br>GTLVTVSA | 18 | QIVLSQSPAILSASPGEKVTMTC<br>RSSSSVSYMHWYQQKPGSSPKPW<br>IYATSNLASGVPGRFSGSGSGTS<br>YSLTISRVEAEDAATYYCQQWGS<br>NPRTFGGGTKLEIK | 53 |
| MTK-15 | QIQLVQSGPELKKPGETVKISC<br>KASGYTFTNYGVHWVKQAPGKG<br>LKWMGWINTYTGEPTYADDFKG<br>RFAFSLETSASTAYLQINNLKN<br>EDMATYFCARGNRYAYMDYWGQ<br>GTSVTVSS | 19 | QIVLSQSPAILSASPGEKVTMTC<br>RASSSVSYMHWYQQKSGSSPKPW<br>IYATSNLASGVPARFSGSGSGTS<br>YSLTISRVEAEDAATYYCQQWSS<br>NPRTFGGGTKLEIK | 54 |
| MTK-16 | LIQLVQSGPELKKPGETVKISC<br>KASGYTFTNHGMNWVKQDPGKG<br>LKWMGWINTYTGEPTYADDFKG<br>RFVFSMETSASAAFLQINNLKN<br>EDTATYFCARKGVTAARYFDYW<br>GQGTTLTVSS | 20 | DIVMTQSPKFMSTSVGDRVSITC<br>KASQNVRTAVAWYKKKPGQSPKA<br>LINLASNRHTGVPDRFTGSGSGT<br>DFTLTISNVQSEDLADYFCLQHW<br>NYPLTFGGGTKLEIK | 55 |
| MTK-17 | QIQLVQSGPELKKPGETVKISC<br>KASGYTFTNFGMNWVKQAPGKG<br>LKWMGWINTYTGEPTYADDFKG<br>RFAFSLETSASTAYLQINNLKN<br>EDTATYFCSRGAVLRAGAMDCW<br>GQGTSVTVSS | 21 | DIQMTQSSSYLSVSLGGRVTITC<br>KASDHINNWLAWYQQKPGNAPRL<br>LISGATSLETGVPSRFSGSGSGK<br>DYTLSITSLQTEDVATYYCQQYW<br>STPRTFGGGTKLEIK | 56 |
| MTK-18 | QIQLVQSGPELKKPGETVKISC<br>KASGYTFTHYGMTWVKQAPGKG<br>LKWMGWINTYTGEPTYADDFKG<br>RFAFSLETSASTAYLQINNLKN<br>EDTATYFCARGGGQLGLRPLDY<br>WGQGTTLTVSS | 22 | DIQMTQTTSSLSASLGDRVTFSC<br>RASQAISNYLNWYQQKPDGTVKL<br>LIYYTSRLHSGVPSRFSGSGSGT<br>DYSLTISNLEQEDIATYFCQQGN<br>TLPWTFGGGTKLEIK | 57 |
| MTK-19 | EVQLQQSGPELVKPGASVKISC<br>KTSGYTFTEYTMHWVKQSHGKS<br>LEWLGGFNPNNVITSYNQRFQG<br>RATLTVDKSSSTAYMELRSLTS<br>DDSAVYYCTRGDLLWSLLLPGN<br>YFDYWGQGTTLTVSS | 23 | DVVMTQSSLTLSVTIGQPASISC<br>KSSQSLLDSDGKTYLNWLLQRPG<br>QSPKRLIYLVSKLDSGVPDRFTG<br>SGSGTDFTLKISRVEAEDLGVYY<br>CWQGTHFPWTFGGGTKLEIK | 58 |
| MTK-20 | QIQLVQSGPELKKPGETVKISC<br>KASGYTFTNYGMTWVKQAPGKG<br>LKWMGWINTYTGEPTYADDFKG<br>RFALSLETSASTAYLQINNLKN<br>EDTATYFCARGGGRLGLRPLDY<br>WGQGTTLTVSS | 24 | DIQMTQTTSSLSASLGDRVTISC<br>RASQDINNYLNWYQQKPDGTVKL<br>LIYYTSRLHSGVPSRFSGSGSGT<br>DYSLTISNLEQEDIATYFCQQGN<br>TLPWTFGGGTKLEIK | 59 |
| MTK-21 | QIQLVQSGPELKKPGETVKISC<br>KASGYTFTNFGMTWVRQAPGMD<br>LKWMGWINTYTGEPKYADDFKG<br>RFALSLETSASTAYLQITNFKN<br>EDTATYFCARGGGRLGLRPLDY<br>WGQGTTLTVSS | 25 | DIQMTOTTSSLSASLGDRVTISC<br>RASQDINNYLNWYQQKPDGTVKL<br>LIYYTSSLHSGVPSRFSGSGSGT<br>DYSLTITNLEQEDIATYFCQQGN<br>TLPWTFGGGTRLEIK | 60 |
| MTK-22 | QVQLQQPGADLVEPGASVKLSC<br>KASGYTFTSYWMHWVKQRPGQG<br>LEWIGEIDPSDSSSNYNQKFKG<br>KATLTVDKSSSTAYMHLNSLTS<br>EDSAVYYCARRYYYGSLYFDNW<br>GQGTTLTVSS | 26 | DVVMTQSHKFMSTSVGDRVSITC<br>KASQDVGTAIAWYQQKPGQSPKL<br>LIYWASTRHTGVPDRFTGSRSGT<br>VFTLTISNVQSEDLADYFCQQYT<br>SYPLTFGSGTKLEIK | 61 |
| MTK-23 | QVQLQQSGADLVRPGASVKISC<br>KAFGYTFTNHHINWVKQRPGQG<br>LDWIGNVDPYNDYSTYNQKFKG<br>KATLTVDKSSSTAYMELSSLTS<br>EDSAVYYCARRVYDGFYVDWYF<br>DVWGAGTTVTVSS | 27 | DIVMTQSHKFMSTPVGDRVSITC<br>KASRDVSTAVAWFHQKPGQSPKL<br>LIYSASYRSTGVPDRFTGSGSGT<br>DFTFTISSVQAEDLAVYYCQQHY<br>SAPLTFGAGTKLELK | 62 |

TABLE 3-continued

| Antibody | Heavy Chain Variable | SEQ ID NO: | Light Chain Variable | SEQ ID NO: |
|---|---|---|---|---|
| MTK-24 | QVQLQQPGAELVKPGASVKLSC KASGYTFTSYWMHWVKQRPGQG LEWIGMIHPNINTNYNEKFKSK ATLTVDISSSTAYMQLSSLTSE DSAVYYCAKRSPYSNYDWYFDV WGTGTTVTVSS | 28 | DIQMTQSPASLSVSVGETVTITC RASENIYSNLAWYQQKQGKSPQL LVYAATNLADGVPSRFSGSGSGT QYSLKINSLQSEDFGSYYCQHFW GTPLTFGAGTKLELK | 63 |
| MTK-25 | EVKLVESEGGLVQPGSSMKLSC TASGFTFSDYYMAWVRQVPEKG LEWVANINYEGSSTYYLGSLKS RFIISRDNAENILYLQMSSLKS EDTATYYCARYYYGSVDYWGQG TTLTVSS | 29 | DIVMTQSQKFMSTSVGDRVSITC KASQNVRTTVAWYQQKPGQSPKT LIYLASNRHTGVPDRFTGSGSGT DFTLTISNVQSEDLADYFCLQLW NYPWTFGGGTKLEIK | 64 |
| MTK-26 | AVQFQESGPGLVKLSQSLSLTC SVTGYSITSGYYWDWIRQFPGN KLEWMGYISYDGSNNYNPSLKN RISITRDTSKNQFFLKLNSVTT EDTATYYCAREGGYYRSMDYWG QGTSVTVSS | 30 | QIVLTQSPAIMSASPGEKVTIAC SASSSVSFMHWFQQKPGTSPRLW IYSTSNLASGVPARFSGSGSGTS YSLTISRMEAEDAATYYCQQRSS YPFTFGSGTKLEIK | 65 |
| MTK-27 | EVQLQQSGTELVRPGASVKLSC TASGFNIKDDYMHWVQQRPEQG LEWIGWIDPENGNTEYASKFQG KATITADASSNTAYLQLSSLTS EDTAVYYCSTLFSNYFDYWGQG TTLTVSS | 31 | DIVMTQSQKFMSTSVGDRVSITC KASQNVRTSVAWYQQKPGQSPKA LIYLASNRHTGVPDRFTGSGSGT DFTLTISNVRSEDLADYFCLQHW NYPYTFGGGTKLEIK | 66 |
| MTK-28 | QIQLVQSGPELKKPGETVKISC KASGYTFTTYGMSWVKQAPGKG LKWMGWINTYSGVPTYADDFKG RFAFSLETSASTAYLQINTLKN EDTTTYFCARFLRYYYFDYWGQ GTTLTVSS | 32 | QIVLSQSPVILSASPGEKVTMTC RASSSVTYMHWYQQQPGSSPKPW IYATSNLASGVPARFSGSGSGTS YSLTISRVETEDAATYYCHQWSG NPTFGGGTKLEIN | 67 |
| MTK-29 | QIQLVQSGPELKKPGETVKISC KSSGFTFTTYGMSWVKQAPGKG LKWMGWINTYSGVPTYTDDFKG RFAFSLETSASTASLQINNLKN EDTATYFCARYTNYGYFDYWGQ GTTLTVSS | 33 | QIVLSQSPAILSASPGEKVTMTC RATSSVGYMHWYQQKPGSSPKPW IYATSNLASGVPARFSGSGSGTS YSLTISRVEAEHAATYYCQQWGS NPFTFGSGTKLEIK | 68 |
| MTK-30 | QVOLQQPGTELVRPGASVKLSC KASGYTFTSYWMHWVKQRPGQG LEWIGNLNPNNGGTYYNEKFKS KATLTVDKSSSTAYMQLSSLTS EDSAVYYCARQILLYFDYWGQG TTLTVSS | 34 | DVLMTQTPLSLPVSLGDQASISC RSSQSIVHSNGDTYLEWYLQKPG QSPKLLIYKVSNRFSGVPDRFSG SGSGTDFTLKISRVEAEDLGVYY CFQGSHVPWTFGGGTKLEIK | 69 |
| MTK-31 | QIQLVQSGPELKKSGETVKISC KASGYTFTSYGMSWVKQAPGKG LKWMGWINTYSGVPTYADDFKG RFAFSLETSASTAYLQINNLKN EDTATYFCASLSYDGSLYHAMD YWGQGTSVTVSS | 35 | DVSMTQTPLSLPVSLGDQASISS RSSQTIVHSNGNTYLEWYLQKPG QSPKLLIYKVSNRFSGVPDRFSG SGSGTDFTLKISRVEAEDLGVYY CFQGSHVPWTFGGGTKLEIK | 70 |
| MTK-32 | QIQLVQSGPELKKPGETVKISC KASGYTFTSYGMSWVHQAPGKG LKWLGWINTYSGVPTYADDFRG RFAFSLDTSVSTASLEINNLQN EDTATYFCAREDNWAWFAYWGQ GTLVTVST | 36 | QIVLSQSPAILSASPGEKVTMTC RATSSVGYMHWYQRKPGSSPKPW IYATSNLASGVPARFSGSGSGTS YSLTISRVEAEDAATYYCQQWSS NPRTFGGGTKLEIK | 71 |
| MTK-33 | QVQLQQPGPELVRPGTSVKLSC KASGYTFTSYWMHWIKQRPGQG LEWIGVIDPSDNYINYNQKFKG KATLTVDTSSSTAYLQLSSLTS EDSAVYYCAREAGTRGYFDYWG QGTTLTVSS | 37 | SIVMTQTPKFLLVSAGDRVIITC KASQSVSNTVAWYQQKPGQSPKL LIYYASNRYTGVPDRFTGSGYGT DFTFTISTVQAEDLAVYFCQQDY RSPFTFGSGTQLEMK | 72 |
| MTK-34 | QVQLQQPGPELVRPGTSVKLSC KASGYTFTSYWMHWIKQRPGQG LEWIGVIDPSDNYINYNQKFKG KATLTVDTSSSTAYLQLSSLTS EDSAVYYCAREAGTRGYFDYWG QGTTLTVSS | 37 | SIVMTQTPKFLLVSAGDRVIITC KASQSVSNTVAWYQQKPGQSPKL LIYYASNRYTGVPDRFTGSGYGT DFTFTISTVQAEDLAVYFCQQDY RSPFTFGSGTQLEMK | 72 |

TABLE 3-continued

| Antibody | Heavy Chain Variable | SEQ ID NO: | Light Chain Variable | SEQ ID NO: |
|---|---|---|---|---|
| MTK-35 | QVLLQQSGPELVKPGASVQLSC KASDYTFTSYDIHWVKQRPGQG LEWIGWIYPRDGYTKYNEIFKG KATLTVDTSSTTAYMELHSLTS EDSAVYFCARAYYTNWYYFDYW GQGTTLTVSS | 38 | EIVLTQSPTTMAASPGEKITITC RASSSISSHYLHWYQQKPGFSPK LLIYRTSNLASGVPARFSGSGSG TSYSLTIGTMEAEDVATYYCQQG STIPLTFGAGTKLVLK | 73 |
| MTK-36 | QVTLKESGPGILQPSQTLSLTC SFSGFSLSTFGMGVGWIRQPSG KGLEWLAHIWWYDDKYYEPALK SRLTISKDSSKNQVFLKIANVD TADTATYYCARIYYGTSYRYFD VWGTGTTVTVSS | 39 | QIVLSQSPAILSAFPGEKVTMTC RATSSVRYMHWYQQKPGSSPKPW IYATYNLTSGVPARFSGSGSGTS YSLTISRVEAEDAATYYCHQWSS NPYTFGGGTKLEIK | 74 |

The CDR sequences according to Kabat for the anti-MerTK antibodies of the present disclosure are provided below in Table 4 (heavy chain) and Table 5 (light chain).

TABLE 4

| Antibody | HVR-H1 | SEQ ID NO: | HVR-H2 | SEQ ID NO: | HVR-H3 | SEQ ID NO: |
|---|---|---|---|---|---|---|
| MTK-01 | NYGMN | 75 | WINTYTGEPT YADDFKG | 99 | RDRYTWFAY | 125 |
| MTK-02 | DYGVN | 76 | WINTYSGEPT YAGDFKG | 100 | RVRYWYFDV | 126 |
| MTK-03 | SGYYWN | 77 | YMSFDGDNKF NPSLKN | 101 | GGYNYGSTE AN | 127 |
| MTK-04 | NYGMN | 75 | WINTYTGEPT YADDFKG | 99 | YDNYAWFAY | 128 |
| MTK-05 | SYWIQ | 78 | EIFPGTGTTY YNEKFKG | 102 | DGAYFDV | 129 |
| MTK-06 | NYGMN | 75 | WINTNTGEPT YAEEFKG | 103 | YYNYWYFDV | 130 |
| MTK-07 | SGYYWN | 77 | YMSFDGDNKF NPSLKN | 101 | GGYNYGSTE AN | 127 |
| MTK-08 | NYGMN | 75 | WINTYTGEPT YADDFKG | 99 | EVRYWYFDV | 131 |
| MTK-09 | NHHIK | 79 | YIDPYNDYTT YNQNFKG | 104 | RAYDGYYVD WYFDV | 132 |
| MTK-10 | TSGMGVG | 80 | HIWSDDDKRS NPALKS | 105 | LTPVREFAY | 133 |
| MTK-11 | DYGVH | 81 | VIWSSGTTDY NEAFIS | 106 | KGHDPYAMD Y | 134 |
| MTK-12 | SHWMH | 82 | MIDPSDGESR LNQKFKD | 107 | GIYYYGITY AMDY | 135 |
| MTK-13 | SGYYWN | 77 | NIDYDGSNKY NPSLKN | 108 | DGGNYRSFA Y | 136 |
| MTK-14 | NYGMN | 75 | WINTYTGEPT YADDFTG | 109 | GGHYAWFAY | 137 |
| MTK-15 | NYGVH | 83 | WINTYTGEPT YADDFKG | 99 | GNRYAYMDY | 138 |
| MTK-16 | NHGMN | 84 | WINTYTGEPT YADDFKG | 99 | KGVTAARYF DY | 139 |
| MTK-17 | NFGMN | 85 | WINTYTGEPT YADDFKG | 99 | GAVLRAGAM DC | 140 |

TABLE 4-continued

| Antibody | HVR-H1 | SEQ ID NO: | HVR-H2 | SEQ ID NO: | HVR-H3 | SEQ ID NO: |
|---|---|---|---|---|---|---|
| MTK-18 | HYGMT | 86 | WINTYTGEPT YADDFKG | 99 | GGGQLGLRP LDY | 141 |
| MTK-19 | EYTMH | 87 | GFNPNNVITS YNQRFQG | 110 | GDLLWSLLL PGNYFDY | 142 |
| MTK-20 | NYGMT | 88 | WINTYTGEPT YADDFKG | 99 | GGGRLGLRP LDY | 143 |
| MTK-21 | NFGMT | 89 | WINTYTGEPK YADDFKG | 111 | GGGRLGLRP LDY | 143 |
| MTK-22 | SYWMH | 90 | EIDPSDSSSN YNQKFKG | 112 | RYYYGSLYF DN | 144 |
| MTK-23 | NHHIN | 91 | NVDPYNDYST YNQKFKG | 113 | RVYDGFYVD WYFDV | 145 |
| MTK-24 | SYWMH | 90 | MIHPNINTNY NEKFKS | 114 | RSPYSNYDW YFDV | 146 |
| MTK-25 | DYYMA | 92 | NINYEGSSTY YLGSLKS | 115 | YYYGSVDY | 147 |
| MTK-26 | SGYYWD | 93 | YISYDGSNNY NPSLKN | 116 | EGGYYRSMD Y | 148 |
| MTK-27 | DDYMH | 94 | WIDPENGNTE YASKFQG | 117 | LFSNYFDY | 149 |
| MTK-28 | TYGMS | 95 | WINTYSGVPT YADDFKG | 118 | FLRYYYFDY | 150 |
| MTK-29 | TYGMS | 95 | WINTYSGVPT YTDDFKG | 119 | YTNYGYFDY | 151 |
| MTK-30 | SYWMH | 90 | NLNPNNGGTY YNEKFKS | 120 | QILLYFDY | 152 |
| MTK-31 | SYGMS | 96 | WINTYSGVPT YADDFKG | 118 | LSYDGSLYH AMDY | 153 |
| MTK-32 | SYGMS | 96 | WINTYSGVPT YADDFRG | 121 | EDNWAWFAY | 154 |
| MTK-33 | SYWMH | 90 | VIDPSDNYIN YNQKFKG | 122 | EAGTRGYFD Y | 155 |
| MTK-34 | SYWMH | 90 | VIDPSDNYIN YNQKFKG | 122 | EAGTRGYFD Y | 155 |
| MTK-35 | SYDIH | 97 | WIYPRDGYTK YNEIFKG | 123 | AYYTNWYYF DY | 156 |
| MTK-36 | TFGMGVG | 98 | HIWWYDDKYY EPALKS | 124 | IYYGTSYRY FDV | 157 |

TABLE 5

| Antibody | HVR-L1 | SEQ ID NO: | HVR-L2 | SEQ ID NO: | HVR-L3 | SEQ ID NO: |
|---|---|---|---|---|---|---|
| MTK-01 | RASSSVS YMH | 158 | ATSNLAS | 187 | QQWSSNPPT | 207 |
| MTK-02 | RANSSVS YMH | 159 | ATSNLAS | 187 | QQWGSNPFT | 208 |
| MTK-03 | SASSSVN YMH | 160 | STSNLAS | 188 | QQRSSYPFT | 209 |
| MTK-04 | RASSSVS YMH | 158 | ATSNLAS | 187 | QQWSSNPRT | 210 |

TABLE 5-continued

| Antibody | HVR-L1 | SEQ ID NO: | HVR-L2 | SEQ ID NO: | HVR-L3 | SEQ ID NO: |
|---|---|---|---|---|---|---|
| MTK-05 | RASENIF SYLA | 161 | NAKTLAE | 189 | LHHYGTPLT | 211 |
| MTK-06 | RASSSVS YMH | 158 | ATSNLAS | 187 | QQWSSKPPT | 212 |
| MTK-07 | SASSSVT YMH | 162 | STSNLAS | 188 | QQRSSYPFT | 209 |
| MTK-08 | RATSSVS YMH | 163 | ATSNLAS | 187 | QHWSGNPRT | 213 |
| MTK-09 | KASQDVT TSVA | 164 | SASYRYT | 190 | QQHYSTPLT | 214 |
| MTK-10 | SASQGIS NYLN | 165 | YTSRLHS | 191 | QQYTKLPYT | 215 |
| MTK-11 | TASSSIS SSYFH | 166 | STSNLPS | 192 | HQYYRSPLT | 216 |
| MTK-12 | SASSSVS YMY | 167 | DTSNLAS | 193 | QQWSSYPLT | 217 |
| MTK-13 | SASSSVS YMY | 167 | STFNLAS | 194 | QQRSSYPFT | 209 |
| MTK-14 | RSSSSVS YMH | 168 | ATSNLAS | 187 | QQWGSNPRT | 218 |
| MTK-15 | RASSSVS YMH | 158 | ATSNLAS | 187 | QQWSSNPRT | 210 |
| MTK-16 | KASQNVR TAVA | 169 | LASNRHT | 195 | LQHWNYPLT | 219 |
| MTK-17 | KASDHIN NWLA | 170 | GATSLET | 196 | QQYWSTPRT | 220 |
| MTK-18 | RASQAIS NYLN | 171 | YTSRLHS | 191 | QQGNTLPWT | 221 |
| MTK-19 | KSSQSLL DSDGKTY LN | 172 | LVSKLDS | 197 | WQGTHFPWT | 222 |
| MTK-20 | RASQDIN NYLN | 173 | YTSRLHS | 191 | QQGNTLPW | 223 |
| MTK-21 | RASQDIN NYLN | 173 | YTSSLHS | 198 | QQGNTLPWT | 221 |
| MTK-22 | KASQDVG TAIA | 174 | WASTRHT | 199 | QQYTSYPLT | 224 |
| MTK-23 | KASRDVS TAVA | 175 | SASYRST | 200 | QQHYSAPLT | 225 |
| MTK-24 | RASENIY SNLA | 176 | AATNLAD | 201 | QHFWGTPLT | 226 |
| MTK-25 | KASQNVR TTVA | 177 | LASNRHT | 195 | LQLWNYPWT | 227 |
| MTK-26 | SASSSVS FMH | 178 | STSNLAS | 188 | QQRSSYPFT | 209 |
| MTK-27 | KASQNVR TSVA | 179 | LASNRHT | 195 | LQHWNYPYT | 228 |
| MTK-28 | RASSSVT YMH | 180 | ATSNLAS | 187 | HQWSGNPT | 229 |
| MTK-29 | RATSSVG YMH | 181 | ATSNLAS | 187 | QQWGSNPFT | 208 |

TABLE 5-continued

| Antibody | HVR-L1 | SEQ ID NO: | HVR-L2 | SEQ ID NO: | HVR-L3 | SEQ ID NO: |
|---|---|---|---|---|---|---|
| MTK-30 | RSSQSIV HSNGDTY LE | 182 | KVSNRFS | 202 | FQGSHVPWT | 230 |
| MTK-31 | RSSQTIV HSNGNTY LE | 183 | KVSNRFS | 202 | FQGSHVPWT | 230 |
| MTK-32 | RATSSVG YMH | 181 | ATSNLAS | 187 | QQWSSNPRT | 210 |
| MTK-33 | KASQSVS NTVA | 184 | YASNRYT | 203 | QQDYRSPFT | 231 |
| MTK-34 | KASQSVS NTVA | 184 | YASNRYT | 203 | QQDYRSPFT | 231 |
| MTK-35 | RASSSIS SHYLH | 185 | RTSNLAS | 204 | QQGSTIPLT | 232 |
| MTK-36 | RATSSVR YMH | 186 | ATYNLTS | 205 | HQWSSNPYT | 233 |

Example 10: Production of Anti-MerTK Antibodies

Anti-MerTK hybridoma clones were cultured in serum free hybridoma media and the anti-MerTK antibodies in the supernatants purified on Hamilton STAR platform (Hamilton Company, Reno, NV) using Protein A tips (Phynexus Inc, San Jose, CA). Anti-MerTK antibodies were also produced via direct cloning of the variable gene regions obtained from the hybridomas into a recombinant expression plasmid for production of chimeric antibodies containing a human Fc domain (human IgG1 containing LALAPS amino acid substitutions described above). Using the Tuna293™ Process (LakePharma, San Carlos, CA), HEK293 cell were seeded into shake flasks and expanded using serum-free chemically defined media. The expression plasmids were transiently transfected into the cells and the culture supernatants were harvested 7 days later. After clarification by centrifugation and filtration, the anti-MerTK antibodies in the supernatants were purified via Protein A chromatography.

Example 11: Blocking Efferocytosis with Recombinant Anti-MerTK Antibodies

The ability of anti-MerTK antibodies of the present disclosure to block efferocytosis by phagocytic cells (e.g., human macrophages or mouse bone-marrow derived macrophages) was evaluated as follows. Human macrophages were differentiated from human monocytes for 7 days in the presence of human M-CSF. Mouse bone marrow derived macrophages were differentiated from mouse bone marrow cells for 7 days in the presence of mouse M-CSF (Peprotech, Cat #315-02). After 7 days, human macrophages and mouse macrophages were harvested (by scraping), resuspended in PBS, and plated on 96-well plates at $5\times10^4$ cells/well. For efferocytosis IC50 determinations, cells were starved for 1 hour followed by the addition of 10 μl of recombinant anti-MerTK antibody to each well for 30 min at 37° C. For other studies described herein, recombinant anti-MerTK antibodies were titrated to a final concentration range of between 66.6 nM to 4 pM and then each serially diluted antibody was added to each well for 30 min at 37° C.

Jurkat cells were treated with 1 M staurosporin (SigmaAldrich) for 3 hours at 37° C. (to induce apoptosis) and labeled with pHrodo (ThermoFisher) for 30 min at room temperature. After washing with PBS, pHrodo labeled Jurkat cells were added into each well at 1:4 ratio (1 macrophage: 4 Jurkat cells) for 1 hour. The plates were washed with PBS and then the cells were stained with APC-conjugated anti-human CD14 or anti-mouse CD11b for 30 minutes on ice in the dark. Cells were then washed twice in FACS buffer (PBS+2% FBS), and flow cytometry was performed on a BD FACS Canto II. Data were analyzed using FlowJo software.

In addition to anti-MerTK antibodies of the present disclosure, the following anti-MerTK antibodies were also used in these efferocytosis studies: rat anti-mouse MerTK antibody DS5MMER (eBioscience, Clone ID DS5MMER, rat IgG2a), mouse anti-human MerTK antibody H1 (BioLegend, Clone ID: 590H11G1E3, mouse IgG1), mouse anti-human MerTK antibody H2 (R&D systems, Clone ID: 125518, mouse IgG2b), mouse anti-human MerTK antibody H3 (R&D systems, Clone ID 125508, mouse IgG2b), mouse anti-human MerTK antibody H6 (eBioscience, Clone ID: A3KCAT, mouse IgG1), mouse anti-human MerTK antibody H7 (Sino Biological, Clone ID: 09, Mouse IgG2b), human anti-human MerTK antibody M6 (disclosed in WO2016/106221, huIgG1 LALAPS), and human anti-human MerTK antibody CDX AB2000-A7 (disclosed in WO2019/084307, huIgG1).

In these experiments, efferocytosis-positive macrophages were identified by setting pHrodo CD14 double positive cells as an analysis gate and then applying this exact gate to all the samples. Baseline efferocytosis levels were established using macrophages cultured with media alone and this was set to 1000 efferocytosis activity. Relative efferocytosis levels were calculated as a percent of efferocytosis observed in cells treated with media alone compared to that observed in cells treated with anti-MerTK antibodies.

In comparison to macrophages in the absence of antibody (media alone treatment), no significant change in efferocytosis with isotype control human IgG1 LALAPS, mouse IgG1, or mouse IgG2b was observed.

Efferocytosis blocking studies were performed by addition of 10 μg/ml of recombinant anti-MerTK antibody of the present disclosure to the macrophages. Table 6 and Table 7 show 00 efferocytosis of anti-MerTK antibodies of the present disclosure on efferocytosis activity by macrophages obtained from various human donors.

TABLE 6

| Antibody | % Efferocytosis at 10 µg/mL | | |
|---|---|---|---|
| | donor 922 | donor 923 | donor 924 |
| MTK-01 | 14.45 | 12.45 | 18.20 |
| MTK-02 | 4.27 | 8.11 | 6.59 |
| MTK-03 | 11.64 | 14.51 | 14.55 |
| MTK-04 | 21.24 | 15.71 | 20.20 |
| MTK-05 | 34.72 | 27.78 | 47.61 |
| MTK-06 | 14.41 | 10.71 | 13.79 |
| MTK-07 | 11.98 | 14.35 | 15.75 |
| MTK-08 | 9.51 | 11.25 | 10.86 |
| MTK-09 | 9.42 | 17.54 | 16.06 |
| MTK-10 | 2.55 | 5.00 | 3.84 |
| MTK-11 | 5.99 | 6.56 | 6.10 |
| MTK-12 | 5.78 | 0.57 | 3.85 |
| MTK-13 | 4.04 | 8.03 | 5.43 |
| MTK-14 | 8.67 | 12.53 | 11.03 |
| MTK-15 | 5.57 | 8.30 | 8.50 |
| MTK-16 | 1.79 | 2.68 | 1.40 |
| MTK-17 | 3.43 | 4.35 | 3.98 |
| MTK-18 | 3.33 | 2.91 | 2.92 |
| MTK-19 | 4.31 | 4.15 | 3.41 |
| MTK-20 | 4.08 | 4.42 | 4.13 |
| MTK-21 | 4.08 | 3.13 | 3.28 |
| MTK-22 | 4.94 | 1.65 | 4.29 |
| MTK-23 | 3.12 | 3.83 | 3.98 |
| huIgG1 LALAPS | 114.35 | 96.22 | 131.70 |
| muIgG1 | 119.37 | 101.26 | 97.44 |
| muIgG2b | 121.88 | 111.35 | 112.12 |
| M6 | 4.52 | 1.04 | 1.22 |
| H1 | 7.87 | 21.38 | 23.36 |
| H2 | 8.96 | 13.50 | 16.60 |
| H3 | 88.8 | 111.35 | 104.56 |
| H6 | 103.04 | 119.11 | 124.14 |
| H7 | 108.9 | 100.1 | 99.22 |

TABLE 7

| Antibody | % Efferocytosis at 10 µg/mL | |
|---|---|---|
| | donor 930 | donor 929 |
| MTK-24 | 26.16 | 11.29 |
| MTK-25 | 30.93 | 41.66 |
| MTK-26 | 23.85 | 13.07 |
| MTK-27 | 35.26 | 17.57 |
| MTK-28 | 33.40 | 19.38 |
| MTK-29 | 41.75 | 20.49 |
| MTK-30 | 38.66 | 20.36 |
| MTK-31 | 22.59 | 18.02 |
| MTK-32 | 48.56 | 28.05 |
| MTK-33 | 24.90 | 21.63 |
| MTK-35 | 30.03 | 19.52 |
| MTK-36 | 21.68 | 21.43 |
| Media | 96.49 | 93.73 |
| M6 | 21.49 | 13.17 |
| H1 | 24.09 | 14.31 |

As shown in Table 6 and Table 7 above, anti-MerTK antibodies of the present disclosure reduced or decreased efferocytosis by human macrophages (e.g., reduced efferocytosis by about 50% to about 98%). Although the efferocytosis blocking activity by anti-MerTK antibodies was different depending on donors, there was a general trend of each antibody.

Figure 4:
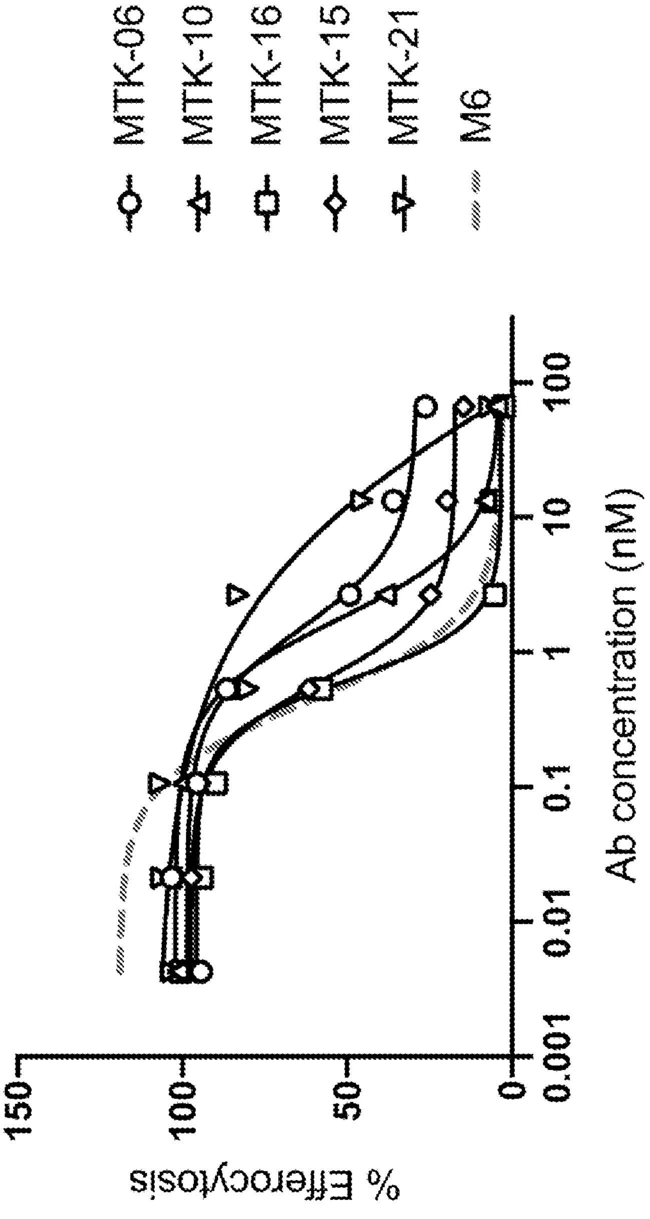
FIG. 4 sets forth data showing the effect of anti-MerTK antibodies of the present disclosure on reducing efferocytosis in human macrophages.
Figure 5:
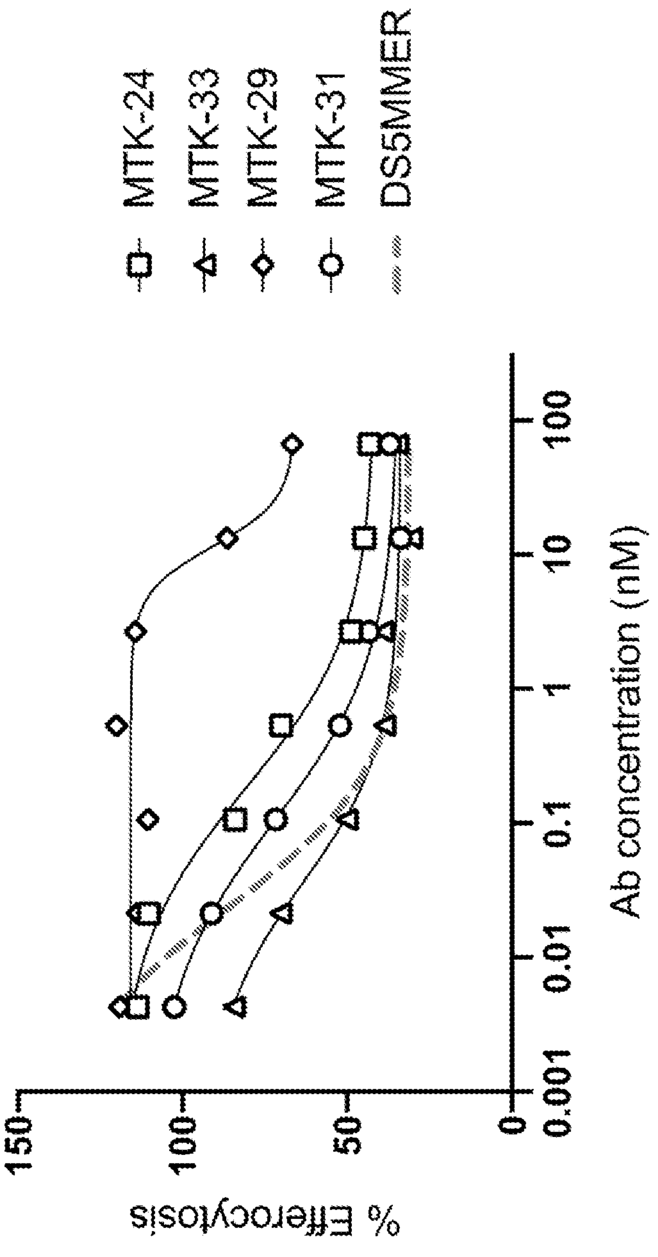
FIG. 5 sets forth data showing the effect of anti-MerTK antibodies of the present disclosure on reducing efferocytosis in mouse bone marrow-derived macrophages.

FIG. 4 and FIG. 5 shows efferocytosis blocking results of exemplary anti-MerTK antibodies of the present disclosure. As shown in FIG. 4, anti-MerTK antibodies MTK-06, MTK-10, MTK-15, MTK-16, and MTK-21 of the present disclosure inhibited efferocytosis of apoptotic cells by human macrophages in a dose dependent manner. These results indicated that anti-MerTK antibodies of the present disclosure are effective at reducing or decreasing efferocytosis activity by human macrophages.

As shown in FIG. 5, anti-MerTK antibodies MTK-24, MTK-29, MTK-31, and MTK-33 of the present disclosure inhibited efferocytosis of apoptotic cells by mouse bone marrow derived macrophages in a dose dependent manner. These results indicated that anti-MerTK antibodies of the present disclosure are effective at reducing or decreasing efferocytosis activity by mouse bone marrow derived macrophages.

Table 8 below shows IC50 values of anti-MerTK antibodies of the present disclosure for reducing or decreasing efferocytosis by human macrophages with a range of IC50 values. As shown in Table 8, anti-MerTK antibodies of the present disclosure reduced or decreased efferocytosis by human macrophages with an IC50 range of about 1.2 nM to about 28 nM.

TABLE 8

| Antibody | Efferocytosis IC50 (nM) donor 940 |
|---|---|
| MTK-01 | 6.91 |
| MTK-02 | 1.20 |
| MTK-03 | 14.16 |
| MTK-05 | 28.12 |
| MTK-06 | 0.77 |
| MTK-08 | 1.31 |
| MTK-10 | 1.45 |
| MTK-11 | 1.36 |
| MTK-13 | 4.90 |
| MTK-14 | 1.79 |
| MTK-15 | 0.86 |
| MTK-16 | 0.80 |
| MTK-17 | 7.76 |
| MTK-18 | 1.53 |
| MTK-19 | 10.50 |
| MTK-20 | 1.42 |
| MTK-21 | 14.11 |
| MTK-22 | 16.62 |
| M6 | 0.56 |

Table 9 and Table 10 show IC50 values of anti-MerTK antibodies of the present disclosure on efferocytosis activity by mouse macrophages and macrophages obtained from various human donors.

TABLE 9

| Antibody | Efferocytosis IC50 (nM) | | |
|---|---|---|---|
| | donor 673 | donor 960 | Mouse Mac |
| MTK-24 | 3.89 | 1.09 | 0.18 |
| MTK-26 | 0.54 | 0.43 | — |
| MTK-27 | 0.71 | 0.21 | — |
| MTK-28 | 0.15 | 0.08 | — |
| MTK-29 | 0.33 | 0.23 | 11.5 |
| MTK-30 | 0.45 | 0.13 | 0.10 |
| MTK-31 | 8.447 | 1.42E+24* | — |
| MTK-32 | 29.95 | 7.04 | — |
| MTK-33 | 0.25 | 0.33 | 0.03607 |
| MTK-35 | 19856 | 3.70 | — |
| MTK-36 | 0.41 | 0.44 | — |
| M6 | 0.11 | 0.12 | |

TABLE 9-continued

| | Efferocytosis IC50 (nM) | | |
|---|---|---|---|
| Antibody | donor 673 | donor 960 | Mouse Mac |
| CDX AB2000-A7 | n.a | 0.09402 | |
| DS5MMER | n.a | — | 0.02361 |

n.a. means data not available
*indicates aberrant value

TABLE 10

| | [nM] | | | |
|---|---|---|---|---|
| Antibody | donor 993 | donor 996 | donor 896 | donor 897 |
| MTK-09 | 0.3418 | 0.7776 | 0.712 | 0.603 |
| MTK-23 | 0.1518 | 0.365 | 0.600 | 0.488 |
| MTK-25 | 0.1125 | 0.1584 | n.a | n.a |
| MTK-27 | 0.3386 | 0.5349 | n.a | n.a |
| MTK-31 | 0.9309 | 5.551 | n.a | n.a |
| MTK-36 | 0.128 | 0.2313 | n.a | n.a |
| CDX AB2000-A7 | 0.1099 | 0.2517 | n.a | n.a |
| H1 | 0.4212 | 1.905 | 1.631 | 0.847 |
| H2 | 0.6921 | 1.474 | n.a | n.a |
| M6 | 0.04335 | 0.1086 | 0.222 | 0.213 |

n.a. means data not available

As shown in Table 8, Table 9, and Table 10 above, anti-MerTK antibodies of the present disclosure were effective at reducing efferocytosis by human macrophages and mouse macrophages. Additionally, these results showed that anti-MerTK antibodies of the present disclosure reduced efferocytosis by human macrophages at an IC50 of about 0.13 nM to about 30 nM.

Example 12: Anti-MerTK Antibodies Bind to SK-MEL-5 Cells and CHO-muMerTK OE Cells To determine whether recombinant anti-human MerTK antibodies of the present disclosure bind to human MerTK endogenously expressed on SK-MEL-5 cells and to CHO cells overexpressing mouse MerTK (CHO-muMerTK OE cells), the following experiments were performed. SK-MEL-5 cells and CHO-muMerTK OE cells were plated at 40,000 cells/well. Anti-MerTK antibodies were titrated to a final concentration range of between 66.6 nM to 4 pM and then added to the cells. After 30 min on ice, cells were washed and then stained with APC-conjugated mouse anti-human Kappa antibody (Southern Biotech Cat #9230-11, Birmingham, AL) and a viability die (Life Technologies) in the presence of Fc block solution on ice for 30 minutes, and then washed twice with cold FACS buffer (2% FBS in PBS). Cells were fixed with 4% paraformaldehyde in PBS. Stained cells were acquired on a BD FACS Canto II cytometer and the mean fluorescence intensity (MFI) was calculated with Flowjo software and K value was calculated with Prism software. Kd values in these results are similar to EC50 values but are calculated by Prism software from data generated by FACS analysis. A lower Kd value reflects higher binding of antibody to cells.

Figure 6:
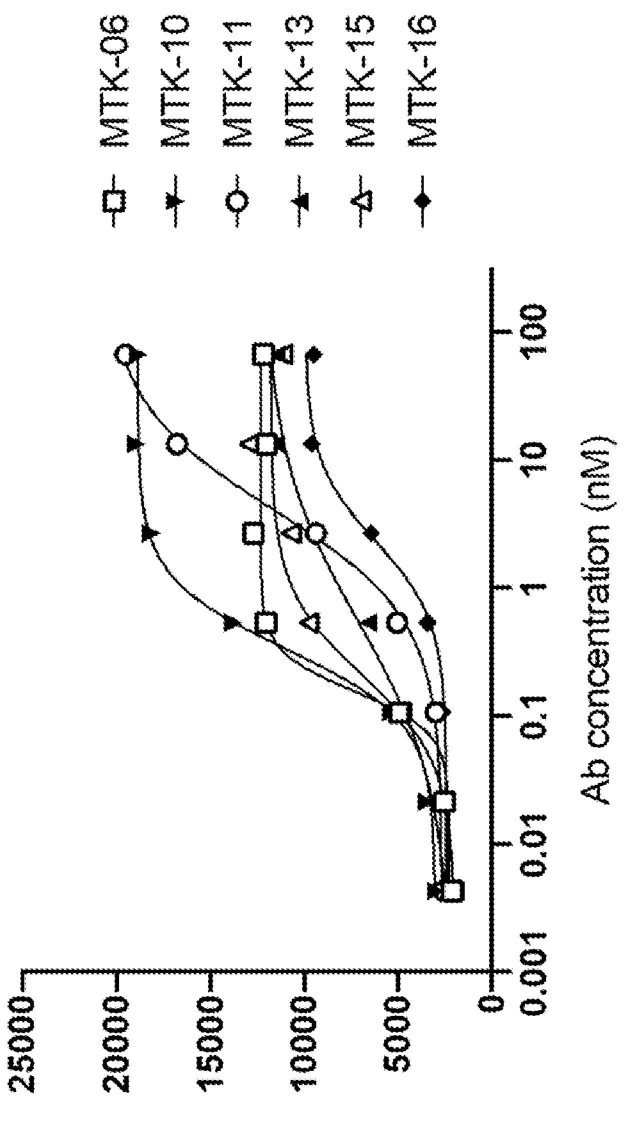
FIG. 6 sets forth data showing anti-MerTK antibodies of the present disclosure bind SK-MEL-5 cells.

FIG. 6 shows anti-human MerTK antibodies MTK-06, MTK-10, MTK-11, MTK-13, MTK-15, and MTK-16 bind to MerTK endogenously expressed on SK-MEL-5 in a dose dependent manner.

Table 11, Table 12, and Table 13 below show Kd values from FACS analysis of anti-MerTK antibodies binding to SK-MEL-5 cells (Table 11 and Table 12) and to CHO-muMerTK-OE cells (Table 13).

TABLE 11

| Antibody | FACS Kd value (nM) |
|---|---|
| MTK-01 | 0.049 |
| MTK-02 | 0.024 |
| MTK-03 | 2.64 |
| MTK-04 | 0.037 |
| MTK-06 | 0.005 |
| MTK-07 | 3.21 |
| MTK-08 | 0.079 |
| MTK-10 | 0.076 |
| MTK-11 | 3.54 |
| MTK-12 | 0.009 |
| MTK-13 | 0.68 |
| MTK-14 | 0.021 |
| MTK-15 | 0.19 |
| MTK-16 | 1.66 |
| MTK-17 | 12.68 |
| MTK-18 | 0.38 |
| MTK-19 | 3.07 |
| MTK-20 | 0.11 |
| MTK-21 | 23.36 |
| MTK-22 | 2.78E−06* |
| M6 | 0.27 |
| H1 | 0.22 |
| H2 | 0.03 |

*indicates aberrant value

TABLE 12

| Antibody | FACS Kd value (nM) |
|---|---|
| MTK-24 | 0.59 |
| MTK-26 | 1.38 |
| MTK-27 | 2.55 |
| MTK-28 | 0.52 |
| MTK-29 | 0.14 |
| MTK-30 | 0.47 |
| MTK-31 | 2.311E−11* |
| MTK-32 | 0.40 |
| MTK-33 | 0.93 |
| MTK-35 | 1.29 |
| MTK-36 | 1.42 |
| M6 | 5.302E−13* |
| CDX AB2000-A7 | 0.19 |
| H1 | 0.06436 |
| H2 | 2.455E−08* |

*indicates aberrant value

TABLE 13

| Antibody | FACS Kd value (nM) |
|---|---|
| MTK-24 | 0.22 |
| MTK-29 | 5.22 |
| MTK-30 | 0.24 |
| MTK-31 | 2.913 |
| MTK-32 | 2.455E−08* |
| MTK-33 | 0.53 |

*indicates aberrant value

Anti-MerTK antibodies binds to SK-MEL-5 or CHO-muMerTK overexpressing cells in a dose dependent manner with Kd value in the picomolar to nanomolar range. Anti-MerTK antibody such as MTK-06 or MTK-12 showed better binding to SK-MEL-5 compared to M6 antibody. Data in Tables 11, 12, and 13 above also show that anti-MerTK antibodies MTK-24, MTK-29, MTK-30, MTK-31, and MTK-33 bind to human MerTK endogenously expressed on human SK-MEL-5 cells and to murine MerTK recombinantly expressed in CHO cells.

Example 13: Anti-MerTK Antibody Blocking of Ligand Gas6 and Ligand ProS Binding to MerTK To determine the ligand blocking activity of anti-MerTK antibodies of the present disclosure, ligand blocking assays was performed to test whether a given anti-MerTK antibody blocks binding of ligand Gas6 or ligand ProS to human MerTK.

Rabbit anti-human IgG polyclonal antibody (Jackson ImmunoResearch, Cat #309-005-008) was captured to a high-protein binding plate at 2 g/ml 4° C. overnight. After washing with 0.05% Tween20 in PBS three times, 5% BSA in PBS was added for 1 hour. Recombinant human MerTK human Fc Chimera protein (R&D systems, Cat #391-MR-100) was added at 2 g/ml for 1 hour and the plates were then washed. Anti-MerTK antibodies were titrated to final concentration range of between 66.6 nM to 4 pM and then 40 µl of serially diluted antibody and 40 µl of His tag-conjugated recombinant Gas6 protein (R&D systems, Cat #885-GSB-050) at 3 g/ml or His tag-conjugated recombinant ProS protein (R&D systems, Cat #9489-PS-100) at 20 g/ml. After a further incubation for 1 hour, plates were washed and incubated for 1 hour with HRP-conjugated anti-6× His tag antibody (Abcam, Cat #ab1187). Plates were then washed and an HRP substrate (TMB) was used to develop the plates. After sufficient color change was observed, the reaction was stopped by adding 50 µl 2N $H_2SO_4$ and the OD was measured using a spectrophotometer (BioTek).

Figure 7:
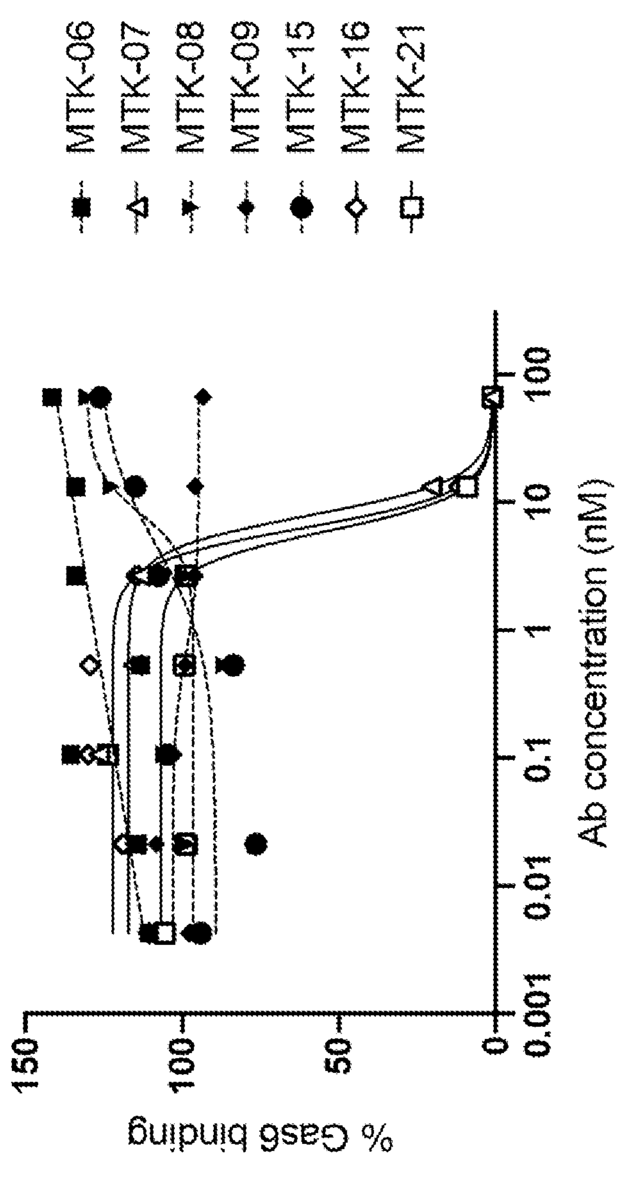
FIG. 7 sets forth data showing anti-MerTK antibodies of the present disclosure blocked Gas6 ligand binding to human MerTK in a dose-dependent manner.

FIG. 7 shows that exemplary anti-MerTK antibodies of the present disclosure (MTK-07, MTK-16, and MTK-21) inhibited (e.g., blocked) Gas6 ligand binding to human MerTK in a dose dependent manner. As shown in FIG. 7, anti-MerTK antibodies MTK-06, MTK-08, MTK-09, and MTK-15 did not block Gas6 ligand binding to human MerTK.

Figure 8:
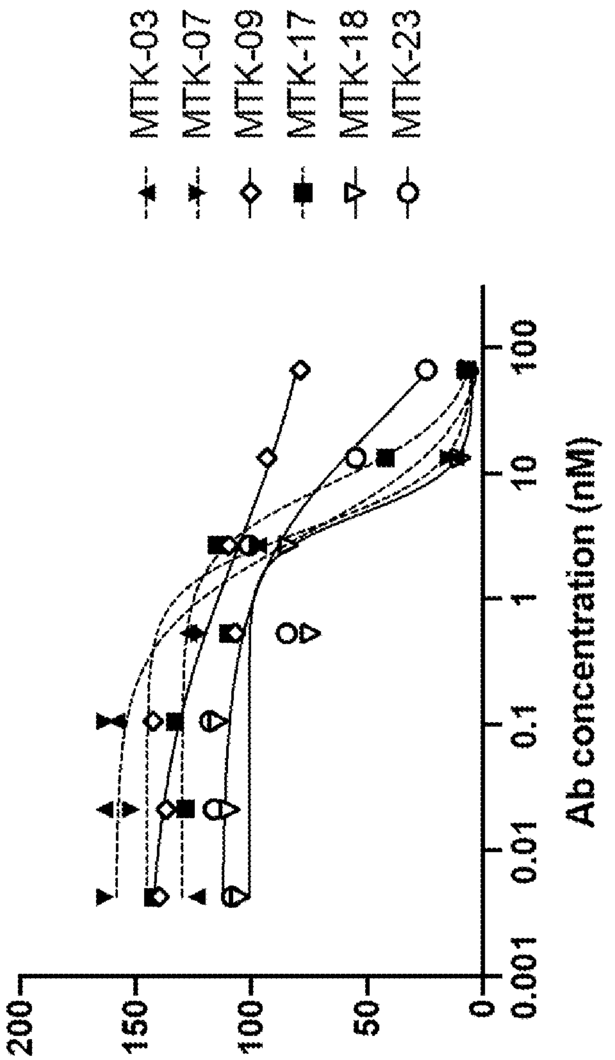
FIG. 8 sets forth data showing anti-MerTK antibodies of the present disclosure blocked ProS ligand binding to human MerTK in a dose-dependent manner.

FIG. 8 shows that exemplary anti-MerTK antibodies of the present disclosure (MTK-03, MTK-07, MTK-09, MTK-17, MTK-18, and MTK-23) inhibited (e.g., blocked) ProS ligand binding to human MerTK in a dose dependent manner.

From these experiments, IC50 values [nM] were determined using OD450 values obtained from the dose-response curves analyzed with Prism software. Table 14 and Table 15 show IC50 values determined for anti-MerTK antibody blocking of Gas6 ligand binding and ProS ligand binding to MerTK. Anti-MerTK antibody MTK-22 did not block Gas6 ligand binding or ProS ligand biding to MerTK; however, anti-MerTK antibody MTK-22 was effective at reducing efferocytosis as shown in Examples above. Dashes indicate lack of significant blocking; "n.a." indicates data not available.

TABLE 14

| Antibody | Gas6 ligand blocking IC50 | ProS ligand blocking IC50 |
|---|---|---|
| MTK-01 | — | 2.85 |
| MTK-02 | — | 3.94 |
| MTK-03 | 8.53 | 3.65 |
| MTK-04 | — | 12.81 |
| MTK-05 | — | 6.51 |
| MTK-06 | — | 2.17 |
| MTK-07 | 7.97 | 3.27 |
| MTK-08 | — | 3.80 |
| MTK-09 | — | 7.84 |
| MTK-10 | 32.38 | 3.80 |
| MTK-11 | — | 24.24 |
| MTK-12 | 25.97 | 3.36 |
| MTK-13 | 18.93 | 3.76 |
| MTK-14 | n.a. | 7.61 |
| MTK-15 | — | 4.20 |
| MTK-16 | 6.32 | 8.59 |
| MTK-17 | 14.47 | 8.35 |
| MTK-18 | 4.22 | 4.76 |
| MTK-19 | n.a. | 11.27 |
| MTK-20 | 4.96 | 5.16 |
| MTK-21 | 5.98 | 13.50 |
| MTK-23 | — | 25.92 |

TABLE 15

| Antibody | Gas6 blocking IC50 | ProS blocking IC50 |
|---|---|---|
| MTK-24 | 0.74 | 0.5792 |
| MTK-26 | 2.93 | 1.203 |
| MTK-27 | 1.42 | 2.543 |
| MTK-28 | — | 2.781 |
| MTK-29 | — | 2.664 |
| MTK-30 | 1.26 | 1.572 |
| MTK-31 | 1.29 | 1.51E+15* |
| MTK-32 | — | 2.781 |
| MTK-33 | n.a. | 0.6005 |
| MTK-35 | 0.31 | 0.924 |
| MTK-36 | 0.29 | 1.402 |
| M6 | 0.28 | 1.339 |
| CDX AB2000-A7 | 0.49 | 2.514 |
| H1 | — | 2.513 |

*indicates aberrant value

In these studies, thirty-five (35) anti-MerTK antibodies of the present disclosure were tested for their ability to block Gas6 ligand binding and/or ProS ligand binding to human MerTK. Nineteen (19) anti-MerTK antibodies of the present disclosure (MTK-03, MTK-07, MTK-10, MTK-12, MTK-13, MTK-16, MTK-17, MTK-18, MTK-20, MTK-21, MTK-24, MTK-25, MTK-26, MTK-27, MTK-30, MTK-31, MTK-33, MTK-35, and MTK-36) blocked the binding of both ProS ligand and Gas6 ligand to recombinant human MerTK protein (herein referred to as ProS/Gas6 double blockers); fifteen (15) anti-MerTK antibodies of the present disclosure (MTK-01, MTK-02, MTK-04, MTK-05, MTK-06, MTK-08, MTK-09, MTK-11, MTK-14, MTK-15, MTK-19, MTK-23, MTK-28, MTK-29, MTK-32) blocked ProS ligand binding (but did not block Gas6 ligand binding) to recombinant human MerTK (herein referred to as ProS specific blockers). Anti-MerTK antibody MTK-22 did not block either ProS ligand or Gas6 ligand binding to recombinant human MerTK protein as measured in this assay; however, anti-MerTK antibody MTK-22 was effective at reducing efferocytosis as shown in Examples above. Anti-MerTK antibody M6 and anti-MerTK antibody CDX AB2000-A7 displayed ProS ligand and Gas6 ligand blocking. Anti-MerTK antibody H1 and anti-MerTK antibody H2 displayed ProS ligand blocking only; neither of these antibodies displayed Gas6 ligand blocking.

These results suggested that anti-MerTK antibodies of the present disclosure can selectively modulate Gas6 and ProS binding to MerTK and can selectively modulate Gas6 and ProS activity.

Example 14: Binding Kinetics of Anti-MerTK Antibodies

Binding kinetics of human anti-MerTK IgG1 LALAPS antibodies of the present disclosure to human, cyno, and murine MerTK were evaluated using a Carterra LSA instrument (Carterra, Salt Lake City, UT). Briefly, anti-MerTK antibodies were prepared by diluting to 10 μg/ml in 10 mM Acetate, pH 4.25 (Carterra), at 300 μl/well. A HC200M sensor chip (Carterra) was activated using the single channel flow cell with a 7-minute injection of a 1:1:1 mixture of 100 mM MES pH 5.5, 100 mM sulfo-NHS, 400 mM EDC (all reconstituted in MES pH 5.5; 100 μl of each mixed in vial immediately before running assay). After switching to the multi-channel array flow cell, the antibodies were injected over the activated chip in a 96-spot array for 15 minutes. The remaining unconjugated active groups on the chip were then blocked by injecting 1M Ethanolamine pH 8.5 (Carterra) for 7 minutes using the single channel flow cell.

After priming with running buffer (HBS-TE, Carterra) with 0.5 mg/ml BSA (Sigma), the immobilized anti-MerTK antibodies were tested for their ability to bind to several forms of recombinant MerTK extracellular domain, including human, cynomolgus, and mouse orthologs as described above. Estimates of affinity were generated by injecting each analyte over the entire antibody array using the single channel flow cell. MerTK analytes were diluted to 33.3, 100, and 300 nM in running buffer, and injected in serial from lowest to highest concentration without regeneration. Two buffer blanks were run between each series (one species per series). Data were processed and analyzed using NextGenKIT high-throughput kinetics analysis software (Carterra).

The equilibrium dissociation constants ($K_D$) were then calculated from the fitted association and dissociation rate constants (k-on and k-off) for anti-MerTK antibodies of the present disclosure. Binding kinetic analysis was also performed on anti-MerTK antibodies H1 (BioLegend, Clone ID: 590H11G1E3), H2 (R&D systems, Clone ID: 125518), M6 (WO2016/106221), and CDX AB2000-A7 hIgG1 (WO2019/084307). The $K_D$ values are summarized in Table 16 below.

TABLE 16

| Antibody | $K_D$ (nM) human | $K_D$ (nM) cyno | $K_D$ (nM) mouse |
|---|---|---|---|
| MTK-01 | NF | 99 | NB |
| MTK-02 | 22 | 24 | NB |
| MTK-03 | 54 | 55 | NB |
| MTK-04 | 33 | 44 | NB |
| MTK-05 | 6.7 | NB | NB |
| MTK-06 | 18 | 17 | NB |
| MTK-07 | 43 | 53 | NB |
| MTK-08 | 37 | 42 | NB |
| MTK-10 | 2.0 | 1.9 | NB |
| MTK-11 | 3.0 | 2.9 | NB |
| MTK-12 | 5.3 | NB | NB |
| MTK-13 | 37 | 39 | NB |
| MTK-14 | 45 | 53 | NB |
| MTK-15 | 2.7 | 3.0 | NB |
| MTK-16 | 1.4 | 1.6 | NB |
| MTK-17 | 25 | 24 | NB |
| MTK-18 | 18 | 18 | NB |
| MTK-19 | 2.4 | 12 | 130 |
| MTK-20 | 9.3 | 9.2 | NB |
| MTK-21 | 40 | 43 | NB |
| MTK-22 | 54 | LB | NB |
| MTK-24 | 41 | 44 | 55 |
| MTK-26 | 30 | 30 | NB |
| MTK-27 | 71 | 71 | NB |

TABLE 16-continued

| Antibody | $K_D$ (nM) human | $K_D$ (nM) cyno | $K_D$ (nM) mouse |
|---|---|---|---|
| MTK-28 | 4.1 | 4.5 | NB |
| MTK-30 | 23 | 24 | 30 |
| MTK-31 | 81 | 91 | 165 |
| MTK-32 | 59 | 107 | 186 |
| MTK-33 | 6.5 | 6.6 | 75 |
| MTK-35 | 14 | 13 | NB |
| MTK-36 | 6.4 | 5.9 | NB |
| CDX AB2000-A7 | 38 | 52 | NB |
| H1 | 7.2 | 6.8 | NB |
| H2 | 18 | 18 | NB |
| H3 | 151 | LB | NB |
| H6 | 26 | 116 | NB |
| H7 | 6.1 | 10 | NB |
| M6 | 5.6 | 5.4 | NB |

NB = No binding; LB = Low binding; NF = No fit, meaning the data obtained did not fit a 1:1 binding equilibrium model.

These results showed that anti-MerTK antibodies of the present disclosure showed a range of affinities to MerTK and species binding specificity. In particular, affinity of anti-MerTK antibodies of the present disclosure for binding to human MerTK ranged from 1.4 nm to 81 nM; affinity of anti-MerTK antibodies of the present disclosure for binding to cyno MerTK ranged from 1.6 nm to 107 nM; and affinity of anti-MerTK antibodies of the present disclosure for binding to murine MerTK ranged from 30 nM to 186 nM.

Example 15: Cross-Reactivity of Anti-MerTK Antibodies to Human, Cyno, and Mouse MerTK Species cross-reactivity of anti-MerTK antibodies of the present disclosure was determined from the binding kinetic analysis data described above. The results of species binding cross-reactivity analysis are shown below in Table 17.

TABLE 17

| Human MerTK Reactive | Human-Cyno MerTK Cross Reactive | Human-Mouse MerTK Cross Reactive |
|---|---|---|
| MTK-05<br>MTK-12 | MTK-01, MTK-02, MTK-03, MTK-04, MTK-06, MTK-07, MTK-08, MTK-09, MTK-10, MTK-11, MTK-13, MTK-14, MTK-15, MTK-16, MTK-17, MTK-18, MTK-19, MTK-20, MTK-21, MTK-22, MTK-24, MTK-26, MTK-27, MTK-28, MTK-30, MTK-31, MTK-32, MTK-33, MTK-34, MTK-35, MTK-36<br>CDX AB2000-A7, H1, H2, H7, M6<br>Weak cross reactivity: H3, H6 | MTK-19, MTK-24, MTK-30, MTK-31, MTK-32, MTK-33 |

These binding experiments showed that the majority of the anti-MerTK antibodies of the present disclosure tested showed binding cross-reactivity to both human and cyno MerTK (MTK-01, MTK-02, MTK-03, MTK-04, MTK-06, MTK-07, MTK-08, MTK-09, MTK-10, MTK-11, MTK-13, MTK-14, MTK-15, MTK-16, MTK-17, MTK-18, MTK-19, MTK-20, MTK-21, MTK-22, MTK-24, MTK-26, MTK-27, MTK-28, MTK-30, MTK-31, MTK-32, MTK-33, MTK-34, MTK-35, and MTK-36). Two anti-MerTK antibodies of the present disclosure showed specific binding only to human MerTK and did not show binding to cyno or mouse MerTK (antibody MTK-05 and antibody MTK-12). Six anti-MerTK antibodies of the present disclosure tested displayed cross-reactivity to both human and mouse MerTK (MTK-19, MTK-24, MTK-30, MTK-31, MTK-32, and MTK-33). Six anti-MerTK antibodies of the present disclosure tested displayed cross-reactivity to human, cyno, and mouse MerTK (MTK-19, MTK-24, MTK-30, MTK-31, MTK-32, and MTK-33). Additionally, Example 12 above showed that anti-MerTK antibodies MTK-24 and MTK-29 also bind to human and murine MerTK.

Example 16: Epitope Binning Analysis of Anti-MerTK Antibodies

Epitope binning analysis was performed on the anti-MerTK antibodies of the present disclosure by performing a tandem injection approach using a Carterra LSA instrument (Carterra, Salt Lake City, UT). Briefly, hybridoma purified mouse anti-MerTK antibodies of the present disclosure, anti-MerTK antibodies H1, H2, H3, H6, and M6, and anti-his IgG were diluted to 15 μg/ml in 10 mM Acetate, pH 4.75 (Carterra), at 300 μl/well. A second set of samples was prepared by 5-fold dilution of the antibodies to 3 μg/ml in the same buffer. A HC200M sensor chip (Carterra) was activated using the single channel flow cell with a 7-minute injection of a 1:1:1 mixture of 100 mM MES pH 5.5, 100 mM sulfo-NHS, 400 mM EDC (as described above). After switching to the multi-channel array flow cell, the 15 μg/ml dilutions of antibodies were injected over the activated chip in a 96-spot array for 15 minutes. A second array was printed by injection of the 3 μg/ml dilutions of the antibodies in a second 96-spot array. The remaining unconjugated active groups on the chip were then blocked by injecting 1M Ethanolamine pH 8.5 (Carterra) over the entire chip surface for 7 minutes using the single channel flow cell.

After priming with running buffer (HBS-TE, Carterra) containing 0.5 mg/ml BSA (Sigma), the immobilized antibodies were tested for their ability to bind to recombinant human MerTK extracellular domain. Bound MerTK was removed by two 30-second injections of 0.425% phosphoric acid (Carterra). For each cycle, MerTK was injected over the chip, followed by a test antibody diluted to 30 μg/ml in running buffer. Data were processed and analyzed using Epitope high-throughput binning analysis software (Carterra). Antibodies which were able to bind antigen captured by an immobilized antibody were designated as "sandwich" or "pairing" antibodies, and these antibodies were assigned into a different epitope bin from that of the immobilized antibody. A matrix of pairing and non-pairing antibodies was constructed from the binding results of these experiments, which allowed for an epitope bin landscape of the anti-MerTK antibodies to be generated.

Figure 9:
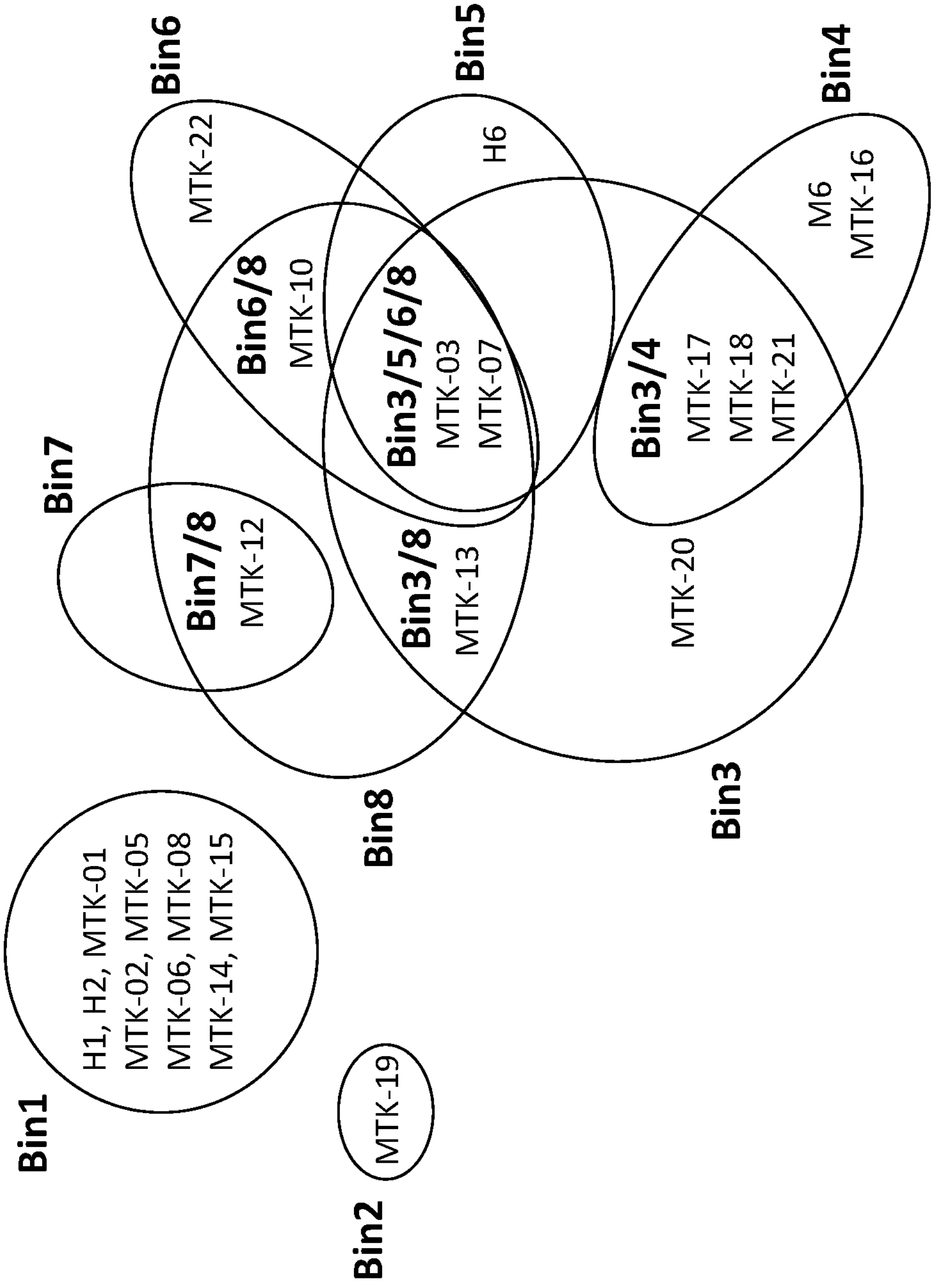
FIG. 9 sets forth data showing epitope binning results of anti-MerTK antibodies of the present disclosure.

The epitope bins identified from these studies for the anti-MerTK antibodies are summarized in FIG. 9. The results showed that most of the ProS ligand-specific blockers belong to Bin 1 group except MTK-19, which is included in Bin 2. Anti-MerTK control antibody H1, a ProS-specific blocker belongs to Bin 1 group. All the ProS/Gas6 double blockers belong to Bin 3 through Bin 8 groups. Some of antibodies recognize partially adjacent epitopes, so have overlapping binning. For example, MTK-03 and MTK-07 have most broad overlapping epitopes of Bin 3, Bin 5, Bin 6, and Bin 8. Anti-MerTK control antibody M6, a ProS/Gas6 double blocker belongs to Bin 4 and H6 belongs to Bin 5 group. These results suggested that ProS and Gas6 may bind to different epitopes or regions on MerTK.

Example 17: Anti-MerTK Antibody Inhibition of Tumor Growth In Vivo

An in vivo efficacy study was performed using MC38 mouse syngeneic colon cancer model to determine the effect of anti-MerTK antibodies on tumor growth. MC38 cells were resuspended at $5\times10^6$ cells/ml in PBS. 100 μl of cells was injected subcutaneously on the shaved right flank of C57BL/6 mice. When tumor size reached approximately 60-100 $mm^3$ in volume, mice were randomized based on tumor volumes into treatment (N=10) or control groups. Treatment groups received 10 mg/kg of control antibodies, 3 mg/kg of anti-PDL1 (clone: BM1) alone, 10 mg/kg of anti-MerTK antibody DS5MMER alone, or 3 mg/kg of anti-PDL1 plus anti-MerTK antibody DS5MMER together. Following the initiation of antibody dosing, mice were weighed, and tumor volume was measured using a caliber twice per week. The study was terminated when tumors in the control group reached approximately 2000 $mm^3$.

Figure 10B:
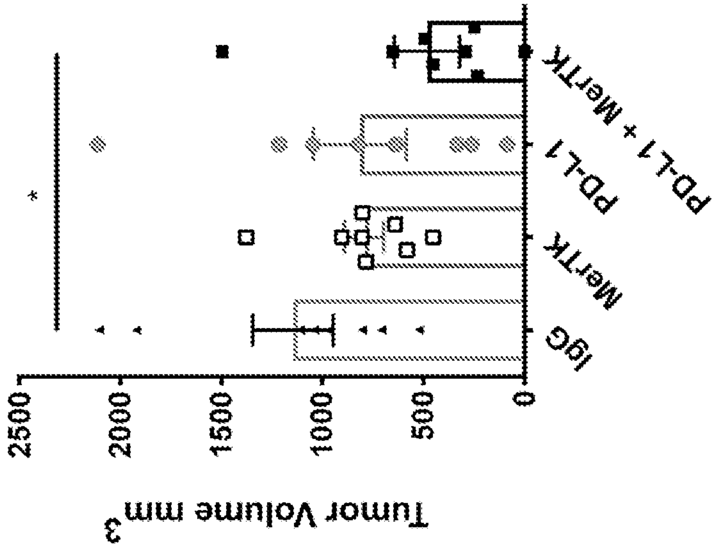
FIGS. 10A and 10B set forth data showing anti-MerTK antibody treatment alone or in combination with anti-PD-L1 antibody treatment reduced tumor growth in vivo.
Figure 10A:
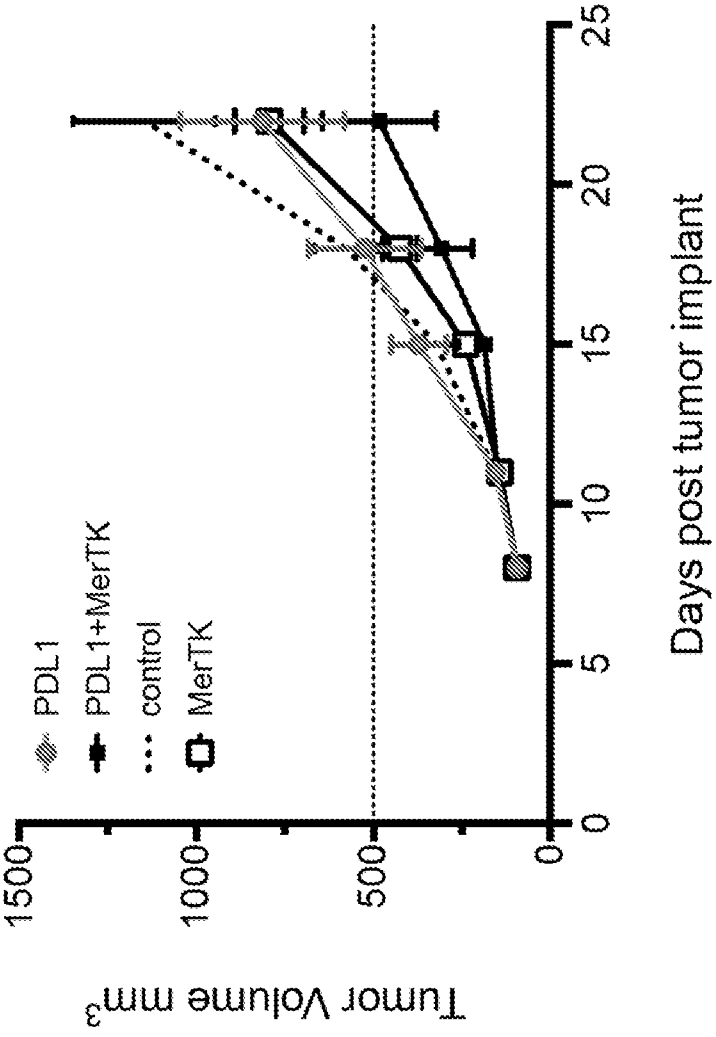
Figure 11A:
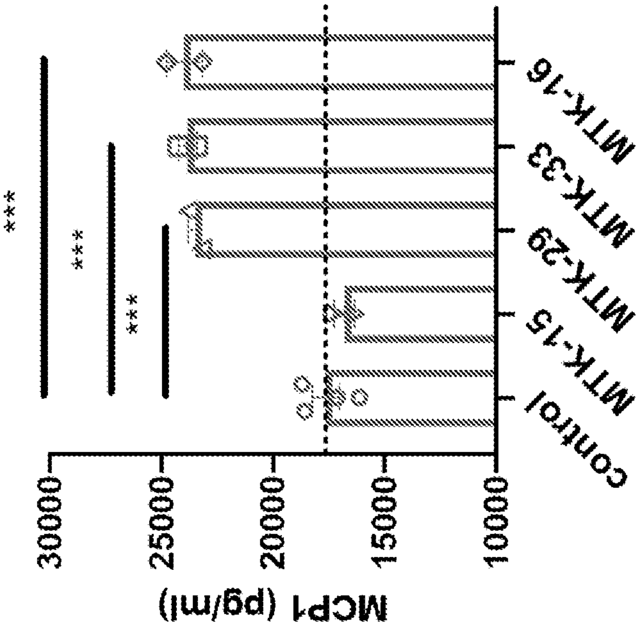
FIGS. 11A, 11B, 11C, and 11D set forth data showing changes in the level of MCP1, MIP-1α, MIP-1, and TNF in human macrophages following overnight treatment with anti-MerTK antibodies of the present disclosure.
Figure 11B:
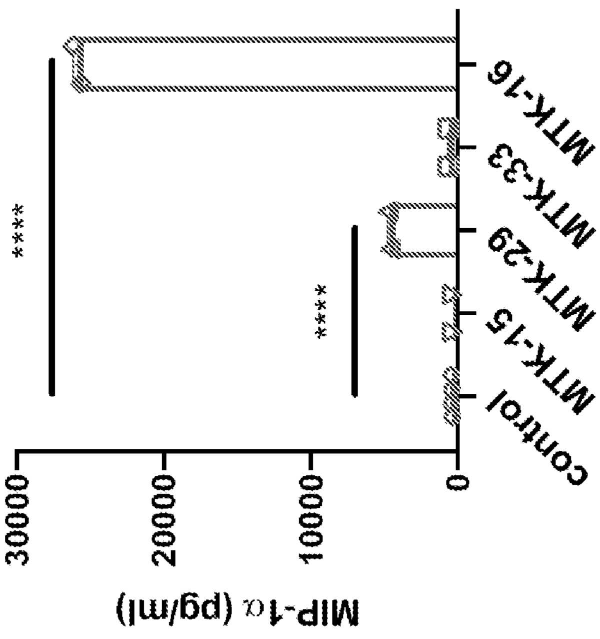
Figure 11C:
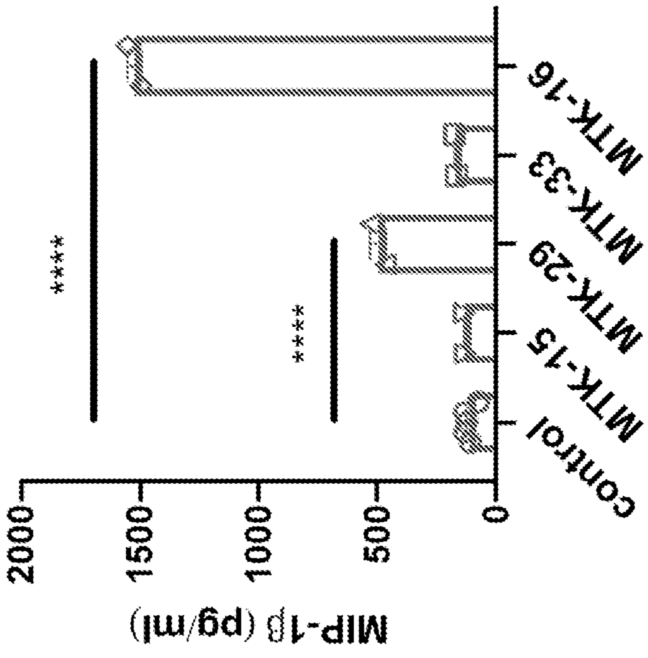
Figure 11D:
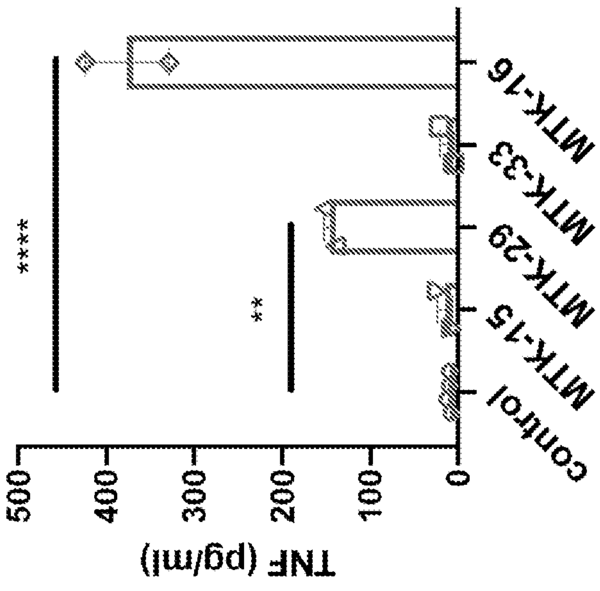

FIGS. 10A and 10B show that either anti-MerTK antibody DS5MMER treatment alone or combination treatment with anti-PDL1 antibody reduced tumor growth in vivo. These results indicated that anti-MerTK antibodies are effective at reducing tumor volume and delaying tumor growth in vivo. These results further showed that anti-MerTK antibodies, when used in combination with an anti-PD-L1 antibody, displayed greater reduction of tumor volume and growth compared to either antibody alone.

Example 18: Modulating Pro-Inflammatory Cytokine Production

The effect of anti-MerTK antibodies on pro-inflammatory cytokine production in myeloid cells was examined as follows. To generate monocyte-derived macrophages and dendritic cells, human primary monocytes were isolated from heparinized human blood (Blood Centers of the Pacific) using RosetteSep Human Monocyte Enrichment Cocktail (STEMCELL Technologies), according to the manufacturer's protocol. Monocytes were seeded in RPMI (Invitrogen) containing 10% Fetal Bovine Serum (Hyclone) and 50 ng/mL IL-4 and GM-CSF (Peprotech) to induce differentiation of dendritic cells or 50 ng/mL M-CSF (Biolegend) to induce differentiation of macrophages. After 6-7 days, dendritic cells or macrophages were harvested by scraping cells. Macrophages or dendritic cells were plated on 96-well plates at $5\times10^4$ cells/well and cultured with 10 g/mL of antibody at 37° C. for overnight. The following day, supernatants were collected and a 13-plex human proinflammatory chemokine and human macrophages/microglia LEGENDplex bead array (BioLegend) was used according to the manufacturer's protocol. All samples were run on BD FACS Canto II and analysis was performed using LEGENDplex analysis software (BioLegend).

FIGS. 11A, 11B, 11C, and 11D show changes in the level of MCP1 (CCL2), MIP-1α(CCL3), MIP-1β (CCL4), and TNF, respectively, from human macrophages following overnight treatment with anti-MerTK antibody MTK-15, MTK-16, MTK-29, or MTK-33. Anti-MerTK antibodies MTK-16 and MTK-29 markedly increased the level of MCP1, MIP-1α, MIP-1P, and TNF in human macrophages. The level of MCP1 significantly increased in response to anti-MerTK antibody MTK-33 compared to that observed upon treatment with control antibody. These results demonstrated that anti-MerTK antibodies MTK-15, MTK-16, MTK-29, and MTK-33 induce pro-inflammatory chemokine or cytokine production in human macrophages in a MerTK-dependent way. These results further showed that anti-MerTK antibodies of the present disclosure are effective at increasing pro-inflammatory cytokines and chemokines in myeloid cells, indicative that anti-MerTK antibodies of the present disclosure are effective at activating myeloid cells (e.g, macrophages). These results also showed that anti-MerTK antibodies of the present disclosure are effective at increasing M1-like macrophage polarization and thus mediating anti-tumor immunity.

Example 19: Effect of Anti-MerTK Antibody Treatment in Colon Cancer In Vivo

The following studies were performed to test the ability of anti-MerTK antibodies of the present disclosure to reduce tumor burden in vivo. In these experiments, 400,000 MC38 mouse colon cancer cells were implanted subcutaneously on the shaved right flank of C57BL/6 mice. When tumor size reached approximately 80-120 $mm^3$ in volume, mice were grouped based on tumor volume to ensure the distribution of starting tumor volume was similar for analyses purposes. Anti-MerTK antibody MTK-29 and MTK33, or control antibody, were administrated via intraperitoneal injection at a dose of 10 mg/kg, twice a week (N=9 per group). At the same time, anti-PDL1 antibody (clone BM1) was administered intraperitoneally at 3 mg/kg to all the treatment groups twice a week. Tumor volume was measured three times per week using a caliber. Mice were humanely euthanized when either tumor volume reached approximately 2000 $mm^3$ or ulceration occurred. Two independent in vivo experiments were performed in these studies.

Figure 12B:
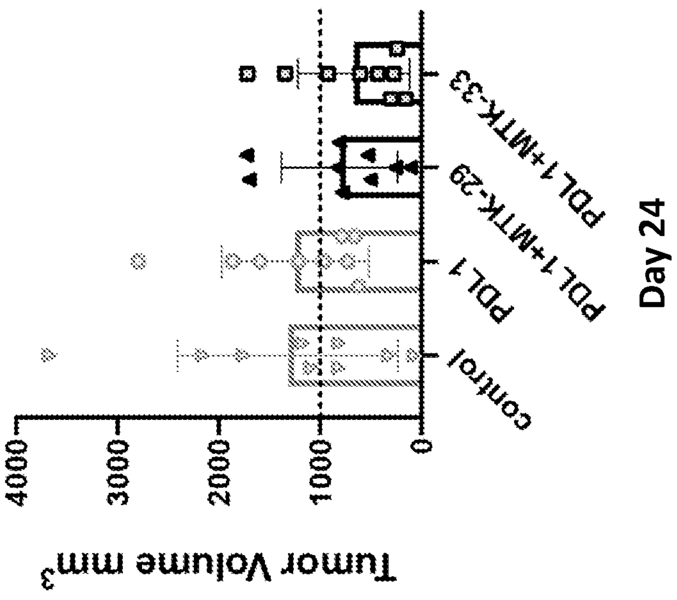
FIGS. 12A and 12B set forth data showing reduced tumor growth in mice administered anti-PDL1 antibody in combination with anti-MerTK antibodies of the present disclosure.
Figure 12A:
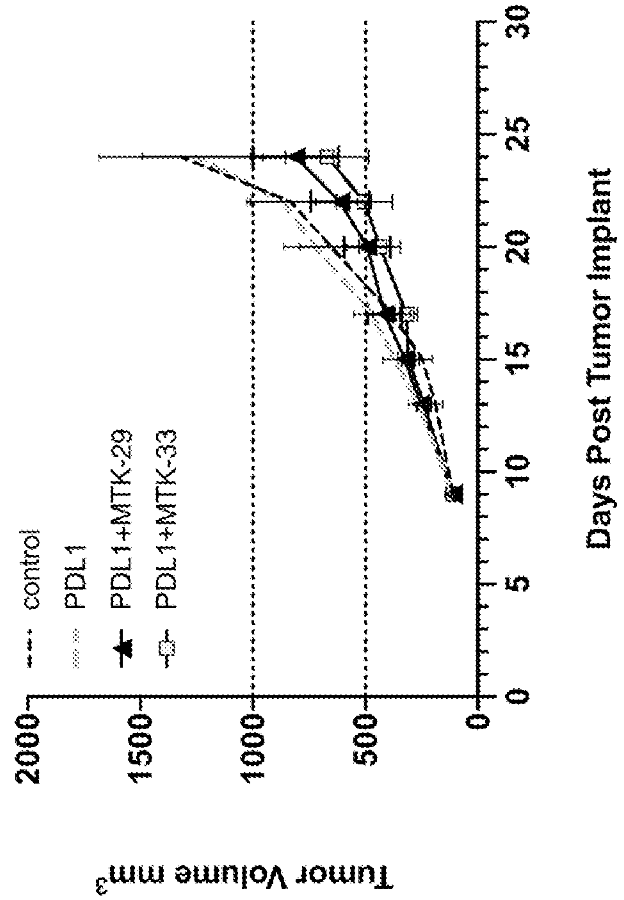

FIG. 12A and FIG. 12B show that treatment of mice with anti-PDL1 antibody and either anti-MerTK antibody MTK-29 or MTK-33 reduced tumor growth rate (shown as tumor volume over time) compared to that observed in mice treated with either anti-PDL1 antibody alone or with control antibody. These results showed that anti-MerTK antibody MTK-29 and MTK-33 are synergistic at reducing tumor volume (reduced tumor growth rate) when administered in combination with anti-PDL1 antibody compared to that observed upon treatment with anti-PDL1 antibody alone.

Figure 13:
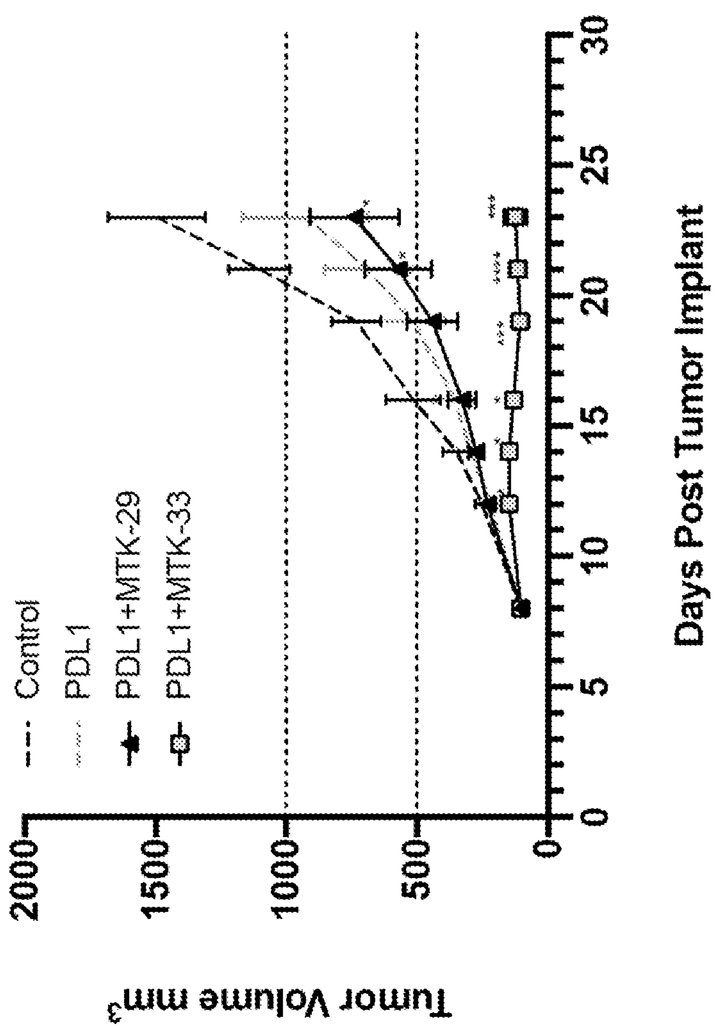
FIG. 13 sets forth data showing reduced tumor growth in mice administered anti-PDL1 antibody in combination with anti-MerTK antibodies of the present disclosure.
Figure 14A:
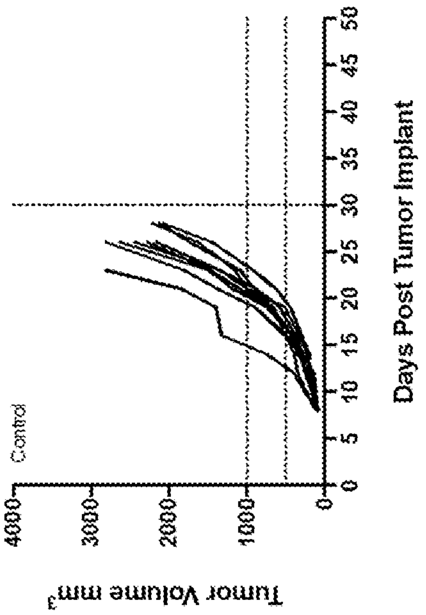
FIGS. 14A, 14B, 14C, and 14D set forth data showing differences in tumor growth rate in mice administered anti-PDL1 antibody in combination with anti-MerTK antibodies of the present disclosure, plotted using a linear scale y-axis.
Figure 14B:
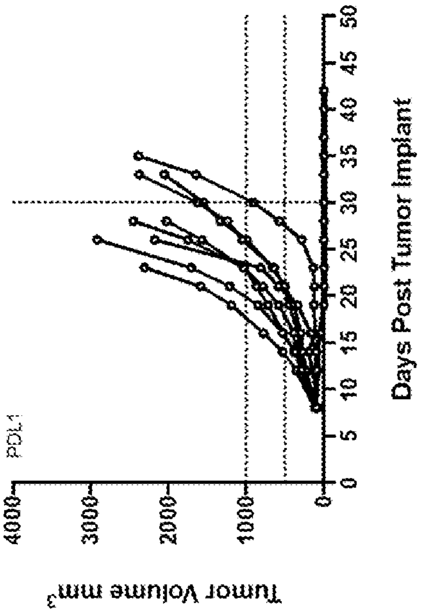
Figure 14C:
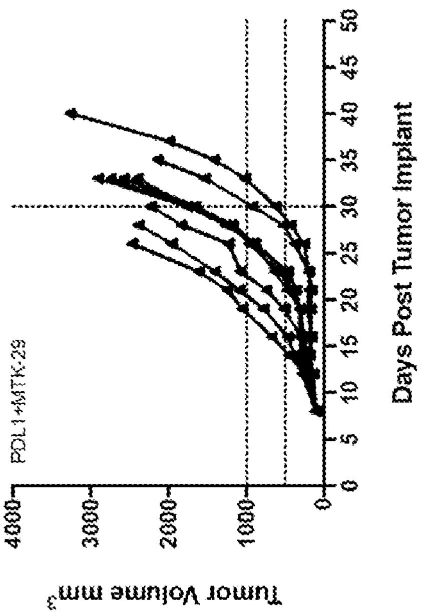
Figure 14D:
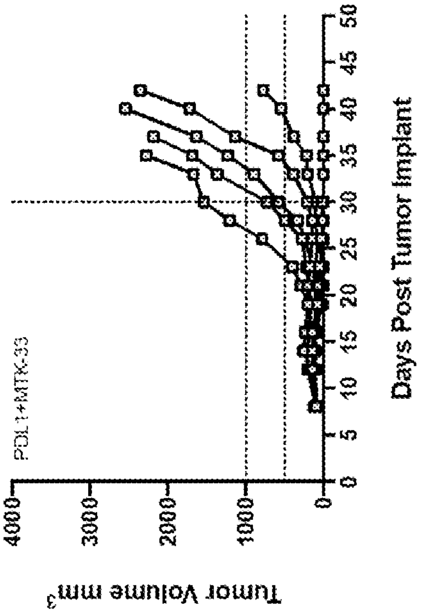
Figure 15A:
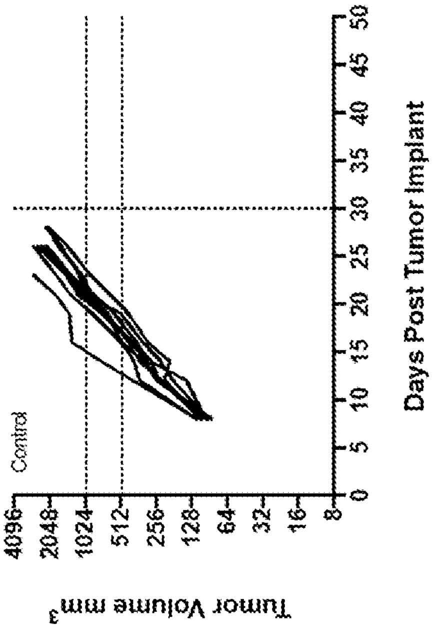
FIGS. 15A, 15B, 15C, and 15D set forth data showing differences in tumor growth rate in mice administered anti-PDL1 antibody in combination with anti-MerTK antibodies of the present disclosure, plotted using a log 2 scale y-axis.
Figure 15B:
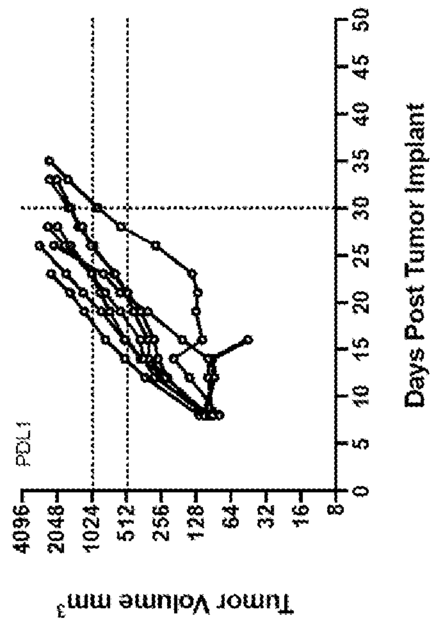
Figure 15C:
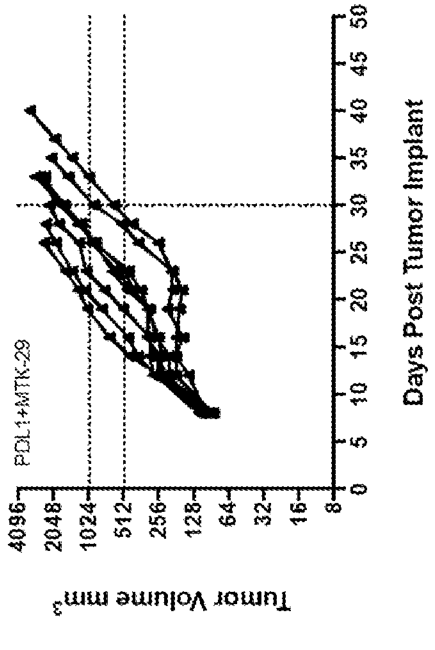
Figure 15D:
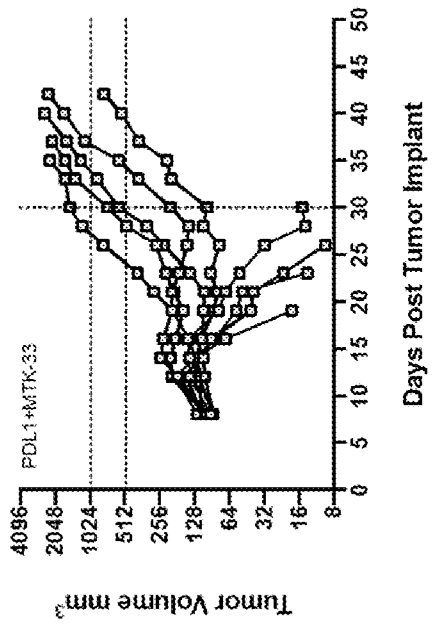

A separate set of in vivo experiments was also performed, using a combination of anti-PDL1 antibody and anti-MerTK antibody MTK-29 or anti-MerTK antibody MTK-33. As shown in FIG. 13, administration of anti-PDL1 antibody lead to reduced tumor volume compared to that observed with control antibody treatment. Administration of a combination of anti-PDL1 antibody and either anti-MerTK antibody MTK-29 or MTK-33 resulted in a greater reduction in tumor volume compared to mice administered anti-PDL1 antibody alone. Specifically, anti-MerTK antibody MTK-29 administered in combination with anti-PDL1 antibody resulted in a significantly greater ($p \leq 0.05$) reduction in tumor growth rate compared to that observed in mice treated with anti-PDL1 antibody alone. Treatment with anti-PDL1 antibody in combination with anti-MerTK antibody MTK-33, in particular, significantly reduced the growth rate of MC38 colon cancer cells in these studies compared to that observed in mice treated with anti-PDL1 antibody alone. Animals treated with 20 mg/kg of anti-MerTK antibody MTK-33 as mono-therapy also showed a reduction in tumor volume compared to that observed in animals treated with control antibody (data not shown).

FIGS. 14A, 14B, 14C, and 14D (as well as FIGS. 15A, 15B, 15C, and 15D) show the differences in tumor growth rate (tumor volume overtime) of individual mice in control, anti-PDL1 antibody alone, anti-PDL1 antibody in combination with anti-MerTK antibody MTK-29, and anti-PDL1 antibody in combination with anti-MerTK antibody MTK-33, respectively. FIGS. 14A, 14B, 14C, and 14D are plotted using a linear scale on the y-axis. FIGS. 15A, 15B, 15C, and 15D are these same results plotted using a Log 2 scale on the y-axis. As shown in these Figures, combination treatment with anti-PDL1 antibody and either anti-MerTK antibody MTK-29 or MTK-33 resulted in near complete regression of tumors in 4 out of 9 mice examined in these studies.

Figure 16:
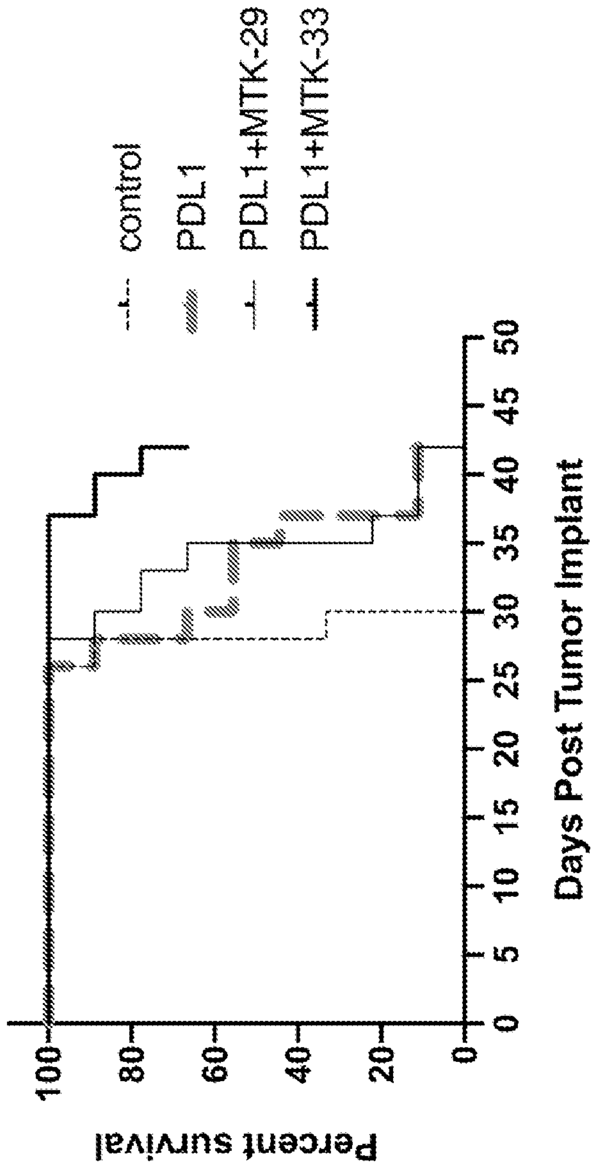
FIG. 16 sets forth data showing survival curves of tumor-bearing mice administered anti-PDL1 antibody in combination with anti-MerTK antibodies of the present disclosure.
Figure 17B:
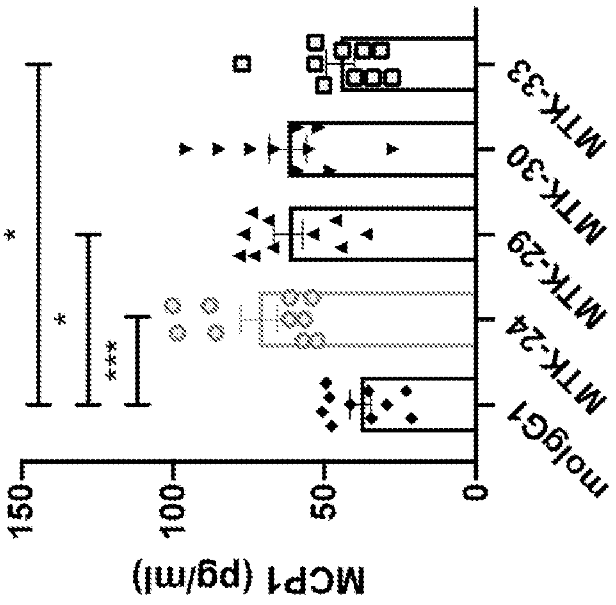
FIGS. 17A, 17B, 17C, 17D, and 17E set forth data showing changes in levels of chemokine (C-X-C motif) ligand 1 (CXCL-1, KC), monocyte chemoattractant protein-1 (MCP1, CCL2), macrophage inflammatory protein-1-alpha (MIP-1α, CCL3), macrophage inflammatory protein-1-beta (MIP-1β, CCL4), and interleukin-6 (IL-6) in plasma from mice following administration of anti-MerTK antibodies of the present disclosure.
Figure 17A:
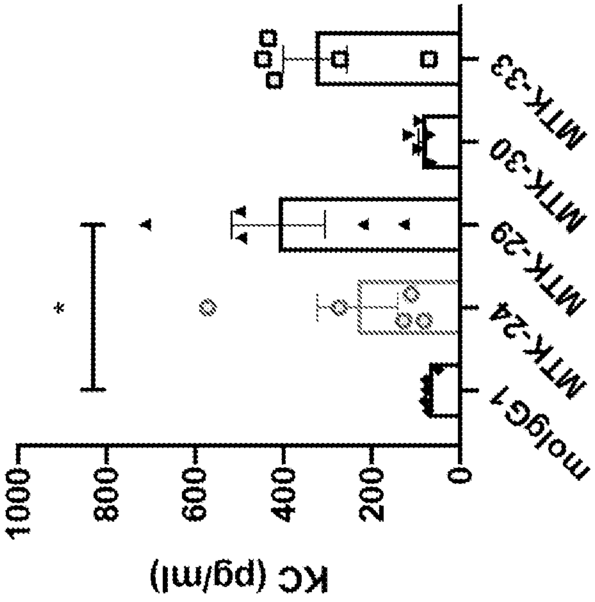
Figure 17C:
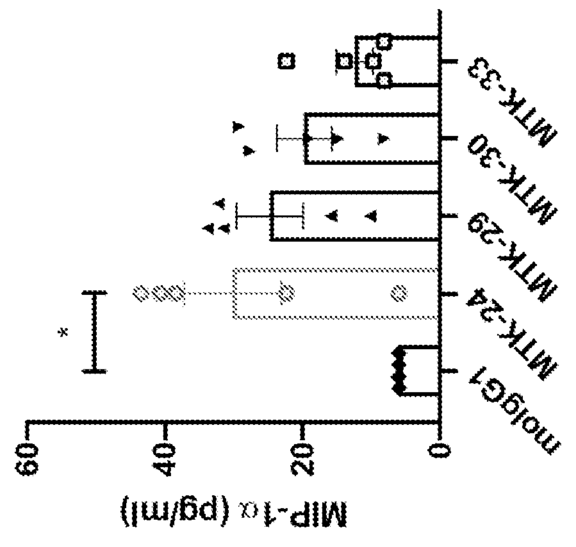
Figure 17D:
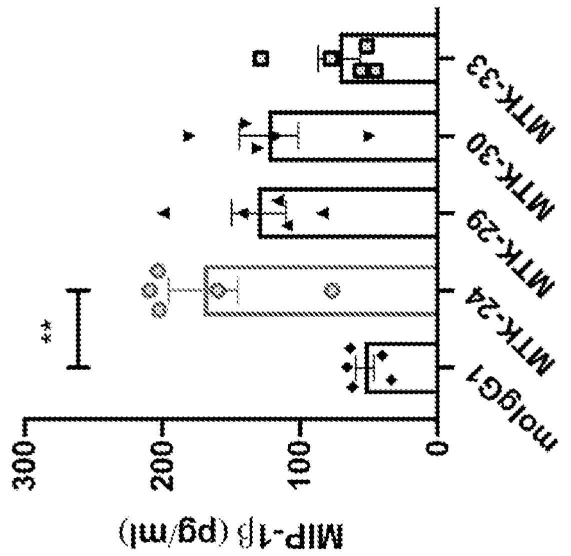
Figure 17E:
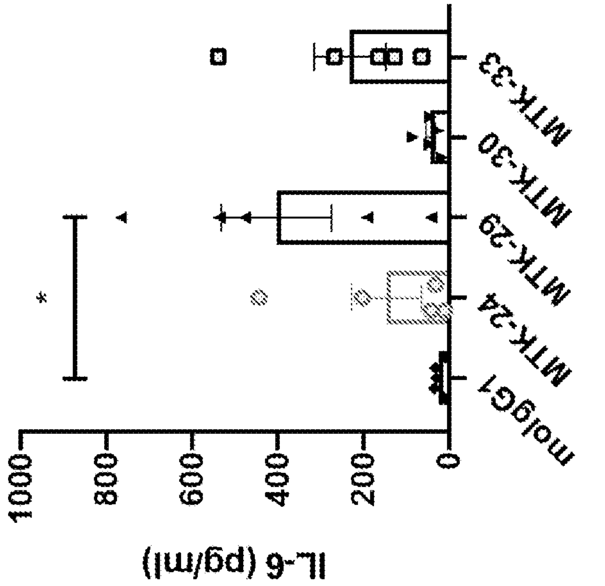
Figure 18A:
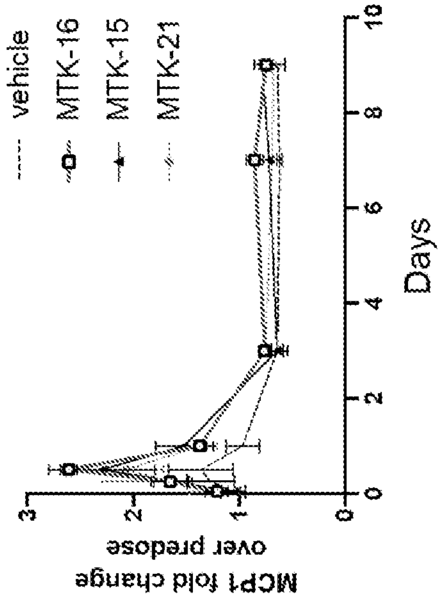
FIGS. 18A, 18B, 18C, and 18D set forth data showing changes in levels of MCP1, MIP-1β, tumor necrosis factor (TNF), and interferon (IFN) in plasma from cynomolgus monkeys administered anti-MerTK antibodies of the present disclosure.
Figure 18B:
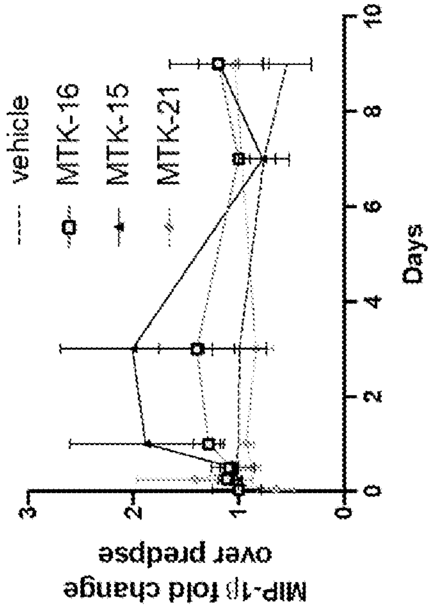
Figure 18C:
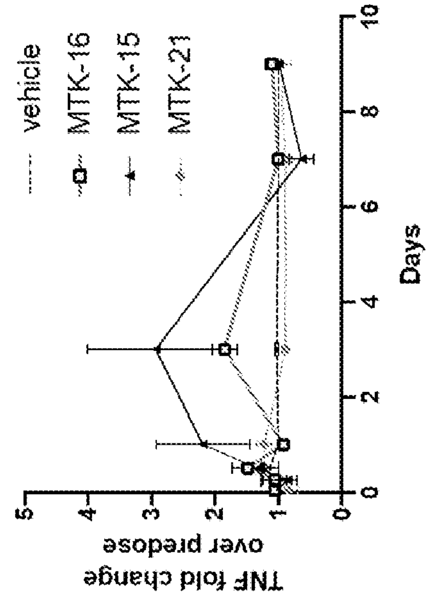
Figure 18D:
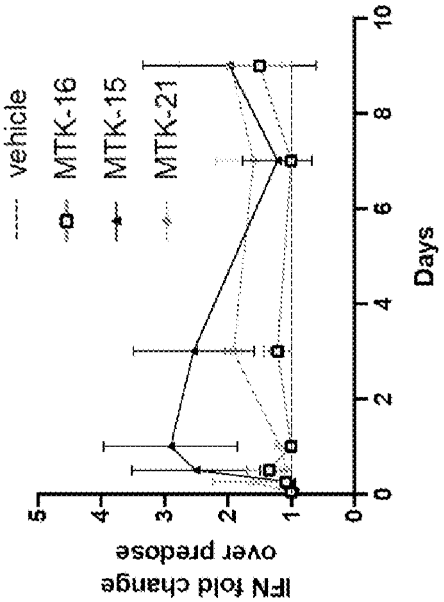

FIG. 16 shows a survival curve of the tumor-bearing mice from these studies. Median survival time of mice administered control antibody was 28 days; median survival time of mice administered anti-PDL1 antibody alone was 35 days; median survival time of mice administered anti-PDL1 antibody in combination with anti-MerTK antibody MTK-29 was 35 days; and median survival time of mice administered anti-PDL1 antibody in combination with anti-MerTK antibody MTK-33 extends beyond the final 42-day post tumor implant time-point: 6 out of 9 mice were still alive on day 42 following this combination treatment. Taken together, the results presented in FIGS. 12A, 12B, 13, 14A, 14B, 14C, 14D, 15A, 15B, 15C, 15D, and 16 demonstrated that anti-MerTK antibodies MTK-29 and MTK-33 in combination with anti-PDL1 antibody have enhanced efficacy in inhibiting tumor growth and improving cancer immunotherapy compared to treatment with anti-PDL1 antibody alone.

Example 20: Modulation of Pro-Inflammatory Cytokine or Chemokine Production in Mice The effect of anti-MerTK antibodies of the present disclosure on pro-inflammatory cytokine or chemokine production in mice was examined as follows. Control antibody or anti-MerTK antibody MTK-24, MTK-29, MTK-30, or MTK-33 was administered to C57BL/6 mice via intraperitoneal injection at a dose of 20 mg/kg (N=5 per group). One hour later, blood was withdrawn from each animal for use in measuring changes in pro-inflammatory cytokine or chemokine levels. LEGENDplex mouse proinflammatory chemokine panel (Biolegend, Catalog #740451) and LEGENDplex mouse macrophage/microglia panel (Biolegend, Catalog #740846) were used according to the manufacturer's instructions as follows. Briefly, serum samples from the mice were diluted 4-fold with Assay Buffer. Standard Cocktail was serially diluted with Assay Buffer. For setting up the standard, 25 μl of Matrix B, 25 μl of standard solution, and 25 μl of Mixed Beads were added. For setting up sample wells, 25 μl of Assay Buffer, 25 μl of diluted serum samples, and 25 μl of Mixed Beads were added. Each plate was placed on a plate shaker at 500 rpm for 2 hours. After washing the plates, 25 μl of Detection Antibodies was added to each well, and then plate was placed on a plate shaker for 1 hour. 25 μl of SA-PE was added, and then plate was shaken for 30 minutes. After washing, samples were resuspended with 1× Wash Buffer and acquired on a BD FACS CantoII (Becton Dickinson, San Jose, CA) and data were analyzed with LEGENDplex software (Biolegend).

FIGS. 17A, 17B, 17C, 17D, and 17E show the levels of KC (CXCL1), MCP1 (CCL2), MIP-1α (CCL3), MIP-1β (CCL4), and IL-6, respectively, in mice following administration of anti-MerTK antibodies of the present disclosure. As shown in these Figures, the level of each of these chemokines or cytokines increased in response to anti-MerTK antibody MTK-24, MTK-29, MTK-30, and MTK-33 administration in mice compared to that observed in mice administered control antibody. These results showed that anti-MerTK antibody MTK-24, MTK-29, MTK-30, or MTK-33 induced pro-inflammatory chemokine or cytokine production in mouse peripheral cells in a MerTK-dependent way. These results also demonstrated that anti-MerTK antibodies of the present disclosure are effective at increasing pro-inflammatory chemokine/cytokine levels in vivo, thus providing further evidence that anti-MerTK antibodies of the present disclosure are effective at activating an anti-tumor immune response.

Example 21: Modulation of Pro-Inflammatory Cytokine or Chemokine Production in Non-Human Primates The effect of anti-MerTK antibodies of the present disclosure on pro-inflammatory cytokine or chemokine production in vivo was tested in cynomolgus monkeys as follows. Anti-MerTK antibody MTK-15, MTK-16, or MTK-21 was given to cynomolgus monkeys via intravenous injection at a dose of 10 mg/kg (N=3 per group). Blood was withdrawn before dosing (pre-dose) and at 1 hour, 6 hours, 12 hours, 24 hours, 72 hours, 168 hours, and 216 hours post-dose. Levels of pro-inflammatory cytokines and chemokines were determined using LEGENDplex NHP Inflammation panel (Biolegend, Catalog #740389) and LEGENDplex NHP Chemokine/cytokine panel (Biolegend, Catalog #740317) according to the manufacturer's instructions. Briefly, plasma samples were diluted 4-fold with Assay Buffer. The Standard Cocktail was serially diluted with Assay Buffer. For setting up standard wells, 25 μl of Matrix B, 25 μl of standard solution, and 25 μl of Mixed Beads was added. For setting up sample wells, 25 μl of Assay Buffer, 25 μl of diluted plasma samples, and 25 μl of Mixed Beads was added. Plates were placed on a plate shaker at 500 rpm for 2 hours. After washing, 25 μl of Detection Antibodies was added, and then plate was shaken for 1 hour. 25 μl of SA-PE was added and then plate was shaken for 30 minutes. After washing, samples were resuspended with 1× Wash Buffer and acquired on a BD FACS CantoII (Becton Dickinson, San Jose, CA) and data were analyzed with LEGENDplex software (Biolegend). Graphs were plotted as fold increase in cytokine/chemokine levels at each specific time point over cytokine/chemokine levels at pre-dose.

FIGS. 18A, 18B, 18C, and 18D show the time course of changes in levels of MCP1 (CCL2), MIP-1β (CCL4), TNF, and IFN, respectively, in plasma obtained from cynomolgus monkeys administered anti-MerTK antibody MTK-15, MTK-16, or MTK-21, or vehicle control. The peak levels of MCP1 occurred around 12 hours post-dose. Administration of anti-MerTK antibody MTK-15 resulted in an increase in the levels of MIP-1β, TNF, and IFN up to 72 hours post-dose. Taken together, these results demonstrated that anti-MerTK antibody MTK15, MTK-16, or MTK-21 increased pro-inflammatory chemokine or cytokine production in cynomolgus monkey peripheral cells in a MerTK-dependent way. These results further indicated that anti-MerTK antibodies of the present disclosure are effective at increasing MCP1, MIP-1b, TNF, and IFN (which are pro-inflammatory cytokines/chemokines) in vivo in non-human primates.

Two additional studies were performed in cynomolgus monkeys administered anti-MerTK antibody MTK-15 or anti-MerTK antibody MTK-29 (both of which block binding of ProS to MerTK but do not block binding of Gas6 to MerTK, and both of which bind to the Ig2 and FN1 domains of MerTK) or administered anti-MerTK antibody MTK-16 (which blocks binding of both ProS and Gas6 to MerTK and which binds to the Ig1 domain of MerTK). In these preliminary studies, animals administered anti-MerTK antibody MTK-16 displayed decreased systemic toxicity compared to animals administered anti-MerTK antibody MTK-15 or anti-MerTK antibody MTK-29. These preliminary results suggested that anti-MerTK antibodies that block binding of both ProS and Gas6 to MerTK may provide a better in vivo safety profile than anti-MerTK antibodies that block binding of ProS to MerTK but that do not block binding of Gas6 to MerTK. These preliminary results also suggested that anti-MerTK antibodies that bind to the Ig 1 domain of MerTK may provide a better in vivo safety profile than anti-MerTK antibodies that bind to both the Ig2 and FN1 domains of MerTK.

Example 22: Phospho-AKT Assay in Human Macrophages

The ability of anti-MerTK antibodies of the present disclosure to block phospho-AKT signaling in the presence of human Gas6 (huGas6) protein was evaluated as follows. Differentiated human macrophages were treated with 100 nM Dexamethasone (Sigma-Aldrich, Cat #D4902) and 10 ng/ml huM-CSF (R&D systems, Cat #216MC25CF) for 2 days to polarize into M2c macrophages. 100,000 cells were seeded in 96-well plate. Next day, cells were serum starved for 4 hours. Cells were treated with anti-MerTK antibodies for 30 min at 37° C. and then 200 nM of huGas6 (R&D systems, Cat #885-GSB-050) was added to the cells. After 30 min incubation, cells were lysed to determine phospho-AKT (pAKT) (CisBio, Cat #63ADK082PEG) or total AKT (CisBio, Cat #64NKTPEG) Homogeneous Time Resolved Fluorescence (HTRF) assays following the manufacturer's instructions. The pAKT signal was normalized to total AKT signal to quantitate the final pAKT activity.

TABLE 18

| Antibody | Average IC50 (nM) From two different donors |
|---|---|
| MTK-01 | 1.28 |
| MTK-03 | 0.019 |
| MTK-05 | 0.2464 |
| MTK-07 | 0.371 |
| MTK-09 | 1.665 |
| MTK-11 | 2.627 |
| MTK-12 | 1.283 |
| MTK-15 | 2.8 |
| MTK-16 | 7.74 |
| MTK-17 | 3.422 |
| MTK-18 | 1.30 |
| MTK-19 | 0.902 |
| MTK-20 | 1.483 |
| MTK-22 | 0.531 |
| MTK-29 | 5.37 |
| MTK-33 | 4.28 |

Figure 19A:
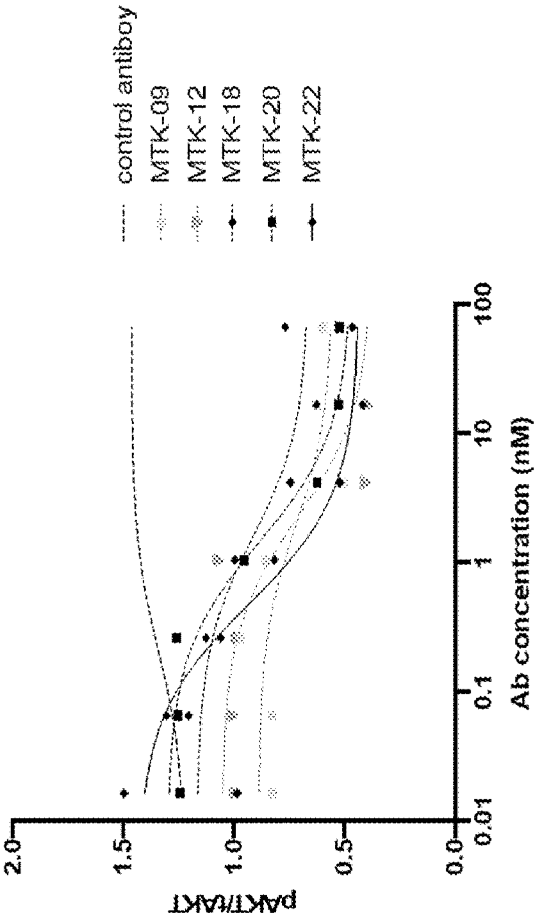
FIGS. 19A and 19B set forth data showing changes in the ratio of phosphor-AKT (pAKT) to total AKT (tAKT) in cells treated with various anti-MerTK antibodies of the present disclosure.
Figure 19B:
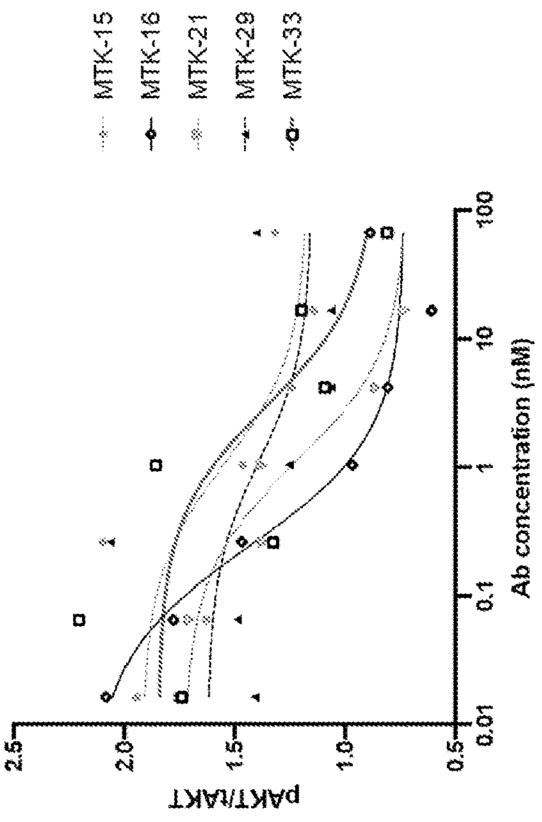

FIGS. 19A and 19B show exemplary anti-MerTK antibodies of the present disclosure (MTK-9, MTK-12, MTK-15, MTK-16, MTK-18, MTK-20, MTK-21, MTK-22, MTK-29, and MTK-33) inhibited Gas6-mediated pAKT activity in a dose-dependent manner. Table 18 above shows IC50 values determined for anti-MerTK antibody blocking of Gas6-mediated pAKT activity. As shown in Table 18. anti-MerTK antibodies of the present disclosure inhibited ligand (e.g., Gas6) mediated MerTK signaling. These results further showed that anti-MerTK antibodies of the present disclosure inhibited Gas6-mediated MerTK signaling, as measured by pAKT levels, with IC50 values ranging from 0.019 nM to 7.74 nM.

Example 23: Domain Binding Analysis of Anti-MerTK Antibodies

The following studies were performed to analyze the binding sites of various anti-MerTK antibodies of the present disclosure on human MerTK.

MerTK is a member of the TAM family, whose members share a unique domain structure containing an N-terminal region (N), two Immunoglobulin-like domains (Ig 1 and Ig2), two Fibronectin type III domains (FN1 and FN2), a juxta-membrane region (JM), and an intracellular tyrosine kinase domain. MerTK also contains less-structured regions both at the N-terminus of the protein and in the juxta-membrane (JM) region of the MerTK protein; cleavage at the juxta-membrane region leads to release of soluble MerTK extracellular domain (ECD). Human MerTK ECD can be divided into the following domains, the amino acid sequences of which are shown below in Table 19:

TABLE 19

| Human MerTK domain | Sequence | SEQ ID NO: |
|---|---|---|
| N-terminal domain (N) of human MerTK ECD | AITEAREEAKPYPLFPGPFPGSLQTDHTPLLSLPHASGY QPALMFSPTQPGRPHTGNVAIPQVTSVE | 449 |
| Immunoglobulin-like domain (Ig1) of human MerTK ECD | SKPLPPLAFKHTVGHIILSEHKGVKFNCSISVPNIYQDT TISWWKDGKELLGAHHAITQFYPDDEVTAIIASFSITSV QRSDNGSYICKMKINNEEIVSDPIYIEVQ | 450 |
| Immunoglobulin-like domain (Ig2) of human MerTK ECD | GLPHFTKQPESMNVTRNTAFNLTCQAVGPPEPVNIFWVQ NSSRVNEQPEKSPSVLTVPGLTEMAVFSCEAHNDKGLTV SKGVQIN | 451 |
| Fibronectin type III domain (FN1) of human MerTK ECD | IKAIPSPPTEVSIRNSTAHSILISWVPGFDGYSPFRNCS IQVKEADPLSNGSVMIFNTSALPHLYQIKQLQALANYSI GVSCMNEIGWSAVSPWILAST | 452 |
| Fibronectin type III domain (FN2) of human MerTK ECD | TEGAPSVAPLNVTVFLNESSDNVDIRWMKPPTKQQDGEL VGYRISHVWQSAGISKELLEEVGQNGSRARISVQVHNAT CTVRIAAVTRGGVGPFSDPV | 453 |
| Juxta membrane domain region (JM) of human MerTK ECD | KIFIPAHGWVDYAPSSTPAPGNADPVLII | 454 |

Axl protein, another member of the TAM family, shares a common domain structure to that of MerTK, having the following domains and associated amino acid sequences in its ECD:

TABLE 20

| Human Axl domain | Sequence | SEQ ID NO: |
|---|---|---|
| N-terminal domain (N) of human Axl ECD | APRGTQAEESPFVGNPGNITGARGLTG | 455 |
| Immunoglobulin-like domain (Ig1) of human Axl ECD | TLRCQLQVQGEPPEVHWLRDGQILELADSTQTQVPLGED EQDDWIVVSQLRITSLQLSDTGQYQCLVFLGHQTFVSQP GYVGLE | 456 |
| Immunoglobulin-like domain (Ig2) of human Axl ECD | GLPYFLEEPEDRTVAANTPFNLSCQAQGPPEPVDLLWLQ DAVPLATAPGHGPQRSLHVPGLNKTSSFSCEAHNAKGVT TSRTATITVLP | 457 |
| Fibronectin type III domain (FN1) of human Axl ECD | QQPRNLHLVSRQPTELEVAWTPGLSGIYPLTHCTLQAVL SDDGMGIQAGEPDPPEEPLTSQASVPPHQLRLGSLHPHT PYHIRVACTSSQGPSSWTHWLPVETPEG | 458 |
| Fibronectin type III domain (FN2) of human Axl ECD | VPLGPPENISATRNGSQAFVHWQEPRAPLQGTLLGYRLA YQGQDTPEVLMDIGLRQEVTLELQGDGSVSNLTVCVAAY TAAGDGPWS | 459 |
| Juxta membrane domain (JM) of human Axl ECD | LPVPLEAWRPGQAQPVHQLVKEPSTPAFSWPWW | 460 |

In these experiments, a series of chimeric proteins were recombinantly expressed in which various domains of human MerTK were swapped with corresponding human Axl domains. The resulting chimeric proteins were recombinantly expressed in Expi293 cells and binding of various anti-MerTK antibodies of the present disclosure were then analyzed for their ability to bind the Axl/MerTK domain-swapped chimeras. DNA encoding the domain-swapped chimeras and deletion mutants, with a signal sequence (MGWSCIILFLVATATGVHS (SEQ ID NO:461) in MerTK constructs, and MGWSCIILFLVATATG (SEQ ID NO:462) in Axl constructs) and a linker+His+Avi tag (GGSGHTKHGGGLNDIFEAQKIEWHE; SEQ ID NO:463) were prepared by gene synthesis and cloned into the expression vector pcDNAtopo3.4 (GeneArt, ThermoFisher). Expi293 cells were transfected with 2 μg of plasmids and ExpiFectamine following recommended procedures (ThermoFisher). Transfected cells were grown in 2 mL cultures with shaking at 37C and 5% $CO_2$ for four days. Cells were pelleted by centrifugation and the supernatants were filtered through 0.2 μM filters by vacuum.

Table 21 shows the configurations of the various Axl/MerTK domain-swapped chimeras that were generated for use in these studies. In Table 21, an M (MerTK) or an A (Axl) indicates from which protein that particular domain was included (i.e., swapped) in the corresponding chimeric protein construct; N (N-terminal domain), Ig1 (immunoglobulin-like domain 1), Ig2 (immunoglobulin-like domain 2), FN1 (fibronectin type III domain 1), FN2 (fibronectin type III domain 2), and JM (juxta-membrane domain).

TABLE 21

| Axl/MerTK Chimeric | N | Ig1 | Ig2 | FN1 | FN2 | JM |
|---|---|---|---|---|---|---|
| Full MerTK | M | M | M | M | M | M |
| MerTK with swapped N | A | M | M | M | M | M |
| MerTK with swapped Ig1 | M | A | M | M | M | M |
| MerTK with swapped Ig2 | M | M | A | M | M | M |
| MerTK with swapped FN1 | M | M | M | A | M | M |
| MerTK with swapped FN2 | M | M | M | M | A | M |
| MerTK with swapped JM | M | M | M | M | M | A |
| Full Axl | A | A | A | A | A | A |
| Axl with swapped N | M | A | A | A | A | A |
| Axl with swapped Ig1 | A | M | A | A | A | A |
| Axl with swapped Ig2 | A | A | M | A | A | A |
| Axl with swapped FN1 | A | A | A | M | A | A |
| Axl with swapped FN2 | A | A | A | A | M | A |
| Axl with swapped JM | A | A | A | A | A | M |
| MerTK with deleted N | | M | M | M | M | M |
| MerTK with deleted N/Ig1 | | | M | M | M | M |
| MerTK with deleted N/Ig1/Ig2 | | | | M | M | M |
| MerTK with deleted N/Ig1/Ig2/FN1 | | | | | M | M |
| MerTK with deleted N/Ig1/Ig2/FN1/FN2 | | | | | | M |

Binding of anti-MerTK antibodies of the present disclosure to these domain-swapped chimera or deletion mutants (prepared as described above) was tested by Surface Plasmon Resonance (SPR) using Carterra LSA. Purified anti-MerTK antibodies were immobilized in duplicate on a HC30M chip (Carterra) by amine coupling, following the manufacturer's instructions (described previously). Supernatants containing the constructs were diluted 1:1 with running buffer containing 0.5 mg/mL BSA (HBS-TE, Carterra) and injected over the immobilized antibodies. The surface was regenerated with 10 mM Glycine pH2.0 after each construct injection. Sensorgrams were analyzed using Carterra Epitope software to identify patterns of construct binding. Loss of binding to MerTK constructs with domains deleted or swapped in from Axl and/or gain of binding to Axl constructs with MerTK domains swapped in were evaluated. Data from these studies was used to construct a domain binding map for anti-MerTK antibodies and their binding to various domains of human MerTK.

In addition to anti-MerTK antibodies of the present disclosure, the following anti-MerTK antibodies were also used in these studies: rat anti-mouse MerTK antibody DS5MMER (eBioscience, Clone ID DS5MMER, rat IgG2a), mouse anti-human MerTK antibody H1 (BioLegend, Clone ID: 590H11G1E3, mouse IgG1), mouse anti-human MerTK antibody H2 (R&D systems, Clone ID: 125518, mouse IgG2b), mouse anti-human MerTK antibody H3 (R&D systems, Clone ID 125508, mouse IgG2b), mouse anti-human MerTK antibody H6 (eBioscience, Clone ID: A3KCAT, mouse IgG1), mouse anti-human MerTK antibody H7 (Sino Biological, Clone ID: 09, Mouse IgG2b), human anti-human MerTK antibody M6 (disclosed in WO2016/106221, huIgG1 LALAPS), and human anti-human MerTK antibody CDX AB3000 (disclosed in WO2020/106461).

TABLE 22

| Antibody | Binding domain |
|---|---|
| H6 | N-terminal |
| MTK-10 | Ig1 |
| MTK-16 | |
| MTK-21 | |
| MTK-25 | |
| MTK-33 | |
| M6 | |
| MTK-22 | |
| MTK-06 | Ig2/FN1 |
| MTK-15 | |
| MTK-29 | |
| MTK-30 | |
| CDX AB3000 | |
| H1 | |
| H2 | |
| H3 | Juxta membrane domain |
| H7 | |

The results of these binding studies are shown above in Table 22. As shown in Table 22, anti-MerTK antibody H6 bound to chimeric protein constructs containing the N-terminal region of human MerTK. Anti-MerTK antibodies MTK-10, MTK-16, MTK-21, MTK-25, MTK-33, and M6 bound to constructs that contained the MerTK Ig 1 domain. Anti-MerTK antibody MTK-22 bound to chimeric protein constructs that contained the MerTK Ig1; however, anti-MerTK antibody MTK-22 binding was affected by the presence of the MerTK FN1 domain. Anti-MerTK antibodies MTK-06, MTK-15, MTK-29, MTK-30, CDX AB3000, H1, and H2 bound only to chimeric protein constructs that contained both the MerTK Ig2 and FN1 domains. Anti-MerTK antibodies H3 and H7 bound to chimeric protein constructs containing the MerTK juxta membrane region. None of the anti-MerTK antibodies tested above bound to the ECD domain of human Axl (data not shown).

These results showed that anti-MetTK antibodies of the present disclosure that blocked binding of both Gas6 and ProS to MerTK generally bound to the Ig1 domain of human MerTK. These results also showed that anti-MerTK antibodies of the present disclosure that blocked binding of only ProS to MerTK generally bound to a combination of both Ig2/FN1 domains.

Example 24: Effect of Anti-MerTK Antibody Treatment in Transgenic Mouse Colon Cancer Model The effect of anti-MerTK antibodies on tumor growth in vivo was performed as follows using an in vivo mouse colon cancer model in which the mice were transgenic to include human MerTK. MC38 mouse cancer cells were implanted subcutaneously on the shaved right flank of huMerTK Knock-In (KI) mice (Ozgene, Perth, Australia), where human MerTK was introduced into the mouse genome. When tumor size reached approximately 80-130 $mm^3$ in volume, mice were treated with 10 mg/kg of MTK-33 plus 3 mg/kg of anti-PDL1 (clone BM1), 10 mg/kg of MTK-16 plus 3 mg/kg of anti-PDL1, 3 mg/kg of anti-PDL1 alone, or 10 mg/kg of control antibody twice a week. Tumor volume was measured three times a week.

Figure 20A:
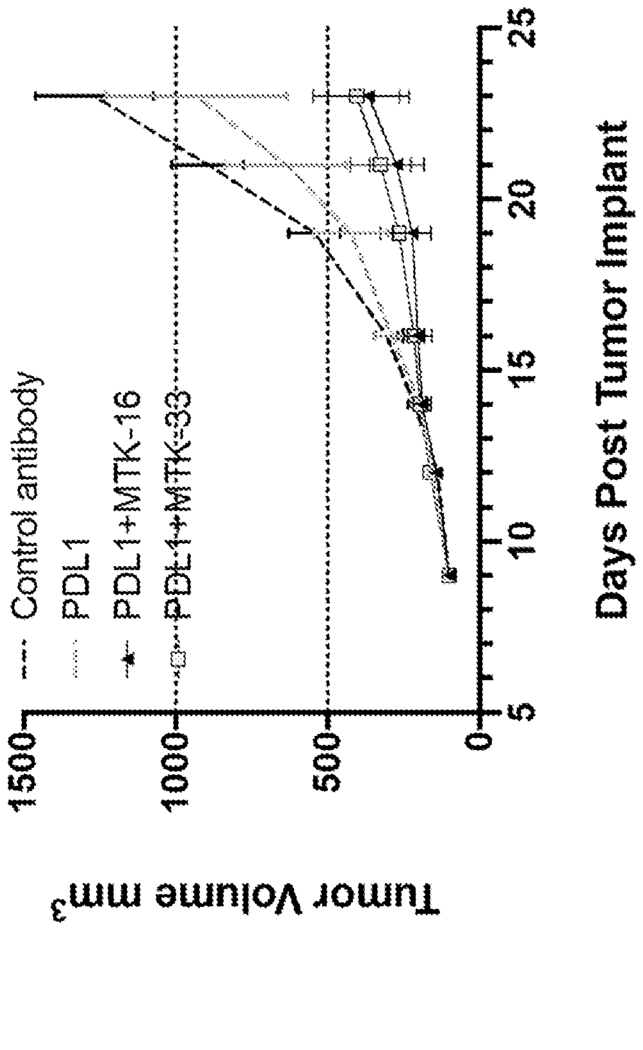
FIGS. 20A, 20B, 20C, 20D, and 20E set forth data showing changes in tumor volume in a MC38 tumor mouse model in vivo in animals administered anti-PDL-1 antibody in combination with various anti-MerTK antibodies of the present disclosure.
Figure 20C:
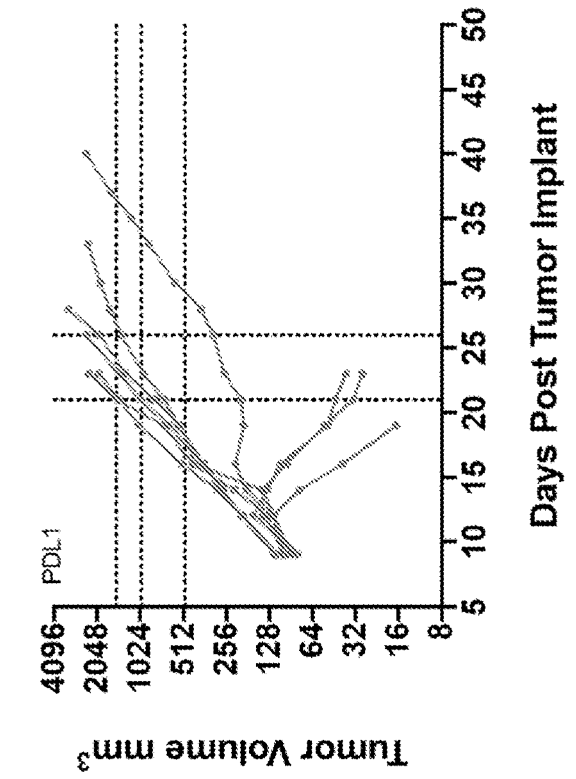
Figure 20B:
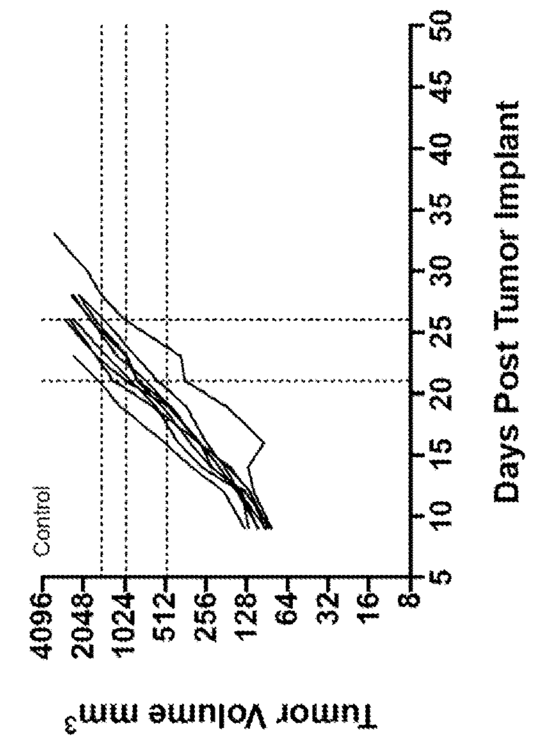
Figure 20E:
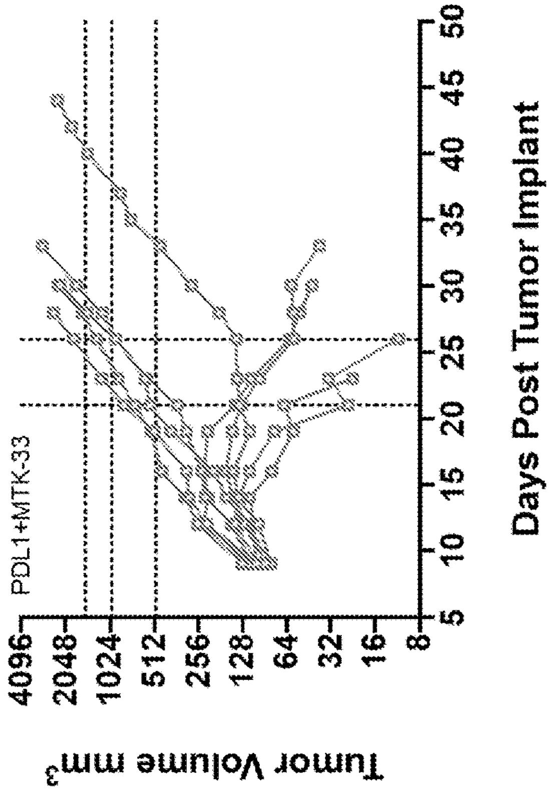
Figure 20D:
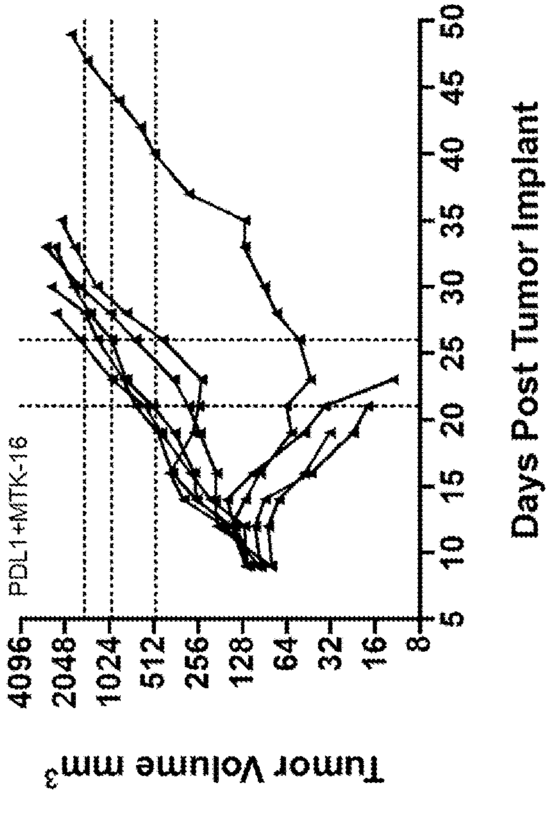
Figure 21:
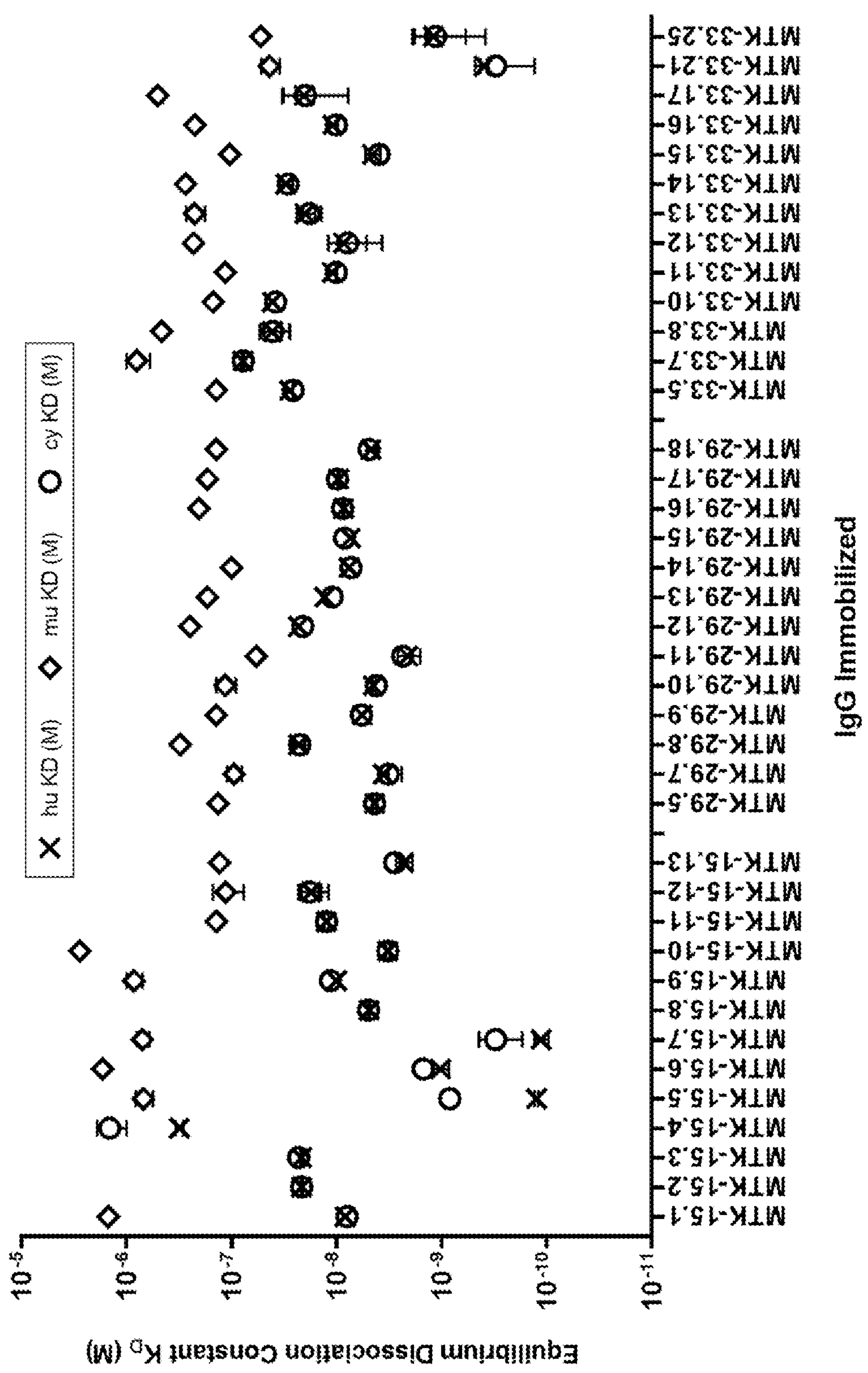
FIG. 21 sets forth data showing binding equilibrium dissociation constants ($K_D$) of anti-MerTK antibodies of the present disclosure to human (hu), murine (mu), and cynomolgus (cy) MerTK protein.

FIG. 20A shows that a combination of anti-PDL1 antibody with either anti-MerTK antibody MTK-16 or anti-MerTK antibody MTK-33 moderately reduced the tumor growth rate compared to that observed in mice treated with either anti-PDL1 antibody alone or with control antibody. FIG. 20B shows the tumor growth of individual mouse in each group and the combination treatment of anti-PDL1 with either MTK-16 or MTK-33 led to the complete regression of tumors from 3 or 4 out of 9 mice. Thus, this data show that human MerTK binding anti-MerTK antibody MTK-16 or MTK-33 in combination with anti-PDL1 antibody improved efficacy in inhibiting tumor growth Example 25: Humanization of murine anti-MERTK mouse antibodies Humanized variants of certain parental mouse anti-MerTK antibodies of the present disclosure were generated as follows.

The parental mouse anti-MerTK antibody MTK-16 contains a heavy chain variable region comprising the amino acid sequence of:

(SEQ ID NO: 55)
DIVMTQSPKFMSTSVGDRVSITCKASQNVRTAVAWYKKKPGQSPKALINL

ASNRHTGVPDRFTGSGSGTDFTLTISNVQSEDLADYFCLQHWNYPLTFGG

GTKLEIK.

and a light chain variable region comprising the amino acid sequence of:

(SEQ ID NO: 20)
LIQLVQSGPELKKPGETVKISCKASGYTFTNHGMNWVKQDPGKGLKWMGW

INTYTGEPTYADDFKGRFVFSMETSASAAFLQINNLKNEDTATYFCARKG

VTAARYFDYWGQGTTLTVSS,

The parental mouse anti-MerTK antibody MTK-33 contains a heavy chain variable region comprising the amino acid sequence of:

(SEQ ID NO: 37)
QVQLQQPGPELVRPGTSVKLSCKASGYTFTSYWMHWIKQRPGQGLEWIGV

IDPSDNYINYNQKFKGKATLTVDTSSSTAYLQLSSLTSEDSAVYYCAREA

GTRGYFDYWGQGTTLTVSS, and a light chain variable region comprising the amino acid sequence of:

(SEQ ID NO: 72)
SIVMTQTPKFLLVSAGDRVIITCKASQSVSNTVAWYQQKPGQSPKLLIYY

ASNRYTGVPDRFTGSGYGTDFTFTISTVQAEDLAVYFCQQDYRSPFTFGS

GTQLEMK.

The parental mouse anti-MerTK antibody MTK-15 contains a heavy chain variable region comprising the amino acid sequence of:

(SEQ ID NO: 19)
QIQLVQSGPELKKPGETVKISCKASGYTFTNYGVHWVKQAPGKGLKWMGW

INTYTGEPTYADDFKGRFAFSLETSASTAYLQINNLKNEDMATYFCARGN

RYAYMDYWGQGTSVTVSS, and a light chain variable region comprising the amino acid sequence of:

(SEQ ID NO: 54)
QIVLSQSPAILSASPGEKVTMTCRASSSVSYMHWYQQKSGSSPKPWIYAT

SNLASGVPARFSGSGSGTSYSLTISRVEAEDAATYYCQQWSSNPRTFGGG

TKLEIK.

The parent mouse anti-MerTK antibody MTK-29 contains a heavy chain variable region comprising the amino acid sequence of:

(SEQ ID NO: 33)
QIQLVQSGPELKKPGETVKISCKSSGFTFTTYGMSWVKQAPGKGLKWMGW

INTYSGVPTYTDDFKGRFAFSLETSASTASLQINNLKNEDTATYFCARYT

NYGYFDYWGQGTTLTVSS, and a light chain variable region comprising the amino acid sequence of:

(SEQ ID NO: 68)
QIVLSQSPAILSASPGEKVTMTCRATSSVGYMHWYQQKPGSSPKPWIYAT

SNLASGVPARFSGSGSGTSYSLTISRVEAEHAATYYCQQWGSNPFTFGSG

TKLEIK.

One method of humanizing non-human antibodies is to transplant the CDRs from a non-human (e.g., murine) antibody onto a human antibody acceptor framework. Such CDR transplantation may result in attenuation or complete loss of affinity of the humanized antibody to its target due to perturbation in its framework. As a result, certain amino acid residues in the human framework may need to be replaced by amino acid residues from the corresponding positions of the murine antibody framework (referred to as back mutations) in order to restore attenuated or lost affinity as a result of humanization. Therefore, the amino acid residues to be replaced in the context of the selected human antibody germline acceptor framework must be determined so that the humanized antibody substantially retains functions and paratopes. In addition, retained or improved thermal stability and solubility are desired for good manufacturability and downstream development.

Briefly, VH and VL amino acid sequences of the mouse anti-MerTK monoclonal antibodies to be humanized were compared to human VL, VH, LJ, and HJ functional germline amino acid sequences taken from IMGT (http://www.imgt.org/). Pseudo-genes and open reading frames were excluded from these analyses. Per one mouse monoclonal antibody (query), one or two of the most similar VH and one of the most similar VL germline amino acid sequences were selected and combined with the most similar VJ and HJ genes, producing one or two humanized amino acid sequences. The CDRs to be transplanted onto the human framework were defined according to the AbM definition.

Structure-based antibody modeling was applied in the process of humanizing mouse anti-MerTK monoclonal antibodies MTK-15 and MTK-29 utilizing the BioMOE module of MOE (Molecular Operating Environment, Chemical Computing Group, Montreal, Canada). Briefly, VH and VL amino acid sequences of the mouse monoclonal antibodies MTK-15 and MTK-29 were compared to human VL, VH, LJ, HJ functional germline amino acid sequences taken from IMGT (http://www.imgt.org/) as mentioned above. Three of the most similar VH and three of the most similar VL germline amino acid sequences were selected and combined with the most similar VJ and HJ genes, producing five to eight humanized amino acid sequences.

The query and the humanized amino acid sequences were used to create Fv homology models using BioMOE module or the Antibody Modeler module of MOE (Molecular Operating Environment, Chemical Computing Group, Montreal, Canada). AMBER10:EHT force field analysis was used for energy minimization through the entire antibody homology modeling process. Based on the Fv homology models obtained, molecular descriptors such as interaction energy between VL and VH, coordinate-based isoelectric point (3D pI), hydrophobic patch, and charged surface area were calculated, analyzed, and sorted by scoring metrics provided by MOE. These molecular descriptors were utilized to prioritize the humanized monoclonal antibodies for downstream experimental procedures, including protein expression, purification, binding affinity studies, and functional assays.

The BioMOE module of MOE provides a tool, Mutation Site Properties, to visualize and classify potential residues for back-mutation. In this context, back-mutation is defined as amino acid substitution which is reverted to the original query amino acid sequence replacing the humanized amino acid sequence. Using this tool, the original query (reference) was compared individually to the selected humanized variants for both the primary amino acid sequence and the 3D structure of the 3D Fv homology model.

Changes between the reference (i.e., parental) antibody and the humanized variant were classified based on amino acid type difference, interaction potential with CDR residues, impact potential for VL/VH pairing, and potential change in hydrophobic and charged surface area in and near the CDRs.

Mutations near the CDRs or the VL/VH interface having a significant charge difference or containing strong H-bond interactions were individually evaluated and the significantly disrupting mutations were reverted to the original query residues.

Affinity maturation of humanized anti-MerTK antibodies MTK-33, MTK-29, and MTK-16 were also performed. Briefly, certain amino acid residues in the heavy chain or light chain were selectively mutagenized and mutants that improved binding were selected through additional rounds of screening. This process simultaneously improved specificity, species cross-reactivity, and developability profiles. Characterization of the affinity-matured anti-MerTK antibodies described herein included SPR affinity measurements on Carterra LSA and efferocytosis blocking assays on human macrophage. After multiple rounds of affinity maturation, anti-MerTK antibodies with desired affinity were obtained. Amino acid sequences of the variable heavy chains (VH) and variable light (VL) chains are provided below in Table 23 (MTK-15 variants), Table 24 (MTK-16 variants), Table 25 (MTK-29 variants), and Table 26 (MTK-33 variants). In Tables 23, 24, 25, and 26, the hypervariable regions (HVR) in each of the chains are underlined.

Table 27 and Table 28 provide amino acid sequences for the heavy chain HVRs and the light chain HVRs, respectively, for anti-MerTK antibody MTK-15 variants. Table 29 and Table 30 provide amino acid sequences for the heavy chain HVRs and the light chain HVRs, respectively, for anti-MerTK antibody MTK-16 variants. Table 31 and Table 32 provide amino acid sequences for the heavy chain HVRs and the light chain HVRs, respectively, for anti-MerTK antibody MTK-29 variants. Table 33 and Table 34 provide amino acid sequences for the heavy chain HVRs and the light chain HVRs, respectively, for anti-MerTK antibody MTK-33 variants.

TABLE 23

| Antibody | Heavy Chain Variable | SEQ ID NO: | Light Chain Variable | SEQ ID NO: |
|---|---|---|---|---|
| MTK-15.1 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYQDYWGQ GTLVTVSS | 234 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.2 | QVQLVQSGSELKKPGASVKVSC KASGYTFTNYGVHWVRQAPGQG LEWMGWGNTYTGEPTYAQGFTG RFVFSLDTSVSTAYLQISSLKA EDTAVYYCARGNRYAYMDYWGQ GTLVTVSS | 235 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.3 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYMDYWGQ GTLVTVSS | 236 | EIVLTQSPATLSLSPGERATLSC RASSHVSYMHWYQQKPGQAPRPL IYATSNLASGIPARFSGSGSGTS YTLTISSLEPEDFAVYYCQQWSS NPRTFGGGTKVEIK | 248 |
| MTK-15.4 | QVQLVQSGSELKKPGASVKVSC KASGYTFTNYGVHWVRQAPGQG LEWMGWINTYTGEPTYAQGFTG | 236 | EIVLTQSPATLSLSPGERATLSC RASSSVGYMHWYQQKPGQAPRPL IYATSNLASGIPARFSGSGSGTS | 249 |

TABLE 23-continued

| Antibody | Heavy Chain Variable | SEQ ID NO: | Light Chain Variable | SEQ ID NO: |
|---|---|---|---|---|
| | RFVFSLDTSVSTAYLQISSLKA EDTAVYYCARGNRYAYMDYWGQ GTLVTVSS | | YTLTISSLEPEDFAVYYCQQWSS NPRTFGGGTKVEIK | |
| MTK-15.5 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCTRGTRYAYMDYWGQ GTLVTVSS | 237 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.6 | QVQLVQSGSELKKPGASVKVSC KASGYTFTNYGVHWVRQAPGQG LEWMGWINTYTGEPYYAQGFTG RFVFSLDTSVSTAYLQISSLKA EDTAVYYCARGNRYAYMDYWGQ GTLVTVSS | 238 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.7 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCVRGNRYAYMDYWGQ GTLVTVSS | 239 | EIVLTQSPATLSLSPGERATLSC RASSGVSYMHWYQQKPGQAPRPL IYATSNLASGIPARFSGSGSGTS YTLTISSLEPEDFAVYYCQQWSS NPRTFGGGTKVEIK | 250 |
| MTK-15.8 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGVRYAYMDYWGQ GTLVTVSS | 240 | EIVLTQSPATLSLSPGERATLSC RASSSVGYMHWYQQKPGQAPRPL IYATSNLASGIPARFSGSGSGTS YTLTISSPEPEDFAVYYCQQWSS NPRTFGGGTKVEIK | 251 |
| MTK-15.9 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGYRYAYMDYWGQ GTLVTVSS | 241 | EIVLTQSPATLSLSPGERATLSC RASSSTSYMHWYQQKPGQAPRPL IYATSNLASGIPARFSGSGSGTS YTLTISSLEPEDFAVYYCQQWSS NPRTFGGGTKVEIK | 252 |
| MTK-15.10 | QVQLVQSGSELKKPGASVKVSC KASGYTFANYGVHWVRQAPGQG LEWMGWINTYQGEPTYAQGFTG RFVFSLDTSVSTAYLQISSLKA EDTAVYYCTRGARYAYMDYWGQ GTLVTVSS | 242 | EIVLTQSPATLSLSPGERATLSC RASSSVGYMHWYQQKPGQAPRPL IYATSNLASGIPARFSGSGSGTS YTLTISSLEPEDFAVYYCQQWSS NPRTFGGGTKVEIK | 249 |
| MTK-15.11 | QVQLVQSGSELKKPGASVKVSC KASGYTFANYGVHWVRQAPGQG LEWMGWINTYEGEPTYAQGFTG RFVFSLDTSVSTAYLQISSLKA EDTAVYYCARGNRYAYQDYWGQ GTLVTVSS | 243 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.12 | QVQLVQSGSELKKPGASVKVSC KASGYTFANYGVHWVRQAPGQG LEWMGWINTYQGEPTYAQGFTG RFVFSLDTSVSTAYLQISSLKA EDTAVYYCARGVRYAYMDYWGQ GTLVTVSS | 244 | EIVLTQSPATLSLSPGERATLSC RASSSVGYMHWYQQKPGQAPRPL IYATSNLASGIPARFSGSGSGTS YTLTISSPEPEDFAVYYCQQWSS NPRTFGGGTKVEIK | 251 |
| MTK-15.13 | QVQLVQSGSELKKPGASVKVSC KASGYTFTNYGVHWVRQAPGQG LEWMGWINTYTGEPTYAQGFTG RFVFSLDTSVSTAYLQISSLKA EDTAVYYCARGNRYAYEDYWGQ GTLVTVSS | 245 | EIVLTQSPATLSLSPGERATLSC RASSSVQYMHWYQQKPGQAPRPL IYATSNLASGIPARFSGSGSGTS YTLTISSLEPEDFAVYYCQQWSS NPRTFGGGTKVEIK | 253 |
| MTK-15.14 | QVQLVQSGSELKKPGASVKVSC KASGYTFTNYGVHWVRQAPGQG LEWMGWINTYTGEPTYAQGFTG RFVFSLDTSVSTAYLQICSLKA EDTAVYYCARGNRYAYMDYWGQ GTLVTVSS | 246 | EIVLTQSPATLSLSPGERATLSC RASSSVSYMHWYQQKPGQAPRPL IYATSNLASGIPARFSGSGSGTS YTLTISSLEPEDFAVYYCQQWSS NPRTFGGGTKVEIK | 247 |
| MTK-15.15 | QVQLVQSGSELKKPGASVKVSC KASGYTFTNYGVHWVRQAPGQG | 246 | QIVLTQSPGTLSLSPGERATLSC RASSSVSYMHWYQQKPGQAPRPL | 254 |

TABLE 23-continued

| Antibody | Heavy Chain Variable | SEQ ID NO: | Light Chain Variable | SEQ ID NO: |
|---|---|---|---|---|
| | LEWMGWINTYTGEPTYAQGFTG RFVFSLDTSVSTAYLQICSLKA EDTAVYYCARGNRYAYMDYWGQ GTLVTVSS | | IYATSNLASGIPDRFSGSGSGTS YTLTISRLEPEDFAVYYCQQWSS NPRTFGGGTKVEIK | |

TABLE 24

| Antibody | Heavy Chain Variable | SEQ ID NO: | Light Chain Variable | SEQ ID NO: |
|---|---|---|---|---|
| MTK-16.1 | QVQLVQSGSELKKPGASVKVSC KASGYTFTNHGMNWVRQAPGQG LEWMGWINTYTGEPTYAQGFTG RFVFSLDTSVSTAYLQISSLKA EDTAVYYCARKGVTAARYFDYW GQGTLVTVSS | 255 | DIQMTQSPSSLSASVGDRVTITC KASQNVRTAVAWYQQKPGKAPKR LIYLASNRHTGVPSRFSGSGSGT EFTLTISNLQPEDFATYYCLQHW NYPLTFGGGTKVEIK | 257 |
| MTK-16.2 | QVQLVQSGSELKKPGASVKVSC KASGYTFTNHGMNWVRQAPGQG LEWMGWINTYTGEPTYADDFKG RFVFSLDTSVSTAYLQISSLKA EDTAVYYCARKGVTAARYFDYW GQGTLVTVSS | 256 | DIQMTQSPSSLSASVGDRVTITC RASQNVRTAVAWYQQKPGKAPKR LIYLASNRHTGVPSRFSGSGSGT EFTLTISNLQPEDFATYYCLQHW NYPLTFGGGTKLEIK | 258 |

TABLE 25

| Antibody | Heavy Chain Variable | SEQ ID NO: | Light Chain Variable | SEQ ID NO: |
|---|---|---|---|---|
| MTK-29.1 | QVQLVQSGSELKKPGASVKVSC KASGYIFTSYGLSWVRQAPGQG LEWMGWINTYSGVPTYAQGFTG RFVFSLDTSVSTAYLQISSLKA EDTAVYYCARYTNYGIFDYWGQ GTLVTVSS | 259 | EIVLTQSPATLSLSPGERATLSC RASSSVGYMHWYQQKPGQAPRPL IYATSNLASGIPARFSGSGSGTD FTLTISRLEPEDFAVYYCQQWGS WPFTFGQGTKLEIK | 274 |
| MTK-29.2 | QVQLVQSGSELKKPGASVKVSC KASGFTFTTYGMSWVRQAPGQG LEWMGWINTYSGVPTYTDDFKG RFVFSLDTSVSTAYLQISSLKA EDTAVYYCARYTNYGIFDYWGQ GTLVTVSS | 260 | DIQLTQSPSFLSASVGDRVTITC RASSSVGYMHWYQQKPGKAPKPL IYATSNLASGVPSRFSGSGSGTE FTLTISSLQPEDFATYYCQQWGS IPFTFGGGTKVEIK | 275 |
| MTK-29.3 | QVQLVQSGSELKKPGASVKVSC KASGFTFTTYGMSWVRQAPGQG LEWMGWINTYSGVPAYTDDFKG RFVFSLDTSVSTAYLQISSLKA EDTAVYYCARYTNYGVFDYWGQ GTLVTVSS | 261 | DIQLTQSPSFLSASVGDRVTITC RASSSVGYMHWYQQKPGKAPKLL IYATSNLASGVPSRFSGSGSGTE FTLTISSLQPEDFATYYCQQWGS LPFTFGQGTKLEIK | 276 |
| MTK-29.4 | QVQLVQSGSELKKPGASVKVSC KASSYTFTTYGMSWVRQAPGQG LEWMGWINTYSGVPTYTDDFKG RFVFSLDTSVSTAYLQISSLKA EDTAVYYCARYTNYGVFDYWGQ GTLVTVSS | 262 | DIQLTQSPSFLSASVGDRVTITC RASSSVGYMHWYQQKPGKAPKLL IYATSNLAQGVPSRFSGSGSGTE FTLTISSLQPEDFATYYCQQWGS LPFTFGQGTKLEIK | 277 |
| MTK-29.5 | QVQLVQSGSELKKPGASVKVSC KASGYIFTSYGLSWVRQAPGQG LEWMGWINTYSGVPTYTDDFKG RFVFSLDTSVSTAYLQISPLKA EDTAVYYCARYTNYGVFDYWGQ GTLVTVSS | 263 | DIQLTQSPSFLSASVGDRVTITC RASSSVGYMHWYQQKPGKAPKLL IYATSNLAQGVPSRFSGSGSGTE FTLTISSLQPEDFATYYCQQWGS LPFTFGQGTKLEIK | 277 |

TABLE 25-continued

| Antibody | Heavy Chain Variable | SEQ ID NO: | Light Chain Variable | SEQ ID NO: |
|---|---|---|---|---|
| MTK-29.6 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.7 | QVQLVQSGSELKKPGASVKVSCKASSYTFTTYGMSWVRQAPGQGLEWMGWINTYSGVPSYTDDFKARFVFSLDTSVSTAYLQISSLKAEDTAVYYCARYTNYGVFDYWGQGTLVTVSS | 265 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.8 | QVQLVQSGSELKKPGASVKVSCKASGYIFTTYGLSWVRQAPGQGLEWMGWINTYSGVPTYTDDFKGRFVFSLDTNVSTAYLQISSLKAEDTAVYYCARYTNYGVFDYWGQGTLVTVSS | 266 | DIQLTQSPSFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 277 |
| MTK-29.9 | QVQLVQSGSELKKPGASVKVSCKASGYIFTSYGLSWVRQAPGQGLEWMGWINTYSGVPTYTDDFKGRFVFSLDTSVSTAYLQISSLKAEDTAVYYCARYTNYGVFDYWGQGTLVTVSS | 267 | DIQLTQSPSFLSASVGDRVTITCRASSSVGYMHWYQQKPGKAPKLLIYATSNLAQGVPSRFSGSGSGTGFTLTISSLQPEDFATYYCQQWGSLPFTFGQGTKLEIK | 278 |
| MTK-29.10 | QVQLVQSGSELKKPGASVKVSCKTSSYTFTTYGMSWVRQAPGQGLEWMGWINTYSGVPTYTDDFKGRFVFSLDTSVSTAYLQISSLKAEDTAVYYCARYTNYGVFDYWGQGTLVTVSS | 268 | EIVLTQSPATLSLSPGERATLSCRASSSVGYMHWYQQKPGQAPRLLIYATSNLASGIPARFSGSGSGTDFTLTISRLEPEDFAVYYCQQWGSLPFTFGGGTKLEIK | 279 |
| MTK-29.11 | QVQLVQSGSELKKPGASVKVSCKASSYTFTTYGMSWVRQAPGQGLEWMGWINTDSGVPTYTDDFKGRFVFSLDTSVSTAYLQISSLKAEDTAVYYCARYTNYGVFDYWGQGTLVTVSS | 269 | EIVLTQSPATLSLSPGERATLSCRASSSVGYMHWYQQKPGQAPRLLIYATSNLASGIPARFSGSGSGTDFTLTISRLEPEDFAVYYCQQWGSLPFTFGGGTKLEIK | 279 |
| MTK-29.12 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPGFLSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 280 |
| MTK-29.13 | QVQLVQSGSELKKPGASVKVSCKASSYTFTTYGMSWVRQAPGQGLEWMGWINTASGVPTYTDDFKGRFVFSLDTSVSTAYLQISSLKAEDTAVYYCARYTNYGVFDYWGQGTLVTVSS | 270 | DIQLTQSPSFLSASVGDRVTITCRASSSVGYMHWYQQEPGKAPKLLIYATSNLAQGVPSRFSGSGSGTEFTLTISSLQPEDFATYYCQQWGSLPFTFGQGTKLEIK | 281 |
| MTK-29.14 | QVQLVQSGSELKKPGASVKVSCKASSYTFTTYGMSWVRQAPGQGLEWMGWINTYSGVPSYTDDFKARFVFSLDTSVSTAYLQISSLKAEDTAVYYCARYTNYGVFDYWGQGTLVTVSS | 265 | DIQLTQSPSFLSASVGDRVTITCRASSSVGYMHWYQQKPGKAPKLLIYATSNLAQGVPSRFSGSGSGTEFTLTIFSLQPEDFATYYCQQWGSLPFTFGQGTKLEIK | 282 |
| MTK-29.15 | QVQLVQSGSELKKPGASVKVSCKASSYTFTTYGMSWVRQAPGQGLEWMGWINTMSGVPTYTDDFKGRFVFSLDTSVSTAYLQISSLKAEDTAVYYCARYTNYGVFDYWGQGTLVTVSS | 264 | DIQLTQSPSFPSASVGDRVTITCRASSSVGYMHWYQQKPGKAPKLLIYATSNLAQGVPSRFSGSGSGTEFTLTISSLQPEDFATYYCQQWGSLPFTFGQGTKLEIK | 283 |
| MTK-29.16 | QVQLVQSGSELKKPGASVKVSCKASGYIFTSYGLSWVRQAPGQGLEWMGWVNTYSGVPTYTDDFKG | 271 | DIQLTQSPSFLSASVGDRVTITCRASSSVGYMHWYQQKPGKAPKLLIYATSNLAQGVPSRFSGSGSGTE | 284 |

TABLE 25-continued

| Antibody | Heavy Chain Variable | SEQ ID NO: | Light Chain Variable | SEQ ID NO: |
|---|---|---|---|---|
| | RFVFSLDTSVSTAYLQISSLKA EDTAVYYCARYTNYGVFDYWGQ GTLVTVSS | | FTLTISSLQPEDFATYYCQQWGR LPFTFGQGTKLEIK | |
| MTK-29.17 | QVQLVQSGSELKKPGASVKVSC KASGYIFTSYGLSWVRQAPGQG LEWMGWINTYSGVPTYAQGFTG RFVFSLDTSVSTAYLQISSLKA EDTAVYYCARYTNYGVFDYWGQ GTLVTVSS | 272 | DIQLTQSPSFLSASVGDRVTITC RSSSSVGYMHWYQQKPGKAPKLL IYATSNLAQGVPSRFSGSGSGTE FTLTISSLQPEDFATYYCQQWGS LPFTFGQGTKLEIK | 285 |
| MTK-29.18 | QVQLVQSGSELKKPGASVKVSC KASGYIFTSYGLSWVRQAPGQG LEWMGWVNTYSGVPTYTDDFKG RFVFSLDTSVSTAYLQISSLKA EDTAVYYCARYTNYGVFDYWGQ GTLVTVSS | 271 | EIVLTQSPATLSLSPGERATLSC RASSTVGYMHWYQQKPGQAPRLL IYATSNLASGIPARFSGSGSGTD FTLTISRLEPEDFAVYYCQQWGS LPFTFGGGTKLEIK | 286 |
| MTK-29.19 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPGTLSLSPGERATLSC RATSSVGYMHWYQQKPGQAPRPL IYATSNLASGIPDRFSGSGSGTS YTLTISRLEPEDFAVYYCQQWGS NPFTFGQGTKLEIK | 287 |
| MTK-29.20 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPATLSLSPGERATLSC RATSSVGYMHWYQQKPGLAPRPL IYATSNLASGIPDRFSGSGSGTS YTLTISRLEPEDFAVYYCQQWGS NPFTFGQGTKLEIK | 288 |
| MTK-29.21 | QVQLVQSGSELKKPGASVKVSC KASGFTFTTYGMSWVRQAPGQG LEWMGWINTYSGVPTYAQGFTG RFVFSLDTSVSTAYLQICSLKA EDTAVYYCARYTNYGYFDYWGQ GTLVTVSS | 273 | QIVLTQSPATLSLSPGERATLSC RATSSVGYMHWYQQKPGQAPRPL IYATSNLASGIPARFSGSGSGTS YTLTISSLEPEDFAVYYCQQWGS NPFTFGQGTKLEIK | 289 |

TABLE 26

| Antibody | Heavy Chain Variable | SEQ ID NO: | Light Chain Variable | SEQ ID NO: |
|---|---|---|---|---|
| MTK-33.1 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFNYWG QGTLVTVSS | 290 | DIQMTQSPSSLSASVGDRVTITC QASQSVSNTVAWYQQKPGKAPKL LIYYASLRYTGVPSRFSGSGSGT DFTFTISSLQPEDIATYYCQQDY RSPFTFGQGTKLEIK | 309 |
| MTK-33.2 | QVQLVQSGAEVKKPGASVKVSC KASGYTSTSYWMHWVRQAPGQG LEWIGVIDPSDNYINYNQKFQG RVTMTRDTSTSTVYMELSSLRS EDTAVYYCAREAGTRGYFDYWG QGTLVTVSS | 291 | DIQMTQSPSSLSASVGDRVTITC QASGSVSNTVAWYQQKPGKAPKL LIYYASNRYTGVPSRFSGSGSGT DFTFTISSLQPEDIATYYCQQDY RSPFTFGQGTKLEIK | 310 |
| MTK-33.3 | QVQLVQSGAEVKKPGASVKVSC KASGYTFTSYWMHWVRQAPGQG LEWIGVIDPSDNYINYNQKFQG RVTMTRDTSTSTVYMELSSLRS EDTAVYYCAREAWTRGYFDYWG QGTLVTVSS | 292 | DIQMTQSPSSLSASVGDRVTITC QASRSVSNTVAWYQQKPGKAPKL LIYYASNRYTGVPSRFSGSGSGT DFTFTISSLQPEDIATYYCQQDY RSPFTFGQGTKLEIK | 311 |
| MTK-33.4 | QVQLVQSGAEVKKPGASVKVSC KASGYTFTSYWMHWVRQAPGQG LEWIGVIDPSDNYINMNQKFQG RVTMTRDTSTSTVYMELSSLRS EDTAVYYCAREAGTRGYFDYWG QGTLVTVSS | 293 | DIQMTQSPSSLSASVGDRVTITC QASQSVSNTVAWYQQKPGKAPKL LIYYASNRYTGVPSRFSGSGSGT DFTFTISSLQPEDIATYYCQQDR RSPFTFGQGTKLEIK | 312 |

TABLE 26-continued

| Antibody | Heavy Chain Variable | SEQ ID NO: | Light Chain Variable | SEQ ID NO: |
|---|---|---|---|---|
| MTK-33.5 | QVQLVQSGAEVKKPGASVKVSCMASGYTFGSYWMHWVRQAPGQGLEWIGVIDPSDNYINYNQKFQGRVTMTRDTSTSTVYMELSSLRSEDTAVYYCAREAGTRGYFDYWGQGTLVTVSS | 294 | DIQMTQSPSSLSASVGDRVTITCQASQSVSNTVAWYQQKPGKAPKLLIYYASNRETGVPSRFSGSGSGTDFTFTISSLQPEDIGTYYCQQDYRSPFTFGQGTKLEIK | 313 |
| MTK-33.6 | QVQLVQSGAEVKKPGASVKVSCMASGYTFRSYWMHWVRQAPGQGLEWIGVIDPSDNYINYNQKFQGRVTMTRDTSTSTVYMELSSLRSEDTAVYYCAREAGTRGYFDYWGQGTLVTVSS | 295 | DIQMTQSPSSLSASVGDRVTITCQASRSVSNTMAWYQQKPGKAPKLLIYYASNRYTGVPSRFSGSGSGTDFTFTISSLQPEDIATYYCQQDYRSPFTFGQGTKLEIK | 314 |
| MTK-33.7 | QVQLVQSGAEVKKPGASVKVSCKASGYTFTSYWMHWVRQAPGQGLEWIGVIDPSDNYINYNAKFQGRVTMTRDTSTSTVYMELSSLRSEDTAVYYCAREAGTRGYFDYWGQGTLVTVSS | 296 | DIQMTQSPSSLSASVGDRVTITCGASQSVSNTVAWYQQKPGKAPKLLIYYASNRYTGVPSRFSGSGSGTDFTFTISSLQPEDIATYYCQQDYRSPFTFGQGTKLEIK | 315 |
| MTK-33.8 | QVQLVQSGAEVKKPGASVKVSCKASGYTFTSYWMHWVRQAPGQGLEWIGVIDPSDNYINYNQKFQGRVTMTRDTSTSTVYMELSSLRSEDTAVYYCAREAWTRGYFNYWGQGTLVTVSS | 290 | DIQMTQSPSSLSASVGDRVTITCQASQSVSRTVAWYQQKPGKAPKLLIYYASNRYTGVPSRFSGSGSGTDFTFTISSLQPEDIATYYCQQDYRSPFTFGQGTKLEIK | 316 |
| MTK-33.9 | QVQLVQSGAEVKKPGASVKVSCKASGYTFTSYWMHWVRQAPGQGLEWIGVIDPSDRYINYNQKFQGRVTMTRDTSTSTVYMELSSLRSEDTAVYYCAREAGTRGYFDYWGQGTLVTVSS | 297 | DIQMTQSPSSLSASVGDRVTITCQASASVSNTVAWYQQKPGKAPKLLIYYASNRYTGVPSRFSGSGSGTDFTFTISSLQPEDIATYYCQQDYRSPFTFGQGTKLEIK | 317 |
| MTK-33.10 | QVQLVQSGAEVKKPGASVKVSCKASSYSFTSYWMHWVRQAPGQGLEWIGVIDPSDNYINYNQKFRGRVTMTRDTSTSTVYMELSSLRSEDTAVYYCAREAGTRGYFDYWGQGTLVTVSS | 298 | DIQMTQSPSSLSASVGDRVTITCQAGQSVSNTVAWYQQKPGKAPKLLIYYASNRYTGVPSRFSGSGSGTDFTFTISSLQPEDIATYYCQQDYRSPFTFGQGTKLEIK | 318 |
| MTK-33.11 | QVQLVQSGAEVKKPGASVKVSCKASGYTFTSYWMHWVRQAPGQGLEWIGVIDPSDNYINYNQKFQGRVTMTRDTSTSTVYMELSSLRSEDTAVYYCAREAWTRGYFDYWGQGTLVTVSS | 292 | DIQMTQSPSSLSASVGDRVTITCQASRSVRNTVAWYQQKPGKAPKLLIYYASNRYTGVPSRFSGSGSGTDFTFTISSLQPEDIATYYCQQDYRSPFTFGQGTKLEIK | 319 |
| MTK-33.12 | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSS | 299 | DIQMTQSPSSLSASVGDRVTITCQASQSVSNTVAWYQQKPGKAPKLLIYYASNRYTGVPSRFSGSGSGTDFTFTISSLQPEDIATYYCRQDTRSPFTFGQGTKLELK | 320 |
| MTK-33.13 | QVQLVQSGAEVKKPGASVKVSCKASGYTFTSYWMHWVRQAPGQGLEWIGVIDPSDNYINYNQKFQGRVTMTRDTSTSTVYMELSSLRSEDTAVYYCAREAGTRGYFDYWGQGTLVTVSS | 300 | DIQMTQSPSSLSASVGDRVTITCQASRSVSNTVAWYQQKPGKAPKLLIYYASNRYTGVPSRFSGSGSGTDFTFTISSLQPEDIATYYCQQDYRSPFTFGQGTKLEIK | 311 |
| MTK-33.14 | QVQLVQSGAEVKKPGASVKVSCKASGYTFTSYWMHWVRQAPGQGLEWIGVIDPSDNYINYNQKFRGRVTMTRDTSTSTVYMELSSLRSEDTAVYYCAREAGTRGYFDYWGQGTLVTVSS | 301 | DIQMTQSPSSLSASVGDRVTITCQASQSVSNTVAWYQQKPGKAPKLLIYYASNRYTGVPSRFSGSGSGTDFTFTISSLQPEDIATYYCQQDYRSPFTFGQGTKLEIK | 321 |
| MTK-33.15 | QVQLVQSGAEVKKPGASVKVSCKASGYTFTSYWMHWVRQAPGQGLEWIGVIDPSDNYINYNQKFQVRVTMTRDTSTSTVYMELSSLRSEDTAVYYCAREAGTRGYFDYWGQGTLVTVSS | 302 | DIQMTQSPSSLSASVGDRVTITCQASRSVSNTVAWYQQKPGKAPKLLIYYASNRYTGVPSRFSGSGSGTDFTFTISSLQPEDIATYYCQQDMRSPFTFGQGTKLEIK | 322 |

TABLE 26-continued

| Antibody | Heavy Chain Variable | SEQ ID NO: | Light Chain Variable | SEQ ID NO: |
|---|---|---|---|---|
| MTK-33.16 | QVQLVQSGAEVKKPGASVKVSC KASWYTFTSYWMHWVRQAPGQG LEWIGVIDPSDNYINYNQKFQG RVTMTRDTSTSTVYMELSSLRS EDTAVYYCAREAGTRGYFDYWG QGTLVTVSS | 303 | DIQMTQSPSSLSASVGDRVTITC QASRSVSNTVAWYQQKPGKAPKL LIYYASNRYTGVPSRFSGSGSGT DFTFTISSLQPEDIATYYCQQDY RSPFTFGQGTKLEIK | 311 |
| MTK-33.17 | QVQLVQSGAEVKKPGASVKVSC KASGYTFTSYWMHWVRQAPGQG LEWIGVIAPSDNYINYNQKFRG RVTMTRDTSTSTVYMELSSLRS EDTAVYYCAREAGTRGYFDYWG QGTLVTVSS | 304 | DIQMTQSPSSLSASVGDRVTITC QASRSVSNTVAWYQQKPGKAPKL LIYYASNRYTGVPSRFSGSGSGT DFTFTISSLQPEDIATYYCQQDM RSPFTFGQGTKLEIK | 322 |
| MTK-33.18 | QVQLVQSGAEVKKPGASVKVSC KASGYTFTSYWMHWVRQAPGQG LEWIGVISPSDNYINYNQKFRG RVTMTRDTSTSTVYMELSSLRS EDTAVYYCAREAGTRGYFDYWG QGTLVTVSS | 305 | DIQMTQSPSSLSASVGDRVTITC QASRSVSNTVAWYQQKPGKAPKL LIYYASNRYTGVPSRFSGSGSGT DFTFTISSLQPEDIATYYCQQDM RSPFTFGQGTKLEIK | 322 |
| MTK-33.19 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGDRVTITC QASRSVSATVAWYQQKPGKAPKL LIYYASNRYTGVPSRFSGSGSGT DFTFTISSLQPEDIATYYCQQDM RSPFTFGQGTKLEIK | 323 |
| MTK-33.20 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGDRVTITC QASRSVSNTVAWYQQKPGKAPKL LIYYASNRYTGVPSRFSGSGSGT DFTFTISSLQPEDIATYYCAQDM RSPFTFGQGTKLEIK | 324 |
| MTK-33.21 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 301 | DIQMTQSPSSLSASVGGRVTITC QASRSVSNTVAWYQQKPGKAPKL LIYYVSNRYTGVPSRFSGSGSGT DFTFTISSLQPEDIATYYCQQDM RSPFTFGQGTKLEIK | 325 |
| MTK-33.22 | QVQLVQSGAEVKKPGASVKVSC KASGYTFTSYWMHWVRQAPGQG LEWIGVIDPSDNYINYNQKLRG RVTMTRDTSTSTVYMELSSLRS EDTAVYYCAREAGTRGYFDYWG QGTLVTVSS | 306 | DIQMTQSPSSLSASVGDRVTITC QASRSVSNTVAWYQQKPGKAPKL LIYYASNRRTGVPSRFSGSGSGT DFTFTISSLQPEDIATYYCQQDM RSPFTFGQGTKLEIK | 326 |
| MTK-33.23 | QVQLVQSGAEVKKPGASVKVSC KASGYTFTSYWMHWVRQAPGQG LEWIGVIDPSDNYINYNQKFRG RVTMTRDTSTSTVYMELSSLRS EDTAVYYCAREAYTRGYFDYWG QGTLVTVSS | 307 | DIQMTQSPSSLSASVGDRVTITC IASRSVSNTVAWYQQKPGKAPKL LIYYASNRYTGVPSRFSGSGSGT DFTFTISSLQPEDIATYYCQQDM RSPFTFGQGTKLEIK | 327 |
| MTK-33.24 | QVQLVQSGAEVKKPGASVKVSC KASSYTFTSYWMHWVRQAPGQG LEWIGVIDPSDNYINYNQKFRG RVTMTRDTSTSTVYMELSSLRS EDTAVYYCAREAGTRGYFDYWG QGTLVTVSS | 308 | DIQMTQSPSSLSASVGDRVTITC QASRSVSRTVAWYQQKPGKAPKL LIYYASNRYTGVPSRFSGSGSGT DFTFTISSLQPEDIATYYCQQDM RSPFTFGQGTKLEIK | 328 |

TABLE 27

| Antibody | HVR-H1 | SEQ ID NO: | HVR-H2 | SEQ ID NO: | HVR-H3 | SEQ ID NO: |
|---|---|---|---|---|---|---|
| MTK-15.1 | NYGVH | 83 | WINTYTGEPT YAQGFTG | 329 | GNRYAYQDY | 334 |
| MTK-15.2 | NYGVH | 83 | WGNTYTGEPT YAQGFTG | 330 | GNRYAYMDY | 138 |
| MTK-15.3 | NYGVH | 83 | WINTYTGEPT YAQGFTG | 329 | GNRYAYMDY | 138 |
| MTK-15.4 | NYGVH | 83 | WINTYTGEPT YAQGFTG | 329 | GNRYAYMDY | 138 |
| MTK-15.5 | NYGVH | 83 | WINTYTGEPT YAQGFTG | 329 | GTRYAYMDY | 335 |
| MTK-15.6 | NYGVH | 83 | WINTYTGEPY YAQGFTG | 331 | GNRYAYMDY | 138 |
| MTK-15.7 | NYGVH | 83 | WINTYTGEPT YAQGFTG | 329 | GNRYAYMDY | 138 |
| MTK-15.8 | NYGVH | 83 | WINTYTGEPT YAQGFTG | 329 | GVRYAYMDY | 336 |
| MTK-15.9 | NYGVH | 83 | WINTYTGEPT YAQGFTG | 329 | GYRYAYMDY | 337 |
| MTK-15.10 | NYGVH | 83 | WINTYQGEPT YAQGFTG | 332 | GARYAYMDY | 338 |
| MTK-15.11 | NYGVH | 83 | WINTYEGEPT YAQGFTG | 333 | GNRYAYQDY | 334 |
| MTK-15.12 | NYGVH | 83 | WINTYQGEPT YAQGFTG | 332 | GVRYAYMDY | 336 |
| MTK-15.13 | NYGVH | 83 | WINTYTGEPT YAQGFTG | 329 | GNRYAYEDY | 339 |
| MTK-15.14 | NYGVH | 83 | WINTYTGEPT YAQGFTG | 329 | GNRYAYMDY | 138 |
| MTK-15.15 | NYGVH | 83 | WINTYTGEPT YAQGFTG | 329 | GNRYAYMDY | 138 |

TABLE 28

| Antibody | HVR-L1 | SEQ ID NO: | HVR-L2 | SEQ ID NO: | HVR-L3 | SEQ ID NO: |
|---|---|---|---|---|---|---|
| MTK-15.1 | RASSSVSYMH | 158 | ATSNLAS | 187 | QQWSSNPRT | 210 |
| MTK-15.2 | RASSSVSYMH | 158 | ATSNLAS | 187 | QQWSSNPRT | 210 |
| MTK-15.3 | RASSHVSYMH | 340 | ATSNLAS | 187 | QQWSSNPRT | 210 |
| MTK-15.4 | RASSSVGYMH | 341 | ATSNLAS | 187 | QQWSSNPRT | 210 |
| MTK-15.5 | RASSSVGYMH | 341 | ATSNLAS | 187 | QQWSSNPRT | 210 |
| MTK-15.6 | RASSSVGYMH | 341 | ATSNLAS | 187 | QQWSSNPRT | 210 |
| MTK-15.7 | RASSGVSYMH | 342 | ATSNLAS | 187 | QQWSSNPRT | 210 |
| MTK-15.8 | RASSSVGYMH | 341 | ATSNLAS | 187 | QQWSSNPRT | 210 |
| MTK-15.9 | RASSSTSYMH | 343 | ATSNLAS | 187 | QQWSSNPRT | 210 |
| MTK-15.10 | RASSSVGYMH | 341 | ATSNLAS | 187 | QQWSSNPRT | 210 |
| MTK-15.11 | RASSSVSYMH | 158 | ATSNLAS | 187 | QQWSSNPRT | 210 |
| MTK-15.12 | RASSSVGYMH | 341 | ATSNLAS | 187 | QQWSSNPRT | 210 |
| MTK-15.13 | RASSSVQYMH | 344 | ATSNLAS | 187 | QQWSSNPRT | 210 |
| MTK-15.14 | RASSSVSYMH | 158 | ATSNLAS | 187 | QQWSSNPRT | 210 |
| MTK15.15 | RASSSVSYMH | 158 | ATSNLAS | 187 | QQWSSNPRT | 210 |

TABLE 29

| Antibody | HVR-H1 | SEQ ID NO: | HVR-H2 | SEQ ID NO: | HVR-H3 | SEQ ID NO: |
|---|---|---|---|---|---|---|
| MTK-16.1 | NHGMN | 84 | WINTYTGEPT YAQGFTG | 329 | KGVTAARYF DY | 139 |
| MTK-16.2 | NHGMN | 84 | WINTYTGEPT YADDFKG | 99 | KGVTAARYF DY | 139 |

TABLE 30

| Antibody | HVR-L1 | SEQ ID NO: | HVR-L2 | SEQ ID NO: | HVR-L3 | SEQ ID NO: |
|---|---|---|---|---|---|---|
| MTK-16.1 | KASQNVRTAVA | 169 | LASNRHT | 195 | LQHWNYPLT | 219 |
| MTK-16.2 | RASQNVRTAVA | 345 | LASNRHT | 195 | LQHWNYPLT | 219 |

TABLE 31

| Antibody | HVR-H1 | SEQ ID NO: | HVR-H2 | SEQ ID NO: | HVR-H3 | SEQ ID NO: |
|---|---|---|---|---|---|---|
| MTK-29.1 | SYGLS | 346 | WINTYSGVPT YAQGFTG | 348 | YTNYGIFDY | 355 |
| MTK-29.2 | TYGMS | 95 | WINTYSGVPT YTDDFKG | 119 | YTNYGIFDY | 355 |
| MTK-29.3 | TYGMS | 95 | WINTYSGVPA YTDDFKG | 349 | YTNYGVFDY | 356 |
| MTK-29.4 | TYGMS | 95 | WINTYSGVPT YTDDFKG | 119 | YTNYGVFDY | 356 |
| MTK-29.5 | SYGLS | 346 | WINTYSGVPT YTDDFKG | 119 | YTNYGVFDY | 356 |
| MTK-29.6 | TYGMS | 95 | WINTMSGVPT YTDDFKG | 350 | YTNYGVFDY | 356 |
| MTK-29.7 | TYGMS | 95 | WINTYSGVPS YTDDFKA | 351 | YTNYGVFDY | 356 |
| MTK-29.8 | TYGLS | 347 | WINTYSGVPT YTDDFKG | 119 | YTNYGVFDY | 356 |
| MTK-29.9 | SYGLS | 346 | WINTYSGVPT YTDDFKG | 119 | YTNYGVFDY | 356 |
| MTK-29.10 | TYGMS | 95 | WINTYSGVPT YTDDFKG | 119 | YTNYGVFDY | 356 |
| MTK-29.11 | TYGMS | 95 | WINTDSGVPT YTDDFKG | 352 | YTNYGVFDY | 356 |
| MTK-29.12 | TYGMS | 95 | WINTMSGVPT YTDDFKG | 350 | YTNYGVFDY | 356 |
| MTK-29.13 | TYGMS | 95 | WINTASGVPT YTDDFKG | 353 | YTNYGVFDY | 356 |
| MTK-29.14 | TYGMS | 95 | WINTYSGVPS YTDDFKA | 351 | YTNYGVFDY | 356 |
| MTK-29.15 | TYGMS | 95 | WINTMSGVPT YTDDFKG | 350 | YTNYGVFDY | 356 |
| MTK-29.16 | SYGLS | 346 | WVNTYSGVPT YTDDFKG | 354 | YTNYGVFDY | 356 |
| MTK-29.17 | SYGLS | 346 | WINTYSGVPT YAQGFTG | 348 | YTNYGVFDY | 356 |
| MTK-29.18 | SYGLS | 346 | WVNTYSGVPT YTDDFKG | 354 | YTNYGVFDY | 356 |
| MTK-29.19 | TYGMS | 95 | WINTYSGVPT YAQGFTG | 348 | YTNYGYFDY | 151 |
| MTK-29.20 | TYGMS | 95 | WINTYSGVPT YAQGFTG | 348 | YTNYGYFDY | 151 |
| MTK-29.21 | TYGMS | 95 | WINTYSGVPT YAQGFTG | 348 | YTNYGYFDY | 151 |

TABLE 32

| Antibody | HVR-L1 | SEQ ID NO: | HVR-L2 | SEQ ID NO: | HVR-L3 | SEQ ID NO: |
|---|---|---|---|---|---|---|
| MTK-29.1 | RASSSVGYMH | 341 | ATSNLAS | 187 | QQWGSWPFT | 360 |
| MTK-29.2 | RASSSVGYMH | 341 | ATSNLAS | 187 | QQWGSIPFT | 361 |
| MTK-29.3 | RASSSVGYMH | 341 | ATSNLAS | 187 | QQWGSLPFT | 362 |
| MTK-29.4 | RASSSVGYMH | 341 | ATSNLAQ | 359 | QQWGSLPFT | 362 |
| MTK-29.5 | RASSSVGYMH | 341 | ATSNLAQ | 359 | QQWGSLPFT | 362 |
| MTK-29.6 | RASSSVGYMH | 341 | ATSNLAQ | 359 | QQWGSLPFT | 362 |
| MTK-29.7 | RASSSVGYMH | 341 | ATSNLAQ | 359 | QQWGSLPFT | 362 |
| MTK-29.8 | RASSSVGYMH | 341 | ATSNLAQ | 359 | QQWGSLPFT | 362 |
| MTK-29.9 | RASSSVGYMH | 341 | ATSNLAQ | 359 | QQWGSLPFT | 362 |
| MTK-29.10 | RASSSVGYMH | 341 | ATSNLAS | 187 | QQWGSLPFT | 362 |
| MTK-29.11 | RASSSVGYMH | 341 | ATSNLAS | 187 | QQWGSLPFT | 362 |
| MTK-29.12 | RASSSVGYMH | 341 | ATSNLAQ | 359 | QQWGSLPFT | 362 |
| MTK-29.13 | RASSSVGYMH | 341 | ATSNLAQ | 359 | QQWGSLPFT | 362 |
| MTK-29.14 | RASSSVGYMH | 341 | ATSNLAQ | 359 | QQWGSLPFT | 362 |
| MTK-29.15 | RASSSVGYMH | 341 | ATSNLAQ | 359 | QQWGSLPFT | 362 |
| MTK-29.16 | RASSSVGYMH | 341 | ATSNLAQ | 359 | QQWGRLPFT | 363 |
| MTK-29.17 | RSSSSVGYMH | 357 | ATSNLAQ | 359 | QQWGSLPFT | 362 |
| MTK-29.18 | RASSTVGYMH | 358 | ATSNLAS | 187 | QQWGSLPFT | 362 |
| MTK-29.19 | RATSSVGYMH | 181 | ATSNLAS | 187 | QQWGSNPFT | 208 |
| MTK-29.20 | RATSSVGYMH | 181 | ATSNLAS | 187 | QQWGSNPFT | 208 |
| MTK-29.21 | RATSSVGYMH | 181 | ATSNLAS | 187 | QQWGSNPFT | 208 |

TABLE 33

| Antibody | HVR-H1 | SEQ ID NO: | HVR-H2 | SEQ ID NO: | HVR-H3 | SEQ ID NO: |
|---|---|---|---|---|---|---|
| MTK-33.1 | SYWMH | 90 | VIDPSDNYIN YNQKFQG | 364 | EAWTRGYFN Y | 373 |
| MTK-33.2 | SYWMH | 90 | VIDPSDNYIN YNQKFQG | 364 | EAGTRGYFD Y | 155 |
| MTK-33.3 | SYWMH | 90 | VIDPSDNYIN YNQKFQG | 364 | EAWTRGYFD Y | 374 |
| MTK-33.4 | SYWMH | 90 | VIDPSDNYIN MNQKFQG | 365 | EAGTRGYFD Y | 155 |
| MTK-33.5 | SYWMH | 90 | VIDPSDNYIN YNQKFQG | 364 | EAGTRGYFD Y | 155 |
| MTK-33.6 | SYWMH | 90 | VIDPSDNYIN YNQKFQG | 364 | EAGTRGYFD Y | 155 |
| MTK-33.7 | SYWMH | 90 | VIDPSDNYIN YNAKFQG | 366 | EAGTRGYFD Y | 155 |
| MTK-33.8 | SYWMH | 90 | VIDPSDNYIN YNQKFQG | 364 | EAWTRGYFN Y | 373 |
| MTK-33.9 | SYWMH | 90 | VIDPSDRYIN YNQKFQG | 367 | EAGTRGYFD Y | 155 |

TABLE 33-continued

| Antibody | HVR-H1 | SEQ ID NO: | HVR-H2 | SEQ ID NO: | HVR-H3 | SEQ ID NO: |
|---|---|---|---|---|---|---|
| MTK-33.10 | SYWMH | 90 | VIDPSDNYIN YNQKFRG | 368 | EAGTRGYFD Y | 155 |
| MTK-33.11 | SYWMH | 90 | VIDPSDNYIN YNQKFQG | 364 | EAWTRGYFD Y | 374 |
| MTK-33.12 | SYWMH | 90 | VIDPSDNYIN YNQKFRG | 368 | EAGTRGYFD Y | 155 |
| MTK-33.13 | SYWMH | 90 | VIDPSDNYIN YNQKFQG | 364 | EAGTRGYFD Y | 155 |
| MTK-33.14 | SYWMH | 90 | VIDPSDNYIN YNQKFRG | 368 | EAGTRGYFD Y | 155 |
| MTK-33.15 | SYWMH | 90 | VIDPSDNYIN YNQKFQV | 369 | EAGTRGYFD Y | 155 |
| MTK-33.16 | SYWMH | 90 | VIDPSDNYIN YNQKFQG | 364 | EAGTRGYFD Y | 155 |
| MTK-33.17 | SYWMH | 90 | VIAPSDNYIN YNQKFRG | 370 | EAGTRGYFD Y | 155 |
| MTK-33.18 | SYWMH | 90 | VISPSDNYIN YNQKFRG | 371 | EAGTRGYFD Y | 155 |

TABLE 33-continued

| Anti-body | HVR-H1 | SEQ ID NO: | HVR-H2 | SEQ ID NO: | HVR-H3 | SEQ ID NO: |
|---|---|---|---|---|---|---|
| MTK-33.19 | SYWMH | 90 | VIDPSDNYIN YNQKFRG | 368 | EAGTRGYFD Y | 155 |
| MTK-33.20 | SYWMH | 90 | VIDPSDNYIN YNQKFRG | 368 | EAGTRGYFD Y | 155 |
| MTK-33.21 | SYWMH | 90 | VIDPSDNYIN YNQKFRG | 368 | EAGTRGYFD Y | 155 |
| MTK-33.22 | SYWMH | 90 | VIDPSDNYIN YNQKLRG | 372 | EAGTRGYFD Y | 155 |
| MTK-33.23 | SYWMH | 90 | VIDPSDNYIN YNQKFRG | 368 | EAYTRGYFD Y | 375 |
| MTK-33.24 | SYWMH | 90 | VIDPSDNYIN YNQKFRG | 368 | EAGTRGYFD Y | 155 |

TABLE 34

| Antibody | HVR-L1 | SEQ ID NO: | HVR-L2 | SEQ ID NO: | HVR-L3 | SEQ ID NO: |
|---|---|---|---|---|---|---|
| MTK-33.1 | QASQSVSNTVA | 376 | YASLRYT | 388 | QQDYRSPFT | 231 |
| MTK-33.2 | QASGSVSNTVA | 377 | YASNRYT | 203 | QQDYRSPFT | 231 |
| MTK-33.3 | QASRSVSNTVA | 378 | YASNRYT | 203 | QQDYRSPFT | 231 |
| MTK-33.4 | QASQSVSNTVA | 376 | YASNRYT | 203 | QQDRRSPFT | 392 |
| MTK-33.5 | QASQSVSNTVA | 376 | YASNRET | 389 | QQDYRSPFT | 231 |
| MTK-33.6 | QASRSVSNTMA | 379 | YASNRYT | 203 | QQDYRSPFT | 231 |
| MTK-33.7 | GASQSVSNTVA | 380 | YASNRYT | 203 | QQDYRSPFT | 231 |
| MTK-33.8 | QASQSVSRTVA | 381 | YASNRYT | 203 | QQDYRSPFT | 231 |
| MTK-33.9 | QASASVSNTVA | 382 | YASNRYT | 203 | QQDYRSPFT | 231 |
| MTK-33.10 | QAGQSVSNTVA | 383 | YASNRYT | 203 | QQDYRSPFT | 231 |
| MTK-33.11 | QASRSVRNTVA | 384 | YASNRYT | 203 | QQDYRSPFT | 231 |
| MTK-33.12 | QASQSVSNTVA | 376 | YASNRYT | 203 | RQDTRSPFT | 393 |
| MTK-33.13 | QASRSVSNTVA | 378 | YASNRYT | 203 | QQDYRSPFT | 231 |
| MTK-33.14 | QASQSVSNTVA | 376 | YASNRYT | 203 | QQDYRSPFT | 231 |
| MTK-33.15 | QASRSVSNTVA | 378 | YASNRYT | 203 | QQDMRSPFT | 394 |
| MTK-33.16 | QASRSVSNTVA | 378 | YASNRYT | 203 | QQDYRSPFT | 231 |
| MTK-33.17 | QASRSVSNTVA | 378 | YASNRYT | 203 | QQDMRSPFT | 394 |
| MTK-33.18 | QASRSVSNTVA | 378 | YASNRYT | 203 | QQDMRSPFT | 394 |
| MTK-33.19 | QASRSVSATVA | 385 | YASNRYT | 203 | QQDMRSPFT | 394 |
| MTK-33.20 | QASRSVSNTVA | 378 | YASNRYT | 203 | AQDMRSPFT | 395 |
| MTK-33.21 | QASRSVSNTVA | 378 | YVSNRYT | 390 | QQDMRSPFT | 394 |
| MTK-33.22 | QASRSVSNTVA | 378 | YASNRRT | 391 | QQDMRSPFT | 394 |
| MTK-33.23 | IASRSVSNTVA | 386 | YASNRYT | 203 | QQDMRSPFT | 394 |
| MTK-33.24 | QASRSVSRTVA | 387 | YASNRYT | 203 | QQDMRSPFT | 394 |

Example 26: Blocking Efferocytosis with Humanized and Affinity-Matured Anti-MerTK Antibodies The ability of humanized and affinity-matured anti-MerTK antibodies of the present disclosure to block efferocytosis was evaluated using methods as described above in Example 11 with the following modifications. Differentiated human macrophages were treated with 100 nM Dexamethasone (Sigma-Aldrich) and 10 μg/ml huM-CSF (R&D systems) for 2 days. 50,000 cells of polarized macrophages were seeded in 96-well plate. Humanized or affinity-matured anti-MerTK antibodies were titrated to a final concentration range of between 66.6 nM to 4 pM and then each serially diluted antibody was added to each well for 30 min at 37° C.

Staurosporin-induced apoptotic Jurkat cells were labeled with pHrodo (ThermoFisher) and then added into each well at 1:4 ratio (1 macrophage: 4 Jurkat cells) for 1 hour. The plates were washed with PBS and then the cells were stained with APC-conjugated anti-human CD14 for 30 minutes on ice in the dark. Cells were then washed twice in FACS buffer (PBS+2% FBS), and flow cytometry was performed on a BD FACS Canto IL. Data were analyzed using FlowJo software. In these experiments, baseline efferocytosis levels were established using macrophages cultured with media alone and this was set to 10000 efferocytosis activity. Relative efferocytosis activity was calculated as a percent of efferocytosis observed in cells treated with media alone compared to that observed in cells treated with anti-MerTK antibodies. The results of these studies are shown below in Table 35.

TABLE 35

| Antibody | Efferocytosis blocking activity average IC50 (nM) from at least three different donors |
|---|---|
| MTK-15.1 | 0.594 |
| MTK-15.2 | 0.867 |
| MTK-15.3 | 1.006 |
| MTK-15.4 | 0.764 |
| MTK-15.5 | 0.556 |
| MTK-15.6 | 0.506 |
| MTK-15.7 | 0.789 |
| MTK-15.8 | 0.648 |
| MTK-15.9 | 2.432 |
| MTK-15.10 | 0.579 |
| MTK-15.11 | 1.014 |
| MTK-15.12 | 1.016 |
| MTK-15.13 | 0.722 |
| MTK-15.14 | 0.902 |
| MTK-15.15 | 0.228 |
| MTK-16.1 | 0.363 |
| MTK-16.2 | 1.010 |
| MTK-29.5 | 0.572 |
| MTK-29.7 | 0.768 |
| MTK-29.8 | 0.844 |
| MTK-29.9 | 0.632 |
| MTK-29.10 | 0.823 |
| MTK-29.11 | 1.006 |
| MTK-29.12 | 1.119 |
| MTK-29.13 | 0.974 |
| MTK-29.14 | 0.719 |
| MTK-29.15 | 0.963 |
| MTK-29.16 | 0.433 |
| MTK-29.17 | 0.963 |
| MTK-29.18 | 0.697 |
| MTK-29.19 | 0.705 |
| MTK-29.20 | 0.500 |
| MTK-29.21 | 0.819 |
| MTK-33.1 | 5.5 |
| MTK-33.5 | 2.248 |
| MTK-33.7 | 7.542 |
| MTK-33.8 | 23.69 |
| MTK-33.10 | 8.850 |
| MTK-33.11 | 0.453 |
| MTK-33.12 | 0.257 |
| MTK-33.13 | 1.641 |
| MTK-33.14 | 3.568 |
| MTK-33.15 | 0.480 |
| MTK-33.16 | 0.807 |
| MTK-33.17 | 7.494 |
| MTK-33.19 | 0.348 |
| MTK-33.20 | 0.457 |
| MTK-33.21 | 0.534 |
| MTK-33.22 | 0.629 |
| MTK-33.23 | 0.405 |
| MTK-33.24 | 0.480 |
| MTK-33.25 | 0.457 |

As shown in Table 35, humanized and affinity-matured anti-MerTK antibodies of the present disclosure were effective at blocking efferocytosis by human macrophages, displaying various IC50 values. Certain affinity-matured variants of anti-MerTK antibodies MTK-15, MTK-16, and MTK-33 displayed similar IC50 values to the corresponding parental anti-MerTK antibodies (see Example 11 above). Certain other affinity matured variants of anti-MerTK antibodies displayed lower IC50 values for blocking efferocytosis (e.g., MTK-15.1, MTK-15.4, MTK-15.5, MTK-15.6, MTK-15.7, MTK-15.8, MTK-15.10, MTK-15.13, MTK-15.15, MTK-16.1, and MTK-33.15) Affinity-matured variants of MTK-15 showed a range of IC50 values of 0.228 nM to 2.4 nM; affinity-matured variants of MTK-16 showed a range of IC50 values of 0.36 nM to 1.01 nM affinity-matured variants of MTK-29 showed a range of IC50 values of 0.5 nM to 1.12 nM; affinity-matured variants of MTK-33 showed a range of IC50 values of 0.41 nM to 23.9 nM.

Example 27: Binding Kinetics of Humanized and Affinity-Matured Anti-MerTK Antibodies Binding kinetics of humanized and affinity-matured anti-MerTK antibodies of the present disclosure to human, murine, and cynomolgus MerTK proteins were evaluated as follows. Briefly, anti-MerTK antibodies were prepared by diluting to 10 μg/ml in 10 mM Acetate, pH 4.25 (Carterra, Salt Lake City, Utah), at 300 μl/well. A HC200M sensor chip (Carterra) was activated using the single channel flow cell with a 7-minute injection of a 1:1:1 mixture of 100 mM MES pH 5.5, 100 mM sulfo-NHS, 400 mM EDC (all reconstituted in MES pH 5.5; 100 μl of each mixed in vial immediately before running assay). After switching to the multi-channel array flow cell, the antibodies were injected over the activated chip in a 96-spot array for 15 minutes. The remaining unconjugated active groups on the chip were then blocked by injecting 1M Ethanolamine pH 8.5 (Carterra) for 7 minutes using the single channel flow cell.

After priming with running buffer (HBS-TE, Carterra) with 0.5 mg/ml BSA (Sigma), the immobilized anti-MerTK antibodies were tested for their ability to bind to several forms of recombinant MerTK extracellular domain, including human, cynomolgus, and mouse orthologs as described above.

Estimates of affinity were generated by injecting each analyte over the entire antibody array using the single channel flow cell. MerTK analytes were diluted to 33.3, 100, and 300 nM in running buffer, and injected in serial from lowest to highest concentration without regeneration. Two buffer blanks were run between each series (one species per series). Data were processed and analyzed using NextGen-KIT high-throughput kinetics analysis software (Carterra). In these experiments, the anti-MerTK antibodies were human IgG1 isotype containing the Fc variant LALAPS.

The equilibrium dissociation constants ($K_D$) were then calculated from the filled association and dissociation rate constants (k-on and k-off) for anti-MerTK antibodies of the present disclosure. The $K_D$ values obtained from these experiments are summarized in Table 36 below.

TABLE 36

| Antibody | $K_D$ (nM) | | |
|---|---|---|---|
| | huMerTK | moMerTK | cynoMerTK |
| MTK-15.1 | 8.3 | 1500 | 8.0 |
| MTK-15.2 | 21.5 | NB | 21.5 |
| MTK-15.3 | 21.5 | NB | 23 |
| MTK-15.4 | NF | NB | 1450 |
| MTK-15.5 | 0.1 | 690 | 0.8 |
| MTK-15.6 | 1.0 | 1700 | 1.5 |
| MTK-15.7 | 0.1 | 705 | 0.3 |
| MTK-15.8 | 4.9 | NB | 5.0 |

TABLE 36-continued

| Antibody | KD (nM) huMerTK | moMerTK | cynoMerTK |
|---|---|---|---|
| MTK-15.9 | 10 | 850 | 11.5 |
| MTK-15.10 | 3.3 | 2800 | 3.3 |
| MTK-15.11 | 12.5 | 140 | 12.5 |
| MTK-15.12 | 17.5 | 114 | 18 |
| MTK-15.13 | 2.3 | 130 | 2.8 |
| MTK-16.1 | 86 | NB | 170 |
| MTK-16.2 | 80 | NB | 160 |
| MTK-29.5 | 4.4 | 135 | 4.4 |
| MTK-29.7 | 3.6 | 95 | 3.2 |
| MTK-29.8 | 23 | 310 | 22.5 |
| MTK-29.9 | 5.7 | 140 | 5.8 |
| MTK-29.10 | 4.5 | 116 | 4.2 |
| MTK-29.11 | 2.1 | 59 | 2.4 |
| MTK-29.12 | 23 | 250 | 21 |
| MTK-29.13 | 13 | 170 | 11 |
| MTK-29.14 | 7.6 | 100 | 7.3 |
| MTK-29.15 | 7.4 | NB | 8.4 |
| MTK-29.16 | 8.6 | 205 | 8.8 |
| MTK-29.17 | 9.6 | 170 | 9.9 |
| MTK-29.18 | 4.7 | 140 | 4.9 |
| MTK-33.5 | 28 | 140 | 26 |
| MTK-33.7 | 78 | 800 | 78 |
| MTK-33.8 | 41 | 465 | 41 |
| MTK-33.10 | 41 | 150 | 38 |
| MTK-33.11 | 11 | 115 | 10.1 |
| MTK-33.12 | 8.6 | 230 | 7.9 |
| MTK-33.13 | 20 | 225 | 18 |
| MTK-33.14 | 30.5 | 275 | 29 |
| MTK-33.15 | 4.6 | 105 | 4.0 |
| MTK-33.16 | 10.9 | 225 | 10.1 |
| MTK-33.17 | 20.4 | 505 | 19.9 |
| MTK-33.21 | 0.4 | 44 | 0.3 |
| MTK-33.25 | 1.2 | 53 | 1.1 |

NB = No binding
NF = No fit, meaning the data obtained did not fit a 1:1 binding equilibrium model These results showed that humanized and affinity-matured anti-MerTK antibodies of the present disclosure displayed a range of affinities to human, cynomolgus, and murine MerTK protein.

These results also showed that humanized and affinity-matured anti-MerTK antibodies of the present disclosure variously displayed species binding specificity and cross-reactivity to human, murine, and cynomolgus MerTK. In particular, affinity of anti-MerTK antibodies of the present disclosure for binding to human MerTK ranged from 0.1 nM to 86 nM; affinity of anti-MerTK antibodies of the present disclosure for binding to cyno MerTK ranged from 0.3 nM to 1450 nM; and affinity of anti-MerTK antibodies of the present disclosure for binding to murine MerTK ranged from 44 nM to 2800 nM. Compared to the parental anti-MerTK antibody MTK-15, certain affinity-matured anti-MerTK antibody MTK-15 variants gained binding activity to mouse MerTK, which ranged from 114 nM to 2800 nM.

Table 37 below sets forth amino acid sequences of various human heavy chain immunoglobulin Fc variants.

TABLE 37

| Human Ig Heavy Chain Fc variants | Sequence | SEQ ID NO |
|---|---|---|
| huIgG1 WT Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 396 |
| huIgG1 WT Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 397 |
| huIgG1 LALAPS Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 398 |
| huIgG1 LALAPS Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 399 |
| huIgG1 NSLF Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSSKAFPAPIEKTISKAKGQPREPQVYTLPPSRDELTKNQVSLTC | 400 |

TABLE 37-continued

| Human Ig Heavy Chain Fc variants | Sequence | SEQ ID NO |
|---|---|---|
| | LVKGFYPSDIAVEWESNGQPENNYKTTPPVLDSDGSFFLYSKLTVDKSRW QQGNVFSCSVMHEALHNHYTQKSLSLSPGK | |
| huIgG1 NSLF Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGK EYKCKVSSKAFPAPIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 401 |
| huIgG1 YTE Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLYITREPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPGK | 402 |
| huIgG1 YTE Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLYITREPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVMHEALHNHYTQKSLSLSPG | 403 |
| huIgG1 LS Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVLHEALHSHYTQKSLSLSPGK | 404 |
| huIgG1 LS Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGQPENNYKTTPPVLDSDGSFFLYSKLTVDKSRW QQGNVFSCSVLHEALHSHYTQKSLSLSPG | 405 |
| huIgG1 LV5-112 Fc with C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGGCALYPTNCGGGQPENNYKTTPPVLDSDGSFF LYSKLTVDKSRWQQGNVFSCSVMHEALHNHYTQKSLSLSPGK | 406 |
| huIgG1 LV5-112 Fc without C-terminal lysine | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEP KSCDKTHTCPPCPAPEAAGGPSVFLFPPKPKDTLMISRTPEVTCVVVDVS HEDPEVKFNWYVDGVEVHNAKTKPREEQYNSTYRVVSVLTVLHQDWLNGK EYKCKVSNKALPASIEKTISKAKGQPREPQVYTLPPSRDELTKNQVSLTC LVKGFYPSDIAVEWESNGGCALYPTNCGGGQPENNYKTTPPVLDSDGSFF LYSKLTVDKSRWQQGNVFSCSVMHEALHNHYTQKSLSLSPG | 407 |
| huIgG2 WT Fc with C-terminal lysine | ASTKGPSVFPLAPCSRSTSESTAALGCLVKDYFPEPVTVSWNSGALTSGV HTFPAVLQSSGLYSLSSVVTVPSSNFGTQTYTCNVDHKPSNTKVDKTVER KCCVECPPCPAPPVAGPSVFLFPPKPKDTLMISRTPEVTCVVVDVSHEDP EVQFNWYVDGVEVHNAKTKPREEQFNSTFRVVSVLTVVHQDWLNGKEYKC KVSNKGLPAPIEKTISKTKGQPREPQVYTLPPSREEMTKNQVSLTCLVKG FYPSDIAVEWESNGQPENNYKTTPPMLDSDGSFFLYSKLTVDKSRWQQGN VFSCSVMHEALHNHYTQKSLSLSPGK | 408 |
| huIgG2 WT Fc without C-terminal lysine | ASTKGPSVFPLAPCSRSTSESTAALGCLVKDYFPEPVTVSWNSGALTSGV HTFPAVLQSSGLYSLSSVVTVPSSNFGTQTYTCNVDHKPSNTKVDKTVER KCCVECPPCPAPPVAGPSVFLFPPKPKDTLMISRTPEVTCVVVDVSHEDP EVQFNWYVDGVEVHNAKTKPREEQFNSTFRVVSVLTVVHQDWLNGKEYKC KVSNKGLPAPIEKTISKTKGQPREPQVYTLPPSREEMTKNQVSLTCLVKG FYPSDIAVEWESNGQPENNYKTTPPMLDSDGSFFLYSKLTVDKSRWQQGN VFSCSVMHEALHNHYTQKSLSLSPG | 409 |

TABLE 37-continued

| Human Ig Heavy Chain Fc variants | Sequence | SEQ ID NO |
|---|---|---|
| huIgG4 WT Fc with C-terminal lysine | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPSCPAPEFLGGPSVFLFPPKPKDTLMISRTPEVTCVVVDVSQED PEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEG NVFSCSVMHEALHNHYTQKSLSLSLGK | 410 |
| huIgG4 WT Fc without C-terminal lysine | ASTKGPSVFPLAPCSRSTSESTAALGCLVKDYFPEPVTVSWNSGALTSGV HTFPAVLQSSGLYSLSSVVTVPSSSLGTKTYTCNVDHKPSNTKVDKRVES KYGPPCPSCPAPEFLGGPSVFLFPPKPKDTLMISRTPEVTCVVVDVSQED PEVQFNWYVDGVEVHNAKTKPREEQFNSTYRVVSVLTVLHQDWLNGKEYK CKVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQEG NVFSCSVMHEALHNHYTQKSLSLSLG | 411 |

Human IgG1 light chain constant region amino acid sequence is set forth below:

(SEQ ID NO: 412)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

Full-length heavy chain amino acid sequences of certain anti-MerTK antibodies of the present disclosure are shown below in Table 38.

TABLE 38

| Antibody | Sequence | SEQ ID NO: |
|---|---|---|
| MTK-16.1 with huIgG1 WT Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 413 |
| MTK-16.1 with huIgG1 WT Fc without C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 414 |
| MTK-16.1 with huIgG1 LALAPS Fc with C-terminal lysine | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 415 |
| MTK-16.1 with hulgG1 LALAPS Fc without C-terminal | QVQLVQSGSELKKPGASVKVSCKASGYTFTNHGMNWVRQAPGQGLEWMGWI NTYTGEPTYAQGFTGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV | 416 |

TABLE 38-continued

| Antibody | Sequence | SEQ ID NO: |
|---|---|---|
| lysine | SVLTVLHQDWLNGKEYKCKVSNKALPASIEKTISKAKGQPREPQVYTLPPS<br>RDELTKNQVSLTCLVKGFYPSDIAVEWESNGQPENNYKTTPPVLDSDGSFF<br>LYSKLTVDKSRWQQGNVFSCSVMHEALHNHYTQKSLSLSPG | |
| MTK-16.1 with huIgG1 NSLF Fc with C-terminal lysine | QVQLVQSGSELKKPGASVKVSCKASGYTFTNHGMNWVRQAPGQGLEWMGWI<br>NTYTGEPTYAQGFTGRFVFSLDTSVSTAYLQISSLKAEDTAVYYCARKGVT<br>AARYFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVV<br>SVLTVLHQDWLNGKEYKCKVSSKAFPAPIEKTISKAKGQPREPQVYTLPPS<br>RDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK | 417 |
| MTK-16.1 with hulgG1 NSLF Fc without C-terminal lysine | QVQLVQSGSELKKPGASVKVSCKASGYTFTNHGMNWVRQAPGQGLEWMGWI<br>NTYTGEPTYAQGFTGRFVFSLDTSVSTAYLQISSLKAEDTAVYYCARKGVT<br>AARYFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVV<br>SVLTVLHQDWLNGKEYKCKVSSKAFPAPIEKTISKAKGQPREPQVYTLPPS<br>RDELTKNQVSLTCLVKGFYPSDIAVEWESNGQPENNYKTTPPVLDSDGSFF<br>LYSKLTVDKSRWQQGNVFSCSVMHEALHNHYTQKSLSLSPG | 418 |
| MTK-16.1 with hulgG4 Fc with C-terminal lysine | QVQLVQSGSELKKPGASVKVSCKASGYTFTNHGMNWVRQAPGQGLEWMGWI<br>NTYTGEPTYAQGFTGRFVFSLDTSVSTAYLQISSLKAEDTAVYYCARKGVT<br>AARYFDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPSCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYS<br>RLTVDKSRWQEGNVFSCSVMHEALHNHYTQKSLSLSLGK | 419 |
| MTK-16.1 with hulgG4 Fc without C-terminal lysine | NTYTGEPTYAQGFTGRFVFSLDTSVSTAYLQISSLKAEDTAVYYCARKGVT<br>AARYFDYWGQGTLVTVSSASTKGPSVFPLAPCSRSTSESTAALGCLVKDYF<br>PEPVTVSWNSGALTSGVHTFPAVLQSSGLYSLSSVVTVPSSSLGTKTYTCN<br>VDHKPSNTKVDKRVESKYGPPCPSCPAPEFLGGPSVFLFPPKPKDTLMISR<br>TPEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYS<br>RLTVDKSRWQEGNVFSCSVMHEALHNHYTQKSLSLSLG | 420 |

MTK-16.1 light chain amino acid sequence is set forth below:

(SEQ ID NO: 421)
DIQMTQSPSSLSASVGDRVTITCKASQNVRTAVAWYQQKPGKAPKRLIYL

ASNRHTGVPSRFSGSGSGTEFTLTISNLQPEDFATYYCLQHWNYPLTFGG

-continued

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full-length heavy chain amino acid sequences of certain anti-MerTK antibodies of the present disclosure are shown below in Table 39.

TABLE 39

| Antibody | Sequence | SEQ ID NO: |
|---|---|---|
| MTK-16.2 with huIgG1 WT Fc with C-terminal lysine | QVQLVQSGSELKKPGASVKVSCKASGYTFTNHGMNWVRQAPGQGLEWMGWI<br>NTYTGEPTYADDFKGRFVFSLDTSVSTAYLQISSLKAEDTAVYYCARKGVT<br>AARYFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLM<br>ISRTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPS<br>RDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK | 422 |
| MTK-16.2 with huIgG1 WT Fc without C- | QVQLVQSGSELKKPGASVKVSCKASGYTFTNHGMNWVRQAPGQGLEWMGWI<br>NTYTGEPTYADDFKGRFVFSLDTSVSTAYLQISSLKAEDTAVYYCARKGVT<br>AARYFDYWGQGTLVTVSSASTKGPSVFPLAPSSKSTSGGTAALGCLVKDYF<br>PEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLM | 423 |

TABLE 39-continued

| Antibody | Sequence | SEQ ID NO: |
|---|---|---|
| terminal lysine | ISRTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | |
| MTK-16.2 with huIgG1 LALAPS Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 424 |
| MTK-16.2 with huIgG1 LALAPS Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPEAAGGPSVFLFPPKPKDTLM ISRTPEVTCVVVDVSHEDPEVKFNWYVDGVEVHNAKTKPREEQYNSTYRVV SVLTVLHQDWLNGKEYKCKVSNKALPASIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 425 |
| MTK-16.2 with huIgG1 NSLF Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPGK | 426 |
| MTK-16.2 with huIgG1 NSLF Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPSSKSTSGGTAALGCLVKDYF PEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVV SVLTVLHQDWLNGKEYKCKVSSKAFPAPIEKTISKAKGQPREPQVYTLPPS RDELTKNQVSLTCLVKGFYPSDIAVEWESNGQPENNYKTTPPVLDSDGSFF LYSKLTVDKSRWQQGNVFSCSVMHEALHNHYTQKSLSLSPG | 427 |
| MTK-16.2 with huIgG4 Fc with C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSSASTKGPSVFPLAPCSRSTSESTAALGCLVKDYF PEPVTVSWNSGALTSGVHTFPAVLQSSGLYSLSSVVTVPSSSLGTKTYTCN VDHKPSNTKVDKRVESKYGPPCPSCPAPEFLGGPSVFLFPPKPKDTLMISR TPEVTCVVVDVSQEDPEVQFNWYVDGVEVHNAKTKPREEQFNSTYRVVSVL TVLHQDWLNGKEYKCKVSNKGLPSSIEKTISKAKGQPREPQVYTLPPSQEE MTKNQVSLTCLVKGFYPSDIAVEWESNGQPENNYKTTPPVLDSDGSFFLYS RLTVDKSRWQEGNVFSCSVMHEALHNHYTQKSLSLSLGK | 428 |
| MTK-16.2 with huIgG4 Fc without C-terminal lysine | QVQLVQSGSELKKPGASVKVSCKASGYTFTNHGMNWVRQAPGQGLEWMGWI NTYTGEPTYADDFKGRFVFSLDTSVSTAYLQISSLKAEDTAVYYCARKGVT AARYFDYWGQGTLVTVSS ASTKGPSVFPLAPCSRSTSESTAALGCLVKDYFPEPVTVSWNSGALTSGVH TFPAVLQSSGLYSLSSVVTVPSSSLGTKTYTCNVDHKPSNTKVDKRVESKY GPPCPSCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPS DIAVEWESNGQPENNYKTTPPVLDSDGSFFLYSRLTVDKSRWQEGNVFSCS VMHEALHNHYTQKSLSLSLGK | 429 |

MTK-16.2 light chain amino acid sequence is set forth below:

(SEQ ID NO: 430)
DIQMTQSPSSLSASVGDRVTITCRASQNVRTAVAWYQQKPGKAPKRLIYL
ASNRHTGVPSRFSGSGSGTEFTLTISNLQPEDFATYYCLQHWNYPLTFGG

-continued

GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Full-length heavy chain amino acid sequences of certain anti-MerTK antibodies of the present disclosure are shown below in Table 40.

TABLE 40

| Antibody | Sequence | SEQ ID NO: |
|---|---|---|
| MTK-33.1 with huIgG1 WT Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 431 |
| MTK-33.1 with huIgG1 WT Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 432 |
| MTK-33.1 with huIgG1 LALAPS Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 433 |
| MTK-33.1 with huIgG1 LALAPS Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPEAAGGPSVFLFPPKPKDTLMI SRTPEVTCVVVDVSHEDPEVKFNWYVDGVEVHNAKTKPREEQYNSTYRVVS VLTVLHQDWLNGKEYKCKVSNKALPASIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 434 |
| MTK-33.1 with huIgG1 NSLF Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPGK | 435 |
| MTK-33.1 with huIgG1 NSLF Fc without C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPSSKSTSGGTAALGCLVKDYFP EPVTVSWNSGALTSGVHTFPAVLQSSGLYSLSSVVTVPSSSLGTQTYICNV NHKPSNTKVDKKVEPKSCDKTHTCPPCPAPELLGGPSVFLFPPKPKDTLMI SRTPEVTCVVVDVSHEDPEVKFNWYVDGVEVHNAKTKPREEQYNSTYRVVS VLTVLHQDWLNGKEYKCKVSSKAFPAPIEKTISKAKGQPREPQVYTLPPSR DELTKNQVSLTCLVKGFYPSDIAVEWESNGQPENNYKTTPPVLDSDGSFFL YSKLTVDKSRWQQGNVFSCSVMHEALHNHYTQKSLSLSPG | 436 |
| MTK-33.1 with huIgG4 Fc with C-terminal lysine | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT RGYFNYWGQGTLVTVSSASTKGPSVFPLAPCSRSTSESTAALGCLVKDYFP EPVTVSWNSGALTSGVHTFPAVLQSSGLYSLSSVVTVPSSSLGTKTYTCNV DHKPSNTKVDKRVESKYGPPCPSCPAPEFLGGPSVFLFPPKPKDTLMISRT PEVTCVVVDVSQEDPEVQFNWYVDGVEVHNAKTKPREEQFNSTYRVVSVLT VLHQDWLNGKEYKCKVSNKGLPSSIEKTISKAKGQPREPQVYTLPPSQEEM TKNQVSLTCLVKGFYPSDIAVEWESNGQPENNYKTTPPVLDSDGSFFLYSR LTVDKSRWQEGNVFSCSVMHEALHNHYTQKSLSLSLGK | 437 |
| MTK-33.1 with | QVQLVQSGAEVKKPGASVKVSCKASGYTFTSYWMHWVRQAPGQGLEWIGVI DPSDNYINYNQKFQGRVTMTRDTSTSTVYMELSSLRSEDTAVYYCAREAWT | 438 |

TABLE 40-continued

| Antibody | Sequence | SEQ ID NO: |
|---|---|---|
| huIgG4 Fc without C-terminal lysine | RGYFNYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG | |

MTK-33.1 light chain amino acid sequence is set forth below:

(SEQ ID NO: 439)

DIQMTQSPSSLSASVGDRVTITCQASQSVSNTVAWYQQKPGKAPKLLIYY

ASLRYTGVPSRFSGSGSGTDFTFTISSLQPEDIATYYCQQDYRSPFTFGQ

-continued

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full-length heavy chain amino acid sequences of certain anti-MerTK antibodies of the present disclosure are shown below in Table 41.

TABLE 41

| Antibody | Sequence | SEQ ID NO: |
|---|---|---|
| MTK-33.12 with huIgG1 WT Fc with C-terminal lysine | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 440 |
| MTK-33.12 with huIgG1 WT Fc without C-terminal lysine | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 441 |
| MTK-33.12 with huIgG1 LALAPS Fc with C-terminal lysine | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 442 |
| MTK-33.12 with huIgG1 LALAPS Fc without C-terminal lysine | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 443 |
| MTK-33.12 with huIgG1 NSLF Fc with C-terminal lysine | QVQLVQSGAEVKKPGASVKVSCKASGYTFVSYWMHWVRQAPGQGLEWIGVIDPSDNYINYNQKFRGRVTMTRDTSTSTVYMELSSLRSEDTAVYYCAREAGTRGYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSSKAFPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 444 |

TABLE 41-continued

| Antibody | Sequence | SEQ ID NO: |
|---|---|---|
| MTK-33.12 with huIgG1 NSLF Fc without C-terminal lysine | DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSSKAFPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG | 445 |
| MTK-33.12 with huIgG4 Fc with C-terminal lysine | QVQLVQSGAEVKKPGASVKVSCKASGYTFVSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPSCPAPEFLGGPSVFLFPPKPKDTLMISRT<br>PEVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSR<br>LTVDKSRWQEGNVFSCSVMHEALHNHYTQKSLSLSLGK | 446 |
| MTK-33.12 with huIgG4 Fc without C-terminal lysine | QVQLVQSGAEVKKPGASVKVSCKASGYTFVSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPSCPAPEFLGGPSVFLFPPKPKDTLMISRT<br>PEVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSR<br>LTVDKSRWQEGNVFSCSVMHEALHNHYTQKSLSLSLG | 447 |

MTK-33.12 light chain amino acid sequence is set forth below:

(SEQ ID NO: 448)

DIQMTQSPSSLSASVGDRVTITCQASQSVSNTVAWYQQKPGKAPKLLIYY

ASNRYTGVPSRFSGSGSGTDFTFTISSLQPEDIATYYCRQDTRSPFTFGQ

-continued

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Full-length heavy chain amino acid sequences of certain anti-MerTK antibodies of the present disclosure are shown below in Table 42.

TABLE 42

| Antibody | Sequence | SEQ ID NO: |
|---|---|---|
| MTK-33.10 with huIgG1 WT Fc with C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPGK | 464 |
| MTK-33.10 with huIgG1 WT Fc without C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG | 465 |
| MTK-33.10 with huIgG1 LALAPS Fc with C-terminal lysine | DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPEAAGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPASIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPGK | 466 |

TABLE 42-continued

| Antibody | Sequence | SEQ ID NO: |
|---|---|---|
| MTK-33.10 with huIgG1 LALAPS Fc without C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPEAAGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSNKALPASIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG | 467 |
| MTK-33.10 with huIgG1 NSLF Fc with C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSSKAFPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPGK | 468 |
| MTK-33.10 with huIgG1 NSLF Fc without C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMI<br>SRTPEVTCVVVDVSHEDPEVKFNWYVDGVEVHNAKTKPREEQYNSTYRVVS<br>VLTVLHQDWLNGKEYKCKVSSKAFPAPIEKTISKAKGQPREPQVYTLPPSR<br>DELTKNQVSLTCLVKGFYPSDIAVEWESNGQPENNYKTTPPVLDSDGSFFL<br>YSKLTVDKSRWQQGNVFSCSVMHEALHNHYTQKSLSLSPG | 469 |
| MTK-33.10 with huIgG4 Fc with C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPSCPAPEFLGGPSVFLFPPKPKDTLMISRT<br>PEVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSR<br>LTVDKSRWQEGNVFSCSVMHEALHNHYTQKSLSLSLGK | 470 |
| MTK-33.10 with huIgG4 Fc without C-terminal lysine | QVQLVQSGAEVKKPGASVKVSCKASSYSFTSYWMHWVRQAPGQGLEWIGVI<br>DPSDNYINYNQKFRGRVTMTRDTSTSTVYMELSSLRSEDTAVYYCAREAGT<br>RGYFDYWGQGTLVTVSSASTKGPSVFPLAPCSRSTSESTAALGCLVKDYFP<br>EPVTVSWNSGALTSGVHTFPAVLQSSGLYSLSSVVTVPSSSLGTKTYTCNV<br>DHKPSNTKVDKRVESKYGPPCPSCPAPEFLGGPSVFLFPPKPKDTLMISRT<br>PEVTCVVVDVSQEDPEVQFNWYVDGVEVHNAKTKPREEQFNSTYRVVSVLT<br>VLHQDWLNGKEYKCKVSNKGLPSSIEKTISKAKGQPREPQVYTLPPSQEEM<br>TKNQVSLTCLVKGFYPSDIAVEWESNGQPENNYKTTPPVLDSDGSFFLYSR<br>LTVDKSRWQEGNVFSCSVMHEALHNHYTQKSLSLSLG | 471 |

MTK-33.10 light chain amino acid sequence is set forth below:

(SEQ ID NO: 472)

DIQMTQSPSSLSASVGDRVTITCQAGQSVSNTVAWYQQKPGKAPKLLIY

YASNRYTGVPSRFSGSGSGTDFTFTISSLQPEDIATYYCQQDYRSPFTF

-continued

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

What is claimed is:

1. A method of treating an individual having cancer, the method comprising administering to an individual in need thereof a therapeutically effective amount an antibody that binds to human MerTK, wherein the antibody comprises an HVR-H1, HVR-H2, HVR-H3, HVR-L1, HVR-L2, and HVR-L3 comprising the amino acid sequences of:

(i) SEQ ID NOs: 75, 99, 125, 158, 187, and 207, respectively;

(ii) SEQ ID NOs: 76, 100, 126, 159, 187, and 208, respectively;

(iii) SEQ ID NOs: 77, 101, 127, 160, 188, and 209, respectively;

(iv) SEQ ID NOs: 75, 99, 128, 158, 187, and 210, respectively;

(v) SEQ ID NOs: 78, 102, 129, 161, 189, and 211, respectively;

(vi) SEQ ID NOs: 75, 103, 130, 158, 187, and 212, respectively;

(vii) SEQ ID NOs: 77, 101, 127, 162, 188, and 209, respectively;

(viii) SEQ ID NOs: 75, 99, 131, 163, 187, and 213, respectively;

(ix) SEQ ID NOs: 79, 104, 132, 164, 190, and 214, respectively;

(x) SEQ ID NOs: 80, 105, 133, 165, 191, and 215, respectively;

(xi) SEQ ID NOs: 81, 106, 134, 166, 192, and 216, respectively;

(xii) SEQ ID NOs: 82, 107, 135, 167, 193, and 217, respectively;

(xiii) SEQ ID NOs: 77, 108, 136, 167, 194, and 209, respectively;

(xiv) SEQ ID NOs: 75, 109, 137, 168, 187, and 218, respectively;

(xv) SEQ ID NOs: 83, 99, 138, 158, 187, and 210, respectively;

(xvi) SEQ ID NOs: 84, 99, 139, 169, 195, and 219, respectively;

(xvii) SEQ ID NOs: 85, 99, 140, 170, 196, and 220, respectively;

(xviii) SEQ ID NOs: 86, 99, 141, 171, 191, and 221, respectively;

(xix) SEQ ID NOs: 87, 110, 142, 172, 197, and 222, respectively;

(xx) SEQ ID NOs: 88, 99, 143, 173, 191, and 223, respectively;

(xxi) SEQ ID NOs: 89, 111, 143, 173, 198, and 221, respectively;

(xxii) SEQ ID NOs: 90, 112, 144, 174, 199, and 224, respectively;

(xxiii) SEQ ID NOs: 91, 113, 145, 175, 200, and 225, respectively;

(xxiv) SEQ ID NOs: 90, 114, 146, 176, 201, and 226, respectively;

(xxv) SEQ ID NOs: 92, 115, 147, 177, 195, and 227, respectively;

(xxvi) SEQ ID NOs: 93, 116, 148, 178, 188, and 209, respectively;
(xxvii) SEQ ID NOs: 94, 117, 149, 179, 195, and 228, respectively;
(xxviii) SEQ ID NOs: 95, 118, 150, 180, 187, and 229, respectively;
(xxix) SEQ ID NOs: 95, 119, 151, 181, 187, and 208, respectively;
(xxx) SEQ ID NOs: 90, 120, 152, 182, 202, and 230, respectively;
(xxxi) SEQ ID NOs: 96, 118, 153, 183, 202, and 230, respectively;
(xxxii) SEQ ID NOs: 96, 121, 154, 181, 187, and 210, respectively;
(xxxiii) SEQ ID NOs: 90, 122, 155, 184, 203, and 231, respectively;
(xxxiv) SEQ ID NOs: 90, 122, 155, 184, 203, and 231, respectively;
(xxxv) SEQ ID NOs: 97, 123, 156, 185, 204, and 232, respectively;
(xxxvi) SEQ ID NOs: 98, 124, 157, 186, 205, and 233, respectively;
(xxxvii) SEQ ID NOs: 83, 329, 334, 158, 187, and 210, respectively;
(xxxviii) SEQ ID NOs: 83, 330, 138, 158, 187, and 210, respectively;
(xxxix) SEQ ID NOs: 83, 329, 138, 340, 187, and 210, respectively;
(xl) SEQ ID NOs: 83, 329, 138, 341, 187, and 210, respectively;
(xli) SEQ ID NOs: 83, 329, 335, 341, 187, and 210, respectively;
(xlii) SEQ ID NOs: 83, 331, 138, 341, 187, and 210, respectively;
(xliii) SEQ ID NOs: 83, 329, 138, 342, 187, and 210, respectively;
(xliv) SEQ ID NOs: 83, 329, 336, 341, 187, and 210, respectively;
(xlv) SEQ ID NOs: 83, 329, 337, 343, 187, and 210, respectively;
(xlvi) SEQ ID NOs: 83, 332, 338, 341, 187, and 210, respectively;
(xlvii) SEQ ID NOs: 83, 333, 334, 158, 187, and 210, respectively;
(xlviii) SEQ ID NOs: 83, 332, 336, 341, 187, and 210, respectively;
(xlix) SEQ ID NOs: 83, 329, 339, 344, 187, and 210, respectively;
(l) SEQ ID NOs: 83, 329, 138, 158, 187, and 210, respectively;
(li) SEQ ID NOs: 84, 329, 139, 169, 195, and 219, respectively;
(lii) SEQ ID NOs: 84, 99, 139, 345, 195, and 219, respectively;
(liii) SEQ ID NOs: 346, 348, 355, 341, 187, and 360, respectively;
(liv) SEQ ID NOs: 95, 119, 355, 341, 187, and 361, respectively;
(lv) SEQ ID NOs: 95, 349, 356, 341, 187, and 362, respectively;
(lvi) SEQ ID NOs: 95, 119, 356, 341, 359, and 362, respectively;
(lvii) SEQ ID NOs: 346, 119, 356, 341, 359, and 362, respectively;
(lviii) SEQ ID NOs: 95, 350, 356, 341, 359, and 362, respectively;
(lix) SEQ ID NOs: 95, 351, 356, 341, 359, and 362, respectively;
(lx) SEQ ID NOs: 347, 119, 356, 341, 359, and 362, respectively;
(lxi) SEQ ID NOs: 346, 119, 356, 341, 359, and 362, respectively;
(lxii) SEQ ID NOs: 95, 119, 356, 341, 187, and 362, respectively;
(lxiii) SEQ ID NOs: 95, 352, 356, 341, 187, and 362, respectively;
(lxiv) SEQ ID NOs: 95, 350, 356, 341, 359, and 362, respectively;
(lxv) SEQ ID NOs: 95, 353, 356, 341, 359, and 362, respectively;
(lxvi) SEQ ID NOs: 95, 351, 356, 341, 359, and 362, respectively;
(lxvii) SEQ ID NOs: 95, 350, 356, 341, 359, and 362, respectively;
(lxviii) SEQ ID NOs: 346, 354, 356, 341, 359, and 363, respectively;
(lxix) SEQ ID NOs: 346, 348, 356, 357, 359, and 362, respectively;
(lxx) SEQ ID NOs: 346, 354, 356, 358, 187, and 362, respectively;
(lxxi) SEQ ID NOs: 95, 348, 151, 181, 187, and 208, respectively;
(lxxii) SEQ ID NOs: 90, 364, 373, 376, 388, and 231, respectively;
(lxxiii) SEQ ID NOs: 90, 364, 155, 377, 203, and 231, respectively;
(lxxiv) SEQ ID NOs: 90, 364, 374, 378, 203, and 231, respectively;
(lxxv) SEQ ID NOs: 90, 365, 155, 376, 203, and 392, respectively;
(lxxvi) SEQ ID NOs: 90, 364, 155, 376, 389, and 231, respectively;
(lxxvii) SEQ ID NOs: 90, 364, 155, 379, 203, and 231, respectively;
(lxxviii) SEQ ID NOs: 90, 366, 155, 380, 203, and 231, respectively;
(lxxix) SEQ ID NOs: 90, 364, 373, 381, 203, and 231, respectively;
(lxxx) SEQ ID NOs: 90, 367, 155, 382, 203, and 231, respectively;
(lxxxi) SEQ ID NOs: 90, 368, 155, 383, 203, and 231, respectively;
(lxxxii) SEQ ID NOs: 90, 364, 374, 384, 203, and 231, respectively;
(lxxxiii) SEQ ID NOs: 90, 368, 155, 376, 203, and 293, respectively;
(lxxxiv) SEQ ID NOs: 90, 364, 155, 378, 203, and 231, respectively;
(lxxxv) SEQ ID NOs: 90, 368, 155, 376, 203, and 231, respectively;
(lxxxvi) SEQ ID NOs: 90, 369, 155, 378, 203, and 394, respectively;
(lxxxvii) SEQ ID NOs: 90, 364, 155, 378, 203, and 231, respectively;
(lxxxviii) SEQ ID NOs: 90, 370, 155, 378, 203, and 394, respectively;
(lxxxix) SEQ ID NOs: 90, 371, 155, 378, 203, and 394, respectively;
(xc) SEQ ID NOs: 90, 368, 155, 385, 203, and 394, respectively;
(xci) SEQ ID NOs: 90, 368, 155, 378, 203, and 395, respectively;

(xcii) SEQ ID NOs: 90, 368, 155, 378, 390, and 394, respectively;

(xciii) SEQ ID NOs: 90, 372, 155, 378, 391, and 394, respectively;

(xciv) SEQ ID NOs: 90, 368, 375, 386, 203, and 394, respectively; or (xcv) SEQ ID NOs: 90, 368, 155, 387, 203, and 394, respectively.

2. The method of claim 1, wherein the cancer is colon cancer, ovarian cancer, liver cancer, or endometrial cancer.

3. The method of claim 1, wherein the administration does not lead to a retinal pathology in the individual.

4. The method of claim 1, further comprising administering an anti-PD-L1 antibody, an anti-PD-L2 antibody, or an anti-PD-1 antibody to the individual.

5. The method of claim 1, wherein the antibody comprises a heavy chain variable region and a light chain variable region comprising the amino acid sequences of SEQ ID NOs:5 and 40, respectively; SEQ ID NOs:6 and 41, respectively; SEQ ID NOs:7 and 42, respectively; SEQ ID NOs:8 and 43, respectively; SEQ ID NOs:9 and 44, respectively; SEQ ID NOs:10 and 45, respectively; SEQ ID NOs:11 and 46, respectively; SEQ ID NOs:12 and 47, respectively; SEQ ID NOs:13 and 48, respectively; SEQ ID NOs:14 and 49, respectively; SEQ ID NOs:15 and 50, respectively; SEQ ID NOs:16 and 51, respectively; SEQ ID NOs:17 and 52, respectively; SEQ ID NOs:18 and 53, respectively; SEQ ID NOs:19 and 54, respectively; SEQ ID NOs:20 and 55, respectively; SEQ ID NOs:21 and 56, respectively; SEQ ID NOs:22 and 57, respectively; SEQ ID NOs:23 and 58, respectively; SEQ ID NOs:24 and 59, respectively; SEQ ID NOs:25 and 60, respectively; SEQ ID NOs:26 and 61, respectively; SEQ ID NOs:27 and 62, respectively; SEQ ID NOs:28 and 63, respectively; SEQ ID NOs:29 and 64, respectively; SEQ ID NOs:30 and 65, respectively; SEQ ID NOs:31 and 66, respectively; SEQ ID NOs:32 and 67, respectively; SEQ ID NOs:33 and 68, respectively; SEQ ID NOs:34 and 69, respectively; SEQ ID NOs:35 and 70, respectively; SEQ ID NOs:36 and 71, respectively; SEQ ID NOs:37 and 72, respectively; SEQ ID NOs:38 and 73, respectively; and SEQ ID NOs:39 and 74, respectively; SEQ ID NOs:234 and 247, respectively; SEQ ID NOs:235 and 247, respectively; SEQ ID NOs:236 and 248, respectively; SEQ ID NOs:236 and 249, respectively; SEQ ID NOs:237 and 249, respectively; SEQ ID NOs:238 and 249, respectively; SEQ ID NOs:239 and 250, respectively; SEQ ID NOs:240 and 251, respectively; SEQ ID NOs:241 and 252, respectively; SEQ ID NOs:242 and 249, respectively; SEQ ID NOs:243 and 247, respectively; SEQ ID NOs:244 and 251, respectively; SEQ ID NOs:245 and 253, respectively; SEQ ID NOs:246 and 247, respectively; SEQ ID NOs:246 and 254, respectively; SEQ ID NOs:255 and 257, respectively; SEQ ID NOs:256 and 258, respectively; SEQ ID NOs:259 and 274, respectively; SEQ ID NOs:260 and 275, respectively; SEQ ID NOs:261 and 276, respectively; SEQ ID NOs:262 and 277, respectively; SEQ ID NOs:263 and 277, respectively; SEQ ID NOs:264 and 277, respectively; SEQ ID NOs:265 and 277, respectively; SEQ ID NOs:266 and 277, respectively; SEQ ID NOs:267 and 278, respectively; SEQ ID NOs:268 and 279, respectively; SEQ ID NOs:269 and 279, respectively; SEQ ID NOs:264 and 280, respectively; SEQ ID NOs:270 and 281, respectively; SEQ ID NOs:265 and 282, respectively; SEQ ID NOs:264 and 283, respectively; SEQ ID NOs:271 and 284, respectively; SEQ ID NOs:272 and 285, respectively; SEQ ID NOs:271 and 286, respectively; SEQ ID NOs:273 and 287, respectively; SEQ ID NOs:273 and 288, respectively; SEQ ID NOs:273 and 289, respectively; SEQ ID NOs:290 and 309, respectively; SEQ ID NOs:291 and 310, respectively; SEQ ID NOs:292 and 311, respectively SEQ ID NOs:293 and 312, respectively; SEQ ID NOs:294 and 313, respectively; SEQ ID NOs:295 and 314, respectively; SEQ ID NOs:296 and 315, respectively; SEQ ID NOs:290 and 316, respectively; SEQ ID NOs:297 and 317, respectively; SEQ ID NOs:298 and 318, respectively; SEQ ID NOs:292 and 319, respectively; SEQ ID NOs:299 and 320, respectively; SEQ ID NOs:300 and 311, respectively; SEQ ID NOs:301 and 321, respectively; SEQ ID NOs:302 and 322, respectively; SEQ ID NOs:303 and 311, respectively; SEQ ID NOs:304 and 322, respectively; SEQ ID NOs:305 and 322, respectively; SEQ ID NOs:301 and 323, respectively; SEQ ID NOs:301 and 324, respectively; SEQ ID NOs:301 and 325, respectively; SEQ ID NOs:306 and 326, respectively; SEQ ID NOs:307 and 327, respectively; or SEQ ID NOs:308 and 328, respectively.

6. The method of claim 5, wherein the antibody comprises (a) a heavy chain comprising the amino acid sequence of SEQ ID NO:466 or 464 and a light chain comprising the amino acid sequence of SEQ ID NO:472; (b) a heavy chain comprising the amino acid sequence of SEQ ID NO: 467, 465, 468, or 469 and a light chain comprising the amino acid sequence of SEQ ID NO: 472; (c) a heavy chain comprising the amino acid sequence of SEQ ID NO:422, 423, 424, 425, or 426 and a light chain comprising the amino acid sequence of SEQ ID NO:430; (d) a heavy chain comprising the amino acid sequence of SEQ ID NO:440, 441, 442, 443, 444, or 445 and a light chain comprising the amino acid sequence of SEQ ID NO:448; or (e) a heavy chain comprising the amino acid sequence of SEQ ID NO:413, 414, 415, 416, 417, or 418 and a light chain comprising the amino acid sequence of SEQ ID NO:421.

7. The method of claim 1, wherein the antibody is a murine antibody, a humanized antibody, a bispecific antibody, a monoclonal antibody, a multivalent antibody, a conjugated antibody, or a chimeric antibody.

8. The method of claim 1, wherein the antibody is of the IgG class, the IgM class, or the IgA class.

9. The method of claim 8, wherein the antibody is of the IgG class and has an IgG1, and IgG2, or an IgG4 isotype.

10. The method of claim 1, wherein the antibody is a full-length antibody.

11. The method of claim 1, wherein the antibody is an antibody fragment.

12. The method of claim 11, wherein the antibody fragment is a Fab, Fab', Fab'-SH, F(ab')2, Fv or scFv.

13. The method of claim 1, wherein the antibody is an scFv.

14. The method of claim 5, wherein the antibody is a bispecific antibody, a monoclonal antibody, a multivalent antibody, or a conjugated antibody.

15. The method of claim 5, wherein the antibody is of the IgG class.

16. The method of claim 15, wherein the antibody is of the IgG class and has an IgG1, and IgG2, or an IgG4 isotype.

17. The method of claim 5, wherein the antibody is a full-length antibody.

18. The method of claim 5, wherein the antibody is an antibody fragment.

19. The method of claim 18, wherein the antibody fragment is a Fab, Fab', Fab'-SH, F(ab')2, Fv or scFv.

20. A method for detecting MerTK in a sample comprising contacting said sample with the antibody of claim 1.

* * * * *

SEQUENCE LISTING

```
Sequence total quantity: 472
SEQ ID NO: 1            moltype = AA  length = 999
FEATURE                 Location/Qualifiers
source                  1..999
                        mol_type = protein
                        organism = Homo sapiens
SEQUENCE: 1
MGPAPLPLLL GLFLPALWRR AITEAREEAK PYPLFPGPFP GSLQTDHTPL LSLPHASGYQ  60
PALMFSPTQP GRPHTGNVAI PQVTSVESKP LPPLAFKHTV GHIILSEHKG VKFNCSISVP  120
NIYQDTTISW WKDGKELLGA HHAITQFYPD DEVTAIIASF SITSVQRSDN GSYICKMKIN  180
```

```
NEEIVSDPIY IEVQGLPHFT KQPESMNVTR NTAFNLTCQA VGPPEPVNIF WVQNSSRVNE  240
QPEKSPSVLT VPGLTEMAVF SCEAHNDKGL TVSKGVQINI KAIPSPPTEV SIRNSTAHSI  300
LISWVPGFDG YSPFRNCSIQ VKEADPLSNG SVMIFNTSAL PHLYQIKQLQ ALANYSIGVS  360
CMNEIGWSAV SPWILASTTE GAPSVAPLNV TVFLNESSDN VDIRWMKPPT KQQDGELVGY  420
RISHVWQSAG ISKELLEEVG QNGSRARISV QVHNATCTVR IAAVTRGGVG PFSDPVKIFI  480
PAHGWVDYAP SSTPAPGNAD PVLIIFGCFC GFILIGLILY ISLAIRKRVQ ETKFGNAFTE  540
EDSELVVNYI AKKSFCRRAI ELTLHSLGVS EELQNKLEDV VIDRNLLILG KILGEGEFGS  600
VMEGNLKQED GTSLKVAVKT MKLDNSSQRE IEEFLSEAAC MKDFSHPNVI RLLGVCIEMS  660
SQGIPKPMVI LPFMKYGDLH TYLLYSRLET GPKHIPLQTL LKFMVDIALG MEYLSNRNFL  720
HRDLAARNCM LRDDMTVCVA DFGLSKKIYS GDYYRQGRIA KMPVKWIAIE SLADRVYTSK  780
SDVWAFGVTM WEIATRGMTP YPGVQNHEMY DYLLHGHRLK QPEDCLDELY EIMYSCWRTD  840
PLDRPTFSVL RLQLEKLLES LPDVRNQADV IYVNTQLLES SEGLAQGSTL APLDLNIDPD  900
SIIASCTPRA AISVVTAEVH DSKPHEGRYI LNGGSEEWED LTSAPSAAVT AEKNSVLPGE  960
RLVRNGVSWS HSSMLPLGSS LPDELLFADD SSEGSEVLM                         999

SEQ ID NO: 2           moltype = AA  length = 505
FEATURE                Location/Qualifiers
source                 1..505
                       mol_type = protein
                       organism = Homo sapiens
SEQUENCE: 2
MGPAPLPLLL GLFLPALWRR AITEAREEAK PYPLFPGPFP GSLQTDHTPL LSLPHASGYQ  60
PALMFSPTQP GRPHTGNVAI PQVTSVESKP LPPLAFKHTV GHIILSEHKG VKFNCSISVP  120
NIYQDTTISW WKDGKELLGA HHAITQFYPD DEVTAIIASF SITSVQRSDN GSYICKMKIN  180
NEEIVSDPIY IEVQGLPHFT KQPESMNVTR NTAFNLTCQA VGPPEPVNIF WVQNSSRVNE  240
QPEKSPSVLT VPGLTEMAVF SCEAHNDKGL TVSKGVQINI KAIPSPPTEV SIRNSTAHSI  300
LISWVPGFDG YSPFRNCSIQ VKEADPLSNG SVMIFNTSAL PHLYQIKQLQ ALANYSIGVS  360
CMNEIGWSAV SPWILASTTE GAPSVAPLNV TVFLNESSDN VDIRWMKPPT KQQDGELVGY  420
RISHVWQSAG ISKELLEEVG QNGSRARISV QVHNATCTVR IAAVTRGGVG PFSDPVKIFI  480
PAHGWVDYAP SSTPAPGNAD PVLII                                        505

SEQ ID NO: 3           moltype = AA  length = 507
FEATURE                Location/Qualifiers
REGION                 1..507
                       note = Cyno MerTK ECD
source                 1..507
                       mol_type = protein
                       organism = synthetic construct
SEQUENCE: 3
MGLAPLPLPL LLGLFLPALW SRAITEAREE AKPYPLFPGP LPGSLQTDHT SLLSLPHTSG  60
YQPALMFSPT QPGRPYTGNV AIPRVTSAGS KLLPPLAFKH TVGHIILSEH KDVKFNCSIS  120
VPNIYQDTTI SWWKDGKELL GAHHAITQFY PDDEVTAIIA SFSITSVQRS DNGSYICKMK  180
INNEEIVSDP IYIEVQGLPH FTKQPESMNV TRNTAFNLTC QAVGPPEPVN IFWVQNSSRV  240
NEQPEKSPSV LTVPGLTEMA VFSCEAHNDK GLTVSKGVQI NIKAIPSPPT EVSIHNSTAH  300
SILISWVPGF DGYSPFRNCS VQVKEVDPLS NGSVMIFNTS ASPHMYQIKQ LQALANYSIG  360
VSCMNEIGWS AVSPWILAST TEGAPSVAPL NVTVFLNESR DNVDIRWMKP LTKRQAGELV  420
GYRISHVWQS AGISKELLEE VGQNNSRAQI SVQVHNATCT VRIAAVTKGG VGPFSDPVKI  480
FIPAHGWVDH APSSTPAPGN ADPVLII                                      507

SEQ ID NO: 4           moltype = AA  length = 497
FEATURE                Location/Qualifiers
REGION                 1..497
                       note = Murine MerTK ECD
source                 1..497
                       mol_type = protein
                       organism = synthetic construct
SEQUENCE: 4
MVLAPLLLGL LLLPALWSGG TAEKWEETEL DQLFSGPLPG RLPVNHRPFS APHSSRDQLP  60
PPQTGRSHPA HTAAPQVTST ASKLLPPVAF NHTIGHIVLS EHKNVKFNCS INIPNTYQET  120
AGISWWKDGK ELLGAHHSIT QFYPDEEGVS IIALFSIASV QRSDNGSYFC KMKVNNREIV  180
SDPIYVEVQG LPYFIKQPES VNVTRNTAFN LTCQAVGPPE PVNIFWVQNS SRVNEKPERS  240
PSVLTVPGLT ETAVFSCEAH NDKGLTVSKG VHINIKVIPS PPTEVHILNS TAHSILVSWV  300
PGFDGYSPLQ NCSIQVKEAD RLSNGSVMVF NTSASPHLYE IQQLQALANY SIAVSCRNEI  360
GWSAVSPWIL ASTTEGAPSV APLNITVFLN ESNNILDIRW TKPPIKRQDG ELVGYRISHV  420
WESAGTYKEL SEEVSQNGSW AQIPVQIHNA TCTVRIAAIT KGGIGPFSEP VNIIIPEHSK  480
VDYAPSSTPA PGNTDSM                                                 497

SEQ ID NO: 5           moltype = AA  length = 118
FEATURE                Location/Qualifiers
REGION                 1..118
                       note = MTK-01 Heavy Chain Variable
source                 1..118
                       mol_type = protein
                       organism = synthetic construct
SEQUENCE: 5
QIQLVQSGPE LKKPGETVKI SCKASGYTFT NYGMNWVKQA PGKGLKCMGW INTYTGEPTY  60
ADDFKGRFAF SLETSATTAY LQINNLKNED TATYFCARRD RYTWFAYWGQ GTLVTVSA    118

SEQ ID NO: 6           moltype = AA  length = 118
```

```
FEATURE                 Location/Qualifiers
REGION                  1..118
                        note = MTK-02 Heavy Chain Variable
source                  1..118
                        mol_type = protein
                        organism = synthetic construct
SEQUENCE: 6
QIQLVQSGPE LKQPGETVKI SCKASGYTFT DYGVNWVKQA PGKGLKWMGW INTYSGEPTY  60
AGDFKGRFAF SLESSASTAF LQINNLKNED MATYFCARRV RYWYFDVWGA GTSVTVSS    118

SEQ ID NO: 7            moltype = AA  length = 120
FEATURE                 Location/Qualifiers
REGION                  1..120
                        note = MTK-03 Heavy Chain Variable
source                  1..120
                        mol_type = protein
                        organism = synthetic construct
SEQUENCE: 7
DVQLQESGPG LVKPSQSLSL TCSVTGYSIT SGYYWNWIRQ FPGNTLEWMG YMSFDGDNKF  60
NPSLKNRISI TRDTSKNQFF LRLNSVTTED TATYYCARGG YNYGSTEANW GQGTLVTVSA  120

SEQ ID NO: 8            moltype = AA  length = 118
FEATURE                 Location/Qualifiers
REGION                  1..118
                        note = MTK-04 Heavy Chain Variable
source                  1..118
                        mol_type = protein
                        organism = synthetic construct
SEQUENCE: 8
QIQLVQSGPE LKKPGETVKI SCKASGYTFT NYGMNWVKQA PGKGLKCMGW INTYTGEPTY  60
ADDFKGRFAF SLETSASTAY LQINNLKNED MATYFCAKYD NYAWFAYWGQ GTLVTVSA    118

SEQ ID NO: 9            moltype = AA  length = 116
FEATURE                 Location/Qualifiers
REGION                  1..116
                        note = MTK-05 Heavy Chain Variable
source                  1..116
                        mol_type = protein
                        organism = synthetic construct
SEQUENCE: 9
QVQLQQSGAE LVQPGTSVRL SCKTSGYTFT SYWIQWVKQR PGQGLGWIGE IFPGTGTTYY  60
NEKFKGKATL TIDTSSSTAY MQLSSLTSED SAVYFCARDG AYFDVWGAGT TVTVSS      116

SEQ ID NO: 10           moltype = AA  length = 118
FEATURE                 Location/Qualifiers
REGION                  1..118
                        note = MTK-06 Heavy Chain Variable
source                  1..118
                        mol_type = protein
                        organism = synthetic construct
SEQUENCE: 10
QIQLVQSGPE LKKPGETVKI SCKASGYTFT NYGMNWVKQA PGKGLKWMGW INTNTGEPTY  60
AEEFKGRFAF SLETSASTAY LQINNLKNED TATYFCARYY NYWYFDVWGA GTTVTVSS    118

SEQ ID NO: 11           moltype = AA  length = 120
FEATURE                 Location/Qualifiers
REGION                  1..120
                        note = MTK-07 Heavy Chain Variable
source                  1..120
                        mol_type = protein
                        organism = synthetic construct
SEQUENCE: 11
DVQLQESGPG LVKPSQSLSL TCSVTGYSIT SGYYWNWIRQ FPGNTLEWMG YMSFDGDNKF  60
NPSLKNRISI TRDTSKNQFF LRLNSVTTED TATYYCARGG YNYGSTEANW GQGTLVTVST  120

SEQ ID NO: 12           moltype = AA  length = 118
FEATURE                 Location/Qualifiers
REGION                  1..118
                        note = MTK-08 Heavy Chain Variable
source                  1..118
                        mol_type = protein
                        organism = synthetic construct
SEQUENCE: 12
QIQLVQSGPE LKKPGETVKI SCKASGYTFT NYGMNWVKQA PGKGLKWMGW INTYTGEPTY  60
ADDFKGRFAF SLETSASTAY LQINNLKNED TATYFCAREV RYWYFDVWGA GTTVTVSS    118

SEQ ID NO: 13           moltype = AA  length = 123
FEATURE                 Location/Qualifiers
```

```
REGION                  1..123
                        note = MTK-09 Heavy Chain Variable
source                  1..123
                        mol_type = protein
                        organism = synthetic construct
SEQUENCE: 13
QVQLQQSGAE LVRPGASVKI SCKAFGYTFT NHHIKWVKQR PGQGLDWIGY IDPYNDYTTY  60
NQNFKGKATL TVDKSSSTAY MELSSLTSED SAVYYCARRA YDGYYVDWYF DVWGAGTTVT  120
VSS                                                                123

SEQ ID NO: 14           moltype = AA  length = 119
FEATURE                 Location/Qualifiers
REGION                  1..119
                        note = MTK-10 Heavy Chain Variable
source                  1..119
                        mol_type = protein
                        organism = synthetic construct
SEQUENCE: 14
QVTLKESGPG ILQPSQTLSL TCSFSGFSLT TSGMGVGWIR QPSGKGLEWL AHIWSDDDKR  60
SNPALKSRLT ISQDSSTNQV FLKIASVDTA DSATYYCSHL TPVREFAYWG PGTLVTVSE   119

SEQ ID NO: 15           moltype = AA  length = 118
FEATURE                 Location/Qualifiers
REGION                  1..118
                        note = MTK-11 Heavy Chain Variable
source                  1..118
                        mol_type = protein
                        organism = synthetic construct
SEQUENCE: 15
QVQLKQSGPG LVQPSQSLSI TCTVSGFSLT DYGVHWVRQS PGKGLEWLGV IWSSGTTDYN  60
EAFISRLSIS KDNSKSHVFF KMNSLQAIDT AIYYCARKGH DPYAMDYWGQ GTSVTVSS    118

SEQ ID NO: 16           moltype = AA  length = 122
FEATURE                 Location/Qualifiers
REGION                  1..122
                        note = MTK-12 Heavy Chain Variable
source                  1..122
                        mol_type = protein
                        organism = synthetic construct
SEQUENCE: 16
QVQLQQSGPQ LVRPGASVKI SCKASGYSFT SHWMHWVKQR PGQGLEWIGM IDPSDGESRL  60
NQKFKDKATL TVDKSSSTAY MQLSSPTFED SAVYYCARGI YYYGITYAMD YWGQGTSVTV  120
SS                                                                 122

SEQ ID NO: 17           moltype = AA  length = 119
FEATURE                 Location/Qualifiers
REGION                  1..119
                        note = MTK-13 Heavy Chain Variable
source                  1..119
                        mol_type = protein
                        organism = synthetic construct
SEQUENCE: 17
DVQLQESGPG LVKPSQSLSL TCSVTGYSIT SGYYWNWIRQ FPGNKLEWMG NIDYDGSNKY  60
NPSLKNRISI TRDTSKNHFF LKLNSVTPED TATYFCARDG GNYRSFAYWG QGTLVTVSA   119

SEQ ID NO: 18           moltype = AA  length = 118
FEATURE                 Location/Qualifiers
REGION                  1..118
                        note = MTK-14 Heavy Chain Variable
source                  1..118
                        mol_type = protein
                        organism = synthetic construct
SEQUENCE: 18
QIQLVQSGPE LKKPGETVKI SCKASGYTFT NYGMNWVKQA PGKDLQWMGW INTYTGEPTY  60
ADDFTGRFAF SLETSASTAY LQINNLKNED TATYFCAKGG HYAWFAYWGQ GTLVTVSA    118

SEQ ID NO: 19           moltype = AA  length = 118
FEATURE                 Location/Qualifiers
REGION                  1..118
                        note = MTK-15 Heavy Chain Variable
source                  1..118
                        mol_type = protein
                        organism = synthetic construct
SEQUENCE: 19
QIQLVQSGPE LKKPGETVKI SCKASGYTFT NYGVHWVKQA PGKGLKWMGW INTYTGEPTY  60
ADDFKGRFAF SLETSASTAY LQINNLKNED MATYFCARGN RYAYMDYWGQ GTSVTVSS    118

SEQ ID NO: 20           moltype = AA  length = 120
FEATURE                 Location/Qualifiers
```

```
REGION                 1..120
                       note = MTK-16 Heavy Chain Variable
source                 1..120
                       mol_type = protein
                       organism = synthetic construct
SEQUENCE: 20
LIQLVQSGPE LKKPGETVKI SCKASGYTFT NHGMNWVKQD PGKGLKWMGW INTYTGEPTY  60
ADDFKGRFVF SMETSASAAF LQINNLKNED TATYFCARKG VTAARYFDYW GQGTTLTVSS  120

SEQ ID NO: 21          moltype = AA  length = 120
FEATURE                Location/Qualifiers
REGION                 1..120
                       note = MTK-17 Heavy Chain Variable
source                 1..120
                       mol_type = protein
                       organism = synthetic construct
SEQUENCE: 21
QIQLVQSGPE LKKPGETVKI SCKASGYTFT NFGMNWVKQA PGKGLKWMGW INTYTGEPTY  60
ADDFKGRFAF SLETSASTAY LQINNLKNED TATYFCSRGA VLRAGAMDCW GQGTSVTVSS  120

SEQ ID NO: 22          moltype = AA  length = 121
FEATURE                Location/Qualifiers
REGION                 1..121
                       note = MTK-18 Heavy Chain Variable
source                 1..121
                       mol_type = protein
                       organism = synthetic construct
SEQUENCE: 22
QIQLVQSGPE LKKPGETVKI SCKASGYTFT HYGMTWVKQA PGKGLKWMGW INTYTGEPTY  60
ADDFKGRFAF SLETSASTAY LQINNLKNED TATYFCARGG GQLGLRPLDY WGQGTTLTVS  120
S                                                                 121

SEQ ID NO: 23          moltype = AA  length = 125
FEATURE                Location/Qualifiers
REGION                 1..125
                       note = MTK-19 Heavy Chain Variable
source                 1..125
                       mol_type = protein
                       organism = synthetic construct
SEQUENCE: 23
EVQLQQSGPE LVKPGASVKI SCKTSGYTFT EYTMHWVKQS HGKSLEWLGG FNPNNVITSY  60
NQRFQGRATL TVDKSSSTAY MELRSLTSDD SAVYYCTRGD LLWSLLLPGN YFDYWGQGTT  120
LTVSS                                                             125

SEQ ID NO: 24          moltype = AA  length = 121
FEATURE                Location/Qualifiers
REGION                 1..121
                       note = MTK-20 Heavy Chain Variable
source                 1..121
                       mol_type = protein
                       organism = synthetic construct
SEQUENCE: 24
QIQLVQSGPE LKKPGETVKI SCKASGYTFT NYGMTWVKQA PGKGLKWMGW INTYTGEPTY  60
ADDFKGRFAL SLETSASTAY LQINNLKNED TATYFCARGG GRLGLRPLDY WGQGTTLTVS  120
S                                                                 121

SEQ ID NO: 25          moltype = AA  length = 121
FEATURE                Location/Qualifiers
REGION                 1..121
                       note = MTK-21 Heavy Chain Variable
source                 1..121
                       mol_type = protein
                       organism = synthetic construct
SEQUENCE: 25
QIQLVQSGPE LKKPGETVKI SCKASGYTFT NFGMTWVRQA PGMDLKWMGW INTYTGEPKY  60
ADDFKGRFAL SLETSASTAY LQITNFKNED TATYFCARGG GRLGLRPLDY WGQGTTLTVS  120
S                                                                 121

SEQ ID NO: 26          moltype = AA  length = 120
FEATURE                Location/Qualifiers
REGION                 1..120
                       note = MTK-22 Heavy Chain Variable
source                 1..120
                       mol_type = protein
                       organism = synthetic construct
SEQUENCE: 26
QVQLQQPGAD LVEPGASVKL SCKASGYTFT SYWMHWVKQR PGQGLEWIGE IDPSDSSSNY  60
NQKFKGKATL TVDKSSSTAY MHLNSLTSED SAVYYCARRY YYGSLYFDNW GQGTTLTVSS  120
```

```
SEQ ID NO: 27          moltype = AA  length = 123
FEATURE                Location/Qualifiers
REGION                 1..123
                       note = MTK-23 Heavy Chain Variable
source                 1..123
                       mol_type = protein
                       organism = synthetic construct
SEQUENCE: 27
QVQLQQSGAD LVRPGASVKI SCKAFGYTFT NHHINWVKQR PGQGLDWIGN VDPYNDYSTY  60
NQKFKGKATL TVDKSSSTAY MELSSLTSED SAVYYCARRV YDGFYVDWYF DVWGAGTTVT  120
VSS                                                               123

SEQ ID NO: 28          moltype = AA  length = 121
FEATURE                Location/Qualifiers
REGION                 1..121
                       note = MTK-24 Heavy Chain Variable
source                 1..121
                       mol_type = protein
                       organism = synthetic construct
SEQUENCE: 28
QVQLQQPGAE LVKPGASVKL SCKASGYTFT SYWMHWVKQR PGQGLEWIGM IHPNINTNYN  60
EKFKSKATLT VDISSSTAYM QLSSLTSEDS AVYYCAKRSP YSNYDWYFDV WGTGTTVTVS  120
S                                                                 121

SEQ ID NO: 29          moltype = AA  length = 117
FEATURE                Location/Qualifiers
REGION                 1..117
                       note = MTK-25 Heavy Chain Variable
source                 1..117
                       mol_type = protein
                       organism = synthetic construct
SEQUENCE: 29
EVKLVESEGG LVQPGSSMKL SCTASGFTFS DYYMAWVRQV PEKGLEWVAN INYEGSSTYY  60
LGSLKSRFII SRDNAENILY LQMSSLKSED TATYYCARYY YGSVDYWGQG TTLTVSS     117

SEQ ID NO: 30          moltype = AA  length = 119
FEATURE                Location/Qualifiers
REGION                 1..119
                       note = MTK-26 Heavy Chain Variable
source                 1..119
                       mol_type = protein
                       organism = synthetic construct
SEQUENCE: 30
AVQFQESGPG LVKLSQSLSL TCSVTGYSIT SGYYWDWIRQ FPGNKLEWMG YISYDGSNNY  60
NPSLKNRISI TRDTSKNQFF LKLNSVTTED TATYYCAREG GYYRSMDYWG QGTSVTVSS   119

SEQ ID NO: 31          moltype = AA  length = 117
FEATURE                Location/Qualifiers
REGION                 1..117
                       note = MTK-27 Heavy Chain Variable
source                 1..117
                       mol_type = protein
                       organism = synthetic construct
SEQUENCE: 31
EVQLQQSGTE LVRPGASVKL SCTASGFNIK DDYMHWVQQR PEQGLEWIGW IDPENGNTEY  60
ASKFQGKATI TADASSNTAY LQLSSLTSED TAVYYCSTLF SNYFDYWGQG TTLTVSS     117

SEQ ID NO: 32          moltype = AA  length = 118
FEATURE                Location/Qualifiers
REGION                 1..118
                       note = MTK-28 Heavy Chain Variable
source                 1..118
                       mol_type = protein
                       organism = synthetic construct
SEQUENCE: 32
QIQLVQSGPE LKKPGETVKI SCKASGYTFT TYGMSWVKQA PGKGLKWMGW INTYSGVPTY  60
ADDFKGRFAF SLETSASTAY LQINTLKNED TTTYFCARFL RYYYFDYWGQ GTTLTVSS    118

SEQ ID NO: 33          moltype = AA  length = 118
FEATURE                Location/Qualifiers
REGION                 1..118
                       note = MTK-29 Heavy Chain Variable
source                 1..118
                       mol_type = protein
                       organism = synthetic construct
SEQUENCE: 33
QIQLVQSGPE LKKPGETVKI SCKSSGFTFT TYGMSWVKQA PGKGLKWMGW INTYSGVPTY  60
TDDFKGRFAF SLETSASTAS LQINNLKNED TATYFCARYT NYGYFDYWGQ GTTLTVSS    118
```

-continued

```
SEQ ID NO: 34          moltype = AA  length = 117
FEATURE                Location/Qualifiers
REGION                 1..117
                       note = MTK-30 Heavy Chain Variable
source                 1..117
                       mol_type = protein
                       organism = synthetic construct
SEQUENCE: 34
QVQLQQPGTE LVRPGASVKL SCKASGYTFT SYWMHWVKQR PGQGLEWIGN LNPNNGGTYY  60
NEKFKSKATL TVDKSSSTAY MQLSSLTSED SAVYYCARQI LLYFDYWGQG TTLTVSS     117

SEQ ID NO: 35          moltype = AA  length = 122
FEATURE                Location/Qualifiers
REGION                 1..122
                       note = MTK-31 Heavy Chain Variable
source                 1..122
                       mol_type = protein
                       organism = synthetic construct
SEQUENCE: 35
QIQLVQSGPE LKKSGETVKI SCKASGYTFT SYGMSWVKQA PGKGLKWMGW INTYSGVPTY  60
ADDFKGRFAF SLETSASTAY LQINNLKNED TATYFCASLS YDGSLYHAMD YWGQGTSVTV  120
SS                                                                 122

SEQ ID NO: 36          moltype = AA  length = 118
FEATURE                Location/Qualifiers
REGION                 1..118
                       note = MTK-32 Heavy Chain Variable
source                 1..118
                       mol_type = protein
                       organism = synthetic construct
SEQUENCE: 36
QIQLVQSGPE LKKPGETVKI SCKASGYTFT SYGMSWVHQA PGKGLKWLGW INTYSGVPTY  60
ADDFRGRFAF SLDTSVSTAS LEINNLQNED TATYFCARED NWAWFAYWGQ GTLVTVST    118

SEQ ID NO: 37          moltype = AA  length = 119
FEATURE                Location/Qualifiers
REGION                 1..119
                       note = MTK-33, 34 Heavy Chain Variable
source                 1..119
                       mol_type = protein
                       organism = synthetic construct
SEQUENCE: 37
QVQLQQPGPE LVRPGTSVKL SCKASGYTFT SYWMHWIKQR PGQGLEWIGV IDPSDNYINY  60
NQKFKGKATL TVDTSSSTAY LQLSSLTSED SAVYYCAREA GTRGYFDYWG QGTTLTVSS   119

SEQ ID NO: 38          moltype = AA  length = 120
FEATURE                Location/Qualifiers
REGION                 1..120
                       note = MTK-35 Heavy Chain Variable
source                 1..120
                       mol_type = protein
                       organism = synthetic construct
SEQUENCE: 38
QVLLQQSGPE LVKPGASVQL SCKASDYTFT SYDIHWVKQR PGQGLEWIGW IYPRDGYTKY  60
NEIFKGKATL TVDTSSTTAY MELHSLTSED SAVYFCARAY YTNWYYFDYW GQGTTLTVSS  120

SEQ ID NO: 39          moltype = AA  length = 122
FEATURE                Location/Qualifiers
REGION                 1..122
                       note = MTK-36 Heavy Chain Variable
source                 1..122
                       mol_type = protein
                       organism = synthetic construct
SEQUENCE: 39
QVTLKESGPG ILQPSQTLSL TCSFSGFSLS TFGMGVGWIR QPSGKGLEWL AHIWWYDDKY  60
YEPALKSRLT ISKDSSKNQV FLKIANVDTA DTATYYCARI YYGTSYRYFD VWGTGTTVTV  120
SS                                                                 122

SEQ ID NO: 40          moltype = AA  length = 106
FEATURE                Location/Qualifiers
REGION                 1..106
                       note = MTK-01 Light Chain Variable
source                 1..106
                       mol_type = protein
                       organism = synthetic construct
SEQUENCE: 40
QIVLSQSPAI LSASPGEKVT MTCRASSSVS YMHWYQQKPG SSPKPWIYAT SNLASGVPAR  60
FSGSGSGTSY SLTISRVEAE DAATYYCQQW SSNPPTFGGG TKLEIK                 106
```

```
SEQ ID NO: 41          moltype = AA  length = 106
FEATURE                Location/Qualifiers
REGION                 1..106
                       note = MTK-02 Light Chain Variable
source                 1..106
                       mol_type = protein
                       organism = synthetic construct
SEQUENCE: 41
QIVLSQSPAI LSASPGERVT MTCRANSSVS YMHWYQQKPG SSPKPWIYAT SNLASGVPAR  60
FSASGSGTSY SLTVSRVEAE DAATYYCQQW GSNPFTFGSG TKLEIK                106

SEQ ID NO: 42          moltype = AA  length = 106
FEATURE                Location/Qualifiers
REGION                 1..106
                       note = MTK-03 Light Chain Variable
source                 1..106
                       mol_type = protein
                       organism = synthetic construct
SEQUENCE: 42
QIVLTQSPAI MSAFPGEKVT ITCSASSSVN YMHWFQQKPG TSPKLWIYST SNLASGVPAR  60
FSGSGSGTSY SLTISRMEAE DAATYYCQQR SSYPFTFGSG TKLEIK                106

SEQ ID NO: 43          moltype = AA  length = 106
FEATURE                Location/Qualifiers
REGION                 1..106
                       note = MTK-04 Light Chain Variable
source                 1..106
                       mol_type = protein
                       organism = synthetic construct
SEQUENCE: 43
QIVLSQSPAF LSASPGEKVT MTCRASSSVS YMHWYLQKPG SSPKPWIYAT SNLASGVPVR  60
FSGSGSGTSY SLTISRVEAE DAATYYCQQW SSNPRTFGGG TKLEIR                106

SEQ ID NO: 44          moltype = AA  length = 107
FEATURE                Location/Qualifiers
REGION                 1..107
                       note = MTK-05 Light Chain Variable
source                 1..107
                       mol_type = protein
                       organism = synthetic construct
SEQUENCE: 44
DIQMTQSPAS LSASVGETVT FTCRASENIF SYLAWYQQKQ GKSPQLLVYN AKTLAEGVPS  60
RFSGSGSGTH FSLKINSLQP EDFGSYYCLH HYGTPLTFGA GTKLELK               107

SEQ ID NO: 45          moltype = AA  length = 106
FEATURE                Location/Qualifiers
REGION                 1..106
                       note = MTK-06 Light Chain Variable
source                 1..106
                       mol_type = protein
                       organism = synthetic construct
SEQUENCE: 45
QIVLSQSPAI LSASPGEKVT MTCRASSSVS YMHWYQQKPG SSPKPWIYAT SNLASGVPAR  60
FSGSGSGTSY SLTISRVEAE DAATYYCQQW SSKPPTFGGG TKLEIK                106

SEQ ID NO: 46          moltype = AA  length = 106
FEATURE                Location/Qualifiers
REGION                 1..106
                       note = MTK-07 Light Chain Variable
source                 1..106
                       mol_type = protein
                       organism = synthetic construct
SEQUENCE: 46
QIVLTQSPAI MSAFPGEKVT ITCSASSSVT YMHWFQQKPG TSPKLWIFST SNLASGVPAR  60
FSGSGSGTSY SLTISRMEAE DAATYYCQQR SSYPFTFGSG TKLEIK                106

SEQ ID NO: 47          moltype = AA  length = 106
FEATURE                Location/Qualifiers
REGION                 1..106
                       note = MTK-08 Light Chain Variable
source                 1..106
                       mol_type = protein
                       organism = synthetic construct
SEQUENCE: 47
QIVLSQSPAI LSASPGEKVT MTCRATSSVS YMHWFQQKPG SSPKPWIYAT SNLASGVPAR  60
FSGSGSGTSY SLTISRVEAE DAAAYYCQHW SGNPRTFGGG TKLEIK                106

SEQ ID NO: 48          moltype = AA  length = 107
FEATURE                Location/Qualifiers
```

```
REGION                 1..107
                       note = MTK-09 Light Chain Variable
source                 1..107
                       mol_type = protein
                       organism = synthetic construct
SEQUENCE: 48
DIVMTQSHKF MSTSVGDRVS ITCKASQDVT TSVAWYHQKP GQSPELLIYS ASYRYTGVPD  60
RFTGSGSGTD FTFTISSVQA EDLAIYYCQQ HYSTPLTFGS GTKLQLK               107

SEQ ID NO: 49          moltype = AA  length = 107
FEATURE                Location/Qualifiers
REGION                 1..107
                       note = MTK-10 Light Chain Variable
source                 1..107
                       mol_type = protein
                       organism = synthetic construct
SEQUENCE: 49
DIQMTQTTSS LSASLGDRVT ISCSASQGIS NYLNWFQQKP DGTVKLLIYY TSRLHSGVPS  60
RFSGSGSGTD FSLTISNLEP EDIATYYCQQ YTKLPYTFGG GTKLEIK               107

SEQ ID NO: 50          moltype = AA  length = 108
FEATURE                Location/Qualifiers
REGION                 1..108
                       note = MTK-11 Light Chain Variable
source                 1..108
                       mol_type = protein
                       organism = synthetic construct
SEQUENCE: 50
QIVLTQSPAI MSASLGERVT MTCTASSSIS SSYFHWYQQK PGSSPKLWIY STSNLPSGVP  60
ARFSGSGSGT SYSLTISSME AEDAATYYCH QYYRSPLTFG AGTKLELK              108

SEQ ID NO: 51          moltype = AA  length = 106
FEATURE                Location/Qualifiers
REGION                 1..106
                       note = MTK-12 Light Chain Variable
source                 1..106
                       mol_type = protein
                       organism = synthetic construct
SEQUENCE: 51
QIVLTQSPAI MSASPGEKVT MTCSASSSVS YMYWYQQKPR SSPRLLIYDT SNLASGVPVR  60
FSGSGSGTSY SLTISRMEAE DAATYYCQQW SSYPLTFGAG TKLELK                106

SEQ ID NO: 52          moltype = AA  length = 106
FEATURE                Location/Qualifiers
REGION                 1..106
                       note = MTK-13 Light Chain Variable
source                 1..106
                       mol_type = protein
                       organism = synthetic construct
SEQUENCE: 52
QIVLTQSPPI MSASPGEKVT ITCSASSSVS YMYWFQQKPG TSPKLWIYST FNLASGVPAR  60
FSGSGSGTSY SLTISRMEAE DVATYYCQQR SSYPFTFGSG TKLEIK                106

SEQ ID NO: 53          moltype = AA  length = 106
FEATURE                Location/Qualifiers
REGION                 1..106
                       note = MTK-14 Light Chain Variable
source                 1..106
                       mol_type = protein
                       organism = synthetic construct
SEQUENCE: 53
QIVLSQSPAI LSASPGEKVT MTCRSSSSVS YMHWYQQKPG SSPKPWIYAT SNLASGVPGR  60
FSGSGSGTSY SLTISRVEAE DAATYYCQQW GSNPRTFGGG TKLEIK                106

SEQ ID NO: 54          moltype = AA  length = 106
FEATURE                Location/Qualifiers
REGION                 1..106
                       note = MTK-15 Light Chain Variable
source                 1..106
                       mol_type = protein
                       organism = synthetic construct
SEQUENCE: 54
QIVLSQSPAI LSASPGEKVT MTCRASSSVS YMHWYQQKSG SSPKPWIYAT SNLASGVPAR  60
FSGSGSGTSY SLTISRVEAE DAATYYCQQW SSNPRTFGGG TKLEIK                106

SEQ ID NO: 55          moltype = AA  length = 107
FEATURE                Location/Qualifiers
REGION                 1..107
                       note = MTK-16 Light Chain Variable
```

```
source                 1..107
                       mol_type = protein
                       organism = synthetic construct
SEQUENCE: 55
DIVMTQSPKF MSTSVGDRVS ITCKASQNVR TAVAWYKKKP GQSPKALINL ASNRHTGVPD  60
RFTGSGSGTD FTLTISNVQS EDLADYFCLQ HWNYPLTFGG GTKLEIK               107

SEQ ID NO: 56          moltype = AA  length = 107
FEATURE                Location/Qualifiers
REGION                 1..107
                       note = MTK-17 Light Chain Variable
source                 1..107
                       mol_type = protein
                       organism = synthetic construct
SEQUENCE: 56
DIQMTQSSSY LSVSLGGRVT ITCKASDHIN NWLAWYQQKP GNAPRLLISG ATSLETGVPS  60
RFSGSGSGKD YTLSITSLQT EDVATYYCQQ YWSTPRTFGG GTKLEIK               107

SEQ ID NO: 57          moltype = AA  length = 107
FEATURE                Location/Qualifiers
REGION                 1..107
                       note = MTK-18 Light Chain Variable
source                 1..107
                       mol_type = protein
                       organism = synthetic construct
SEQUENCE: 57
DIQMTQTTSS LSASLGDRVT FSCRASQAIS NYLNWYQQKP DGTVKLLIYY TSRLHSGVPS  60
RFSGSGSGTD YSLTISNLEQ EDIATYFCQQ GNTLPWTFGG GTKLEIK               107

SEQ ID NO: 58          moltype = AA  length = 112
FEATURE                Location/Qualifiers
REGION                 1..112
                       note = MTK-19 Light Chain Variable
source                 1..112
                       mol_type = protein
                       organism = synthetic construct
SEQUENCE: 58
DVVMTQSSLT LSVTIGQPAS ISCKSSQSLL DSDGKTYLNW LLQRPGQSPK RLIYLVSKLD  60
SGVPDRFTGS GSGTDFTLKI SRVEAEDLGV YYCWQGTHFP WTFGGGTKLE IK          112

SEQ ID NO: 59          moltype = AA  length = 107
FEATURE                Location/Qualifiers
REGION                 1..107
                       note = MTK-20 Light Chain Variable
source                 1..107
                       mol_type = protein
                       organism = synthetic construct
SEQUENCE: 59
DIQMTQTTSS LSASLGDRVT ISCRASQDIN NYLNWYQQKP DGTVKLLIYY TSRLHSGVPS  60
RFSGSGSGTD YSLTISNLEQ EDIATYFCQQ GNTLPWTFGG GTKLEIK               107

SEQ ID NO: 60          moltype = AA  length = 107
FEATURE                Location/Qualifiers
REGION                 1..107
                       note = MTK-21 Light Chain Variable
source                 1..107
                       mol_type = protein
                       organism = synthetic construct
SEQUENCE: 60
DIQMTQTTSS LSASLGDRVT ISCRASQDIN NYLNWYQQKP DGTVKLLIYY TSSLHSGVPS  60
RFSGSGSGTD YSLTITNLEQ EDIATYFCQQ GNTLPWTFGG GTRLEIK               107

SEQ ID NO: 61          moltype = AA  length = 107
FEATURE                Location/Qualifiers
REGION                 1..107
                       note = MTK-22 Light Chain Variable
source                 1..107
                       mol_type = protein
                       organism = synthetic construct
SEQUENCE: 61
DVVMTQSHKF MSTSVGDRVS ITCKASQDVG TAIAWYQQKP GQSPKLLIYW ASTRHTGVPD  60
RFTGSRSGTV FTLTISNVQS EDLADYFCQQ YTSYPLTFGS GTKLEIK               107

SEQ ID NO: 62          moltype = AA  length = 107
FEATURE                Location/Qualifiers
REGION                 1..107
                       note = MTK-23 Light Chain Variable
```

```
source                  1..107
                        mol_type = protein
                        organism = synthetic construct
SEQUENCE: 62
DIVMTQSHKF MSTPVGDRVS ITCKASRDVS TAVAWFHQKP GQSPKLLIYS ASYRSTGVPD  60
RFTGSGSGTD FTFTISSVQA EDLAVYYCQQ HYSAPLTFGA GTKLELK               107

SEQ ID NO: 63           moltype = AA  length = 107
FEATURE                 Location/Qualifiers
REGION                  1..107
                        note = MTK-24 Light Chain Variable
source                  1..107
                        mol_type = protein
                        organism = synthetic construct
SEQUENCE: 63
DIQMTQSPAS LSVSVGETVT ITCRASENIY SNLAWYQQKQ GKSPQLLVYA ATNLADGVPS  60
RFSGSGSGTQ YSLKINSLQS EDFGSYYCQH FWGTPLTFGA GTKLELK               107

SEQ ID NO: 64           moltype = AA  length = 107
FEATURE                 Location/Qualifiers
REGION                  1..107
                        note = MTK-25 Light Chain Variable
source                  1..107
                        mol_type = protein
                        organism = synthetic construct
SEQUENCE: 64
DIVMTQSQKF MSTSVGDRVS ITCKASQNVR TTVAWYQQKP GQSPKTLIYL ASNRHTGVPD  60
RFTGSGSGTD FTLTISNVQS EDLADYFCLQ LWNYPWTFGG GTKLEIK               107

SEQ ID NO: 65           moltype = AA  length = 106
FEATURE                 Location/Qualifiers
REGION                  1..106
                        note = MTK-26 Light Chain Variable
source                  1..106
                        mol_type = protein
                        organism = synthetic construct
SEQUENCE: 65
QIVLTQSPAI MSASPGEKVT IACSASSSVS FMHWFQQKPG TSPRLWIYST SNLASGVPAR  60
FSGSGSGTSY SLTISRMEAE DAATYYCQQR SSYPFTFGSG TKLEIK                106

SEQ ID NO: 66           moltype = AA  length = 107
FEATURE                 Location/Qualifiers
REGION                  1..107
                        note = MTK-27 Light Chain Variable
source                  1..107
                        mol_type = protein
                        organism = synthetic construct
SEQUENCE: 66
DIVMTQSQKF MSTSVGDRVS ITCKASQNVR TSVAWYQQKP GQSPKALIYL ASNRHTGVPD  60
RFTGSGSGTD FTLTISNVRS EDLADYFCLQ HWNYPYTFGG GTKLEIK               107

SEQ ID NO: 67           moltype = AA  length = 105
FEATURE                 Location/Qualifiers
REGION                  1..105
                        note = MTK-28 Light Chain Variable
source                  1..105
                        mol_type = protein
                        organism = synthetic construct
SEQUENCE: 67
QIVLSQSPVI LSASPGEKVT MTCRASSSVT YMHWYQQQPG SSPKPWIYAT SNLASGVPAR  60
FSGSGSGTSY SLTISRVETE DAATYYCHQW SGNPTFGGGT KLEIN                 105

SEQ ID NO: 68           moltype = AA  length = 106
FEATURE                 Location/Qualifiers
REGION                  1..106
                        note = MTK-29 Light Chain Variable
source                  1..106
                        mol_type = protein
                        organism = synthetic construct
SEQUENCE: 68
QIVLSQSPAI LSASPGEKVT MTCRATSSVG YMHWYQQKPG SSPKPWIYAT SNLASGVPAR  60
FSGSGSGTSY SLTISRVEAE HAATYYCQQW GSNPFTFGSG TKLEIK                106

SEQ ID NO: 69           moltype = AA  length = 112
FEATURE                 Location/Qualifiers
REGION                  1..112
                        note = MTK-30 Light Chain Variable
```

```
source                  1..112
                        mol_type = protein
                        organism = synthetic construct
SEQUENCE: 69
DVLMTQTPLS LPVSLGDQAS ISCRSSQSIV HSNGDTYLEW YLQKPGQSPK LLIYKVSNRF  60
SGVPDRFSGS GSGTDFTLKI SRVEAEDLGV YYCFQGSHVP WTFGGGTKLE IK          112

SEQ ID NO: 70           moltype = AA  length = 112
FEATURE                 Location/Qualifiers
REGION                  1..112
                        note = MTK-31 Light Chain Variable
source                  1..112
                        mol_type = protein
                        organism = synthetic construct
SEQUENCE: 70
DVSMTQTPLS LPVSLGDQAS ISSRSSQTIV HSNGNTYLEW YLQKPGQSPK LLIYKVSNRF  60
SGVPDRFSGS GSGTDFTLKI SRVEAEDLGV YYCFQGSHVP WTFGGGTKLE IK          112

SEQ ID NO: 71           moltype = AA  length = 106
FEATURE                 Location/Qualifiers
REGION                  1..106
                        note = MTK-32 Light Chain Variable
source                  1..106
                        mol_type = protein
                        organism = synthetic construct
SEQUENCE: 71
QIVLSQSPAI LSASPGEKVT MTCRATSSVG YMHWYQRKPG SSPKPWIYAT SNLASGVPAR  60
FSGSGSGTSY SLTISRVEAE DAATYYCQQW SSNPRTFGGG TKLEIK                106

SEQ ID NO: 72           moltype = AA  length = 107
FEATURE                 Location/Qualifiers
REGION                  1..107
                        note = MTK-33, 34 Light Chain Variable
source                  1..107
                        mol_type = protein
                        organism = synthetic construct
SEQUENCE: 72
SIVMTQTPKF LLVSAGDRVI ITCKASQSVS NTVAWYQQKP GQSPKLLIYY ASNRYTGVPD  60
RFTGSGYGTD FTFTISTVQA EDLAVYFCQQ DYRSPFTFGS GTQLEMK               107

SEQ ID NO: 73           moltype = AA  length = 108
FEATURE                 Location/Qualifiers
REGION                  1..108
                        note = MTK-35 Light Chain Variable
source                  1..108
                        mol_type = protein
                        organism = synthetic construct
SEQUENCE: 73
EIVLTQSPTT MAASPGEKIT ITCRASSSIS SHYLHWYQQK PGFSPKLLIY RTSNLASGVP  60
ARFSGSGSGT SYSLTIGTME AEDVATYYCQ QGSTIPLTFG AGTKLVLK              108

SEQ ID NO: 74           moltype = AA  length = 106
FEATURE                 Location/Qualifiers
REGION                  1..106
                        note = MTK-36 Light Chain Variable
source                  1..106
                        mol_type = protein
                        organism = synthetic construct
SEQUENCE: 74
QIVLSQSPAI LSAFPGEKVT MTCRATSSVR YMHWYQQKPG SSPKPWIYAT YNLTSGVPAR  60
FSGSGSGTSY SLTISRVEAE DAATYYCHQW SSNPYTFGGG TKLEIK                106

SEQ ID NO: 75           moltype = AA  length = 5
FEATURE                 Location/Qualifiers
REGION                  1..5
                        note = MTK-01, 04, 06, 08, 14 HVR-H1
source                  1..5
                        mol_type = protein
                        organism = synthetic construct
SEQUENCE: 75
NYGMN                                                             5

SEQ ID NO: 76           moltype = AA  length = 5
FEATURE                 Location/Qualifiers
REGION                  1..5
                        note = MTK-02 HVR-H1
source                  1..5
                        mol_type = protein
                        organism = synthetic construct
```

```
SEQUENCE: 76
DYGVN                                                        5

SEQ ID NO: 77          moltype = AA  length = 6
FEATURE                Location/Qualifiers
REGION                 1..6
                       note = MTK-03, 07, 13 HVR-H1
source                 1..6
                       mol_type = protein
                       organism = synthetic construct
SEQUENCE: 77
SGYYWN                                                       6

SEQ ID NO: 78          moltype = AA  length = 5
FEATURE                Location/Qualifiers
REGION                 1..5
                       note = MTK-05 HVR-H1
source                 1..5
                       mol_type = protein
                       organism = synthetic construct
SEQUENCE: 78
SYWIQ                                                        5

SEQ ID NO: 79          moltype = AA  length = 5
FEATURE                Location/Qualifiers
REGION                 1..5
                       note = MTK-09 HVR-H1
source                 1..5
                       mol_type = protein
                       organism = synthetic construct
SEQUENCE: 79
NHHIK                                                        5

SEQ ID NO: 80          moltype = AA  length = 7
FEATURE                Location/Qualifiers
REGION                 1..7
                       note = MTK-10 HVR-H1
source                 1..7
                       mol_type = protein
                       organism = synthetic construct
SEQUENCE: 80
TSGMGVG                                                      7

SEQ ID NO: 81          moltype = AA  length = 5
FEATURE                Location/Qualifiers
REGION                 1..5
                       note = MTK-11 HVR-H1
source                 1..5
                       mol_type = protein
                       organism = synthetic construct
SEQUENCE: 81
DYGVH                                                        5

SEQ ID NO: 82          moltype = AA  length = 5
FEATURE                Location/Qualifiers
REGION                 1..5
                       note = MTK-12 HVR-H1
source                 1..5
                       mol_type = protein
                       organism = synthetic construct
SEQUENCE: 82
SHWMH                                                        5

SEQ ID NO: 83          moltype = AA  length = 5
FEATURE                Location/Qualifiers
REGION                 1..5
                       note = MTK-15, 15.1, 15.2, 15.3, 15.4, 15.5, 15.6, 15.7,
                        15.8, 15.9, 15.10, 15.11, 15.12, 15.13, 15.14, 15.15 HVR-H1
source                 1..5
                       mol_type = protein
                       organism = synthetic construct
SEQUENCE: 83
NYGVH                                                        5

SEQ ID NO: 84          moltype = AA  length = 5
FEATURE                Location/Qualifiers
REGION                 1..5
                       note = MTK-16, 16.1, 16.2 HVR-H1
```

```
source                  1..5
                        mol_type = protein
                        organism = synthetic construct
SEQUENCE: 84
NHGMN                                                                       5

SEQ ID NO: 85           moltype = AA  length = 5
FEATURE                 Location/Qualifiers
REGION                  1..5
                        note = MTK-17 HVR-H1
source                  1..5
                        mol_type = protein
                        organism = synthetic construct
SEQUENCE: 85
NFGMN                                                                       5

SEQ ID NO: 86           moltype = AA  length = 5
FEATURE                 Location/Qualifiers
REGION                  1..5
                        note = MTK-18 HVR-H1
source                  1..5
                        mol_type = protein
                        organism = synthetic construct
SEQUENCE: 86
HYGMT                                                                       5

SEQ ID NO: 87           moltype = AA  length = 5
FEATURE                 Location/Qualifiers
REGION                  1..5
                        note = MTK-19 HVR-H1
source                  1..5
                        mol_type = protein
                        organism = synthetic construct
SEQUENCE: 87
EYTMH                                                                       5

SEQ ID NO: 88           moltype = AA  length = 5
FEATURE                 Location/Qualifiers
REGION                  1..5
                        note = MTK-20 HVR-H1
source                  1..5
                        mol_type = protein
                        organism = synthetic construct
SEQUENCE: 88
NYGMT                                                                       5

SEQ ID NO: 89           moltype = AA  length = 5
FEATURE                 Location/Qualifiers
REGION                  1..5
                        note = MTK-21 HVR-H1
source                  1..5
                        mol_type = protein
                        organism = synthetic construct
SEQUENCE: 89
NFGMT                                                                       5

SEQ ID NO: 90           moltype = AA  length = 5
FEATURE                 Location/Qualifiers
REGION                  1..5
                        note = MTK-22, 24, 30, 33, 33.1, 33.2, 33.3, 33.4, 33.5,
                         33.6, 33.7, 33.8, 33.9, 33.10, 33.11, 33.12, 33.13, 33.14,
                         33.15, 33.16, 33.17, 33.18, 33.19, 33.20, 33.21, 33.22,
                         33.23, 33.24, 34 HVR-H1
source                  1..5
                        mol_type = protein
                        organism = synthetic construct
SEQUENCE: 90
SYWMH                                                                       5

SEQ ID NO: 91           moltype = AA  length = 5
FEATURE                 Location/Qualifiers
REGION                  1..5
                        note = MTK-23 HVR-H1
source                  1..5
                        mol_type = protein
                        organism = synthetic construct
SEQUENCE: 91
NHHIN                                                                       5
```

```
SEQ ID NO: 92           moltype = AA  length = 5
FEATURE                 Location/Qualifiers
REGION                  1..5
                        note = MTK-25 HVR-H1
source                  1..5
                        mol_type = protein
                        organism = synthetic construct
SEQUENCE: 92
DYYMA                                                                        5

SEQ ID NO: 93           moltype = AA  length = 6
FEATURE                 Location/Qualifiers
REGION                  1..6
                        note = MTK-26 HVR-H1
source                  1..6
                        mol_type = protein
                        organism = synthetic construct
SEQUENCE: 93
SGYYWD                                                                       6

SEQ ID NO: 94           moltype = AA  length = 5
FEATURE                 Location/Qualifiers
REGION                  1..5
                        note = MTK-27 HVR-H1
source                  1..5
                        mol_type = protein
                        organism = synthetic construct
SEQUENCE: 94
DDYMH                                                                        5

SEQ ID NO: 95           moltype = AA  length = 5
FEATURE                 Location/Qualifiers
REGION                  1..5
                        note = MTK-28, 29, 29.2, 29.3, 29.4, 29.6, 29.7, 29.10,
                         29.11, 29.12, 29.13, 29.14, 29.15, 29.19, 29.20, 29.21
                         HVR-H1
source                  1..5
                        mol_type = protein
                        organism = synthetic construct
SEQUENCE: 95
TYGMS                                                                        5

SEQ ID NO: 96           moltype = AA  length = 5
FEATURE                 Location/Qualifiers
REGION                  1..5
                        note = MTK-31, 32 HVR-H1
source                  1..5
                        mol_type = protein
                        organism = synthetic construct
SEQUENCE: 96
SYGMS                                                                        5

SEQ ID NO: 97           moltype = AA  length = 5
FEATURE                 Location/Qualifiers
REGION                  1..5
                        note = MTK-35 HVR-H1
source                  1..5
                        mol_type = protein
                        organism = synthetic construct
SEQUENCE: 97
SYDIH                                                                        5

SEQ ID NO: 98           moltype = AA  length = 7
FEATURE                 Location/Qualifiers
REGION                  1..7
                        note = MTK-36 HVR-H1
source                  1..7
                        mol_type = protein
                        organism = synthetic construct
SEQUENCE: 98
TFGMGVG                                                                      7

SEQ ID NO: 99           moltype = AA  length = 17
FEATURE                 Location/Qualifiers
REGION                  1..17
                        note = MTK-01, 04, 08, 15, 16, 16.2, 17, 18, 20 HVR-H2
source                  1..17
                        mol_type = protein
                        organism = synthetic construct
```

```
SEQUENCE: 99
WINTYTGEPT YADDFKG                                                    17

SEQ ID NO: 100        moltype = AA  length = 17
FEATURE               Location/Qualifiers
REGION                1..17
                      note = MTK-02 HVR-H2
source                1..17
                      mol_type = protein
                      organism = synthetic construct
SEQUENCE: 100
WINTYSGEPT YAGDFKG                                                    17

SEQ ID NO: 101        moltype = AA  length = 16
FEATURE               Location/Qualifiers
REGION                1..16
                      note = MTK-03, 07 HVR-H2
source                1..16
                      mol_type = protein
                      organism = synthetic construct
SEQUENCE: 101
YMSFDGDNKF NPSLKN                                                     16

SEQ ID NO: 102        moltype = AA  length = 17
FEATURE               Location/Qualifiers
REGION                1..17
                      note = MTK-05 HVR-H2
source                1..17
                      mol_type = protein
                      organism = synthetic construct
SEQUENCE: 102
EIFPGTGTTY YNEKFKG                                                    17

SEQ ID NO: 103        moltype = AA  length = 17
FEATURE               Location/Qualifiers
REGION                1..17
                      note = MTK-06 HVR-H2
source                1..17
                      mol_type = protein
                      organism = synthetic construct
SEQUENCE: 103
WINTNTGEPT YAEEFKG                                                    17

SEQ ID NO: 104        moltype = AA  length = 17
FEATURE               Location/Qualifiers
REGION                1..17
                      note = MTK-09 HVR-H2
source                1..17
                      mol_type = protein
                      organism = synthetic construct
SEQUENCE: 104
YIDPYNDYTT YNQNFKG                                                    17

SEQ ID NO: 105        moltype = AA  length = 16
FEATURE               Location/Qualifiers
REGION                1..16
                      note = MTK-10 HVR-H2
source                1..16
                      mol_type = protein
                      organism = synthetic construct
SEQUENCE: 105
HIWSDDDKRS NPALKS                                                     16

SEQ ID NO: 106        moltype = AA  length = 16
FEATURE               Location/Qualifiers
REGION                1..16
                      note = MTK-11 HVR-H2
source                1..16
                      mol_type = protein
                      organism = synthetic construct
SEQUENCE: 106
VIWSSGTTDY NEAFIS                                                     16

SEQ ID NO: 107        moltype = AA  length = 17
FEATURE               Location/Qualifiers
REGION                1..17
                      note = MTK-12 HVR-H2
```

```
source                  1..17
                        mol_type = protein
                        organism = synthetic construct
SEQUENCE: 107
MIDPSDGESR LNQKFKD                                                  17

SEQ ID NO: 108          moltype = AA  length = 16
FEATURE                 Location/Qualifiers
REGION                  1..16
                        note = MTK-13 HVR-H2
source                  1..16
                        mol_type = protein
                        organism = synthetic construct
SEQUENCE: 108
NIDYDGSNKY NPSLKN                                                   16

SEQ ID NO: 109          moltype = AA  length = 17
FEATURE                 Location/Qualifiers
REGION                  1..17
                        note = MTK-14 HVR-H2
source                  1..17
                        mol_type = protein
                        organism = synthetic construct
SEQUENCE: 109
WINTYTGEPT YADDFTG                                                  17

SEQ ID NO: 110          moltype = AA  length = 17
FEATURE                 Location/Qualifiers
REGION                  1..17
                        note = MTK-19 HVR-H2
source                  1..17
                        mol_type = protein
                        organism = synthetic construct
SEQUENCE: 110
GFNPNNVITS YNQRFQG                                                  17

SEQ ID NO: 111          moltype = AA  length = 17
FEATURE                 Location/Qualifiers
REGION                  1..17
                        note = MTK-21 HVR-H2
source                  1..17
                        mol_type = protein
                        organism = synthetic construct
SEQUENCE: 111
WINTYTGEPK YADDFKG                                                  17

SEQ ID NO: 112          moltype = AA  length = 17
FEATURE                 Location/Qualifiers
REGION                  1..17
                        note = MTK-22 HVR-H2
source                  1..17
                        mol_type = protein
                        organism = synthetic construct
SEQUENCE: 112
EIDPSDSSSN YNQKFKG                                                  17

SEQ ID NO: 113          moltype = AA  length = 17
FEATURE                 Location/Qualifiers
REGION                  1..17
                        note = MTK-23 HVR-H2
source                  1..17
                        mol_type = protein
                        organism = synthetic construct
SEQUENCE: 113
NVDPYNDYST YNQKFKG                                                  17

SEQ ID NO: 114          moltype = AA  length = 16
FEATURE                 Location/Qualifiers
REGION                  1..16
                        note = MTK-24 HVR-H2
source                  1..16
                        mol_type = protein
                        organism = synthetic construct
SEQUENCE: 114
MIHPNINTNY NEKFKS                                                   16

SEQ ID NO: 115          moltype = AA  length = 17
FEATURE                 Location/Qualifiers
```

```
REGION                  1..17
                        note = MTK-25 HVR-H2
source                  1..17
                        mol_type = protein
                        organism = synthetic construct
SEQUENCE: 115
NINYEGSSTY YLGSLKS                                                    17

SEQ ID NO: 116          moltype = AA  length = 16
FEATURE                 Location/Qualifiers
REGION                  1..16
                        note = MTK-26 HVR-H2
source                  1..16
                        mol_type = protein
                        organism = synthetic construct
SEQUENCE: 116
YISYDGSNNY NPSLKN                                                     16

SEQ ID NO: 117          moltype = AA  length = 17
FEATURE                 Location/Qualifiers
REGION                  1..17
                        note = MTK-27 HVR-H2
source                  1..17
                        mol_type = protein
                        organism = synthetic construct
SEQUENCE: 117
WIDPENGNTE YASKFQG                                                    17

SEQ ID NO: 118          moltype = AA  length = 17
FEATURE                 Location/Qualifiers
REGION                  1..17
                        note = MTK-28, 31 HVR-H2
source                  1..17
                        mol_type = protein
                        organism = synthetic construct
SEQUENCE: 118
WINTYSGVPT YADDFKG                                                    17

SEQ ID NO: 119          moltype = AA  length = 17
FEATURE                 Location/Qualifiers
REGION                  1..17
                        note = MTK-29, 29.2, 29.4, 29.5, 29.8, 29.9, 29.10 HVR-H2
source                  1..17
                        mol_type = protein
                        organism = synthetic construct
SEQUENCE: 119
WINTYSGVPT YTDDFKG                                                    17

SEQ ID NO: 120          moltype = AA  length = 17
FEATURE                 Location/Qualifiers
REGION                  1..17
                        note = MTK-30 HVR-H2
source                  1..17
                        mol_type = protein
                        organism = synthetic construct
SEQUENCE: 120
NLNPNNGGTY YNEKFKS                                                    17

SEQ ID NO: 121          moltype = AA  length = 17
FEATURE                 Location/Qualifiers
REGION                  1..17
                        note = MTK-32 HVR-H2
source                  1..17
                        mol_type = protein
                        organism = synthetic construct
SEQUENCE: 121
WINTYSGVPT YADDFRG                                                    17

SEQ ID NO: 122          moltype = AA  length = 17
FEATURE                 Location/Qualifiers
REGION                  1..17
                        note = MTK-33, 34 HVR-H2
source                  1..17
                        mol_type = protein
                        organism = synthetic construct
SEQUENCE: 122
VIDPSDNYIN YNQKFKG                                                    17

SEQ ID NO: 123          moltype = AA  length = 17
```

```
FEATURE                Location/Qualifiers
REGION                 1..17
                       note = MTK-35 HVR-H2
source                 1..17
                       mol_type = protein
                       organism = synthetic construct
SEQUENCE: 123
WIYPRDGYTK YNEIFKG                                                    17

SEQ ID NO: 124         moltype = AA  length = 16
FEATURE                Location/Qualifiers
REGION                 1..16
                       note = MTK-36 HVR-H2
source                 1..16
                       mol_type = protein
                       organism = synthetic construct
SEQUENCE: 124
HIWWYDDKYY EPALKS                                                     16

SEQ ID NO: 125         moltype = AA  length = 9
FEATURE                Location/Qualifiers
REGION                 1..9
                       note = MTK-01 HVR-H3
source                 1..9
                       mol_type = protein
                       organism = synthetic construct
SEQUENCE: 125
RDRYTWFAY                                                             9

SEQ ID NO: 126         moltype = AA  length = 9
FEATURE                Location/Qualifiers
REGION                 1..9
                       note = MTK-02 HVR-H3
source                 1..9
                       mol_type = protein
                       organism = synthetic construct
SEQUENCE: 126
RVRYWYFDV                                                             9

SEQ ID NO: 127         moltype = AA  length = 11
FEATURE                Location/Qualifiers
REGION                 1..11
                       note = MTK-03, 07 HVR-H3
source                 1..11
                       mol_type = protein
                       organism = synthetic construct
SEQUENCE: 127
GGYNYGSTEA N                                                          11

SEQ ID NO: 128         moltype = AA  length = 9
FEATURE                Location/Qualifiers
REGION                 1..9
                       note = MTK-04 HVR-H3
source                 1..9
                       mol_type = protein
                       organism = synthetic construct
SEQUENCE: 128
YDNYAWFAY                                                             9

SEQ ID NO: 129         moltype = AA  length = 7
FEATURE                Location/Qualifiers
REGION                 1..7
                       note = MTK-05 HVR-H3
source                 1..7
                       mol_type = protein
                       organism = synthetic construct
SEQUENCE: 129
DGAYFDV                                                               7

SEQ ID NO: 130         moltype = AA  length = 9
FEATURE                Location/Qualifiers
REGION                 1..9
                       note = MTK-06 HVR-H3
source                 1..9
                       mol_type = protein
                       organism = synthetic construct
SEQUENCE: 130
YYNYWYFDV                                                             9
```

```
SEQ ID NO: 131          moltype = AA  length = 9
FEATURE                 Location/Qualifiers
REGION                  1..9
                        note = MTK-08 HVR-H3
source                  1..9
                        mol_type = protein
                        organism = synthetic construct
SEQUENCE: 131
EVRYWYFDV                                                                    9

SEQ ID NO: 132          moltype = AA  length = 14
FEATURE                 Location/Qualifiers
REGION                  1..14
                        note = MTK-09 HVR-H3
source                  1..14
                        mol_type = protein
                        organism = synthetic construct
SEQUENCE: 132
RAYDGYYVDW YFDV                                                              14

SEQ ID NO: 133          moltype = AA  length = 9
FEATURE                 Location/Qualifiers
REGION                  1..9
                        note = MTK-10 HVR-H3
source                  1..9
                        mol_type = protein
                        organism = synthetic construct
SEQUENCE: 133
LTPVREFAY                                                                    9

SEQ ID NO: 134          moltype = AA  length = 10
FEATURE                 Location/Qualifiers
REGION                  1..10
                        note = MTK-11 HVR-H3
source                  1..10
                        mol_type = protein
                        organism = synthetic construct
SEQUENCE: 134
KGHDPYAMDY                                                                   10

SEQ ID NO: 135          moltype = AA  length = 13
FEATURE                 Location/Qualifiers
REGION                  1..13
                        note = MTK-12 HVR-H3
source                  1..13
                        mol_type = protein
                        organism = synthetic construct
SEQUENCE: 135
GIYYYGITYA MDY                                                               13

SEQ ID NO: 136          moltype = AA  length = 10
FEATURE                 Location/Qualifiers
REGION                  1..10
                        note = MTK-13 HVR-H3
source                  1..10
                        mol_type = protein
                        organism = synthetic construct
SEQUENCE: 136
DGGNYRSFAY                                                                   10

SEQ ID NO: 137          moltype = AA  length = 9
FEATURE                 Location/Qualifiers
REGION                  1..9
                        note = MTK-14 HVR-H3
source                  1..9
                        mol_type = protein
                        organism = synthetic construct
SEQUENCE: 137
GGHYAWFAY                                                                    9

SEQ ID NO: 138          moltype = AA  length = 9
FEATURE                 Location/Qualifiers
REGION                  1..9
                        note = MTK-15, 15.2, 15.3, 15.4, 15.6, 15.7, 15.14, 15.15
                         HVR-H3
source                  1..9
                        mol_type = protein
                        organism = synthetic construct
SEQUENCE: 138
```

```
GNRYAYMDY                                               9

SEQ ID NO: 139         moltype = AA  length = 11
FEATURE                Location/Qualifiers
REGION                 1..11
                       note = MTK-16, 16.1, 16.2 HVR-H3
source                 1..11
                       mol_type = protein
                       organism = synthetic construct
SEQUENCE: 139
KGVTAARYFD Y                                            11

SEQ ID NO: 140         moltype = AA  length = 11
FEATURE                Location/Qualifiers
REGION                 1..11
                       note = MTK-17 HVR-H3
source                 1..11
                       mol_type = protein
                       organism = synthetic construct
SEQUENCE: 140
GAVLRAGAMD C                                            11

SEQ ID NO: 141         moltype = AA  length = 12
FEATURE                Location/Qualifiers
REGION                 1..12
                       note = MTK-18 HVR-H3
source                 1..12
                       mol_type = protein
                       organism = synthetic construct
SEQUENCE: 141
GGGQLGLRPL DY                                           12

SEQ ID NO: 142         moltype = AA  length = 16
FEATURE                Location/Qualifiers
REGION                 1..16
                       note = MTK-19 HVR-H3
source                 1..16
                       mol_type = protein
                       organism = synthetic construct
SEQUENCE: 142
GDLLWSLLLP GNYFDY                                       16

SEQ ID NO: 143         moltype = AA  length = 12
FEATURE                Location/Qualifiers
REGION                 1..12
                       note = MTK-20, 21 HVR-H3
source                 1..12
                       mol_type = protein
                       organism = synthetic construct
SEQUENCE: 143
GGGRLGLRPL DY                                           12

SEQ ID NO: 144         moltype = AA  length = 11
FEATURE                Location/Qualifiers
REGION                 1..11
                       note = MTK-22 HVR-H3
source                 1..11
                       mol_type = protein
                       organism = synthetic construct
SEQUENCE: 144
RYYYGSLYFD N                                            11

SEQ ID NO: 145         moltype = AA  length = 14
FEATURE                Location/Qualifiers
REGION                 1..14
                       note = MTK-23 HVR-H3
source                 1..14
                       mol_type = protein
                       organism = synthetic construct
SEQUENCE: 145
RVYDGFYVDW YFDV                                         14

SEQ ID NO: 146         moltype = AA  length = 13
FEATURE                Location/Qualifiers
REGION                 1..13
                       note = MTK-24 HVR-H3
source                 1..13
                       mol_type = protein
                       organism = synthetic construct
```

```
SEQUENCE: 146
RSPYSNYDWY FDV                                               13

SEQ ID NO: 147          moltype = AA  length = 8
FEATURE                 Location/Qualifiers
REGION                  1..8
                        note = MTK-25 HVR-H3
source                  1..8
                        mol_type = protein
                        organism = synthetic construct
SEQUENCE: 147
YYYGSVDY                                                     8

SEQ ID NO: 148          moltype = AA  length = 10
FEATURE                 Location/Qualifiers
REGION                  1..10
                        note = MTK-26 HVR-H3
source                  1..10
                        mol_type = protein
                        organism = synthetic construct
SEQUENCE: 148
EGGYYRSMDY                                                   10

SEQ ID NO: 149          moltype = AA  length = 8
FEATURE                 Location/Qualifiers
REGION                  1..8
                        note = MTK-27 HVR-H3
source                  1..8
                        mol_type = protein
                        organism = synthetic construct
SEQUENCE: 149
LFSNYFDY                                                     8

SEQ ID NO: 150          moltype = AA  length = 9
FEATURE                 Location/Qualifiers
REGION                  1..9
                        note = MTK-28 HVR-H3
source                  1..9
                        mol_type = protein
                        organism = synthetic construct
SEQUENCE: 150
FLRYYYFDY                                                    9

SEQ ID NO: 151          moltype = AA  length = 9
FEATURE                 Location/Qualifiers
REGION                  1..9
                        note = MTK-29, 29.19, 29.20, 29.21 HVR-H3
source                  1..9
                        mol_type = protein
                        organism = synthetic construct
SEQUENCE: 151
YTNYGYFDY                                                    9

SEQ ID NO: 152          moltype = AA  length = 8
FEATURE                 Location/Qualifiers
REGION                  1..8
                        note = MTK-30 HVR-H3
source                  1..8
                        mol_type = protein
                        organism = synthetic construct
SEQUENCE: 152
QILLYFDY                                                     8

SEQ ID NO: 153          moltype = AA  length = 13
FEATURE                 Location/Qualifiers
REGION                  1..13
                        note = MTK-31 HVR-H3
source                  1..13
                        mol_type = protein
                        organism = synthetic construct
SEQUENCE: 153
LSYDGSLYHA MDY                                               13

SEQ ID NO: 154          moltype = AA  length = 9
FEATURE                 Location/Qualifiers
REGION                  1..9
                        note = MTK-32 HVR-H3
```

```
source                  1..9
                        mol_type = protein
                        organism = synthetic construct
SEQUENCE: 154
EDNWAWFAY                                                              9

SEQ ID NO: 155          moltype = AA  length = 10
FEATURE                 Location/Qualifiers
REGION                  1..10
                        note = MTK-33, 33.2, 33.4, 33.5, 33.6, 33.7, 33.9, 33.10,
                         33.12, 33.13, 33.14, 33.15, 33.16, 33.17, 33.18, 33.19,
                         33.20, 33.21, 33.22, 33.24, 34 HVR-H3
source                  1..10
                        mol_type = protein
                        organism = synthetic construct
SEQUENCE: 155
EAGTRGYFDY                                                             10

SEQ ID NO: 156          moltype = AA  length = 11
FEATURE                 Location/Qualifiers
REGION                  1..11
                        note = MTK-35 HVR-H3
source                  1..11
                        mol_type = protein
                        organism = synthetic construct
SEQUENCE: 156
AYYTNWYYFD Y                                                           11

SEQ ID NO: 157          moltype = AA  length = 12
FEATURE                 Location/Qualifiers
REGION                  1..12
                        note = MTK-36 HVR-H3
source                  1..12
                        mol_type = protein
                        organism = synthetic construct
SEQUENCE: 157
IYYGTSYRYF DV                                                          12

SEQ ID NO: 158          moltype = AA  length = 10
FEATURE                 Location/Qualifiers
REGION                  1..10
                        note = MTK-01, 04, 06, 15, 15.1, 15.2, 15.11, 15.14, 15.15
                         HVR-L1
source                  1..10
                        mol_type = protein
                        organism = synthetic construct
SEQUENCE: 158
RASSSVSYMH                                                             10

SEQ ID NO: 159          moltype = AA  length = 10
FEATURE                 Location/Qualifiers
REGION                  1..10
                        note = MTK-02 HVR-L1
source                  1..10
                        mol_type = protein
                        organism = synthetic construct
SEQUENCE: 159
RANSSVSYMH                                                             10

SEQ ID NO: 160          moltype = AA  length = 10
FEATURE                 Location/Qualifiers
REGION                  1..10
                        note = MTK-03 HVR-L1
source                  1..10
                        mol_type = protein
                        organism = synthetic construct
SEQUENCE: 160
SASSSVNYMH                                                             10

SEQ ID NO: 161          moltype = AA  length = 11
FEATURE                 Location/Qualifiers
REGION                  1..11
                        note = MTK-05 HVR-L1
source                  1..11
                        mol_type = protein
                        organism = synthetic construct
SEQUENCE: 161
RASENIFSYL A                                                           11
```

```
SEQ ID NO: 162          moltype = AA  length = 10
FEATURE                 Location/Qualifiers
REGION                  1..10
                        note = MTK-07 HVR-L1
source                  1..10
                        mol_type = protein
                        organism = synthetic construct
SEQUENCE: 162
SASSSVTYMH                                                          10

SEQ ID NO: 163          moltype = AA  length = 10
FEATURE                 Location/Qualifiers
REGION                  1..10
                        note = MTK-08 HVR-L1
source                  1..10
                        mol_type = protein
                        organism = synthetic construct
SEQUENCE: 163
RATSSVSYMH                                                          10

SEQ ID NO: 164          moltype = AA  length = 11
FEATURE                 Location/Qualifiers
REGION                  1..11
                        note = MTK-09 HVR-L1
source                  1..11
                        mol_type = protein
                        organism = synthetic construct
SEQUENCE: 164
KASQDVTTSV A                                                        11

SEQ ID NO: 165          moltype = AA  length = 11
FEATURE                 Location/Qualifiers
REGION                  1..11
                        note = MTK-10 HVR-L1
source                  1..11
                        mol_type = protein
                        organism = synthetic construct
SEQUENCE: 165
SASQGISNYL N                                                        11

SEQ ID NO: 166          moltype = AA  length = 12
FEATURE                 Location/Qualifiers
REGION                  1..12
                        note = MTK-11 HVR-L1
source                  1..12
                        mol_type = protein
                        organism = synthetic construct
SEQUENCE: 166
TASSSISSSY FH                                                       12

SEQ ID NO: 167          moltype = AA  length = 10
FEATURE                 Location/Qualifiers
REGION                  1..10
                        note = MTK-12, 13 HVR-L1
source                  1..10
                        mol_type = protein
                        organism = synthetic construct
SEQUENCE: 167
SASSSVSYMY                                                          10

SEQ ID NO: 168          moltype = AA  length = 10
FEATURE                 Location/Qualifiers
REGION                  1..10
                        note = MTK-14 HVR-L1
source                  1..10
                        mol_type = protein
                        organism = synthetic construct
SEQUENCE: 168
RSSSSVSYMH                                                          10

SEQ ID NO: 169          moltype = AA  length = 11
FEATURE                 Location/Qualifiers
REGION                  1..11
                        note = MTK-16, 16.1 HVR-L1
source                  1..11
                        mol_type = protein
                        organism = synthetic construct
SEQUENCE: 169
KASQNVRTAV A                                                        11
```

```
SEQ ID NO: 170          moltype = AA  length = 11
FEATURE                 Location/Qualifiers
REGION                  1..11
                        note = MTK-17 HVR-L1
source                  1..11
                        mol_type = protein
                        organism = synthetic construct
SEQUENCE: 170
KASDHINNWL A                                                        11

SEQ ID NO: 171          moltype = AA  length = 11
FEATURE                 Location/Qualifiers
REGION                  1..11
                        note = MTK-18 HVR-L1
source                  1..11
                        mol_type = protein
                        organism = synthetic construct
SEQUENCE: 171
RASQAISNYL N                                                        11

SEQ ID NO: 172          moltype = AA  length = 16
FEATURE                 Location/Qualifiers
REGION                  1..16
                        note = MTK-19 HVR-L1
source                  1..16
                        mol_type = protein
                        organism = synthetic construct
SEQUENCE: 172
KSSQSLLDSD GKTYLN                                                   16

SEQ ID NO: 173          moltype = AA  length = 11
FEATURE                 Location/Qualifiers
REGION                  1..11
                        note = MTK-20, 21 HVR-L1
source                  1..11
                        mol_type = protein
                        organism = synthetic construct
SEQUENCE: 173
RASQDINNYL N                                                        11

SEQ ID NO: 174          moltype = AA  length = 11
FEATURE                 Location/Qualifiers
REGION                  1..11
                        note = MTK-22 HVR-L1
source                  1..11
                        mol_type = protein
                        organism = synthetic construct
SEQUENCE: 174
KASQDVGTAI A                                                        11

SEQ ID NO: 175          moltype = AA  length = 11
FEATURE                 Location/Qualifiers
REGION                  1..11
                        note = MTK-23 HVR-L1
source                  1..11
                        mol_type = protein
                        organism = synthetic construct
SEQUENCE: 175
KASRDVSTAV A                                                        11

SEQ ID NO: 176          moltype = AA  length = 11
FEATURE                 Location/Qualifiers
REGION                  1..11
                        note = MTK-24 HVR-L1
source                  1..11
                        mol_type = protein
                        organism = synthetic construct
SEQUENCE: 176
RASENIYSNL A                                                        11

SEQ ID NO: 177          moltype = AA  length = 11
FEATURE                 Location/Qualifiers
REGION                  1..11
                        note = MTK-25 HVR-L1
source                  1..11
                        mol_type = protein
                        organism = synthetic construct
```

```
SEQUENCE: 177
KASQNVRTTV A                                                        11

SEQ ID NO: 178          moltype = AA  length = 10
FEATURE                 Location/Qualifiers
REGION                  1..10
                        note = MTK-26 HVR-L1
source                  1..10
                        mol_type = protein
                        organism = synthetic construct
SEQUENCE: 178
SASSSVSFMH                                                          10

SEQ ID NO: 179          moltype = AA  length = 11
FEATURE                 Location/Qualifiers
REGION                  1..11
                        note = MTK-27 HVR-L1
source                  1..11
                        mol_type = protein
                        organism = synthetic construct
SEQUENCE: 179
KASQNVRTSV A                                                        11

SEQ ID NO: 180          moltype = AA  length = 10
FEATURE                 Location/Qualifiers
REGION                  1..10
                        note = MTK-28 HVR-L1
source                  1..10
                        mol_type = protein
                        organism = synthetic construct
SEQUENCE: 180
RASSSVTYMH                                                          10

SEQ ID NO: 181          moltype = AA  length = 10
FEATURE                 Location/Qualifiers
REGION                  1..10
                        note = MTK-29, 29.19, 29.20, 29.21, 32 HVR-L1
source                  1..10
                        mol_type = protein
                        organism = synthetic construct
SEQUENCE: 181
RATSSVGYMH                                                          10

SEQ ID NO: 182          moltype = AA  length = 16
FEATURE                 Location/Qualifiers
REGION                  1..16
                        note = MTK-30 HVR-L1
source                  1..16
                        mol_type = protein
                        organism = synthetic construct
SEQUENCE: 182
RSSQSIVHSN GDTYLE                                                   16

SEQ ID NO: 183          moltype = AA  length = 16
FEATURE                 Location/Qualifiers
REGION                  1..16
                        note = MTK-31 HVR-L1
source                  1..16
                        mol_type = protein
                        organism = synthetic construct
SEQUENCE: 183
RSSQTIVHSN GNTYLE                                                   16

SEQ ID NO: 184          moltype = AA  length = 11
FEATURE                 Location/Qualifiers
REGION                  1..11
                        note = MTK-33, 34 HVR-L1
source                  1..11
                        mol_type = protein
                        organism = synthetic construct
SEQUENCE: 184
KASQSVSNTV A                                                        11

SEQ ID NO: 185          moltype = AA  length = 12
FEATURE                 Location/Qualifiers
REGION                  1..12
                        note = MTK-35 HVR-L1
```

```
source                 1..12
                       mol_type = protein
                       organism = synthetic construct
SEQUENCE: 185
RASSSISSHY LH                                                12

SEQ ID NO: 186         moltype = AA  length = 10
FEATURE                Location/Qualifiers
REGION                 1..10
                       note = MTK-36 HVR-L1
source                 1..10
                       mol_type = protein
                       organism = synthetic construct
SEQUENCE: 186
RATSSVRYMH                                                   10

SEQ ID NO: 187         moltype = AA  length = 7
FEATURE                Location/Qualifiers
REGION                 1..7
                       note = MTK-01, 02, 04, 06, 08, 14, 15, 15.1, 15.2, 15.3,
                        15.4, 15.5, 15.6, 15.7, 15.8, 15.9, 15.10, 15.11, 15.12,
                        15.13, 15.14, 15.15, 28, 29, 29.1, 29.2, 29.3, 29.10,
                        29.11, 29.18, 29.19, 29.20, 29.21, 32 HVR-L2
source                 1..7
                       mol_type = protein
                       organism = synthetic construct
SEQUENCE: 187
ATSNLAS                                                      7

SEQ ID NO: 188         moltype = AA  length = 7
FEATURE                Location/Qualifiers
REGION                 1..7
                       note = MTK-03, 07, 26 HVR-L2
source                 1..7
                       mol_type = protein
                       organism = synthetic construct
SEQUENCE: 188
STSNLAS                                                      7

SEQ ID NO: 189         moltype = AA  length = 7
FEATURE                Location/Qualifiers
REGION                 1..7
                       note = MTK-05 HVR-L2
source                 1..7
                       mol_type = protein
                       organism = synthetic construct
SEQUENCE: 189
NAKTLAE                                                      7

SEQ ID NO: 190         moltype = AA  length = 7
FEATURE                Location/Qualifiers
REGION                 1..7
                       note = MTK-09 HVR-L2
source                 1..7
                       mol_type = protein
                       organism = synthetic construct
SEQUENCE: 190
SASYRYT                                                      7

SEQ ID NO: 191         moltype = AA  length = 7
FEATURE                Location/Qualifiers
REGION                 1..7
                       note = MTK-10, 18, 20 HVR-L2
source                 1..7
                       mol_type = protein
                       organism = synthetic construct
SEQUENCE: 191
YTSRLHS                                                      7

SEQ ID NO: 192         moltype = AA  length = 7
FEATURE                Location/Qualifiers
REGION                 1..7
                       note = MTK-11 HVR-L2
source                 1..7
                       mol_type = protein
                       organism = synthetic construct
SEQUENCE: 192
STSNLPS                                                      7
```

```
SEQ ID NO: 193          moltype = AA  length = 7
FEATURE                 Location/Qualifiers
REGION                  1..7
                        note = MTK-12 HVR-L2
source                  1..7
                        mol_type = protein
                        organism = synthetic construct
SEQUENCE: 193
DTSNLAS                                                                7

SEQ ID NO: 194          moltype = AA  length = 7
FEATURE                 Location/Qualifiers
REGION                  1..7
                        note = MTK-13 HVR-L2
source                  1..7
                        mol_type = protein
                        organism = synthetic construct
SEQUENCE: 194
STFNLAS                                                                7

SEQ ID NO: 195          moltype = AA  length = 7
FEATURE                 Location/Qualifiers
REGION                  1..7
                        note = MTK-16, 16.1, 16.2, 25, 27 HVR-L2
source                  1..7
                        mol_type = protein
                        organism = synthetic construct
SEQUENCE: 195
LASNRHT                                                                7

SEQ ID NO: 196          moltype = AA  length = 7
FEATURE                 Location/Qualifiers
REGION                  1..7
                        note = MTK-17 HVR-L2
source                  1..7
                        mol_type = protein
                        organism = synthetic construct
SEQUENCE: 196
GATSLET                                                                7

SEQ ID NO: 197          moltype = AA  length = 7
FEATURE                 Location/Qualifiers
REGION                  1..7
                        note = MTK-19 HVR-L2
source                  1..7
                        mol_type = protein
                        organism = synthetic construct
SEQUENCE: 197
LVSKLDS                                                                7

SEQ ID NO: 198          moltype = AA  length = 7
FEATURE                 Location/Qualifiers
REGION                  1..7
                        note = MTK-21 HVR-L2
source                  1..7
                        mol_type = protein
                        organism = synthetic construct
SEQUENCE: 198
YTSSLHS                                                                7

SEQ ID NO: 199          moltype = AA  length = 7
FEATURE                 Location/Qualifiers
REGION                  1..7
                        note = MTK-22 HVR-L2
source                  1..7
                        mol_type = protein
                        organism = synthetic construct
SEQUENCE: 199
WASTRHT                                                                7

SEQ ID NO: 200          moltype = AA  length = 7
FEATURE                 Location/Qualifiers
REGION                  1..7
                        note = MTK-23 HVR-L2
source                  1..7
                        mol_type = protein
                        organism = synthetic construct
SEQUENCE: 200
SASYRST                                                                7
```

```
SEQ ID NO: 201          moltype = AA  length = 7
FEATURE                 Location/Qualifiers
REGION                  1..7
                        note = MTK-24 HVR-L2
source                  1..7
                        mol_type = protein
                        organism = synthetic construct
SEQUENCE: 201
AATNLAD                                                      7

SEQ ID NO: 202          moltype = AA  length = 7
FEATURE                 Location/Qualifiers
REGION                  1..7
                        note = MTK-30, 31 HVR-L2
source                  1..7
                        mol_type = protein
                        organism = synthetic construct
SEQUENCE: 202
KVSNRFS                                                      7

SEQ ID NO: 203          moltype = AA  length = 7
FEATURE                 Location/Qualifiers
REGION                  1..7
                        note = MTK-33, 33.2, 33.3, 33.4, 33.6, 33.7, 33.8, 33.9,
                         33.10, 33.11, 33.12, 33.13, 33.14, 33.15, 33.16, 33.17,
                         33.18, 33.19, 33.20, 33.23, 33.24, 34 HVR-L2
source                  1..7
                        mol_type = protein
                        organism = synthetic construct
SEQUENCE: 203
YASNRYT                                                      7

SEQ ID NO: 204          moltype = AA  length = 7
FEATURE                 Location/Qualifiers
REGION                  1..7
                        note = MTK-35 HVR-L2
source                  1..7
                        mol_type = protein
                        organism = synthetic construct
SEQUENCE: 204
RTSNLAS                                                      7

SEQ ID NO: 205          moltype = AA  length = 7
FEATURE                 Location/Qualifiers
REGION                  1..7
                        note = MTK-36 HVR-L2
source                  1..7
                        mol_type = protein
                        organism = synthetic construct
SEQUENCE: 205
ATYNLTS                                                      7

SEQ ID NO: 206          moltype =   length =
SEQUENCE: 206
000

SEQ ID NO: 207          moltype = AA  length = 9
FEATURE                 Location/Qualifiers
REGION                  1..9
                        note = MTK-01 HVR-L3
source                  1..9
                        mol_type = protein
                        organism = synthetic construct
SEQUENCE: 207
QQWSSNPPT                                                    9

SEQ ID NO: 208          moltype = AA  length = 9
FEATURE                 Location/Qualifiers
REGION                  1..9
                        note = MTK-02, 29, 29.19, 29.20, 29.21 HVR-L3
source                  1..9
                        mol_type = protein
                        organism = synthetic construct
SEQUENCE: 208
QQWGSNPFT                                                    9

SEQ ID NO: 209          moltype = AA  length = 9
FEATURE                 Location/Qualifiers
```

```
REGION                  1..9
                        note = MTK-03, 07, 13, 26 HVR-L3
source                  1..9
                        mol_type = protein
                        organism = synthetic construct
SEQUENCE: 209
QQRSSYPFT                                                                   9

SEQ ID NO: 210          moltype = AA  length = 9
FEATURE                 Location/Qualifiers
REGION                  1..9
                        note = MTK-04, 15, 15.1, 15.2, 15.3, 15.4, 15.5, 15.6,
                         15.7, 15.8, 15.9, 15.10, 15.11, 15.12, 15.13, 15.14,
                         15.15, 32 HVR-L3
source                  1..9
                        mol_type = protein
                        organism = synthetic construct
SEQUENCE: 210
QQWSSNPRT                                                                   9

SEQ ID NO: 211          moltype = AA  length = 9
FEATURE                 Location/Qualifiers
REGION                  1..9
                        note = MTK-05 HVR-L3
source                  1..9
                        mol_type = protein
                        organism = synthetic construct
SEQUENCE: 211
LHHYGTPLT                                                                   9

SEQ ID NO: 212          moltype = AA  length = 9
FEATURE                 Location/Qualifiers
REGION                  1..9
                        note = MTK-06 HVR-L3
source                  1..9
                        mol_type = protein
                        organism = synthetic construct
SEQUENCE: 212
QQWSSKPPT                                                                   9

SEQ ID NO: 213          moltype = AA  length = 9
FEATURE                 Location/Qualifiers
REGION                  1..9
                        note = MTK-08 HVR-L3
source                  1..9
                        mol_type = protein
                        organism = synthetic construct
SEQUENCE: 213
QHWSGNPRT                                                                   9

SEQ ID NO: 214          moltype = AA  length = 9
FEATURE                 Location/Qualifiers
REGION                  1..9
                        note = MTK-09 HVR-L3
source                  1..9
                        mol_type = protein
                        organism = synthetic construct
SEQUENCE: 214
QQHYSTPLT                                                                   9

SEQ ID NO: 215          moltype = AA  length = 9
FEATURE                 Location/Qualifiers
REGION                  1..9
                        note = MTK-10 HVR-L3
source                  1..9
                        mol_type = protein
                        organism = synthetic construct
SEQUENCE: 215
QQYTKLPYT                                                                   9

SEQ ID NO: 216          moltype = AA  length = 9
FEATURE                 Location/Qualifiers
REGION                  1..9
                        note = MTK-11 HVR-L3
source                  1..9
                        mol_type = protein
                        organism = synthetic construct
SEQUENCE: 216
HQYYRSPLT                                                                   9
```

```
SEQ ID NO: 217          moltype = AA  length = 9
FEATURE                 Location/Qualifiers
REGION                  1..9
                        note = MTK-12 HVR-L3
source                  1..9
                        mol_type = protein
                        organism = synthetic construct
SEQUENCE: 217
QQWSSYPLT                                                          9

SEQ ID NO: 218          moltype = AA  length = 9
FEATURE                 Location/Qualifiers
REGION                  1..9
                        note = MTK-14 HVR-L3
source                  1..9
                        mol_type = protein
                        organism = synthetic construct
SEQUENCE: 218
QQWGSNPRT                                                          9

SEQ ID NO: 219          moltype = AA  length = 9
FEATURE                 Location/Qualifiers
REGION                  1..9
                        note = MTK-16, 16.1, 16.2 HVR-L3
source                  1..9
                        mol_type = protein
                        organism = synthetic construct
SEQUENCE: 219
LQHWNYPLT                                                          9

SEQ ID NO: 220          moltype = AA  length = 9
FEATURE                 Location/Qualifiers
REGION                  1..9
                        note = MTK-17 HVR-L3
source                  1..9
                        mol_type = protein
                        organism = synthetic construct
SEQUENCE: 220
QQYWSTPRT                                                          9

SEQ ID NO: 221          moltype = AA  length = 9
FEATURE                 Location/Qualifiers
REGION                  1..9
                        note = MTK-18, 21 HVR-L3
source                  1..9
                        mol_type = protein
                        organism = synthetic construct
SEQUENCE: 221
QQGNTLPWT                                                          9

SEQ ID NO: 222          moltype = AA  length = 9
FEATURE                 Location/Qualifiers
REGION                  1..9
                        note = MTK-19 HVR-L3
source                  1..9
                        mol_type = protein
                        organism = synthetic construct
SEQUENCE: 222
WQGTHFPWT                                                          9

SEQ ID NO: 223          moltype = AA  length = 8
FEATURE                 Location/Qualifiers
REGION                  1..8
                        note = MTK-20 HVR-L3
source                  1..8
                        mol_type = protein
                        organism = synthetic construct
SEQUENCE: 223
QQGNTLPW                                                           8

SEQ ID NO: 224          moltype = AA  length = 9
FEATURE                 Location/Qualifiers
REGION                  1..9
                        note = MTK-22 HVR-L3
source                  1..9
                        mol_type = protein
                        organism = synthetic construct
```

```
SEQUENCE: 224
QQYTSYPLT                                                            9

SEQ ID NO: 225          moltype = AA  length = 9
FEATURE                 Location/Qualifiers
REGION                  1..9
                        note = MTK-23 HVR-L3
source                  1..9
                        mol_type = protein
                        organism = synthetic construct
SEQUENCE: 225
QQHYSAPLT                                                            9

SEQ ID NO: 226          moltype = AA  length = 9
FEATURE                 Location/Qualifiers
REGION                  1..9
                        note = MTK-24 HVR-L3
source                  1..9
                        mol_type = protein
                        organism = synthetic construct
SEQUENCE: 226
QHFWGTPLT                                                            9

SEQ ID NO: 227          moltype = AA  length = 9
FEATURE                 Location/Qualifiers
REGION                  1..9
                        note = MTK-25 HVR-L3
source                  1..9
                        mol_type = protein
                        organism = synthetic construct
SEQUENCE: 227
LQLWNYPWT                                                            9

SEQ ID NO: 228          moltype = AA  length = 9
FEATURE                 Location/Qualifiers
REGION                  1..9
                        note = MTK-27 HVR-L3
source                  1..9
                        mol_type = protein
                        organism = synthetic construct
SEQUENCE: 228
LQHWNYPYT                                                            9

SEQ ID NO: 229          moltype = AA  length = 8
FEATURE                 Location/Qualifiers
REGION                  1..8
                        note = MTK-28 HVR-L3
source                  1..8
                        mol_type = protein
                        organism = synthetic construct
SEQUENCE: 229
HQWSGNPT                                                             8

SEQ ID NO: 230          moltype = AA  length = 9
FEATURE                 Location/Qualifiers
REGION                  1..9
                        note = MTK-30, 31 HVR-L3
source                  1..9
                        mol_type = protein
                        organism = synthetic construct
SEQUENCE: 230
FQGSHVPWT                                                            9

SEQ ID NO: 231          moltype = AA  length = 9
FEATURE                 Location/Qualifiers
REGION                  1..9
                        note = MTK-33, 33.1, 33.2, 33.3, 33.5, 33.6, 33.7, 33.8,
                         33.9, 33.10, 33.11, 33.13, 33.14, 33.16, 34 HVR-L3
source                  1..9
                        mol_type = protein
                        organism = synthetic construct
SEQUENCE: 231
QQDYRSPFT                                                            9

SEQ ID NO: 232          moltype = AA  length = 9
FEATURE                 Location/Qualifiers
REGION                  1..9
                        note = MTK-35 HVR-L3
```

```
source                  1..9
                        mol_type = protein
                        organism = synthetic construct
SEQUENCE: 232
QQGSTIPLT                                                         9

SEQ ID NO: 233          moltype = AA  length = 9
FEATURE                 Location/Qualifiers
REGION                  1..9
                        note = MTK-36 HVR-L3
source                  1..9
                        mol_type = protein
                        organism = synthetic construct
SEQUENCE: 233
HQWSSNPYT                                                         9

SEQ ID NO: 234          moltype = AA  length = 118
FEATURE                 Location/Qualifiers
REGION                  1..118
                        note = MTK-15.1 Heavy Chain Variable
source                  1..118
                        mol_type = protein
                        organism = synthetic construct
SEQUENCE: 234
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCARGN RYAYQDYWGQ GTLVTVSS    118

SEQ ID NO: 235          moltype = AA  length = 118
FEATURE                 Location/Qualifiers
REGION                  1..118
                        note = MTK-15.2 Heavy Chain Variable
source                  1..118
                        mol_type = protein
                        organism = synthetic construct
SEQUENCE: 235
QVQLVQSGSE LKKPGASVKV SCKASGYTFT NYGVHWVRQA PGQGLEWMGW GNTYTGEPTY  60
AQGFTGRFVF SLDTSVSTAY LQISSLKAED TAVYYCARGN RYAYMDYWGQ GTLVTVSS    118

SEQ ID NO: 236          moltype = AA  length = 118
FEATURE                 Location/Qualifiers
REGION                  1..118
                        note = MTK-15.3, 15.4 Heavy Chain Variable
source                  1..118
                        mol_type = protein
                        organism = synthetic construct
SEQUENCE: 236
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCARGN RYAYMDYWGQ GTLVTVSS    118

SEQ ID NO: 237          moltype = AA  length = 118
FEATURE                 Location/Qualifiers
REGION                  1..118
                        note = MTK-15.5 Heavy Chain Variable
source                  1..118
                        mol_type = protein
                        organism = synthetic construct
SEQUENCE: 237
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCTRGT RYAYMDYWGQ GTLVTVSS    118

SEQ ID NO: 238          moltype = AA  length = 118
FEATURE                 Location/Qualifiers
REGION                  1..118
                        note = MTK-15.6 Heavy Chain Variable
source                  1..118
                        mol_type = protein
                        organism = synthetic construct
SEQUENCE: 238
QVQLVQSGSE LKKPGASVKV SCKASGYTFT NYGVHWVRQA PGQGLEWMGW INTYTGEPYY  60
AQGFTGRFVF SLDTSVSTAY LQISSLKAED TAVYYCARGN RYAYMDYWGQ GTLVTVSS    118

SEQ ID NO: 239          moltype = AA  length = 118
FEATURE                 Location/Qualifiers
REGION                  1..118
                        note = MTK-15.7 Heavy Chain Variable
source                  1..118
                        mol_type = protein
                        organism = synthetic construct
```

```
SEQUENCE: 239
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCVRGN RYAYMDYWGQ GTLVTVSS    118

SEQ ID NO: 240         moltype = AA  length = 118
FEATURE                Location/Qualifiers
REGION                 1..118
                       note = MTK-15.8 Heavy Chain Variable
source                 1..118
                       mol_type = protein
                       organism = synthetic construct
SEQUENCE: 240
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCARGV RYAYMDYWGQ GTLVTVSS    118

SEQ ID NO: 241         moltype = AA  length = 118
FEATURE                Location/Qualifiers
REGION                 1..118
                       note = MTK-15.9 Heavy Chain Variable
source                 1..118
                       mol_type = protein
                       organism = synthetic construct
SEQUENCE: 241
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCARGY RYAYMDYWGQ GTLVTVSS    118

SEQ ID NO: 242         moltype = AA  length = 118
FEATURE                Location/Qualifiers
REGION                 1..118
                       note = MTK-15.10 Heavy Chain Variable
source                 1..118
                       mol_type = protein
                       organism = synthetic construct
SEQUENCE: 242
QVQLVQSGSE LKKPGASVKV SCKASGYTFA NYGVHWVRQA PGQGLEWMGW INTYQGEPTY  60
AQGFTGRFVF SLDTSVSTAY LQISSLKAED TAVYYCTRGA RYAYMDYWGQ GTLVTVSS    118

SEQ ID NO: 243         moltype = AA  length = 118
FEATURE                Location/Qualifiers
REGION                 1..118
                       note = MTK-15.11 Heavy Chain Variable
source                 1..118
                       mol_type = protein
                       organism = synthetic construct
SEQUENCE: 243
QVQLVQSGSE LKKPGASVKV SCKASGYTFA NYGVHWVRQA PGQGLEWMGW INTYEGEPTY  60
AQGFTGRFVF SLDTSVSTAY LQISSLKAED TAVYYCARGN RYAYQDYWGQ GTLVTVSS    118

SEQ ID NO: 244         moltype = AA  length = 118
FEATURE                Location/Qualifiers
REGION                 1..118
                       note = MTK-15.12 Heavy Chain Variable
source                 1..118
                       mol_type = protein
                       organism = synthetic construct
SEQUENCE: 244
QVQLVQSGSE LKKPGASVKV SCKASGYTFA NYGVHWVRQA PGQGLEWMGW INTYQGEPTY  60
AQGFTGRFVF SLDTSVSTAY LQISSLKAED TAVYYCARGV RYAYMDYWGQ GTLVTVSS    118

SEQ ID NO: 245         moltype = AA  length = 118
FEATURE                Location/Qualifiers
REGION                 1..118
                       note = MTK-15.13 Heavy Chain Variable
source                 1..118
                       mol_type = protein
                       organism = synthetic construct
SEQUENCE: 245
QVQLVQSGSE LKKPGASVKV SCKASGYTFT NYGVHWVRQA PGQGLEWMGW INTYTGEPTY  60
AQGFTGRFVF SLDTSVSTAY LQISSLKAED TAVYYCARGN RYAYEDYWGQ GTLVTVSS    118

SEQ ID NO: 246         moltype = AA  length = 118
FEATURE                Location/Qualifiers
REGION                 1..118
                       note = MTK-15.14, 15.15 Heavy Chain Variable
source                 1..118
                       mol_type = protein
                       organism = synthetic construct
```

```
SEQUENCE: 246
QVQLVQSGSE LKKPGASVKV SCKASGYTFT NYGVHWVRQA PGQGLEWMGW INTYTGEPTY  60
AQGFTGRFVF SLDTSVSTAY LQICSLKAED TAVYYCARGN RYAYMDYWGQ GTLVTVSS    118

SEQ ID NO: 247         moltype = AA  length = 106
FEATURE                Location/Qualifiers
REGION                 1..106
                       note = MTK-15.1, 15.2, 15.11, 15.14 Light Chain Variable
source                 1..106
                       mol_type = protein
                       organism = synthetic construct
SEQUENCE: 247
EIVLTQSPAT LSLSPGERAT LSCRASSSVS YMHWYQQKPG QAPRPLIYAT SNLASGIPAR  60
FSGSGSGTSY TLTISSLEPE DFAVYYCQQW SSNPRTFGGG TKVEIK                106

SEQ ID NO: 248         moltype = AA  length = 106
FEATURE                Location/Qualifiers
REGION                 1..106
                       note = MTK-15.3 Light Chain Variable
source                 1..106
                       mol_type = protein
                       organism = synthetic construct
SEQUENCE: 248
EIVLTQSPAT LSLSPGERAT LSCRASSHVS YMHWYQQKPG QAPRPLIYAT SNLASGIPAR  60
FSGSGSGTSY TLTISSLEPE DFAVYYCQQW SSNPRTFGGG TKVEIK                106

SEQ ID NO: 249         moltype = AA  length = 106
FEATURE                Location/Qualifiers
REGION                 1..106
                       note = MTK-15.4, 15.5, 15.6, 15.10 Light Chain Variable
source                 1..106
                       mol_type = protein
                       organism = synthetic construct
SEQUENCE: 249
EIVLTQSPAT LSLSPGERAT LSCRASSSVG YMHWYQQKPG QAPRPLIYAT SNLASGIPAR  60
FSGSGSGTSY TLTISSLEPE DFAVYYCQQW SSNPRTFGGG TKVEIK                106

SEQ ID NO: 250         moltype = AA  length = 106
FEATURE                Location/Qualifiers
REGION                 1..106
                       note = MTK-15.7 Light Chain Variable
source                 1..106
                       mol_type = protein
                       organism = synthetic construct
SEQUENCE: 250
EIVLTQSPAT LSLSPGERAT LSCRASSGVS YMHWYQQKPG QAPRPLIYAT SNLASGIPAR  60
FSGSGSGTSY TLTISSLEPE DFAVYYCQQW SSNPRTFGGG TKVEIK                106

SEQ ID NO: 251         moltype = AA  length = 106
FEATURE                Location/Qualifiers
REGION                 1..106
                       note = MTK-15.8, 15.12 Light Chain Variable
source                 1..106
                       mol_type = protein
                       organism = synthetic construct
SEQUENCE: 251
EIVLTQSPAT LSLSPGERAT LSCRASSSVG YMHWYQQKPG QAPRPLIYAT SNLASGIPAR  60
FSGSGSGTSY TLTISSPEPE DFAVYYCQQW SSNPRTFGGG TKVEIK                106

SEQ ID NO: 252         moltype = AA  length = 106
FEATURE                Location/Qualifiers
REGION                 1..106
                       note = MTK-15.9 Light Chain Variable
source                 1..106
                       mol_type = protein
                       organism = synthetic construct
SEQUENCE: 252
EIVLTQSPAT LSLSPGERAT LSCRASSSTS YMHWYQQKPG QAPRPLIYAT SNLASGIPAR  60
FSGSGSGTSY TLTISSLEPE DFAVYYCQQW SSNPRTFGGG TKVEIK                106

SEQ ID NO: 253         moltype = AA  length = 106
FEATURE                Location/Qualifiers
REGION                 1..106
                       note = MTK-15.13 Light Chain Variable
source                 1..106
                       mol_type = protein
                       organism = synthetic construct
```

```
SEQUENCE: 253
EIVLTQSPAT LSLSPGERAT LSCRASSSVQ YMHWYQQKPG QAPRPLIYAT SNLASGIPAR  60
FSGSGSGTSY TLTISSLEPE DFAVYYCQQW SSNPRTFGGG TKVEIK                 106

SEQ ID NO: 254          moltype = AA  length = 106
FEATURE                 Location/Qualifiers
REGION                  1..106
                        note = MTK-15.15 Light Chain Variable
source                  1..106
                        mol_type = protein
                        organism = synthetic construct
SEQUENCE: 254
QIVLTQSPGT LSLSPGERAT LSCRASSSVS YMHWYQQKPG QAPRPLIYAT SNLASGIPDR  60
FSGSGSGTSY TLTISRLEPE DFAVYYCQQW SSNPRTFGGG TKVEIK                 106

SEQ ID NO: 255          moltype = AA  length = 120
FEATURE                 Location/Qualifiers
REGION                  1..120
                        note = MTK-16.1 Heavy Chain Variable
source                  1..120
                        mol_type = protein
                        organism = synthetic construct
SEQUENCE: 255
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120

SEQ ID NO: 256          moltype = AA  length = 120
FEATURE                 Location/Qualifiers
REGION                  1..120
                        note = MTK-16.2 Heavy Chain Variable
source                  1..120
                        mol_type = protein
                        organism = synthetic construct
SEQUENCE: 256
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120

SEQ ID NO: 257          moltype = AA  length = 107
FEATURE                 Location/Qualifiers
REGION                  1..107
                        note = MTK-16.1 Light Chain Variable
source                  1..107
                        mol_type = protein
                        organism = synthetic construct
SEQUENCE: 257
DIQMTQSPSS LSASVGDRVT ITCKASQNVR TAVAWYQQKP GKAPKRLIYL ASNRHTGVPS  60
RFSGSGSGTE FTLTISNLQP EDFATYYCLQ HWNYPLTFGG GTKVEIK                107

SEQ ID NO: 258          moltype = AA  length = 107
FEATURE                 Location/Qualifiers
REGION                  1..107
                        note = MTK-16.2 Light Chain Variable
source                  1..107
                        mol_type = protein
                        organism = synthetic construct
SEQUENCE: 258
DIQMTQSPSS LSASVGDRVT ITCRASQNVR TAVAWYQQKP GKAPKRLIYL ASNRHTGVPS  60
RFSGSGSGTE FTLTISNLQP EDFATYYCLQ HWNYPLTFGG GTKLEIK                107

SEQ ID NO: 259          moltype = AA  length = 118
FEATURE                 Location/Qualifiers
REGION                  1..118
                        note = MTK-29.1 Heavy Chain Variable
source                  1..118
                        mol_type = protein
                        organism = synthetic construct
SEQUENCE: 259
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARYT NYGIFDYWGQ GTLVTVSS    118

SEQ ID NO: 260          moltype = AA  length = 118
FEATURE                 Location/Qualifiers
REGION                  1..118
                        note = MTK-29.2 Heavy Chain Variable
source                  1..118
                        mol_type = protein
                        organism = synthetic construct
```

```
SEQUENCE: 260
QVQLVQSGSE LKKPGASVKV SCKASGFTFT TYGMSWVRQA PGQGLEWMGW INTYSGVPTY  60
TDDFKGRFVF SLDTSVSTAY LQISSLKAED TAVYYCARYT NYGIFDYWGQ GTLVTVSS    118

SEQ ID NO: 261         moltype = AA  length = 118
FEATURE                Location/Qualifiers
REGION                 1..118
                       note = MTK-29.3 Heavy Chain Variable
source                 1..118
                       mol_type = protein
                       organism = synthetic construct
SEQUENCE: 261
QVQLVQSGSE LKKPGASVKV SCKASGFTFT TYGMSWVRQA PGQGLEWMGW INTYSGVPAY  60
TDDFKGRFVF SLDTSVSTAY LQISSLKAED TAVYYCARYT NYGVFDYWGQ GTLVTVSS    118

SEQ ID NO: 262         moltype = AA  length = 118
FEATURE                Location/Qualifiers
REGION                 1..118
                       note = MTK-29.4 Heavy Chain Variable
source                 1..118
                       mol_type = protein
                       organism = synthetic construct
SEQUENCE: 262
QVQLVQSGSE LKKPGASVKV SCKASSYTFT TYGMSWVRQA PGQGLEWMGW INTYSGVPTY  60
TDDFKGRFVF SLDTSVSTAY LQISSLKAED TAVYYCARYT NYGVFDYWGQ GTLVTVSS    118

SEQ ID NO: 263         moltype = AA  length = 118
FEATURE                Location/Qualifiers
REGION                 1..118
                       note = MTK-29.5 Heavy Chain Variable
source                 1..118
                       mol_type = protein
                       organism = synthetic construct
SEQUENCE: 263
QVQLVQSGSE LKKPGASVKV SCKASGYIFT SYGLSWVRQA PGQGLEWMGW INTYSGVPTY  60
TDDFKGRFVF SLDTSVSTAY LQISPLKAED TAVYYCARYT NYGVFDYWGQ GTLVTVSS    118

SEQ ID NO: 264         moltype = AA  length = 118
FEATURE                Location/Qualifiers
REGION                 1..118
                       note = MTK-29.6, 29.12, 29.15 Heavy Chain Variable
source                 1..118
                       mol_type = protein
                       organism = synthetic construct
SEQUENCE: 264
QVQLVQSGSE LKKPGASVKV SCKASSYTFT TYGMSWVRQA PGQGLEWMGW INTMSGVPTY  60
TDDFKGRFVF SLDTSVSTAY LQISSLKAED TAVYYCARYT NYGVFDYWGQ GTLVTVSS    118

SEQ ID NO: 265         moltype = AA  length = 118
FEATURE                Location/Qualifiers
REGION                 1..118
                       note = MTK-29.7, 29.14 Heavy Chain Variable
source                 1..118
                       mol_type = protein
                       organism = synthetic construct
SEQUENCE: 265
QVQLVQSGSE LKKPGASVKV SCKASSYTFT TYGMSWVRQA PGQGLEWMGW INTYSGVPSY  60
TDDFKARFVF SLDTSVSTAY LQISSLKAED TAVYYCARYT NYGVFDYWGQ GTLVTVSS    118

SEQ ID NO: 266         moltype = AA  length = 118
FEATURE                Location/Qualifiers
REGION                 1..118
                       note = MTK-29.8 Heavy Chain Variable
source                 1..118
                       mol_type = protein
                       organism = synthetic construct
SEQUENCE: 266
QVQLVQSGSE LKKPGASVKV SCKASGYIFT TYGLSWVRQA PGQGLEWMGW INTYSGVPTY  60
TDDFKGRFVF SLDTNVSTAY LQISSLKAED TAVYYCARYT NYGVFDYWGQ GTLVTVSS    118

SEQ ID NO: 267         moltype = AA  length = 118
FEATURE                Location/Qualifiers
REGION                 1..118
                       note = MTK-29.9 Heavy Chain Variable
source                 1..118
                       mol_type = protein
                       organism = synthetic construct
```

```
SEQUENCE: 267
QVQLVQSGSE LKKPGASVKV SCKASGYIFT SYGLSWVRQA PGQGLEWMGW INTYSGVPTY  60
TDDFKGRFVF SLDTSVSTAY LQISSLKAED TAVYYCARYT NYGVFDYWGQ GTLVTVSS    118

SEQ ID NO: 268         moltype = AA  length = 118
FEATURE                Location/Qualifiers
REGION                 1..118
                       note = MTK-29.10 Heavy Chain Variable
source                 1..118
                       mol_type = protein
                       organism = synthetic construct
SEQUENCE: 268
QVQLVQSGSE LKKPGASVKV SCKTSSYTFT TYGMSWVRQA PGQGLEWMGW INTYSGVPTY  60
TDDFKGRFVF SLDTSVSTAY LQISSLKAED TAVYYCARYT NYGVFDYWGQ GTLVTVSS    118

SEQ ID NO: 269         moltype = AA  length = 118
FEATURE                Location/Qualifiers
REGION                 1..118
                       note = MTK-29.11 Heavy Chain Variable
source                 1..118
                       mol_type = protein
                       organism = synthetic construct
SEQUENCE: 269
QVQLVQSGSE LKKPGASVKV SCKASSYTFT TYGMSWVRQA PGQGLEWMGW INTDSGVPTY  60
TDDFKGRFVF SLDTSVSTAY LQISSLKAED TAVYYCARYT NYGVFDYWGQ GTLVTVSS    118

SEQ ID NO: 270         moltype = AA  length = 118
FEATURE                Location/Qualifiers
REGION                 1..118
                       note = MTK-29.13 Heavy Chain Variable
source                 1..118
                       mol_type = protein
                       organism = synthetic construct
SEQUENCE: 270
QVQLVQSGSE LKKPGASVKV SCKASSYTFT TYGMSWVRQA PGQGLEWMGW INTASGVPTY  60
TDDFKGRFVF SLDTSVSTAY LQISSLKAED TAVYYCARYT NYGVFDYWGQ GTLVTVSS    118

SEQ ID NO: 271         moltype = AA  length = 118
FEATURE                Location/Qualifiers
REGION                 1..118
                       note = MTK-29.16, 29.18 Heavy Chain Variable
source                 1..118
                       mol_type = protein
                       organism = synthetic construct
SEQUENCE: 271
QVQLVQSGSE LKKPGASVKV SCKASGYIFT SYGLSWVRQA PGQGLEWMGW VNTYSGVPTY  60
TDDFKGRFVF SLDTSVSTAY LQISSLKAED TAVYYCARYT NYGVFDYWGQ GTLVTVSS    118

SEQ ID NO: 272         moltype = AA  length = 118
FEATURE                Location/Qualifiers
REGION                 1..118
                       note = MTK-29.17 Heavy Chain Variable
source                 1..118
                       mol_type = protein
                       organism = synthetic construct
SEQUENCE: 272
QVQLVQSGSE LKKPGASVKV SCKASGYIFT SYGLSWVRQA PGQGLEWMGW INTYSGVPTY  60
AQGFTGRFVF SLDTSVSTAY LQISSLKAED TAVYYCARYT NYGVFDYWGQ GTLVTVSS    118

SEQ ID NO: 273         moltype = AA  length = 118
FEATURE                Location/Qualifiers
REGION                 1..118
                       note = MTK-29.19, 29.20, 29.21 Heavy Chain Variable
source                 1..118
                       mol_type = protein
                       organism = synthetic construct
SEQUENCE: 273
QVQLVQSGSE LKKPGASVKV SCKASGFTFT TYGMSWVRQA PGQGLEWMGW INTYSGVPTY  60
AQGFTGRFVF SLDTSVSTAY LQICSLKAED TAVYYCARYT NYGYFDYWGQ GTLVTVSS    118

SEQ ID NO: 274         moltype = AA  length = 106
FEATURE                Location/Qualifiers
REGION                 1..106
                       note = MTK-29.1 Light Chain Variable
source                 1..106
                       mol_type = protein
                       organism = synthetic construct
```

```
SEQUENCE: 274
EIVLTQSPAT LSLSPGERAT LSCRASSSVG YMHWYQQKPG QAPRPLIYAT SNLASGIPAR  60
FSGSGSGTDF TLTISRLEPE DFAVYYCQQW GSWPFTFGQG TKLEIK                106

SEQ ID NO: 275         moltype = AA  length = 106
FEATURE                Location/Qualifiers
REGION                 1..106
                       note = MTK-29.2 Light Chain Variable
source                 1..106
                       mol_type = protein
                       organism = synthetic construct
SEQUENCE: 275
DIQLTQSPSF LSASVGDRVT ITCRASSSVG YMHWYQQKPG KAPKPLIYAT SNLASGVPSR  60
FSGSGSGTEF TLTISSLQPE DFATYYCQQW GSIPFTFGGG TKVEIK                106

SEQ ID NO: 276         moltype = AA  length = 106
FEATURE                Location/Qualifiers
REGION                 1..106
                       note = MTK-29.3 Light Chain Variable
source                 1..106
                       mol_type = protein
                       organism = synthetic construct
SEQUENCE: 276
DIQLTQSPSF LSASVGDRVT ITCRASSSVG YMHWYQQKPG KAPKLLIYAT SNLASGVPSR  60
FSGSGSGTEF TLTISSLQPE DFATYYCQQW GSLPFTFGQG TKLEIK                106

SEQ ID NO: 277         moltype = AA  length = 106
FEATURE                Location/Qualifiers
REGION                 1..106
                       note = MTK-29.4, 29.5, 29.6, 29.7, 29.8 Light Chain Variable
source                 1..106
                       mol_type = protein
                       organism = synthetic construct
SEQUENCE: 277
DIQLTQSPSF LSASVGDRVT ITCRASSSVG YMHWYQQKPG KAPKLLIYAT SNLAQGVPSR  60
FSGSGSGTEF TLTISSLQPE DFATYYCQQW GSLPFTFGQG TKLEIK                106

SEQ ID NO: 278         moltype = AA  length = 106
FEATURE                Location/Qualifiers
REGION                 1..106
                       note = MTK-29.9 Light Chain Variable
source                 1..106
                       mol_type = protein
                       organism = synthetic construct
SEQUENCE: 278
DIQLTQSPSF LSASVGDRVT ITCRASSSVG YMHWYQQKPG KAPKLLIYAT SNLAQGVPSR  60
FSGSGSGTGF TLTISSLQPE DFATYYCQQW GSLPFTFGQG TKLEIK                106

SEQ ID NO: 279         moltype = AA  length = 106
FEATURE                Location/Qualifiers
REGION                 1..106
                       note = MTK-29.10, 29.11 Light Chain Variable
source                 1..106
                       mol_type = protein
                       organism = synthetic construct
SEQUENCE: 279
EIVLTQSPAT LSLSPGERAT LSCRASSSVG YMHWYQQKPG QAPRLLIYAT SNLASGIPAR  60
FSGSGSGTDF TLTISRLEPE DFAVYYCQQW GSLPFTFGGG TKLEIK                106

SEQ ID NO: 280         moltype = AA  length = 106
FEATURE                Location/Qualifiers
REGION                 1..106
                       note = MTK-29.12 Light Chain Variable
source                 1..106
                       mol_type = protein
                       organism = synthetic construct
SEQUENCE: 280
DIQLTQSPGF LSASVGDRVT ITCRASSSVG YMHWYQQKPG KAPKLLIYAT SNLAQGVPSR  60
FSGSGSGTEF TLTISSLQPE DFATYYCQQW GSLPFTFGQG TKLEIK                106

SEQ ID NO: 281         moltype = AA  length = 106
FEATURE                Location/Qualifiers
REGION                 1..106
                       note = MTK-29.13 Light Chain Variable
source                 1..106
                       mol_type = protein
                       organism = synthetic construct
```

```
SEQUENCE: 281
DIQLTQSPSF LSASVGDRVT ITCRASSSVG YMHWYQQEPG KAPKLLIYAT SNLAQGVPSR  60
FSGSGSGTEF TLTISSLQPE DFATYYCQQW GSLPFTFGQG TKLEIK                106

SEQ ID NO: 282         moltype = AA  length = 106
FEATURE                Location/Qualifiers
REGION                 1..106
                       note = MTK-29.14 Light Chain Variable
source                 1..106
                       mol_type = protein
                       organism = synthetic construct
SEQUENCE: 282
DIQLTQSPSF LSASVGDRVT ITCRASSSVG YMHWYQQKPG KAPKLLIYAT SNLAQGVPSR  60
FSGSGSGTEF TLTIFSLQPE DFATYYCQQW GSLPFTFGQG TKLEIK                106

SEQ ID NO: 283         moltype = AA  length = 106
FEATURE                Location/Qualifiers
REGION                 1..106
                       note = MTK-29.15 Light Chain Variable
source                 1..106
                       mol_type = protein
                       organism = synthetic construct
SEQUENCE: 283
DIQLTQSPSF PSASVGDRVT ITCRASSSVG YMHWYQQKPG KAPKLLIYAT SNLAQGVPSR  60
FSGSGSGTEF TLTISSLQPE DFATYYCQQW GSLPFTFGQG TKLEIK                106

SEQ ID NO: 284         moltype = AA  length = 106
FEATURE                Location/Qualifiers
REGION                 1..106
                       note = MTK-29.16 Light Chain Variable
source                 1..106
                       mol_type = protein
                       organism = synthetic construct
SEQUENCE: 284
DIQLTQSPSF LSASVGDRVT ITCRASSSVG YMHWYQQKPG KAPKLLIYAT SNLAQGVPSR  60
FSGSGSGTEF TLTISSLQPE DFATYYCQQW GRLPFTFGQG TKLEIK                106

SEQ ID NO: 285         moltype = AA  length = 106
FEATURE                Location/Qualifiers
REGION                 1..106
                       note = MTK-29.17 Light Chain Variable
source                 1..106
                       mol_type = protein
                       organism = synthetic construct
SEQUENCE: 285
DIQLTQSPSF LSASVGDRVT ITCRSSSSVG YMHWYQQKPG KAPKLLIYAT SNLAQGVPSR  60
FSGSGSGTEF TLTISSLQPE DFATYYCQQW GSLPFTFGQG TKLEIK                106

SEQ ID NO: 286         moltype = AA  length = 106
FEATURE                Location/Qualifiers
REGION                 1..106
                       note = MTK-29.18 Light Chain Variable
source                 1..106
                       mol_type = protein
                       organism = synthetic construct
SEQUENCE: 286
EIVLTQSPAT LSLSPGERAT LSCRASSTVG YMHWYQQKPG QAPRLLIYAT SNLASGIPAR  60
FSGSGSGTDF TLTISRLEPE DFAVYYCQQW GSLPFTFGGG TKLEIK                106

SEQ ID NO: 287         moltype = AA  length = 106
FEATURE                Location/Qualifiers
REGION                 1..106
                       note = MTK-29.19 Light Chain Variable
source                 1..106
                       mol_type = protein
                       organism = synthetic construct
SEQUENCE: 287
QIVLTQSPGT LSLSPGERAT LSCRATSSVG YMHWYQQKPG QAPRPLIYAT SNLASGIPDR  60
FSGSGSGTSY TLTISRLEPE DFAVYYCQQW GSNPFTFGQG TKLEIK                106

SEQ ID NO: 288         moltype = AA  length = 106
FEATURE                Location/Qualifiers
REGION                 1..106
                       note = MTK-29.20 Light Chain Variable
source                 1..106
                       mol_type = protein
                       organism = synthetic construct
```

```
SEQUENCE: 288
QIVLTQSPAT LSLSPGERAT LSCRATSSVG YMHWYQQKPG LAPRPLIYAT SNLASGIPDR  60
FSGSGSGTSY TLTISRLEPE DFAVYYCQQW GSNPFTFGQG TKLEIK                106

SEQ ID NO: 289         moltype = AA  length = 106
FEATURE                Location/Qualifiers
REGION                 1..106
                       note = MTK-29.21 Light Chain Variable
source                 1..106
                       mol_type = protein
                       organism = synthetic construct
SEQUENCE: 289
QIVLTQSPAT LSLSPGERAT LSCRATSSVG YMHWYQQKPG QAPRPLIYAT SNLASGIPAR  60
FSGSGSGTSY TLTISSLEPE DFAVYYCQQW GSNPFTFGQG TKLEIK                106

SEQ ID NO: 290         moltype = AA  length = 119
FEATURE                Location/Qualifiers
REGION                 1..119
                       note = MTK-33.1, 33.8 Heavy Chain Variable
source                 1..119
                       mol_type = protein
                       organism = synthetic construct
SEQUENCE: 290
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSS   119

SEQ ID NO: 291         moltype = AA  length = 119
FEATURE                Location/Qualifiers
REGION                 1..119
                       note = MTK-33.2 Heavy Chain Variable
source                 1..119
                       mol_type = protein
                       organism = synthetic construct
SEQUENCE: 291
QVQLVQSGAE VKKPGASVKV SCKASGYTST SYWMHWVRQA PGQGLEWIGV IDPSDNYINY  60
NQKFQGRVTM TRDTSTSTVY MELSSLRSED TAVYYCAREA GTRGYFDYWG QGTLVTVSS   119

SEQ ID NO: 292         moltype = AA  length = 119
FEATURE                Location/Qualifiers
REGION                 1..119
                       note = MTK-33.3, 33.11 Heavy Chain Variable
source                 1..119
                       mol_type = protein
                       organism = synthetic construct
SEQUENCE: 292
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFDYWG QGTLVTVSS   119

SEQ ID NO: 293         moltype = AA  length = 119
FEATURE                Location/Qualifiers
REGION                 1..119
                       note = MTK-33.4 Heavy Chain Variable
source                 1..119
                       mol_type = protein
                       organism = synthetic construct
SEQUENCE: 293
QVQLVQSGAE VKKPGASVKV SCKASGYTFT SYWMHWVRQA PGQGLEWIGV IDPSDNYINM  60
NQKFQGRVTM TRDTSTSTVY MELSSLRSED TAVYYCAREA GTRGYFDYWG QGTLVTVSS   119

SEQ ID NO: 294         moltype = AA  length = 119
FEATURE                Location/Qualifiers
REGION                 1..119
                       note = MTK-33.5 Heavy Chain Variable
source                 1..119
                       mol_type = protein
                       organism = synthetic construct
SEQUENCE: 294
QVQLVQSGAE VKKPGASVKV SCMASGYTFG SYWMHWVRQA PGQGLEWIGV IDPSDNYINY  60
NQKFQGRVTM TRDTSTSTVY MELSSLRSED TAVYYCAREA GTRGYFDYWG QGTLVTVSS   119

SEQ ID NO: 295         moltype = AA  length = 119
FEATURE                Location/Qualifiers
REGION                 1..119
                       note = MTK-33.6 Heavy Chain Variable
source                 1..119
                       mol_type = protein
                       organism = synthetic construct
```

```
SEQUENCE: 295
QVQLVQSGAE VKKPGASVKV SCMASGYTFR SYWMHWVRQA PGQGLEWIGV IDPSDNYINY  60
NQKFQGRVTM TRDTSTSTVY MELSSLRSED TAVYYCAREA GTRGYFDYWG QGTLVTVSS   119

SEQ ID NO: 296         moltype = AA  length = 119
FEATURE                Location/Qualifiers
REGION                 1..119
                       note = MTK-33.7 Heavy Chain Variable
source                 1..119
                       mol_type = protein
                       organism = synthetic construct
SEQUENCE: 296
QVQLVQSGAE VKKPGASVKV SCKASGYTFT SYWMHWVRQA PGQGLEWIGV IDPSDNYINY  60
NAKFQGRVTM TRDTSTSTVY MELSSLRSED TAVYYCAREA GTRGYFDYWG QGTLVTVSS   119

SEQ ID NO: 297         moltype = AA  length = 119
FEATURE                Location/Qualifiers
REGION                 1..119
                       note = MTK-33.9 Heavy Chain Variable
source                 1..119
                       mol_type = protein
                       organism = synthetic construct
SEQUENCE: 297
QVQLVQSGAE VKKPGASVKV SCKASGYTFT SYWMHWVRQA PGQGLEWIGV IDPSDRYINY  60
NQKFQGRVTM TRDTSTSTVY MELSSLRSED TAVYYCAREA GTRGYFDYWG QGTLVTVSS   119

SEQ ID NO: 298         moltype = AA  length = 119
FEATURE                Location/Qualifiers
REGION                 1..119
                       note = MTK-33.10 Heavy Chain Variable
source                 1..119
                       mol_type = protein
                       organism = synthetic construct
SEQUENCE: 298
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSS   119

SEQ ID NO: 299         moltype = AA  length = 119
FEATURE                Location/Qualifiers
REGION                 1..119
                       note = MTK-33.12 Heavy Chain Variable
source                 1..119
                       mol_type = protein
                       organism = synthetic construct
SEQUENCE: 299
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSS   119

SEQ ID NO: 300         moltype = AA  length = 119
FEATURE                Location/Qualifiers
REGION                 1..119
                       note = MTK-33.13 Heavy Chain Variable
source                 1..119
                       mol_type = protein
                       organism = synthetic construct
SEQUENCE: 300
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA GTRGYFDYWG QGTLVTVSS   119

SEQ ID NO: 301         moltype = AA  length = 119
FEATURE                Location/Qualifiers
REGION                 1..119
                       note = MTK-33.14, 33.19, 33.20, 33.21 Heavy Chain Variable
source                 1..119
                       mol_type = protein
                       organism = synthetic construct
SEQUENCE: 301
QVQLVQSGAE VKKPGASVKV SCKASGYTFT SYWMHWVRQA PGQGLEWIGV IDPSDNYINY  60
NQKFRGRVTM TRDTSTSTVY MELSSLRSED TAVYYCAREA GTRGYFDYWG QGTLVTVSS   119

SEQ ID NO: 302         moltype = AA  length = 119
FEATURE                Location/Qualifiers
REGION                 1..119
                       note = MTK-33.15 Heavy Chain Variable
source                 1..119
                       mol_type = protein
                       organism = synthetic construct
```

```
SEQUENCE: 302
QVQLVQSGAE VKKPGASVKV SCKASGYTFT SYWMHWVRQA PGQGLEWIGV IDPSDNYINY  60
NQKFQVRVTM TRDTSTSTVY MELSSLRSED TAVYYCAREA GTRGYFDYWG QGTLVTVSS   119

SEQ ID NO: 303         moltype = AA  length = 119
FEATURE                Location/Qualifiers
REGION                 1..119
                       note = MTK-33.16 Heavy Chain Variable
source                 1..119
                       mol_type = protein
                       organism = synthetic construct
SEQUENCE: 303
QVQLVQSGAE VKKPGASVKV SCKASWYTFT SYWMHWVRQA PGQGLEWIGV IDPSDNYINY  60
NQKFQGRVTM TRDTSTSTVY MELSSLRSED TAVYYCAREA GTRGYFDYWG QGTLVTVSS   119

SEQ ID NO: 304         moltype = AA  length = 119
FEATURE                Location/Qualifiers
REGION                 1..119
                       note = MTK-33.17 Heavy Chain Variable
source                 1..119
                       mol_type = protein
                       organism = synthetic construct
SEQUENCE: 304
QVQLVQSGAE VKKPGASVKV SCKASGYTFT SYWMHWVRQA PGQGLEWIGV IAPSDNYINY  60
NQKFRGRVTM TRDTSTSTVY MELSSLRSED TAVYYCAREA GTRGYFDYWG QGTLVTVSS   119

SEQ ID NO: 305         moltype = AA  length = 119
FEATURE                Location/Qualifiers
REGION                 1..119
                       note = MTK-33.18 Heavy Chain Variable
source                 1..119
                       mol_type = protein
                       organism = synthetic construct
SEQUENCE: 305
QVQLVQSGAE VKKPGASVKV SCKASGYTFT SYWMHWVRQA PGQGLEWIGV ISPSDNYINY  60
NQKFRGRVTM TRDTSTSTVY MELSSLRSED TAVYYCAREA GTRGYFDYWG QGTLVTVSS   119

SEQ ID NO: 306         moltype = AA  length = 119
FEATURE                Location/Qualifiers
REGION                 1..119
                       note = MTK-33.22 Heavy Chain Variable
source                 1..119
                       mol_type = protein
                       organism = synthetic construct
SEQUENCE: 306
QVQLVQSGAE VKKPGASVKV SCKASGYTFT SYWMHWVRQA PGQGLEWIGV IDPSDNYINY  60
NQKLRGRVTM TRDTSTSTVY MELSSLRSED TAVYYCAREA GTRGYFDYWG QGTLVTVSS   119

SEQ ID NO: 307         moltype = AA  length = 119
FEATURE                Location/Qualifiers
REGION                 1..119
                       note = MTK-33.23 Heavy Chain Variable
source                 1..119
                       mol_type = protein
                       organism = synthetic construct
SEQUENCE: 307
QVQLVQSGAE VKKPGASVKV SCKASGYTFT SYWMHWVRQA PGQGLEWIGV IDPSDNYINY  60
NQKFRGRVTM TRDTSTSTVY MELSSLRSED TAVYYCAREA YTRGYFDYWG QGTLVTVSS   119

SEQ ID NO: 308         moltype = AA  length = 119
FEATURE                Location/Qualifiers
REGION                 1..119
                       note = MTK-33.24 Heavy Chain Variable
source                 1..119
                       mol_type = protein
                       organism = synthetic construct
SEQUENCE: 308
QVQLVQSGAE VKKPGASVKV SCKASSYTFT SYWMHWVRQA PGQGLEWIGV IDPSDNYINY  60
NQKFRGRVTM TRDTSTSTVY MELSSLRSED TAVYYCAREA GTRGYFDYWG QGTLVTVSS   119

SEQ ID NO: 309         moltype = AA  length = 107
FEATURE                Location/Qualifiers
REGION                 1..107
                       note = MTK-33.1 Light Chain Variable
source                 1..107
                       mol_type = protein
                       organism = synthetic construct
```

```
SEQUENCE: 309
DIQMTQSPSS LSASVGDRVT ITCQASQSVS NTVAWYQQKP GKAPKLLIYY ASLRYTGVPS  60
RFSGSGSGTD FTFTISSLQP EDIATYYCQQ DYRSPFTFGQ GTKLEIK               107

SEQ ID NO: 310         moltype = AA  length = 107
FEATURE                Location/Qualifiers
REGION                 1..107
                       note = MTK-33.2 Light Chain Variable
source                 1..107
                       mol_type = protein
                       organism = synthetic construct
SEQUENCE: 310
DIQMTQSPSS LSASVGDRVT ITCQASGSVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 311         moltype = AA  length = 107
FEATURE                Location/Qualifiers
REGION                 1..107
                       note = MTK-33.3, 33.13, 33.16 Light Chain Variable
source                 1..107
                       mol_type = protein
                       organism = synthetic construct
SEQUENCE: 311
DIQMTQSPSS LSASVGDRVT ITCQASRSVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 312         moltype = AA  length = 107
FEATURE                Location/Qualifiers
REGION                 1..107
                       note = MTK-33.4 Light Chain Variable
source                 1..107
                       mol_type = protein
                       organism = synthetic construct
SEQUENCE: 312
DIQMTQSPSS LSASVGDRVT ITCQASQSVS NTVAWYQQKP GKAPKLLIYY ASNRYTGVPS  60
RFSGSGSGTD FTFTISSLQP EDIATYYCQQ DRRSPFTFGQ GTKLEIK               107

SEQ ID NO: 313         moltype = AA  length = 107
FEATURE                Location/Qualifiers
REGION                 1..107
                       note = MTK-33.5 Light Chain Variable
source                 1..107
                       mol_type = protein
                       organism = synthetic construct
SEQUENCE: 313
DIQMTQSPSS LSASVGDRVT ITCQASQSVS NTVAWYQQKP GKAPKLLIYY ASNRETGVPS  60
RFSGSGSGTD FTFTISSLQP EDIGTYYCQQ DYRSPFTFGQ GTKLEIK               107

SEQ ID NO: 314         moltype = AA  length = 107
FEATURE                Location/Qualifiers
REGION                 1..107
                       note = MTK-33.6 Light Chain Variable
source                 1..107
                       mol_type = protein
                       organism = synthetic construct
SEQUENCE: 314
DIQMTQSPSS LSASVGDRVT ITCQASRSVS NTMAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 315         moltype = AA  length = 107
FEATURE                Location/Qualifiers
REGION                 1..107
                       note = MTK-33.7 Light Chain Variable
source                 1..107
                       mol_type = protein
                       organism = synthetic construct
SEQUENCE: 315
DIQMTQSPSS LSASVGDRVT ITCGASQSVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 316         moltype = AA  length = 107
FEATURE                Location/Qualifiers
REGION                 1..107
                       note = MTK-33.8 Light Chain Variable
source                 1..107
                       mol_type = protein
                       organism = synthetic construct
```

```
SEQUENCE: 316
DIQMTQSPSS LSASVGDRVT ITCQASQSVS RTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 317          moltype = AA  length = 107
FEATURE                 Location/Qualifiers
REGION                  1..107
                        note = MTK-33.9 Light Chain Variable
source                  1..107
                        mol_type = protein
                        organism = synthetic construct
SEQUENCE: 317
DIQMTQSPSS LSASVGDRVT ITCQASASVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 318          moltype = AA  length = 107
FEATURE                 Location/Qualifiers
REGION                  1..107
                        note = MTK-33.10 Light Chain Variable
source                  1..107
                        mol_type = protein
                        organism = synthetic construct
SEQUENCE: 318
DIQMTQSPSS LSASVGDRVT ITCQAGQSVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 319          moltype = AA  length = 107
FEATURE                 Location/Qualifiers
REGION                  1..107
                        note = MTK-33.11 Light Chain Variable
source                  1..107
                        mol_type = protein
                        organism = synthetic construct
SEQUENCE: 319
DIQMTQSPSS LSASVGDRVT ITCQASRSVR NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 320          moltype = AA  length = 107
FEATURE                 Location/Qualifiers
REGION                  1..107
                        note = MTK-33.12 Light Chain Variable
source                  1..107
                        mol_type = protein
                        organism = synthetic construct
SEQUENCE: 320
DIQMTQSPSS LSASVGDRVT ITCQASQSVS NTVAWYQQKP GKAPKLLIYY ASNRYTGVPS  60
RFSGSGSGTD FTFTISSLQP EDIATYYCRQ DTRSPFTFGQ GTKLELK               107

SEQ ID NO: 321          moltype = AA  length = 107
FEATURE                 Location/Qualifiers
REGION                  1..107
                        note = MTK-33.14 Light Chain Variable
source                  1..107
                        mol_type = protein
                        organism = synthetic construct
SEQUENCE: 321
DIQMTQSPSS LSASVGDRVT ITCQASQSVS NTVAWYQQKP GKAPKLLIYY ASNRYTGVPS  60
RFSGSGSGTD FTFTISSLQP EDIATYYCQQ DYRSPFTFGQ GTKLEIK               107

SEQ ID NO: 322          moltype = AA  length = 107
FEATURE                 Location/Qualifiers
REGION                  1..107
                        note = MTK-33.15, 33.17, 33.18 Light Chain Variable
source                  1..107
                        mol_type = protein
                        organism = synthetic construct
SEQUENCE: 322
DIQMTQSPSS LSASVGDRVT ITCQASRSVS NTVAWYQQKP GKAPKLLIYY ASNRYTGVPS  60
RFSGSGSGTD FTFTISSLQP EDIATYYCQQ DMRSPFTFGQ GTKLEIK               107

SEQ ID NO: 323          moltype = AA  length = 107
FEATURE                 Location/Qualifiers
REGION                  1..107
                        note = MTK-33.19 Light Chain Variable
source                  1..107
                        mol_type = protein
                        organism = synthetic construct
```

```
SEQUENCE: 323
DIQMTQSPSS LSASVGDRVT ITCQASRSVS ATVAWYQQKP GKAPKLLIYY ASNRYTGVPS  60
RFSGSGSGTD FTFTISSLQP EDIATYYCQQ DMRSPFTFGQ GTKLEIK               107

SEQ ID NO: 324          moltype = AA  length = 107
FEATURE                 Location/Qualifiers
REGION                  1..107
                        note = MTK-33.20 Light Chain Variable
source                  1..107
                        mol_type = protein
                        organism = synthetic construct
SEQUENCE: 324
DIQMTQSPSS LSASVGDRVT ITCQASRSVS NTVAWYQQKP GKAPKLLIYY ASNRYTGVPS  60
RFSGSGSGTD FTFTISSLQP EDIATYYCAQ DMRSPFTFGQ GTKLEIK               107

SEQ ID NO: 325          moltype = AA  length = 107
FEATURE                 Location/Qualifiers
REGION                  1..107
                        note = MTK-33.21 Light Chain Variable
source                  1..107
                        mol_type = protein
                        organism = synthetic construct
SEQUENCE: 325
DIQMTQSPSS LSASVGGRVT ITCQASRSVS NTVAWYQQKP GKAPKLLIYY VSNRYTGVPS  60
RFSGSGSGTD FTFTISSLQP EDIATYYCQQ DMRSPFTFGQ GTKLEIK               107

SEQ ID NO: 326          moltype = AA  length = 107
FEATURE                 Location/Qualifiers
REGION                  1..107
                        note = MTK-33.22 Light Chain Variable
source                  1..107
                        mol_type = protein
                        organism = synthetic construct
SEQUENCE: 326
DIQMTQSPSS LSASVGDRVT ITCQASRSVS NTVAWYQQKP GKAPKLLIYY ASNRRTGVPS  60
RFSGSGSGTD FTFTISSLQP EDIATYYCQQ DMRSPFTFGQ GTKLEIK               107

SEQ ID NO: 327          moltype = AA  length = 107
FEATURE                 Location/Qualifiers
REGION                  1..107
                        note = MTK-33.23 Light Chain Variable
source                  1..107
                        mol_type = protein
                        organism = synthetic construct
SEQUENCE: 327
DIQMTQSPSS LSASVGDRVT ITCIASRSVS NTVAWYQQKP GKAPKLLIYY ASNRYTGVPS  60
RFSGSGSGTD FTFTISSLQP EDIATYYCQQ DMRSPFTFGQ GTKLEIK               107

SEQ ID NO: 328          moltype = AA  length = 107
FEATURE                 Location/Qualifiers
REGION                  1..107
                        note = MTK-33.24 Light Chain Variable
source                  1..107
                        mol_type = protein
                        organism = synthetic construct
SEQUENCE: 328
DIQMTQSPSS LSASVGDRVT ITCQASRSVS RTVAWYQQKP GKAPKLLIYY ASNRYTGVPS  60
RFSGSGSGTD FTFTISSLQP EDIATYYCQQ DMRSPFTFGQ GTKLEIK               107

SEQ ID NO: 329          moltype = AA  length = 17
FEATURE                 Location/Qualifiers
REGION                  1..17
                        note = MTK-15.1, 15.3, 15.4, 15.5, 15.7, 15.8, 15.9, 15.13,
                         15.14, 15.15, 16.1 HVR-H2
source                  1..17
                        mol_type = protein
                        organism = synthetic construct
SEQUENCE: 329
WINTYTGEPT YAQGFTG                                                17

SEQ ID NO: 330          moltype = AA  length = 17
FEATURE                 Location/Qualifiers
REGION                  1..17
                        note = MTK-15.2 HVR-H2
source                  1..17
                        mol_type = protein
                        organism = synthetic construct
```

```
SEQUENCE: 330
WGNTYTGEPT YAQGFTG                                              17

SEQ ID NO: 331          moltype = AA  length = 17
FEATURE                 Location/Qualifiers
REGION                  1..17
                        note = MTK-15.6 HVR-H2
source                  1..17
                        mol_type = protein
                        organism = synthetic construct
SEQUENCE: 331
WINTYTGEPY YAQGFTG                                              17

SEQ ID NO: 332          moltype = AA  length = 17
FEATURE                 Location/Qualifiers
REGION                  1..17
                        note = MTK-15.10, 15.12 HVR-H2
source                  1..17
                        mol_type = protein
                        organism = synthetic construct
SEQUENCE: 332
WINTYQGEPT YAQGFTG                                              17

SEQ ID NO: 333          moltype = AA  length = 17
FEATURE                 Location/Qualifiers
REGION                  1..17
                        note = MTK-15.11 HVR-H2
source                  1..17
                        mol_type = protein
                        organism = synthetic construct
SEQUENCE: 333
WINTYEGEPT YAQGFTG                                              17

SEQ ID NO: 334          moltype = AA  length = 9
FEATURE                 Location/Qualifiers
REGION                  1..9
                        note = MTK-15.1, 15.11 HVR-H3
source                  1..9
                        mol_type = protein
                        organism = synthetic construct
SEQUENCE: 334
GNRYAYQDY                                                       9

SEQ ID NO: 335          moltype = AA  length = 9
FEATURE                 Location/Qualifiers
REGION                  1..9
                        note = MTK-15.5 HVR-H3
source                  1..9
                        mol_type = protein
                        organism = synthetic construct
SEQUENCE: 335
GTRYAYMDY                                                       9

SEQ ID NO: 336          moltype = AA  length = 9
FEATURE                 Location/Qualifiers
REGION                  1..9
                        note = MTK-15.8, 15.12 HVR-H3
source                  1..9
                        mol_type = protein
                        organism = synthetic construct
SEQUENCE: 336
GVRYAYMDY                                                       9

SEQ ID NO: 337          moltype = AA  length = 9
FEATURE                 Location/Qualifiers
REGION                  1..9
                        note = MTK-15.9 HVR-H3
source                  1..9
                        mol_type = protein
                        organism = synthetic construct
SEQUENCE: 337
GYRYAYMDY                                                       9

SEQ ID NO: 338          moltype = AA  length = 9
FEATURE                 Location/Qualifiers
```

```
REGION                1..9
                      note = MTK-15.10 HVR-H3
source                1..9
                      mol_type = protein
                      organism = synthetic construct
SEQUENCE: 338
GARYAYMDY                                                   9

SEQ ID NO: 339        moltype = AA  length = 9
FEATURE               Location/Qualifiers
REGION                1..9
                      note = MTK-15.13 HVR-H3
source                1..9
                      mol_type = protein
                      organism = synthetic construct
SEQUENCE: 339
GNRYAYEDY                                                   9

SEQ ID NO: 340        moltype = AA  length = 10
FEATURE               Location/Qualifiers
REGION                1..10
                      note = MTK-15.3 HVR-L1
source                1..10
                      mol_type = protein
                      organism = synthetic construct
SEQUENCE: 340
RASSHVSYMH                                                  10

SEQ ID NO: 341        moltype = AA  length = 10
FEATURE               Location/Qualifiers
REGION                1..10
                      note = MTK-15.4, 15.5, 15.6, 15.8, 15.10, 15.12, 29.1,
                       29.2, 29.3, 29.4, 29.5, 29.6, 29.7, 29.8, 29.9, 29.10,
                       29.11, 29.12, 29.13, 29.14, 29.15, 29.16 HVR-L1
source                1..10
                      mol_type = protein
                      organism = synthetic construct
SEQUENCE: 341
RASSSVGYMH                                                  10

SEQ ID NO: 342        moltype = AA  length = 10
FEATURE               Location/Qualifiers
REGION                1..10
                      note = MTK-15.7 HVR-L1
source                1..10
                      mol_type = protein
                      organism = synthetic construct
SEQUENCE: 342
RASSGVSYMH                                                  10

SEQ ID NO: 343        moltype = AA  length = 10
FEATURE               Location/Qualifiers
REGION                1..10
                      note = MTK-15.9 HVR-L1
source                1..10
                      mol_type = protein
                      organism = synthetic construct
SEQUENCE: 343
RASSSTSYMH                                                  10

SEQ ID NO: 344        moltype = AA  length = 10
FEATURE               Location/Qualifiers
REGION                1..10
                      note = MTK-15.13 HVR-L1
source                1..10
                      mol_type = protein
                      organism = synthetic construct
SEQUENCE: 344
RASSSVQYMH                                                  10

SEQ ID NO: 345        moltype = AA  length = 11
FEATURE               Location/Qualifiers
REGION                1..11
                      note = MTK-16.2 HVR-L1
source                1..11
                      mol_type = protein
                      organism = synthetic construct
SEQUENCE: 345
RASQNVRTAV A                                                11
```

```
SEQ ID NO: 346          moltype = AA  length = 5
FEATURE                 Location/Qualifiers
REGION                  1..5
                        note = MTK-29.1, 29.5, 29.9, 29.16, 29.17, 29.18 HVR-H1
source                  1..5
                        mol_type = protein
                        organism = synthetic construct
SEQUENCE: 346
SYGLS                                                                       5

SEQ ID NO: 347          moltype = AA  length = 5
FEATURE                 Location/Qualifiers
REGION                  1..5
                        note = MTK-29.8 HVR-H1
source                  1..5
                        mol_type = protein
                        organism = synthetic construct
SEQUENCE: 347
TYGLS                                                                       5

SEQ ID NO: 348          moltype = AA  length = 17
FEATURE                 Location/Qualifiers
REGION                  1..17
                        note = MTK-29.1, 29.17, 29.19, 29.20, 29.21 HVR-H2
source                  1..17
                        mol_type = protein
                        organism = synthetic construct
SEQUENCE: 348
WINTYSGVPT YAQGFTG                                                          17

SEQ ID NO: 349          moltype = AA  length = 17
FEATURE                 Location/Qualifiers
REGION                  1..17
                        note = MTK-29.3 HVR-H2
source                  1..17
                        mol_type = protein
                        organism = synthetic construct
SEQUENCE: 349
WINTYSGVPA YTDDFKG                                                          17

SEQ ID NO: 350          moltype = AA  length = 17
FEATURE                 Location/Qualifiers
REGION                  1..17
                        note = MTK-29.6, 29.12, 29.15 HVR-H2
source                  1..17
                        mol_type = protein
                        organism = synthetic construct
SEQUENCE: 350
WINTMSGVPT YTDDFKG                                                          17

SEQ ID NO: 351          moltype = AA  length = 17
FEATURE                 Location/Qualifiers
REGION                  1..17
                        note = MTK-29.7, 29.14 HVR-H2
source                  1..17
                        mol_type = protein
                        organism = synthetic construct
SEQUENCE: 351
WINTYSGVPS YTDDFKA                                                          17

SEQ ID NO: 352          moltype = AA  length = 17
FEATURE                 Location/Qualifiers
REGION                  1..17
                        note = MTK-29.11 HVR-H2
source                  1..17
                        mol_type = protein
                        organism = synthetic construct
SEQUENCE: 352
WINTDSGVPT YTDDFKG                                                          17

SEQ ID NO: 353          moltype = AA  length = 17
FEATURE                 Location/Qualifiers
REGION                  1..17
                        note = MTK-29.13 HVR-H2
source                  1..17
                        mol_type = protein
                        organism = synthetic construct
```

```
SEQUENCE: 353
WINTASGVPT YTDDFKG                                              17

SEQ ID NO: 354          moltype = AA  length = 17
FEATURE                 Location/Qualifiers
REGION                  1..17
                        note = MTK-29.16, 29.18 HVR-H2
source                  1..17
                        mol_type = protein
                        organism = synthetic construct
SEQUENCE: 354
WVNTYSGVPT YTDDFKG                                              17

SEQ ID NO: 355          moltype = AA  length = 17
FEATURE                 Location/Qualifiers
REGION                  1..17
                        note = MTK-29.1, 29.2 HVR-H3
source                  1..17
                        mol_type = protein
                        organism = synthetic construct
SEQUENCE: 355
WINTYSGVPT YAQGFTG                                              17

SEQ ID NO: 356          moltype = AA  length = 9
FEATURE                 Location/Qualifiers
REGION                  1..9
                        note = MTK-29.3, 29.4, 29.5, 29.6, 29.7, 29.8, 29.9, 29.10,
                         29.11, 29.12, 29.13, 29.14, 29.15, 29.16, 29.17, 29.18
                         HVR-H3
source                  1..9
                        mol_type = protein
                        organism = synthetic construct
SEQUENCE: 356
YTNYGVFDY                                                       9

SEQ ID NO: 357          moltype = AA  length = 10
FEATURE                 Location/Qualifiers
REGION                  1..10
                        note = MTK-29.17 HVR-L1
source                  1..10
                        mol_type = protein
                        organism = synthetic construct
SEQUENCE: 357
RSSSSVGYMH                                                      10

SEQ ID NO: 358          moltype = AA  length = 10
FEATURE                 Location/Qualifiers
REGION                  1..10
                        note = MTK-29.18 HVR-L1
source                  1..10
                        mol_type = protein
                        organism = synthetic construct
SEQUENCE: 358
RASSTVGYMH                                                      10

SEQ ID NO: 359          moltype = AA  length = 7
FEATURE                 Location/Qualifiers
REGION                  1..7
                        note = MTK-29.4, 29.5, 29.6, 29.7, 29.8, 29.9, 29.12,
                         29.13, 29.14, 29.15, 29.16, 29.17 HVR-L2
source                  1..7
                        mol_type = protein
                        organism = synthetic construct
SEQUENCE: 359
ATSNLAQ                                                         7

SEQ ID NO: 360          moltype = AA  length = 9
FEATURE                 Location/Qualifiers
REGION                  1..9
                        note = MTK-29.1 HVR-L3
source                  1..9
                        mol_type = protein
                        organism = synthetic construct
SEQUENCE: 360
QQWGSWPFT                                                       9

SEQ ID NO: 361          moltype = AA  length = 9
FEATURE                 Location/Qualifiers
```

```
REGION                  1..9
                        note = MTK-29.2 HVR-L3
source                  1..9
                        mol_type = protein
                        organism = synthetic construct
SEQUENCE: 361
QQWGSIPFT                                                                  9

SEQ ID NO: 362          moltype = AA  length = 9
FEATURE                 Location/Qualifiers
REGION                  1..9
                        note = MTK-29.3, 29.4, 29.5, 29.6, 29.7, 29.8, 29.9, 29.10,
                         29.11, 29.12, 29.13, 29.14, 29.15, 29.17, 29.18 HVR-L3
source                  1..9
                        mol_type = protein
                        organism = synthetic construct
SEQUENCE: 362
QQWGSLPFT                                                                  9

SEQ ID NO: 363          moltype = AA  length = 9
FEATURE                 Location/Qualifiers
REGION                  1..9
                        note = MTK-29.16 HVR-L3
source                  1..9
                        mol_type = protein
                        organism = synthetic construct
SEQUENCE: 363
QQWGRLPFT                                                                  9

SEQ ID NO: 364          moltype = AA  length = 17
FEATURE                 Location/Qualifiers
REGION                  1..17
                        note = MTK-33.1, 33.2, 33.3, 33.5, 33.6, 33.8, 33.11,
                         33.13, 33.16 HVR-H2
source                  1..17
                        mol_type = protein
                        organism = synthetic construct
SEQUENCE: 364
VIDPSDNYIN YNQKFQG                                                         17

SEQ ID NO: 365          moltype = AA  length = 17
FEATURE                 Location/Qualifiers
REGION                  1..17
                        note = MTK-33.4 HVR-H2
source                  1..17
                        mol_type = protein
                        organism = synthetic construct
SEQUENCE: 365
VIDPSDNYIN MNQKFQG                                                         17

SEQ ID NO: 366          moltype = AA  length = 17
FEATURE                 Location/Qualifiers
REGION                  1..17
                        note = MTK-33.7 HVR-H2
source                  1..17
                        mol_type = protein
                        organism = synthetic construct
SEQUENCE: 366
VIDPSDNYIN YNAKFQG                                                         17

SEQ ID NO: 367          moltype = AA  length = 17
FEATURE                 Location/Qualifiers
REGION                  1..17
                        note = MTK-33.9 HVR-H2
source                  1..17
                        mol_type = protein
                        organism = synthetic construct
SEQUENCE: 367
VIDPSDRYIN YNQKFQG                                                         17

SEQ ID NO: 368          moltype = AA  length = 17
FEATURE                 Location/Qualifiers
REGION                  1..17
                        note = MTK-33.10, 33.12, 33.14, 33.19, 33.20, 33.21, 33.23,
                         33.24 HVR-H2
source                  1..17
                        mol_type = protein
                        organism = synthetic construct
```

```
SEQUENCE: 368
VIDPSDNYIN YNQKFRG                                                17

SEQ ID NO: 369          moltype = AA  length = 17
FEATURE                 Location/Qualifiers
REGION                  1..17
                        note = MTK-33.15 HVR-H2
source                  1..17
                        mol_type = protein
                        organism = synthetic construct
SEQUENCE: 369
VIDPSDNYIN YNQKFQV                                                17

SEQ ID NO: 370          moltype = AA  length = 17
FEATURE                 Location/Qualifiers
REGION                  1..17
                        note = MTK-33.17 HVR-H2
source                  1..17
                        mol_type = protein
                        organism = synthetic construct
SEQUENCE: 370
VIAPSDNYIN YNQKFRG                                                17

SEQ ID NO: 371          moltype = AA  length = 17
FEATURE                 Location/Qualifiers
REGION                  1..17
                        note = MTK-33.18 HVR-H2
source                  1..17
                        mol_type = protein
                        organism = synthetic construct
SEQUENCE: 371
VISPSDNYIN YNQKFRG                                                17

SEQ ID NO: 372          moltype = AA  length = 17
FEATURE                 Location/Qualifiers
REGION                  1..17
                        note = MTK-33.22 HVR-H2
source                  1..17
                        mol_type = protein
                        organism = synthetic construct
SEQUENCE: 372
VIDPSDNYIN YNQKLRG                                                17

SEQ ID NO: 373          moltype = AA  length = 10
FEATURE                 Location/Qualifiers
REGION                  1..10
                        note = MTK-33.1, 33.8 HVR-H3
source                  1..10
                        mol_type = protein
                        organism = synthetic construct
SEQUENCE: 373
EAWTRGYFNY                                                        10

SEQ ID NO: 374          moltype = AA  length = 10
FEATURE                 Location/Qualifiers
REGION                  1..10
                        note = MTK-33.3, 33.11 HVR-H3
source                  1..10
                        mol_type = protein
                        organism = synthetic construct
SEQUENCE: 374
EAWTRGYFDY                                                        10

SEQ ID NO: 375          moltype = AA  length = 10
FEATURE                 Location/Qualifiers
REGION                  1..10
                        note = MTK-33.23 HVR-H3
source                  1..10
                        mol_type = protein
                        organism = synthetic construct
SEQUENCE: 375
EAYTRGYFDY                                                        10

SEQ ID NO: 376          moltype = AA  length = 11
FEATURE                 Location/Qualifiers
REGION                  1..11
                        note = MTK-33.1, 33.4, 33.5, 33.12, 33.14 HVR-L1
```

```
source                  1..11
                        mol_type = protein
                        organism = synthetic construct
SEQUENCE: 376
QASQSVSNTV A                                                              11

SEQ ID NO: 377          moltype = AA  length = 11
FEATURE                 Location/Qualifiers
REGION                  1..11
                        note = MTK-33.2 HVR-L1
source                  1..11
                        mol_type = protein
                        organism = synthetic construct
SEQUENCE: 377
QASGSVSNTV A                                                              11

SEQ ID NO: 378          moltype = AA  length = 11
FEATURE                 Location/Qualifiers
REGION                  1..11
                        note = MTK-33.3, 33.13, 33.15, 33.16, 33.17, 33.18, 33.20,
                         33.21, 33.22 HVR-L1
source                  1..11
                        mol_type = protein
                        organism = synthetic construct
SEQUENCE: 378
QASRSVSNTV A                                                              11

SEQ ID NO: 379          moltype = AA  length = 11
FEATURE                 Location/Qualifiers
REGION                  1..11
                        note = MTK-33.6 HVR-L1
source                  1..11
                        mol_type = protein
                        organism = synthetic construct
SEQUENCE: 379
QASRSVSNTM A                                                              11

SEQ ID NO: 380          moltype = AA  length = 11
FEATURE                 Location/Qualifiers
REGION                  1..11
                        note = MTK-33.7 HVR-L1
source                  1..11
                        mol_type = protein
                        organism = synthetic construct
SEQUENCE: 380
GASQSVSNTV A                                                              11

SEQ ID NO: 381          moltype = AA  length = 11
FEATURE                 Location/Qualifiers
REGION                  1..11
                        note = MTK-33.8 HVR-L1
source                  1..11
                        mol_type = protein
                        organism = synthetic construct
SEQUENCE: 381
QASQSVSRTV A                                                              11

SEQ ID NO: 382          moltype = AA  length = 11
FEATURE                 Location/Qualifiers
REGION                  1..11
                        note = MTK-33.9 HVR-L1
source                  1..11
                        mol_type = protein
                        organism = synthetic construct
SEQUENCE: 382
QASASVSNTV A                                                              11

SEQ ID NO: 383          moltype = AA  length = 11
FEATURE                 Location/Qualifiers
REGION                  1..11
                        note = MTK-33.10 HVR-L1
source                  1..11
                        mol_type = protein
                        organism = synthetic construct
SEQUENCE: 383
QAGQSVSNTV A                                                              11

SEQ ID NO: 384          moltype = AA  length = 11
FEATURE                 Location/Qualifiers
```

```
REGION                  1..11
                        note = MTK-33.11 HVR-L1
source                  1..11
                        mol_type = protein
                        organism = synthetic construct
SEQUENCE: 384
QASRSVRNTV A                                                        11

SEQ ID NO: 385          moltype = AA  length = 11
FEATURE                 Location/Qualifiers
REGION                  1..11
                        note = MTK-33.19 HVR-L1
source                  1..11
                        mol_type = protein
                        organism = synthetic construct
SEQUENCE: 385
QASRSVSATV A                                                        11

SEQ ID NO: 386          moltype = AA  length = 11
FEATURE                 Location/Qualifiers
REGION                  1..11
                        note = MTK-33.23 HVR-L1
source                  1..11
                        mol_type = protein
                        organism = synthetic construct
SEQUENCE: 386
IASRSVSNTV A                                                        11

SEQ ID NO: 387          moltype = AA  length = 11
FEATURE                 Location/Qualifiers
REGION                  1..11
                        note = MTK-33.24 HVR-L1
source                  1..11
                        mol_type = protein
                        organism = synthetic construct
SEQUENCE: 387
QASRSVSRTV A                                                        11

SEQ ID NO: 388          moltype = AA  length = 7
FEATURE                 Location/Qualifiers
REGION                  1..7
                        note = MTK-33.1 HVR-L2
source                  1..7
                        mol_type = protein
                        organism = synthetic construct
SEQUENCE: 388
YASLRYT                                                             7

SEQ ID NO: 389          moltype = AA  length = 7
FEATURE                 Location/Qualifiers
REGION                  1..7
                        note = MTK-33.5 HVR-L2
source                  1..7
                        mol_type = protein
                        organism = synthetic construct
SEQUENCE: 389
YASNRET                                                             7

SEQ ID NO: 390          moltype = AA  length = 7
FEATURE                 Location/Qualifiers
REGION                  1..7
                        note = MTK-33.21 HVR-L2
source                  1..7
                        mol_type = protein
                        organism = synthetic construct
SEQUENCE: 390
YVSNRYT                                                             7

SEQ ID NO: 391          moltype = AA  length = 7
FEATURE                 Location/Qualifiers
REGION                  1..7
                        note = MTK-33.22 HVR-L2
source                  1..7
                        mol_type = protein
                        organism = synthetic construct
SEQUENCE: 391
YASNRRT                                                             7

SEQ ID NO: 392          moltype = AA  length = 9
```

```
FEATURE                Location/Qualifiers
REGION                 1..9
                       note = MTK-33.4 HVR-L3
source                 1..9
                       mol_type = protein
                       organism = synthetic construct
SEQUENCE: 392
QQDRRSPFT                                                          9

SEQ ID NO: 393         moltype = AA  length = 9
FEATURE                Location/Qualifiers
REGION                 1..9
                       note = MTK-33.12 HVR-L3
source                 1..9
                       mol_type = protein
                       organism = synthetic construct
SEQUENCE: 393
RQDTRSPFT                                                          9

SEQ ID NO: 394         moltype = AA  length = 9
FEATURE                Location/Qualifiers
REGION                 1..9
                       note = MTK-33.15, 33.17, 33.18, 33.19, 33.21, 33.22, 33.23,
                        33.24 HVR-L3
source                 1..9
                       mol_type = protein
                       organism = synthetic construct
SEQUENCE: 394
QQDMRSPFT                                                          9

SEQ ID NO: 395         moltype = AA  length = 9
FEATURE                Location/Qualifiers
REGION                 1..9
                       note = MTK-33.20 HVR-L3
source                 1..9
                       mol_type = protein
                       organism = synthetic construct
SEQUENCE: 395
AQDMRSPFT                                                          9

SEQ ID NO: 396         moltype = AA  length = 330
FEATURE                Location/Qualifiers
REGION                 1..330
                       note = huIgG1 WT Fc with C-terminal lysine
source                 1..330
                       mol_type = protein
                       organism = synthetic construct
SEQUENCE: 396
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 397         moltype = AA  length = 329
FEATURE                Location/Qualifiers
REGION                 1..329
                       note = huIgG1 WT Fc without C-terminal lysine
source                 1..329
                       mol_type = protein
                       organism = synthetic construct
SEQUENCE: 397
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 398         moltype = AA  length = 330
FEATURE                Location/Qualifiers
REGION                 1..330
                       note = huIgG1 LALAPS Fc with C-terminal lysine
source                 1..330
                       mol_type = protein
                       organism = synthetic construct
```

SEQUENCE: 398
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPEAAGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPASIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 399 moltype = AA length = 329
FEATURE Location/Qualifiers
REGION 1..329
note = huIgG1 LALAPS Fc without C-terminal lysine
source 1..329
mol_type = protein
organism = synthetic construct
SEQUENCE: 399
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPEAAGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPASIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPG 329

SEQ ID NO: 400 moltype = AA length = 330
FEATURE Location/Qualifiers
REGION 1..330
note = huIgG1 NSLF Fc with C-terminal lysine
source 1..330
mol_type = protein
organism = synthetic construct
SEQUENCE: 400
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSSKA FPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 401 moltype = AA length = 329
FEATURE Location/Qualifiers
REGION 1..329
note = huIgG1 NSLF Fc without C-terminal lysine
source 1..329
mol_type = protein
organism = synthetic construct
SEQUENCE: 401
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSSKA FPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPG 329

SEQ ID NO: 402 moltype = AA length = 330
FEATURE Location/Qualifiers
REGION 1..330
note = huIgG1 YTE Fc with C-terminal lysine
source 1..330
mol_type = protein
organism = synthetic construct
SEQUENCE: 402
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPEAAGG 120
PSVFLFPPKP KDTLYITREP EVTCVVVDVS HEDPEVKFNW YVDGVEVHNA KTKPREEQYN 180
STYRVVSVLT VLHQDWLNGK EYKCKVSNKA LPASIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK 330

SEQ ID NO: 403 moltype = AA length = 329
FEATURE Location/Qualifiers
REGION 1..329
note = huIgG1 YTE Fc without C-terminal lysine
source 1..329
mol_type = protein
organism = synthetic construct
SEQUENCE: 403
ASTKGPSVFP LAPSSKSTSG GTAALGCLVK DYFPEPVTVS WNSGALTSGV HTFPAVLQSS 60
GLYSLSSVVT VPSSSLGTQT YICNVNHKPS NTKVDKKVEP KSCDKTHTCP PCPAPEAAGG 120
PSVFLFPPKP KDTLYITREP EVTCVVVDVS HEDPEVKFNW YVDGVEVHNA KTKPREEQYN 180

```
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 404         moltype = AA  length = 330
FEATURE                Location/Qualifiers
REGION                 1..330
                       note = huIgG1 LS Fc with C-terminal lysine
source                 1..330
                       mol_type = protein
                       organism = synthetic construct
SEQUENCE: 404
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 405         moltype = AA  length = 329
FEATURE                Location/Qualifiers
REGION                 1..329
                       note = huIgG1 LS Fc without C-terminal lysine
source                 1..329
                       mol_type = protein
                       organism = synthetic construct
SEQUENCE: 405
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 406         moltype = AA  length = 342
FEATURE                Location/Qualifiers
REGION                 1..342
                       note = huIgG1 LV5-112 Fc with C-terminal lysine
source                 1..342
                       mol_type = protein
                       organism = synthetic construct
SEQUENCE: 406
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGGC ALYPTNCGGG QPENNYKTTP PVLDSDGSFF  300
LYSKLTVDKS RWQQGNVFSC SVMHEALHNH YTQKSLSLSP GK                     342

SEQ ID NO: 407         moltype = AA  length = 341
FEATURE                Location/Qualifiers
REGION                 1..341
                       note = huIgG1 LV5-112 Fc without C-terminal lysine
source                 1..341
                       mol_type = protein
                       organism = synthetic construct
SEQUENCE: 407
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPASIEKTIS KAKGQPREPQ VYTLPPSRDE  240
LTKNQVSLTC LVKGFYPSDI AVEWESNGGC ALYPTNCGGG QPENNYKTTP PVLDSDGSFF  300
LYSKLTVDKS RWQQGNVFSC SVMHEALHNH YTQKSLSLSP G                      341

SEQ ID NO: 408         moltype = AA  length = 326
FEATURE                Location/Qualifiers
REGION                 1..326
                       note = huIgG2 WT Fc with C-terminal lysine
source                 1..326
                       mol_type = protein
                       organism = synthetic construct
SEQUENCE: 408
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326
```

```
SEQ ID NO: 409          moltype = AA  length = 325
FEATURE                 Location/Qualifiers
REGION                  1..325
                        note = huIgG2 WT Fc without C-terminal lysine
source                  1..325
                        mol_type = protein
                        organism = synthetic construct
SEQUENCE: 409
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPG                                       325

SEQ ID NO: 410          moltype = AA  length = 327
FEATURE                 Location/Qualifiers
REGION                  1..327
                        note = huIgG4 WT Fc with C-terminal lysine
source                  1..327
                        mol_type = protein
                        organism = synthetic construct
SEQUENCE: 410
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 411          moltype = AA  length = 326
FEATURE                 Location/Qualifiers
REGION                  1..326
                        note = huIgG4 WT Fc without C-terminal lysine
source                  1..326
                        mol_type = protein
                        organism = synthetic construct
SEQUENCE: 411
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 412          moltype = AA  length = 107
FEATURE                 Location/Qualifiers
REGION                  1..107
                        note = Human IgG1 light chain constant region
source                  1..107
                        mol_type = protein
                        organism = synthetic construct
SEQUENCE: 412
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 413          moltype = AA  length = 450
FEATURE                 Location/Qualifiers
REGION                  1..450
                        note = MTK-16.1 with huIgG1 WT Fc with C-terminal lysine
source                  1..450
                        mol_type = protein
                        organism = synthetic construct
SEQUENCE: 413
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 414          moltype = AA  length = 449
FEATURE                 Location/Qualifiers
REGION                  1..449
                        note = MTK-16.1 with huIgG1 WT Fc without C-terminal lysine
```

```
source                  1..449
                        mol_type = protein
                        organism = synthetic construct
SEQUENCE: 414
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 415          moltype = AA  length = 450
FEATURE                 Location/Qualifiers
REGION                  1..450
                        note = MTK-16.1 with huIgG1 LALAPS Fc with C-terminal lysine
source                  1..450
                        mol_type = protein
                        organism = synthetic construct
SEQUENCE: 415
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPASIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 416          moltype = AA  length = 449
FEATURE                 Location/Qualifiers
REGION                  1..449
                        note = MTK-16.1 with huIgG1 LALAPS Fc without C-terminal
                         lysine
source                  1..449
                        mol_type = protein
                        organism = synthetic construct
SEQUENCE: 416
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPASIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                  449

SEQ ID NO: 417          moltype = AA  length = 450
FEATURE                 Location/Qualifiers
REGION                  1..450
                        note = MTK-16.1 with huIgG1 NSLF Fc with C-terminal lysine
source                  1..450
                        mol_type = protein
                        organism = synthetic construct
SEQUENCE: 417
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSSKA FPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                 450

SEQ ID NO: 418          moltype = AA  length = 449
FEATURE                 Location/Qualifiers
REGION                  1..449
                        note = MTK-16.1 with huIgG1 NSLF Fc without C-terminal
                         lysine
source                  1..449
                        mol_type = protein
                        organism = synthetic construct
SEQUENCE: 418
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
```

```
STYRVVSVLT VLHQDWLNGK EYKCKVSSKA FPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 419         moltype = AA  length = 447
FEATURE                Location/Qualifiers
REGION                 1..447
                       note = MTK-16.1 with huIgG4 Fc with C-terminal lysine
source                 1..447
                       mol_type = protein
                       organism = synthetic construct
SEQUENCE: 419
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPSCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

SEQ ID NO: 420         moltype = AA  length = 446
FEATURE                Location/Qualifiers
REGION                 1..446
                       note = MTK-16.1 with huIgG4 Fc without C-terminal lysine
source                 1..446
                       mol_type = protein
                       organism = synthetic construct
SEQUENCE: 420
QVQLVQSGSE LKKPGASVKV SCKASGYTFT NHGMNWVRQA PGQGLEWMGW INTYTGEPTY  60
AQGFTGRFVF SLDTSVSTAY LQISSLKAED TAVYYCARKG VTAARYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPSCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLG                                      446

SEQ ID NO: 421         moltype = AA  length = 214
FEATURE                Location/Qualifiers
REGION                 1..214
                       note = MTK-16.1 light chain
source                 1..214
                       mol_type = protein
                       organism = synthetic construct
SEQUENCE: 421
DIQMTQSPSS LSASVGDRVT ITCKASQNVR TAVAWYQQKP GKAPKRLIYL ASNRHTGVPS  60
RFSGSGSGTE FTLTISNLQP EDFATYYCLQ HWNYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 422         moltype = AA  length = 450
FEATURE                Location/Qualifiers
REGION                 1..450
                       note = MTK-16.2 with huIgG1 WT Fc with C-terminal lysine
source                 1..450
                       mol_type = protein
                       organism = synthetic construct
SEQUENCE: 422
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 423         moltype = AA  length = 449
FEATURE                Location/Qualifiers
REGION                 1..449
                       note = MTK-16.2 with huIgG1 WT Fc without C-terminal lysine
source                 1..449
                       mol_type = protein
                       organism = synthetic construct
SEQUENCE: 423
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
```

```
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 424          moltype = AA  length = 450
FEATURE                 Location/Qualifiers
REGION                  1..450
                        note = MTK-16.2 with huIgG1 LALAPS Fc with C-terminal lysine
source                  1..450
                        mol_type = protein
                        organism = synthetic construct
SEQUENCE: 424
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPASIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 425          moltype = AA  length = 449
FEATURE                 Location/Qualifiers
REGION                  1..449
                        note = MTK-16.2 with huIgG1 LALAPS Fc without C-terminal
                         lysine
source                  1..449
                        mol_type = protein
                        organism = synthetic construct
SEQUENCE: 425
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPASIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 426          moltype = AA  length = 450
FEATURE                 Location/Qualifiers
REGION                  1..450
                        note = MTK-16.2 with huIgG1 NSLF Fc with C-terminal lysine
source                  1..450
                        mol_type = protein
                        organism = synthetic construct
SEQUENCE: 426
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSSKA FPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 427          moltype = AA  length = 449
FEATURE                 Location/Qualifiers
REGION                  1..449
                        note = MTK-16.2 with huIgG1 NSLF Fc without C-terminal
                         lysine
source                  1..449
                        mol_type = protein
                        organism = synthetic construct
SEQUENCE: 427
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSSKA FPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 428          moltype = AA  length = 447
FEATURE                 Location/Qualifiers
```

```
REGION                  1..447
                        note = MTK-16.2 with huIgG4 Fc with C-terminal lysine
source                  1..447
                        mol_type = protein
                        organism = synthetic construct
SEQUENCE: 428
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPSCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 429          moltype = AA  length = 447
FEATURE                 Location/Qualifiers
REGION                  1..447
                        note = MTK-16.2 with huIgG4 Fc without C-terminal lysine
source                  1..447
                        mol_type = protein
                        organism = synthetic construct
SEQUENCE: 429
QVQLVQSGSE LKKPGASVKV SCKASGYTFT NHGMNWVRQA PGQGLEWMGW INTYTGEPTY  60
ADDFKGRFVF SLDTSVSTAY LQISSLKAED TAVYYCARKG VTAARYFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPSCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 430          moltype = AA  length = 214
FEATURE                 Location/Qualifiers
REGION                  1..214
                        note = MTK-16.2 light chain
source                  1..214
                        mol_type = protein
                        organism = synthetic construct
SEQUENCE: 430
DIQMTQSPSS LSASVGDRVT ITCRASQNVR TAVAWYQQKP GKAPKRLIYL ASNRHTGVPS  60
RFSGSGSGTE FTLTISNLQP EDFATYYCLQ HWNYPLTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 431          moltype = AA  length = 449
FEATURE                 Location/Qualifiers
REGION                  1..449
                        note = MTK-33.1 with huIgG1 WT Fc with C-terminal lysine
source                  1..449
                        mol_type = protein
                        organism = synthetic construct
SEQUENCE: 431
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 432          moltype = AA  length = 448
FEATURE                 Location/Qualifiers
REGION                  1..448
                        note = MTK-33.1 with huIgG1 WT Fc without C-terminal lysine
source                  1..448
                        mol_type = protein
                        organism = synthetic construct
SEQUENCE: 432
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448
```

```
SEQ ID NO: 433          moltype = AA  length = 449
FEATURE                 Location/Qualifiers
REGION                  1..449
                        note = MTK-33.1 with huIgG1 LALAPS Fc with C-terminal lysine
source                  1..449
                        mol_type = protein
                        organism = synthetic construct
SEQUENCE: 433
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 434          moltype = AA  length = 448
FEATURE                 Location/Qualifiers
REGION                  1..448
                        note = MTK-33.1 with huIgG1 LALAPS Fc without C-terminal
                         lysine
source                  1..448
                        mol_type = protein
                        organism = synthetic construct
SEQUENCE: 434
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 435          moltype = AA  length = 449
FEATURE                 Location/Qualifiers
REGION                  1..449
                        note = MTK-33.1 with huIgG1 NSLF Fc with C-terminal lysine
source                  1..449
                        mol_type = protein
                        organism = synthetic construct
SEQUENCE: 435
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 436          moltype = AA  length = 448
FEATURE                 Location/Qualifiers
REGION                  1..448
                        note = MTK-33.1 with huIgG1 NSLF Fc without C-terminal
                         lysine
source                  1..448
                        mol_type = protein
                        organism = synthetic construct
SEQUENCE: 436
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 437          moltype = AA  length = 446
FEATURE                 Location/Qualifiers
REGION                  1..446
                        note = MTK-33.1 with huIgG4 Fc with C-terminal lysine
source                  1..446
                        mol_type = protein
                        organism = synthetic construct
```

```
SEQUENCE: 437
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 438          moltype = AA  length = 445
FEATURE                 Location/Qualifiers
REGION                  1..445
                        note = MTK-33.1 with huIgG4 Fc without C-terminal lysine
source                  1..445
                        mol_type = protein
                        organism = synthetic construct
SEQUENCE: 438
QVQLVQSGAE VKKPGASVKV SCKASGYTFT SYWMHWVRQA PGQGLEWIGV IDPSDNYINY  60
NQKFQGRVTM TRDTSTSTVY MELSSLRSED TAVYYCAREA WTRGYFNYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLG                                       445

SEQ ID NO: 439          moltype = AA  length = 214
FEATURE                 Location/Qualifiers
REGION                  1..214
                        note = MTK-33.1 light chain
source                  1..214
                        mol_type = protein
                        organism = synthetic construct
SEQUENCE: 439
DIQMTQSPSS LSASVGDRVT ITCQASQSVS NTVAWYQQKP GKAPKLLIYY ASLRYTGVPS  60
RFSGSGSGTD FTFTISSLQP EDIATYYCQQ DYRSPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 440          moltype = AA  length = 449
FEATURE                 Location/Qualifiers
REGION                  1..449
                        note = MTK-33.12 with huIgG1 WT Fc with C-terminal lysine
source                  1..449
                        mol_type = protein
                        organism = synthetic construct
SEQUENCE: 440
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 441          moltype = AA  length = 448
FEATURE                 Location/Qualifiers
REGION                  1..448
                        note = MTK-33.12 with huIgG1 WT Fc without C-terminal lysine
source                  1..448
                        mol_type = protein
                        organism = synthetic construct
SEQUENCE: 441
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 442          moltype = AA  length = 449
FEATURE                 Location/Qualifiers
REGION                  1..449
                        note = MTK-33.12 with huIgG1 LALAPS Fc with C-terminal
                         lysine
```

```
source                  1..449
                        mol_type = protein
                        organism = synthetic construct
SEQUENCE: 442
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 443          moltype = AA  length = 448
FEATURE                 Location/Qualifiers
REGION                  1..448
                        note = MTK-33.12 with huIgG1 LALAPS Fc without C-terminal
                         lysine
source                  1..448
                        mol_type = protein
                        organism = synthetic construct
SEQUENCE: 443
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 444          moltype = AA  length = 449
FEATURE                 Location/Qualifiers
REGION                  1..449
                        note = MTK-33.12 with huIgG1 NSLF Fc with C-terminal lysine
source                  1..449
                        mol_type = protein
                        organism = synthetic construct
SEQUENCE: 444
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 445          moltype = AA  length = 448
FEATURE                 Location/Qualifiers
REGION                  1..448
                        note = MTK-33.12 with huIgG1 NSLF Fc without C-terminal
                         lysine
source                  1..448
                        mol_type = protein
                        organism = synthetic construct
SEQUENCE: 445
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 446          moltype = AA  length = 446
FEATURE                 Location/Qualifiers
REGION                  1..446
                        note = MTK-33.12 with huIgG4 Fc with C-terminal lysine
source                  1..446
                        mol_type = protein
                        organism = synthetic construct
SEQUENCE: 446
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
```

```
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                      446

SEQ ID NO: 447         moltype = AA  length = 445
FEATURE                Location/Qualifiers
REGION                 1..445
                       note = MTK-33.12 with huIgG4 Fc without C-terminal lysine
source                 1..445
                       mol_type = protein
                       organism = synthetic construct
SEQUENCE: 447
QVQLVQSGAE VKKPGASVKV SCKASGYTFV SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLG                                       445

SEQ ID NO: 448         moltype = AA  length = 214
FEATURE                Location/Qualifiers
REGION                 1..214
                       note = MTK-33.12 light chain
source                 1..214
                       mol_type = protein
                       organism = synthetic construct
SEQUENCE: 448
DIQMTQSPSS LSASVGDRVT ITCQASQSVS NTVAWYQQKP GKAPKLLIYY ASNRYTGVPS  60
RFSGSGSGTD FTFTISSLQP EDIATYYCRQ DTRSPFTFGQ GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 449         moltype = AA  length = 67
FEATURE                Location/Qualifiers
REGION                 1..67
                       note = N-terminal domain (N) of human MerTK ECD
source                 1..67
                       mol_type = protein
                       organism = synthetic construct
SEQUENCE: 449
AITEAREEAK PYPLFPGPFP GSLQTDHTPL LSLPHASGYQ PALMFSPTQP GRPHTGNVAI  60
PQVTSVE                                                           67

SEQ ID NO: 450         moltype = AA  length = 107
FEATURE                Location/Qualifiers
REGION                 1..107
                       note = Immunoglobulin-like domain (Ig1) of human MerTK ECD
source                 1..107
                       mol_type = protein
                       organism = synthetic construct
SEQUENCE: 450
SKPLPPLAFK HTVGHIILSE HKGVKFNCSI SVPNIYQDTT ISWWKDGKEL LGAHHAITQF  60
YPDDEVTAII ASFSITSVQR SDNGSYICKM KINNEEIVSD PIYIEVQ               107

SEQ ID NO: 451         moltype = AA  length = 85
FEATURE                Location/Qualifiers
REGION                 1..85
                       note = Immunoglobulin-like domain (Ig2) of human MerTK ECD
source                 1..85
                       mol_type = protein
                       organism = synthetic construct
SEQUENCE: 451
GLPHFTKQPE SMNVTRNTAF NLTCQAVGPP EPVNIFWVQN SSRVNEQPEK SPSVLTVPGL  60
TEMAVFSCEA HNDKGLTVSK GVQIN                                       85

SEQ ID NO: 452         moltype = AA  length = 99
FEATURE                Location/Qualifiers
REGION                 1..99
                       note = Fibronectin type III domain (FN1) of human MerTK ECD
source                 1..99
                       mol_type = protein
                       organism = synthetic construct
SEQUENCE: 452
IKAIPSPPTE VSIRNSTAHS ILISWVPGFD GYSPFRNCSI QVKEADPLSN GSVMIFNTSA  60
LPHLYQIKQL QALANYSIGV SCMNEIGWSA VSPWILAST                        99

SEQ ID NO: 453         moltype = AA  length = 98
```

```
FEATURE                 Location/Qualifiers
REGION                  1..98
                        note = Fibronectin type III domain (FN2) of human MerTK ECD
source                  1..98
                        mol_type = protein
                        organism = synthetic construct
SEQUENCE: 453
TEGAPSVAPL NVTVFLNESS DNVDIRWMKP PTKQQDGELV GYRISHVWQS AGISKELLEE  60
VGQNGSRARI SVQVHNATCT VRIAAVTRGG VGPFSDPV                          98

SEQ ID NO: 454          moltype = AA  length = 29
FEATURE                 Location/Qualifiers
REGION                  1..29
                        note = Juxta membrane domain region (JM) of human MerTK ECD
source                  1..29
                        mol_type = protein
                        organism = synthetic construct
SEQUENCE: 454
KIFIPAHGWV DYAPSSTPAP GNADPVLII                                    29

SEQ ID NO: 455          moltype = AA  length = 27
FEATURE                 Location/Qualifiers
REGION                  1..27
                        note = N-terminal domain (N) of human Axl ECD
source                  1..27
                        mol_type = protein
                        organism = synthetic construct
SEQUENCE: 455
APRGTQAEES PFVGNPGNIT GARGLTG                                      27

SEQ ID NO: 456          moltype = AA  length = 84
FEATURE                 Location/Qualifiers
REGION                  1..84
                        note = Immunoglobulin-like domain (Ig1) of human Axl ECD
source                  1..84
                        mol_type = protein
                        organism = synthetic construct
SEQUENCE: 456
TLRCQLQVQG EPPEVHWLRD GQILELADST QTQVPLGEDE QDDWIVVSQL RITSLQLSDT  60
GQYQCLVFLG HQTFVSQPGY VGLE                                         84

SEQ ID NO: 457          moltype = AA  length = 89
FEATURE                 Location/Qualifiers
REGION                  1..89
                        note = Immunoglobulin-like domain (Ig2) of human Axl ECD
source                  1..89
                        mol_type = protein
                        organism = synthetic construct
SEQUENCE: 457
GLPYFLEEPE DRTVAANTPF NLSCQAQGPP EPVDLLWLQD AVPLATAPGH GPQRSLHVPG  60
LNKTSSFSCE AHNAKGVTTS RTATITVLP                                    89

SEQ ID NO: 458          moltype = AA  length = 106
FEATURE                 Location/Qualifiers
REGION                  1..106
                        note = Fibronectin type III domain (FN1) of human Axl ECD
source                  1..106
                        mol_type = protein
                        organism = synthetic construct
SEQUENCE: 458
QQPRNLHLVS RQPTELEVAW TPGLSGIYPL THCTLQAVLS DDGMGIQAGE PDPPEEPLTS  60
QASVPPHQLR LGSLHPHTPY HIRVACTSSQ GPSSWTHWLP VETPEG                 106

SEQ ID NO: 459          moltype = AA  length = 87
FEATURE                 Location/Qualifiers
REGION                  1..87
                        note = Fibronectin type III domain (FN2) of human Axl ECD
source                  1..87
                        mol_type = protein
                        organism = synthetic construct
SEQUENCE: 459
VPLGPPENIS ATRNGSQAFV HWQEPRAPLQ GTLLGYRLAY QGQDTPEVLM DIGLRQEVTL  60
ELQGDGSVSN LTVCVAAYTA AGDGPWS                                      87
```

```
SEQ ID NO: 460         moltype = AA  length = 33
FEATURE                Location/Qualifiers
REGION                 1..33
                       note = Juxta membrane domain (JM) of human Axl ECD
source                 1..33
                       mol_type = protein
                       organism = synthetic construct
SEQUENCE: 460
LPVPLEAWRP GQAQPVHQLV KEPSTPAFSW PWW                              33

SEQ ID NO: 461         moltype = AA  length = 19
FEATURE                Location/Qualifiers
REGION                 1..19
                       note = MerTK construct signal sequence
source                 1..19
                       mol_type = protein
                       organism = synthetic construct
SEQUENCE: 461
MGWSCIILFL VATATGVHS                                              19

SEQ ID NO: 462         moltype = AA  length = 16
FEATURE                Location/Qualifiers
REGION                 1..16
                       note = Axl construct signal sequence
source                 1..16
                       mol_type = protein
                       organism = synthetic construct
SEQUENCE: 462
MGWSCIILFL VATATG                                                 16

SEQ ID NO: 463         moltype = AA  length = 27
FEATURE                Location/Qualifiers
REGION                 1..27
                       note = Linker+His+Avi tag
source                 1..27
                       mol_type = protein
                       organism = synthetic construct
SEQUENCE: 463
GGSGHHHHHH GGGLNDIFEA QKIEWHE                                     27

SEQ ID NO: 464         moltype = AA  length = 449
FEATURE                Location/Qualifiers
REGION                 1..449
                       note = MTK-33.10 with huIgG1 WT Fc with C-terminal lysine
source                 1..449
                       mol_type = protein
                       organism = synthetic construct
SEQUENCE: 464
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 465         moltype = AA  length = 448
FEATURE                Location/Qualifiers
REGION                 1..448
                       note = MTK-33.10 with huIgG1 WT Fc without C-terminal lysine
source                 1..448
                       mol_type = protein
                       organism = synthetic construct
SEQUENCE: 465
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448
```

```
SEQ ID NO: 466          moltype = AA  length = 449
FEATURE                 Location/Qualifiers
REGION                  1..449
                        note = MTK-33.10 with huIgG1 LALAPS Fc with C-terminal
                         lysine
source                  1..449
                        mol_type = protein
                        organism = synthetic construct
SEQUENCE: 466
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 467          moltype = AA  length = 448
FEATURE                 Location/Qualifiers
REGION                  1..448
                        note = MTK-33.10 with huIgG1 LALAPS Fc without C-terminal
                         lysine
source                  1..448
                        mol_type = protein
                        organism = synthetic construct
SEQUENCE: 467
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PASIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 468          moltype = AA  length = 449
FEATURE                 Location/Qualifiers
REGION                  1..449
                        note = MTK-33.10 with huIgG1 NSLF Fc with C-terminal lysine
source                  1..449
                        mol_type = protein
                        organism = synthetic construct
SEQUENCE: 468
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 469          moltype = AA  length = 448
FEATURE                 Location/Qualifiers
REGION                  1..448
                        note = MTK-33.10 with huIgG1 NSLF Fc without C-terminal
                         lysine
source                  1..448
                        mol_type = protein
                        organism = synthetic construct
SEQUENCE: 469
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSSKAF PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 470          moltype = AA  length = 446
FEATURE                 Location/Qualifiers
REGION                  1..446
                        note = MTK-33.10 with huIgG4 Fc with C-terminal lysine
```

```
source                  1..446
                        mol_type = protein
                        organism = synthetic construct
SEQUENCE: 470
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 471          moltype = AA  length = 445
FEATURE                 Location/Qualifiers
REGION                  1..445
                        note = MTK-33.10 with huIgG4 Fc without C-terminal lysine
source                  1..445
                        mol_type = protein
                        organism = synthetic construct
SEQUENCE: 471
QVQLVQSGAE VKKPGASVKV SCKASSYSFT SYWMHWVRQA PGQGLEWIGV IDPSDNYINY  60
NQKFRGRVTM TRDTSTSTVY MELSSLRSED TAVYYCAREA GTRGYFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPSCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLG                                        445

SEQ ID NO: 472          moltype = AA  length = 214
FEATURE                 Location/Qualifiers
REGION                  1..214
                        note = MTK-33.10 light chain
source                  1..214
                        mol_type = protein
                        organism = synthetic construct
SEQUENCE: 472
DIQMTQSPSS LSASVGDRVT ITCQAGQSVS NTVAWYQQKP GKAPKLLIYY ASNRYTGVPS  60
RFSGSGSGTD FTFTISSLQP EDIATYYCQQ DYRSPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```